(12) United States Patent
Croce et al.

(10) Patent No.: US 8,658,370 B2
(45) Date of Patent: Feb. 25, 2014

(54) MICRORNA-BASED METHODS AND COMPOSITIONS FOR THE DIAGNOSIS, PROGNOSIS AND TREATMENT OF BREAST CANCER

(75) Inventors: Carlo M. Croce, Columbus, OH (US); George A. Calin, Pearland, TX (US)

(73) Assignee: The Ohio State University Research Foundation, Columbus, OH (US)

( * ) Notice: Subject to any disclaimer, the term of this patent is extended or adjusted under 35 U.S.C. 154(b) by 1144 days.

(21) Appl. No.: 12/012,235

(22) Filed: Jan. 31, 2008

(65) Prior Publication Data

US 2008/0261908 A1 Oct. 23, 2008

(51) Int. Cl.
| C12Q 1/68 | (2006.01) |
| C07H 21/02 | (2006.01) |
| C07H 21/04 | (2006.01) |

(52) U.S. Cl.
USPC .......................... 435/6.14; 435/6.1; 536/23.1

(58) Field of Classification Search
USPC ..................................... 435/6, 91.1, 325, 375
See application file for complete search history.

(56) References Cited

U.S. PATENT DOCUMENTS

| 4,172,124 A | 10/1979 | Koprowski et al. |
| 4,196,265 A | 4/1980 | Koprowski et al. |
| 4,608,337 A | 8/1986 | Croce |
| 4,693,975 A | 9/1987 | Kozbor et al. |
| 4,701,409 A | 10/1987 | Croce |
| 5,015,568 A | 5/1991 | Tsujimoto et al. |
| 5,149,628 A | 9/1992 | Croce |
| 5,198,338 A | 3/1993 | Croce |
| 5,202,429 A | 4/1993 | Tsujimoto et al. |
| 5,459,251 A | 10/1995 | Tsujimoto et al. |
| 5,506,106 A | 4/1996 | Croce et al. |
| 5,506,344 A | 4/1996 | Tsujimoto et al. |
| 5,523,393 A | 6/1996 | Tsujimoto et al. |
| 5,567,586 A | 10/1996 | Croce |
| 5,595,869 A | 1/1997 | Tsujimoto et al. |
| 5,633,135 A | 5/1997 | Croce et al. |
| 5,633,136 A | 5/1997 | Croce et al. |
| 5,674,682 A | 10/1997 | Croce et al. |
| 5,688,649 A | 11/1997 | Croce et al. |
| 5,695,944 A | 12/1997 | Croce et al. |
| 5,928,884 A | 7/1999 | Croce et al. |
| 5,939,258 A | 8/1999 | Croce et al. |
| 5,985,598 A | 11/1999 | Russo et al. |
| 6,040,140 A | 3/2000 | Croce et al. |
| 6,130,201 A | 10/2000 | Croce et al. |
| 6,187,536 B1 | 2/2001 | Weinberg et al. |

(Continued)

FOREIGN PATENT DOCUMENTS

| CA | 2533701 A1 | 2/2005 |
| CA | 2587189 | 12/2006 |

(Continued)

OTHER PUBLICATIONS

Lu et al., MicroRNA expression profiles classify human cancers. Nature Jun. 9, 2004, 435:835-838.

(Continued)

*Primary Examiner* — Terra Cotta Gibbs
(74) *Attorney, Agent, or Firm* — MacMillan, Sobanski & Todd, LLC

(57) ABSTRACT

The present invention provides novel methods and compositions for the diagnosis, prognosis and treatment of breast cancer. The invention also provides methods of identifying anti-breast cancer agents.

10 Claims, 4 Drawing Sheets
(2 of 4 Drawing Sheet(s) Filed in Color)

(56) References Cited

U.S. PATENT DOCUMENTS

| | | |
|---|---|---|
| 6,242,212 B1 | 6/2001 | Croce et al. |
| 6,255,293 B1 | 7/2001 | Kimchi |
| 6,258,541 B1 | 7/2001 | Chapkin et al. |
| 6,774,217 B1 | 8/2004 | Croce et al. |
| 6,924,414 B2 | 8/2005 | Croce et al. |
| 7,060,811 B2 | 6/2006 | Aldaz et al. |
| 7,141,417 B1 | 11/2006 | Croce et al. |
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,585,969 B2 | 9/2009 | Stoffel et al. |
| 7,592,441 B2 | 9/2009 | Bentwich et al. |
| 7,618,814 B2 | 11/2009 | Bentwich et al. |
| 7,642,348 B2 | 1/2010 | Bentwich et al. |
| 7,667,090 B2 | 2/2010 | Croce |
| 7,670,840 B2 | 3/2010 | Croce et al. |
| 7,709,616 B2 | 5/2010 | Bentwich et al. |
| 7,723,030 B2 | 5/2010 | Croce et al. |
| 7,723,035 B2 | 5/2010 | Croce et al. |
| 7,728,189 B2 | 6/2010 | Croce |
| 7,749,715 B2 | 7/2010 | Russo et al. |
| 7,777,005 B2 | 8/2010 | Croce et al. |
| 7,888,010 B2 | 2/2011 | Brown et al. |
| 7,919,245 B2 | 4/2011 | Brown et al. |
| 2001/0026796 A1 | 10/2001 | Croce et al. |
| 2002/0086331 A1 | 7/2002 | Croce et al. |
| 2002/0116726 A1 | 8/2002 | Croce et al. |
| 2002/0132290 A1 | 9/2002 | Frazer |
| 2004/0033502 A1 | 2/2004 | Williams et al. |
| 2004/0078834 A1 | 4/2004 | Croce |
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0112630 A1 | 5/2005 | Shaughnessy et al. |
| 2005/0164252 A1 | 7/2005 | Yeung |
| 2005/0176025 A1 | 8/2005 | McSwiggen et al. |
| 2005/0181385 A1 | 8/2005 | Linsley et al. |
| 2005/0186589 A1 | 8/2005 | Kowalik et al. |
| 2005/0256072 A1 | 11/2005 | Aronin et al. |
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0127895 A1 | 6/2006 | Sabapathy |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0247448 A1 | 11/2006 | Boivin et al. |
| 2006/0292616 A1 | 12/2006 | Neely et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0099196 A1 | 5/2007 | Kauppinen et al. |
| 2007/0123482 A1 | 5/2007 | Stoffel et al. |
| 2007/0161004 A1 | 7/2007 | Brown et al. |
| 2007/0178105 A1 | 8/2007 | Croce et al. |
| 2007/0178502 A1 | 8/2007 | Reed |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2008/0026951 A1 | 1/2008 | Brown et al. |
| 2008/0050744 A1 | 2/2008 | Brown et al. |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0254473 A1 | 10/2008 | Chen et al. |
| 2008/0256650 A1 | 10/2008 | Croce |
| 2008/0261908 A1 | 10/2008 | Croce et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004322 A1 | 1/2010 | Croce |
| 2010/0048681 A1 | 2/2010 | Croce |
| 2010/0099200 A1 | 4/2010 | Nazabal et al. |
| 2010/0104662 A1 | 4/2010 | Oren et al. |
| 2010/0120898 A1 | 5/2010 | Croce et al. |
| 2010/0137410 A1 | 6/2010 | Croce |
| 2010/0144850 A1 | 6/2010 | Croce |
| 2010/0173319 A1 | 7/2010 | Croce et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0196426 A1 | 8/2010 | Skog et al. |
| 2010/0197770 A1 | 8/2010 | Wang et al. |
| 2010/0197774 A1 | 8/2010 | Croce et al. |
| 2010/0203544 A1 | 8/2010 | Croce et al. |
| 2010/0234241 A1 | 9/2010 | Croce et al. |
| 2010/0249213 A1 | 9/2010 | Croce |
| 2010/0257618 A1 | 10/2010 | Croce et al. |
| 2010/0317610 A1 | 12/2010 | Croce |

FOREIGN PATENT DOCUMENTS

| | | |
|---|---|---|
| FR | 2877350 A1 | 5/2006 |
| WO | 90/15156 | 12/1990 |
| WO | 91/00364 | 1/1991 |
| WO | 91/07424 | 5/1991 |
| WO | 93/12136 | 6/1993 |
| WO | 94/10343 | 5/1994 |
| WO | 94/24308 | 10/1994 |
| WO | 94/26930 | 11/1994 |

(56) References Cited

FOREIGN PATENT DOCUMENTS

| | | |
|---|---|---|
| WO | 96/13514 | 5/1996 |
| WO | 96/35124 | 11/1996 |
| WO | 97/29119 | 8/1997 |
| WO | 98/09510 | 3/1998 |
| WO | 00/03685 | 1/2000 |
| WO | 00/50565 | 8/2000 |
| WO | 00/55169 | 9/2000 |
| WO | 0076524 | 12/2000 |
| WO | 01/44466 | 6/2001 |
| WO | 01/68666 | 9/2001 |
| WO | 01/77343 | 10/2001 |
| WO | 01/87958 | 11/2001 |
| WO | 02/064171 | 8/2002 |
| WO | 02/064172 | 8/2002 |
| WO | 03/029459 | 4/2003 |
| WO | 03/078662 | 9/2003 |
| WO | 03/092370 | 11/2003 |
| WO | 2004/033659 | 4/2004 |
| WO | 2004/043387 | 5/2004 |
| WO | 2004043387 A2 | 5/2004 |
| WO | 2004/079013 | 9/2004 |
| WO | 2004/098377 | 11/2004 |
| WO | 2005/017711 | 2/2005 |
| WO | 2005013901 A3 | 2/2005 |
| WO | 2005/020795 | 3/2005 |
| WO | 2005060661 | 7/2005 |
| WO | 2005/078139 | 8/2005 |
| WO | 2005078139 A2 | 8/2005 |
| WO | 2005/080601 | 9/2005 |
| WO | 2005079397 A2 | 9/2005 |
| WO | 2005103298 A2 | 11/2005 |
| WO | 2005/118806 | 12/2005 |
| WO | 2006/105486 | 10/2006 |
| WO | 2006/108718 | 10/2006 |
| WO | 2006108718 A1 | 10/2006 |
| WO | 2006/119266 | 11/2006 |
| WO | 2006/133022 | 12/2006 |
| WO | 2006/137941 | 12/2006 |
| WO | 2007/016548 | 2/2007 |
| WO | 2007016548 A2 | 2/2007 |
| WO | 2007/033023 | 3/2007 |
| WO | 2007/044413 | 4/2007 |
| WO | 2007/081680 | 7/2007 |
| WO | 2007/081720 | 7/2007 |
| WO | 2007/081740 | 7/2007 |
| WO | 2007/084486 | 7/2007 |
| WO | 2007/109236 | 9/2007 |
| WO | 2007112097 | 10/2007 |
| WO | 2007112754 A2 | 10/2007 |
| WO | 2007/127190 | 11/2007 |
| WO | 2008/008430 | 1/2008 |
| WO | 2008/036168 A2 | 3/2008 |
| WO | 2008/036776 | 3/2008 |
| WO | 2008/054828 | 5/2008 |
| WO | 2008/054828 C | 5/2008 |
| WO | 2008/070082 | 6/2008 |
| WO | 2008/073920 | 6/2008 |
| WO | 2008073915 A2 | 6/2008 |
| WO | 2008/094545 | 8/2008 |
| WO | 2008/097277 | 8/2008 |
| WO | 2008/136971 | 11/2008 |
| WO | 2008/153987 | 12/2008 |
| WO | 2008/157319 | 12/2008 |
| WO | 2009/018303 | 2/2009 |
| WO | 2009/020905 | 2/2009 |
| WO | 2009/026487 | 2/2009 |
| WO | 2009/033140 | 3/2009 |
| WO | 2009/049129 | 4/2009 |
| WO | 2009/055773 | 4/2009 |
| WO | 2009/064590 | 5/2009 |
| WO | 2009/070653 | 6/2009 |
| WO | 2009/100029 | 8/2009 |
| WO | 2009/108853 | 9/2009 |
| WO | 2009/108856 | 9/2009 |
| WO | 2009/108860 | 9/2009 |
| WO | 2009/108866 | 9/2009 |
| WO | 2009/152300 | 12/2009 |
| WO | 2010/019694 | 2/2010 |
| WO | 2010/059779 | 5/2010 |
| WO | 2010/065156 | 6/2010 |
| WO | 2010/099161 | 9/2010 |

OTHER PUBLICATIONS

Calin et al., Human MicroRNA genes frequently located at fragile sites and genomic regions involved in cancers. Proc. Natl. Acad. Sci. USA. Mar. 2, 2004, 101(9): 2999-3004.

Iorio et al., MicroRNA Gene Expression Deregulation in Human Breast Cancer. Cancer Res. Aug. 15, 2005, 65(16):7065-7070.

Mattie et al., Optimized high-throughput microRNA expression profiling provides novel biomarker assessment of clinical prostate and breast cancer biopsies. Molecular Cancer. Jun. 19, 2006, 5:24-37.

Zhang et al., MicroRNAs exhibit high frequency genomic alterations in human cancer. Proc. Natl. Acad. Sci. USA. Jun. 13, 2006, 103(24):9136-9141.

Calin et al., MicroRNA Signature Associated with Prognosis and Progression in Chronic Lymphocytic Leukemia. N. Engl. J. Med. Oct. 27, 2005, 353:1793-1801.

Akahoshi, M. et al., "Myeloproliferative Disorders Terminating in Acute Megakaryoblastic Leukemia with Chromosome 3q26 Abnormality," Cancer, 1987, pp. 2654-2661, vol. 60.

Akao, Y. et al., "let-7 MicroRNA Functions as a Potential Growth Suppressor in Human Colon Cancer Cells," Biol. Pharm. Bull., May 2006, pp. 903-906, vol. 29, No. 5.

Ambs, S. et al., "Genomic Profiling of MicroRNA and Messenger RNA Reveals Deregulated MicroRNA Expression in Prostate Cancer," Cancer Research, Aug. 2008, pp. 6162-6170, vol. 68, No. 15.

Aqeilan, R. I. et al., "Targeted Deletion of WWOX Reveals a Tumor Suppressor Function," PNAS, Mar. 2007, pp. 3949-3954, vol. 104, No. 10.

Bandres, E. et al., "Identification by Real-Time PCR of 13 Mature MicroRNAs Differentially Expressed in Colorectal Cancer and Non-Tumoral Tissues," Molecular Cancer, Jul. 2006, 10 pages, vol. 5, No. 29.

Bartel, D. P., "MicroRNAs: Target Recognition and Regulatory Functions," Cell, Jan. 2009, pp. 215-233, vol. 136.

Bednarek, A. K. et al., "WWOX, the FRA16D Gene, Behaves as a Suppressor of Tumor Growth," Cancer Research, Nov. 2001, pp. 8068-8073, vol. 61.

Bejenaro, etal., "Ultraconserved Elements in the Human Genome," Electronic Suppl. Data, Science, 2004.

Bejerano, G. et al., "Ultraconserved Elements in the Human Genome," Science, May 2004, pp. 1321-1325, vol. 304.

Bell, D. A., "Origins and Molecular Pathology of Ovarian Cancer," Modern Pathology, 2005, pp. S19-S32, vol. 18.

Bichi, R. et al., "Human Chronic Lymphocytic Leukemia Modeled in Mouse by Targeted TCL1 Expression," PNAS, May 2002, pp. 6955-6960, vol. 99, No. 10.

Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.

Budhu, A. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.

Budhu, A. et al., "Identification of Metastasis-Related MicroRNAs in Hepatocellular Carcinoma," Hepatology, Mar. 2008, pp. 897-907, vol. 47, No. 3.

Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.

Calin, G. A. et al., "Chromosomal Rearrangements and MicroRNAs: A New Cancer Link with Clinical Implications," The Journal of Clinical Investigation, Aug. 2007, pp. 2059-2066, vol. 117, No. 8.

Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.

(56) References Cited

OTHER PUBLICATIONS

Calin, G. A. et al., "Human MicroRNA Genes are Frequently Located at Fragile Sites and Genomic Regions Involved in Cancers," PNAS, Mar. 2004, pp. 2999-3004, vol. 101, No. 9.
Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.
Calin, G. A. et al., "MicroRNA Signatures in Human Cancers," Nature Reviews Cancer, Nov. 2006, pp. 857-866, vol. 6.
Calin, G. A. et al., "MiR-15a and MiR-16-1 Cluster Functions in Human Leukemia," PNAS, Apr. 2008, pp. 5166-5171, vol. 105, No. 13.
Calin, G. A. et al., "Ultraconserved Regions Encoding ncRNAs are Altered in Human Leukemias and Carcinomas," Cancer Cell, Sep. 2007, pp. 215-229, vol. 12.
Chan, J. A. et al., "MicroRNA-21 is an Antiapoptotic Factor in Human Glioblastoma Cells," Cancer Research, Jul. 2005, pp. 6029-6033, vol. 65, No. 14.
Chang, N.-S. et al., "Molecular Mechanisms Underlying WOX1 Activation During Apoptotic and Stress Responses," Biochemical Pharmacology, 2003, pp. 1347-1354, vol. 66.
Chang, T.-C. et al., "Widespread MicroRNA Repression by Myc Contributes to Tumorigenesis," Nat Genet., Jan. 2008, pp. 43-50, vol. 40, No. 1.
Chen, C.-Z. et al., "MicroRNAs as Regulators of Mammalian Hematopoiesis," Seminars in Immunology, 2005, pp. 155-165, vol. 17.
Cheng, A. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.
Ciafre, S. A. et al., "Extensive Modulation of a Set of MicroRNAs in Primary Glioblastoma," Biochemical and Biophysical Research Communications, 2005, pp. 1351-1358, vol. 334.
Cimmino, A. et al., "miR-15 and miR-16 Induce Apoptosis by Targeting BCL2," PNAS, Sep. 2005, pp. 13944-13949, vol. 102, No. 39.
Cimmino, A. et al., Corrections to "miR-15 and miR-16 Induce Apoptosis by Targeting BCL2," PNAS, Feb. 2006, pp. 2464-2465, vol. 103, No. 7.
Costinean, S. et al., "Pre-B Cell Proliferation and Lymphoblastic Leukemia/ High-Grade Lymphoma in Eµ-miR155 Transgenic Mice," PNAS, May 2006, pp. 7024-7029, vol. 103, No. 18.
Croce, C. M. et al., "miRNAs, Cancer, and Stem Cell Division," Cell, 2005, pp. 6-7, vol. 36.
Croce, C. M. et al., "Role of FHIT in Human Cancer," Journal of Clinical Oncology, May 1999, pp. 1618-1624, vol. 17, No. 5.
Croce, C. M., "Causes and Consequences of MicroRNA Dysregulation in Cancer," Nature Reviews Genetics, Oct. 2009, pp. 704-714, vol. 10.
Croce, C. M., "Oncogenes and Cancer," the New England Journal of Medicine, Jan. 2008, pp. 502-511, vol. 358, No. 5.
Dalmay, T. et al., "MicroRNAs and the Hallmarks of Cancer," Oncogene, 2006, pp. 6170-6175, vol. 25.
Davies, F. E. et al., "Insights into the Multistep Transformation of MGUS to Myeloma Using Microarray Expression Analysis," Blood, Dec. 2003, pp. 4504-4511, vol. 102, No. 13.
Dohner, H. et al., "Genomic Aberrations and Survival in Chronic Lymphocytic Leukemia," The New England Journal of Medicine, Dec. 2000, pp. 1910-1916, vol. 343, No. 26.
Druck, etal., "FHIT," Atlas of Genetics and Cytogenetics in Oncology and Haematology, 2007, pp. 171-178, vol. 2.
Eis, P. S. et al., "Accumulation of miR-155 and BIC RNA in Human B Cell Lymphomas," PNAS, Mar. 2005, pp. 3627-3632, vol. 102, No. 10.
European Patent Application, EP 1795203 A2, Croce et al., Application No. 06010581.4, filed Feb. 7, 1997, published Jun. 13, 2007.
European Search Report, Application No. 06800599.0 dated Oct. 19, 2009.
European Search Report, Application No. 06814375.9 dated Oct. 8, 2009.
European Search Report, Application No. 06825457.2 dated Sep. 16, 2009.
European Search Report, Application No. 07716208.9 dated Nov. 10, 2009.
European Search Report, Application No. 07717734.3 dated Nov. 9, 2009.
European Search Report, Application No. 07717903.4 dated Oct. 23, 2009.
European Search Report, Application No. 07753450.1 dated Jan. 12, 2009.
European Search Report, Application No. 07810382.7 dated Sep.14, 2009.
European Search Report, Application No. 07867402.5 dated Mar. 16, 2010.
European Search Report, Application No. 07872618.9 dated Jul. 5, 2010.
European Search Report, Application No. 08767439.6 dated May 12, 2010.
European Search Report, Application No. 08768266.2 dated Jul. 1, 2010.
European Search Report, Application No. 08796821.0 dated Aug. 4, 2010.
European Search Report, Application No. 08841700.1 dated Jun. 2, 2010.
Fabbri, M. et al., "MicroRNA-29 Family Reverts Aberrant Methylation in Lung Cancer by Targeting DNA Methyltransferases 3A and 3B," PNAS, Oct. 2007, pp. 15805-15810, vol. 104, No. 40.
Fabbri, M. et al., "MicroRNAs," The Cancer Journal, Jan./Feb. 2008, pp. 1-6, vol. 14, No. 1.
Fabbri, M. et al., "WWOX Gene Restoration Prevents Lung Cancer Growth in Vitro and in Vivo," PNAS, Oct. 2005, pp. 15611-15616, vol. 102, No. 43.
Fong, Y. et al., "Muir-Torre-Like Syndrome in FHIT-Deficient Mice," PNAS, Apr. 2000, pp. 4742-4747, vol. 97, No. 9.
Fox, T. et al., "A Single Amino Acid Substitution Makes ERK2 Susceptible to Pyridinyl Imidazole Inhibitors of p38 Map Kinase," Protein Science, 1998, pp. 2249-2255, vol. 7.
Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.
Garzon, R. et al., "MicroRNA Fingerprints During Human Megakaryocytopoiesis," PNAS, Mar. 2006, pp. 5078-5083, vol. 103, No. 13.
Garzon, R. et al., "MicroRNA Signatures Associated with Cytogenetics and Prognosis in Acute Myeloid Leukemia," Blood, Published Online Jan. 2008, DOI: 10.1182/blood-2007-07-098749.
Godlewski, J. et al., "Targeting of the Bmi-1 Oncogene/Stem Cell Renewal Factor by MicroRNA-128 Inhibits Glioma Proliferation and Self-Renewal," Cancer Research, Nov. 2008, pp. 9125-9130, vol. 68, No. 22.
Gourley, C. et al., "WWOX Gene Expression Abolishes Ovarian Cancer Tumorigenicity in Vivo and Decreases Attachment to Fibronectin via Integrin α3," Cancer Research, Jun. 2009, pp. 4835-4842, vol. 69, No. 11.
Griffiths-Jones, S. et al., "miRBase: MicroRNA Sequences, Targets and Gene Nomenclature," Nucleic Acids Research, 2006, pp. D140-D144, vol. 34.
Guimaraes-Sternberg, C. et al., "MicroRNA Modulation of Megakaryoblast Fate Involves Cholinergic Signaling," Leukemia Research, 2006, pp. 583-595, vol. 30.
Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.
Havelange, V. et al., "MicroRNAs: New Players in Acute Myeloid Leukemia," British Journal of Cancer, 2009, pp. 743-748, vol. 101.
Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.
Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.

(56) References Cited

OTHER PUBLICATIONS

Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.

Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.

Iliopoulos, D. et al., "Fragile Genes as Biomarkers: Epigenetic Control of WWOX and FHIT in Lung, Breast and Bladder Cancer," Oncogene, 2005, pp. 1625-1633, vol. 24.

Iliopoulos, D. et al., "Inhibition of Breast Cancer Growth InVitro and in Vivo: Effect of Restoration of WWOX Expression," Clin. Cancer Research, Jan. 2007, pp. 268-274, vol. 13, No. 1.

Iorio, M. V. et al., "MicroRNA Gene Expression Deregulation in Human Breast Cancer," Cancer Research, Aug. 2005, pp. 7065-7070, vol. 65, No. 16.

Iorio, M. V. et al., "MicroRNA Signatures in Human Ovarian Cancer," Cancer Research, Sep. 2007, pp. 8699-8707, vol. 67, No. 18.

Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.

Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.

Ji, J. et al., "MicroRNA Expression, Survival, and Response to Interferon in Liver Cancer," The New England Journal of Medicine, Oct. 2009, pp. 1437-1447, vol. 361, No. 15.

Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.

Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.

Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.

Jiang, J. et al., "Real-Time Expression Profiling of MicroRNA Precursors in Human Cancer Cell Lines," Nucleic Acids Research, 2005, pp. 5394-5403, vol. 33, No. 17.

John, B. et al., "Human MicroRNA Targets," PLOS Biology, Nov. 2004, pp. 1862-1879, vol. 2, Issue 11.

Johnson, S. M. et al., "RAS is Regulated by the let-7 MicroRNA Family," Cell, Mar. 2005, pp. 635-647, vol. 120.

Johnson, S. M. et al., "RAS is Regulated by the let-7 MicroRNA Family," Supplemental Data, Cell, Mar. 2005, pp. 635-647, vol. 120.

Kawasaki, H. et al., "MicroRNA-196 Inhibits HOXB8 Expression in Myeloid Differentiation of HL60 Cells," Nucleic Acids Symposium Series, 2004, pp. 211-212, No. 48.

Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.

Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, Apr. 14-18, 2007, Los Angeles, CA: AACR, 2007, 2 pages, Abstract No. 1780.

Koturbash, I. et al., "Role of Epigenetic Effectors in Maintenance of the Long-Term Persistent Bystander Effect in Spleen in Vivo," Carcinogenesis, 2007, pp. 1831-1838, vol. 28, No. 8.

Krek, A. et al., "Combinatorial MicroRNA Target Predictions," Nature Genetics, May 2005, pp. 495-500, vol. 37, No. 5.

Kulshreshtha, R. et al., "A MicroRNA Signature of Hypoxia," Molecular and Cellular Biology, Mar. 2007, pp. 1859-1867, vol. 27, No. 5.

Kuroki, et al., "Genetic Alterations of the Tumor Suppressor Gene WWOX in Esophageal Squamous Cell Carcinoma," Cancer Research, Apr. 2002, pp. 2258-2260, vol. 62.

Kutay, H. et al., "Downregulation of miR-122 in the Rodent and Human Hepatocellular Carcinomas," Journal of Cellular Biochemistry, 2006, pp. 671-678, vol. 99.

Lagos-Quintana, M. et al., "New MicroRNAs From Mouse to Human," RNA, 2003, pp. 175-179, vol. 9, No. 2.

Landi, M. T. et al., "Gene Expression Signature of Cigarette Smoking and Its Role in Lung Adenocarcinoma Development and Survival," PLOS One, Feb. 2008, pp. 1-8, vol. 3, Issue 2.

Lee, E. J. et al., "Expression Profiling Identifies MicroRNA Signature in Pancreatic Cancer," Int. J. Cancer, 2006, pp. 1046-1054, vol. 120.

Lewis, B. P. et al., "Prediction of Mammalian MicroRNA Targets," Cell, Dec. 2003, pp. 787-798, vol. 115.

Lin, R.-K. et al., "Alteration of DNA Methyltransferases Contributes to 5'CpG Methylation and Poor Prognosis in Lung Cancer," Lung Cancer, 2007, pp. 205-213, vol. 55.

Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.

Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.

Lu, J. et al., "MicroRNA Expression Profiles Classify Human Cancers," Nature, Jun. 2005, pp. 834-838, vol. 435, Supplementary Information.

Lu, J. et al., "MicroRNA Expression Profiles Classify Human Cancers," Nature, Jun. 2005, pp. 834-838, vol. 435.

Ma, G. et al., "Expression of Programmed Cell Death 4 and Its Clinicopathological Significance in Human Pancreatic Cancer," Department of General Surgery, the First Affiliated Hospital, China Medical University, Oct. 2005, pp. 597-600.

Mack, G. S., "MicroRNA Gets Down to Business," Nature Biotechnology, Jun. 2007, pp. 631-638, vol. 25, No. 6.

Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.

Marcucci, et al., "MicroRNA Expression in Cytogenetically Normal Acute Myeloid Leukemia," NEJM May 2008, pp. 1919-1928, vol. 358, No. 18.

Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pages, vol. 5, No. 24.

McManus, M. T., "MicroRNAs and Cancer," Seminars in Cancer Biology, 2003, pp. 253-258, vol. 13.

Megraw, M. et al., "miRGen: A Database for the Study of Animal MicroRNA Genomic Organization and Function," Nucleic Acids Research, 2007, pp. D149-D155, vol. 35.

Meng, F. et al., "Involvement of Human MicroRNA in Growth and Response to Chemotherapy in Human Cholangiocarcinoma Cell Lines," Gastroenterology, 2006, pp. 2113-2129, vol. 130.

Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.

Michael, M. Z. et al., "Reduced Accumulation of Specific MicroRNAs in Colorectal Neoplasia," Molecular Cancer Research, Oct. 2003, pp. 882-891, vol. 1.

Miller, M. K. et al., "Concurrent Chronic Lymphocytic Leukemia Cutis and Acute Myelogenous Leukemia Cutis in a Patient with Untreated CLL," The American Journal of Dermatopathology, 2001, pp. 334-340, vol. 23, No. 4.

Mitchell, P. S. et al., "Circulating MicroRNAs as Stable Blood-Based Markers for Cancer Detection," Pnas, Jul. 2008, pp. 10513-10518, vol. 105, No. 30.

Mitrovic, T. et al., "Cancer Gene Therapy," Arch. Oncology, 2005, pp. 23-26, vol. 13, No. 1.

(56) References Cited

OTHER PUBLICATIONS

Mountzios, G. et al., "Mechanisms of Disease: Signal Transduction in Lung Carcinogenesis-A Comparison of Smokers and Never-Smokers," Nature Clinical Practice Oncology, Oct. 2008, pp. 610-618, vol. 5, No. 10.
Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.
Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.
Negrini, M. et al., "MicroRNAs in Human Cancer: From Research to Therapy," Journal of Cell Science, Apr. 2007, pp. 1833-1840, vol. 120.
Notice of Allowance and Fees Due in U.S. Appl. No. 12/160,064, filed Jul. 3, 2008, mailing date Nov. 20, 2009.
Notice of Allowance and Fees Due in U.S. Appl. No. 12/298,221, filed Nov. 10, 2008, mailing date Nov. 30, 2009.
Office Action issued in U.S. Appl. No. 12/083,067, filed Jun. 20, 2008, mailing date Jul. 8, 2010.
Office Action issued in U.S. Appl. No. 12/160,034, filed Jul. 3, 2008, mailing date Jun. 7, 2010.
Office Action issued in U.S. Appl. No. 12/160,061, filed Jul. 3, 2008, mailing date Mar. 12, 2010.
Office Action issued in U.S. Appl. No. 12/160,061, filed Jul. 3, 2008, mailing date Apr. 24, 2009.
Office Action issued in U.S. Appl. No. 12/160,061, filed Jul. 3, 2008, mailing date Oct. 30, 2009.
Office Action issued in U.S. Appl. No. 12/160,064, filed Jul. 3, 2008, mailing date Aug. 10, 2009.
Office Action issued in U.S. Appl. No. 12/293,471, filed Oct. 9, 2008, mailing date Jun. 8, 2010.
Office Action issued in U.S. Appl. No. 12/373,358, filed Feb. 11, 2009, mailing date Aug. 20, 2010.
Office Action issued in U.S. Appl. No. 12/442,018, filed Mar. 27, 2009, mailing date Apr. 15, 2010.
Palamarchuk, A. et al., "Akt Phosphorylates Tcl1 Oncoprotein and Inhibits Its Repressor Activity," Cancer Research, Jun. 2005, pp. 4515-4519, vol. 65, No. 11.
Pawelczyk, T. et al., "Expression in *Escherichia coli* and Simple Purification of Human Fhit Protein," Protein Expr. Purlf., Apr. 2000, pp. 320-326, vol. 18, No. 3.
PCT International Preliminary Report on Patentability, PCT/US/2007/023660 filed Nov. 1, 2007, dated May 5, 2009.
PCT International Preliminary Report on Patentability, PCT/US/2008/072081 filed Aug. 4, 2008, dated Feb. 9, 2010.
PCT International Preliminary Report on Patentability, PCT/US2006/029889 filed Jul. 31, 2006, dated Feb. 5, 2008.
PCT International Preliminary Report on Patentability, PCT/US2006/035100 filed Sep. 11, 2006, dated Mar. 18, 2008.
PCT International Preliminary Report on Patentability, PCT/US2006/038824 filed Oct. 4, 2006, dated Apr. 9, 2008.
PCT International Preliminary Report on Patentability, PCT/US2007/000024 filed Jan. 3, 2007, dated Jul. 8, 2008.
PCT International Preliminary Report on Patentability, PCT/US2007/000103 filed Jan. 3, 2007, dated Jul. 8, 2008.
PCT International Preliminary Report on Patentability, PCT/US2007/000159 filed Jan. 3, 2007, dated Jul. 8, 2008.
PCT International Preliminary Report on Patentability, PCT/US2007/006824 filed Mar. 19, 2007, dated Sep. 23, 2008.
PCT International Preliminary Report on Patentability, PCT/US2007/009910 filed Apr. 24, 2007, dated Oct. 28, 2008.
PCT International Preliminary Report on Patentability, PCT/US2007/015892 filed Jul. 12, 2007, dated Jan. 13, 2009.
PCT International Preliminary Report on Patentability, PCT/US2007/020215 filed Sep. 17, 2007, dated Mar. 24, 2009.
PCT International Preliminary Report on Patentability, PCT/US2008/001157 filed Jan. 29, 2008, dated Aug. 4, 2009.
PCT International Preliminary Report on Patentability, PCT/US2008/005503 filed Apr. 29, 2008, dated Nov. 3, 2009.
PCT International Preliminary Report on Patentability, PCT/US2008/007196 filed Jun. 9, 2008, dated Dec. 11, 2009.
PCT International Preliminary Report on Patentability, PCT/US2008/066870 filed Jun. 13, 2008, dated Dec. 17, 2009.
PCT International Preliminary Report on Patentability, PCT/US2008/071532 filed Jul. 30, 2008, dated Feb. 2, 2010.
PCT International Preliminary Report on Patentability, PCT/US2008/073964 filed Aug. 22, 2008, dated Feb. 24, 2010.
PCT International Preliminary Report on Patentability, PCT/US2008/075565 filed Sep. 8, 2008, dated Mar. 9, 2010.
PCT International Preliminary Report on Patentability, PCT/US2008/079482 filed Oct. 10, 2008, dated Apr. 13, 2010.
PCT International Preliminary Report on Patentability, PCT/US2008/081294 filed Oct. 27, 2008, dated Apr. 27, 2010.
PCT International Preliminary Report on Patentability, PCT/US2009/035458 filed Feb. 27, 2009, dated Aug. 31, 2010.
PCT International Preliminary Report on Patentability, PCT/US2009/035463 filed Feb. 27, 2009, dated Aug. 31, 2010.
PCT International Preliminary Report on Patentability, PCT/US2009/035470 filed Feb. 27, 2009, dated Aug. 31, 2010.
PCT International Preliminary Report on Patentability, PCT/US2009/035482 filed Feb. 27, 2009, dated Aug. 31, 2010.
PCT International Search Report and the Written Opinion, PCT/US2007/006824 filed Mar. 19, 2007, dated Mar. 3, 2008.
PCT International Search Report and the Written Opinion, PCT/US2006/29889 filed Jul. 31, 2006, dated Jul. 10, 2007.
PCT International Search Report and the Written Opinion, PCT/US2006/35100 filed Sep. 11, 2006, dated Sep. 5, 2007.
PCT International Search Report and the Written Opinion, PCT/US2006/38824 filed Oct. 4, 2006, dated Aug. 9, 2007
PCT International Search Report and the Written Opinion, PCT/US2007/00024 filed Jan. 3, 2007, dated Nov. 5, 2007.
PCT International Search Report and the Written Opinion, PCT/US2007/00103 filed Jan. 3, 2007, dated Dec. 3, 2007.
PCT International Search Report and the Written Opinion, PCT/US2007/00159 filed Jan. 3, 2007, dated Apr. 11, 2008.
PCT International Search Report and the Written Opinion, PCT/US2007/006824 filed Mar. 19, 2007, dated May 14, 2008.
PCT International Search Report and the Written Opinion, PCT/US2007/09910 filed Apr. 24, 2007, dated Feb. 13, 2008.
PCT International Search Report and the Written Opinion, PCT/US2007/15892 filed Jul. 12, 2007, dated Sep. 30, 2008.
PCT International Search Report and the Written Opinion, PCT/US2007/20215 filed Sep. 17, 2007, dated Jul. 25, 2008.
PCT International Search Report and the Written Opinion, PCT/US2007/23660 filed Nov. 1, 2007, dated Sep. 16, 2008.
PCT International Search Report and the Written Opinion, PCT/US2008/01157 filed Jan. 29, 2008, dated Aug. 7, 2008.
PCT International Search Report and the Written Opinion, PCT/US2008/05503 filed Apr. 29, 2008, dated Sep. 25, 2008.
PCT International Search Report and the Written Opinion, PCT/US2008/07196 filed Jun. 9, 2008, dated Nov. 19, 2008.
PCT International Search Report and the Written Opinion, PCT/US2008/66870 filed Jun. 13, 2008, dated Nov. 10, 2008.
PCT International Search Report and the Written Opinion, PCT/US2008/71532 filed Jul. 30, 2008, dated Apr. 17, 2009.
PCT International Search Report and the Written Opinion, PCT/US2008/72081 filed Aug. 4, 2008, dated Jan. 14, 2009.
PCT International Search Report and the Written Opinion, PCT/US2008/73964 filed Aug. 22, 2008, dated Dec. 24, 2008.
PCT International Search Report and the Written Opinion, PCT/US2008/75565 filed Sep. 8, 2008, dated Dec. 9, 2008.
PCT International Search Report and the Written Opinion, PCT/US2008/79482 filed Oct. 10, 2008, dated Dec. 22, 2008.
PCT International Search Report and the Written Opinion, PCT/US2008/81294 filed Oct. 27, 2008, dated Mar. 26, 2009.
PCT International Search Report and the Written Opinion, PCT/US2008/84821 filed Nov. 26, 2008, dated Feb. 17, 2009.
PCT International Search Report and the Written Opinion, PCT/US2009/35458 filed Feb. 27, 2009, dated Jul. 28, 2009.

(56) References Cited

OTHER PUBLICATIONS

PCT International Search Report and the Written Opinion, PCT/US2009/35463 filed Feb. 27, 2009, dated Aug. 13, 2009.
PCT International Search Report and the Written Opinion, PCT/US2009/35470 filed Feb. 27, 2009, dated Jun. 16, 2009.
PCT International Search Report and the Written Opinion, PCT/US2009/35482 filed Feb. 27, 2009, dated Jul. 17, 2009.
PCT International Search Report and the Written Opinion, PCT/US2009/38214 filed Mar. 25, 2009, dated Aug. 14, 2009.
PCT International Search Report and the Written Opinion, PCT/US2009/46999 filed Jun. 11, 2009, dated Nov. 23, 2009.
PCT International Search Report and the Written Opinion, PCT/US2009/53586 filed Aug. 12, 2009, dated Oct. 28, 2009.
PCT International Search Report and the Written Opinion, PCT/US2009/65072 filed Nov. 19, 2009, dated Mar. 3, 2010.
PCT International Search Report and the Written Opinion, PCT/US2010/025173 filed Feb. 24, 2010, dated Jul. 6, 2010.
Pedersen, I. M. et al., "Interferon Modulation of Cellular MicroRNAs as an Antiviral Mechanism," Nature, Oct. 2007, pp. 919-922, vol. 449.
Pekarsky, Y. et al., "Animal Models for Chronic Lymphocytic Leumekia," Journal of Cellular Biochemistry, 2007, pp. 1109-1118, vol. 100.
Pekarsky, Y. et al., "Tcl1 Enhances Akt Kinase Activity and Mediates Its Nuclear Translocation," PNAS, Mar. 2000, pp. 3028-3033, vol. 97, No. 7.
Pekarsky, Y. et al., "Tcl1 Expression in Chronic Lymphocytic Leukemia is Regulated by miR-29 and miR-181," Cancer Research, Dec. 2006, pp. 11590-11593, vol. 66, No. 24.
Pekarsky, Y. et al., "Tcl1 Functions as a Transcriptional Regulator and is Directly Involved in the Pathogenesis of CLL," PNAS, Dec. 2008, pp. 19643-19648, vol. 105, No. 50.
Petrocca, F. et al., "E2F1-Regulated MicroRNAs Impair TGFβ-Dependent Cell-Cycle Arrest and Apoptosis in Gastric Cancer," Cancer Cell, Mar. 2008, pp. 272-286, vol. 13.
Prueitt, R. L. et al., "Expression of MicroRNAs and Protein-Coding Genes Associated with Perineural Invasion in Prostate Cancer," The Prostate, 2008, pp. 1152-1164, vol. 68.
Qin, H. R. et al., "A Role for the WWOX Gene in Prostate Cancer," Cancer Research, Jul. 2006, pp. 6477-6481, vol. 66, No. 13.
Ramkissoon, S. H, et al., "Hematopoietic-Specific MicroRNA Expression in Human Cells," Leukemia Research, 2006, pp. 643-647, vol. 30.
Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.
Rozovskaia, T. et al., "Expression Profiles of Acute Lymphoblastic and Myeloblastic Leukemias with ALL-1 Rearrangements," PNAS, Jun. 2003, pp. 7853-7858, vol. 100, No. 13.
Schetter, A. J. et al., "MicroRNA Expression Profiles Associated With Prognosis and Therapeutic Outcome in Colon Adenocarcinoma," JAMA, Jan. 2008, pp. 425-436, vol. 299, No. 4.
Schmittgen, T. D. et al., "A High-Throughput Method to Monitor the Expression of MicroRNA Precursors," Nucleic Acids Research, Feb. 2004, vol. 32, No. 4.
Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.
Seike, M. et al., "MiR-21 is an EGFR-Regulated Anti-Apoptotic Factor in Lung Cancer in Never-Smokers," Supporting Information, PNAS, Jul. 2009, pp. 12085-12090. vol. 106, No. 29.
Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.
Seth, P., "Vector-Mediated Cancer Gene Therapy," Cancer Biology & Therapy, May 2005, pp. 512-517, vol. 4, Issue 5.
Sevinsky, J. R. et al., "Extracellular Signal-Regulated Kinase Induces the Megakaryocyte GPIIb/CD41 Gene Through MafB/Kreisler," Molecular and Cellular Biology, May 2004, pp. 4534-4545, vol. 24, No. 10.
Sharma, S. et al., "Development of Inhalational Agents for Oncologic Use," Journal of Clinical Oncology, Mar. 2001, Abstract, vol. 19, Issue 6.
Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.
Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.
Tang, X. et al., "A Simple Array Platform for MicroRNA Analysis and Its Application in Mouse Tissues," RNA, Aug. 2007, pp. 1-20, vol. 13.
Thomson, J. M. et al., "A Custom Microarray Platform for Analysis of MicroRNA Gene Expression," Nature Methods, Oct. 2004, pp. 1-7, vol. 1, No. 1.
Thorgeirsson, S. S. et al., "Functional Genomics of Hepatocellular Carcinoma," Hepatology, Feb. 2006, pp. S145-S150, vol. 43, No. 2, Suppl. 1.
Tockman, M. S. et al., "Considerations in Bringing a Cancer Biomarker to Clinical Application," Cancer Research, May 1992, pp. 2711s-2718s, vol. 52.
Trapasso, F. et al., "Fhit Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.
Tricoli, J. V. et al., "MicroRNA: Potential for Cancer Detection, Diagnosis, and Prognosis," Cancer Research, May 2007, pp. 4553-4555, vol. 67, No. 10.
Ueda, T. et al., "Relation Between MicroRNA Expression and Progression and Prognosis of Gastric Cancer: A MicroRNA Expression Analysis," Published Online; www.thelancet.com/oncology, Dec. 2009, DOI:10.1016/S1470-2045(09)70343-2.
Valeri, N. et al., "Epigenetics, miRNAs, and Human Cancer: A New Chapter in Human Gene Regulation," Mamm Genome, Aug. 2009, pp. 573-580, vol. 20.
Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.
Virgilio, L. et al., "Identification of the TCL1 Gene Involved in T-Call Malignancies," Proc. Natl. Acad. Sci., Dec. 1994, pp. 12530-12534, vol. 91.
Visone, R. et al., "MiRNAs and Cancer," The American Journal of Pathology, Apr. 2009, pp. 1131-1138, vol. 174, No. 4.
Volinia, et al., "Reprogramming of MirRNA Networks in Cancer and Leukemia," Genome Research, 2010, pp. 589-599, vol. 20.
Volinia, S. et al., "A MicroRNA Expression Signature of Human Solid Tumors Defines Cancer Gene Targets," PNAS, Feb. 2006, pp. 2257-2261, vol. 103, No. 7.
Wang, E. et al., "Ontogeny and Oncogenesis Balance the Transcriptional Profile of Renal Cell Cancer," Cancer Research, Oct. 2004, pp. 7279-7287, vol. 64.
Wang, X. et al., "Association Between CpG Island Methylation of the WWOX Gene and Its Expression in Breast Cancers," Tumor Biology, Feb. 2009, pp. 8-14, vol. 30.
Weidhaas, J., "Using MicroRNAs to Understand Cancer Biology," Published Online Dec. 21, 2009, DOI: 10.1016/S1470-2045(09)70386-9.
Yamashita, T. et al., "Activation of Hepatic Stem Cell Marker EpCAM by Wnt-β-Catenin Signaling in Hepatocellular Carcinoma," Cancer Research, Nov. 2007, pp. 10831-10839, vol. 67, No. 22.
Yamashita, T. et al., "EpCAM and α-Fetoprotein Expression Defines Novel Prognostic Subtypes of Hepatocellular Carcinoma," Cancer Research, Mar. 2008, pp. 1451-1461, vol. 68, No. 5.
Yanaihara, N. et al., "Unique MicroRNA Molecular Profiles in Lung Cancer Diagnosis and Prognosis," Cancer Cell, Mar. 2006, pp. 189-198, vol. 9.

(56) References Cited

OTHER PUBLICATIONS

Yang, J. et al., "Analysis of Sequence Variations in 59 MicroRNAs in Hepatocellular Carcinomas," Mutation Research, Aug. 2008, pp. 205-209, vol. 638.
Yendamuri, S. et al., "WW Domain Containing Oxidoreductase Gene Expression is Altered in Non-Small Cell Lung Cancer," Cancer Research, Feb. 2003, pp. 878-881, vol. 63.
Yoon, S. et al., "Prediction of Regulatory Modules Comprising MicroRNAs and Target Genes," Bioinformatics Genes and Genomes, 2005. pp. ii93-ii100, vol. 21, Suppl. 2.
Yu, L.-G. et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin," The Journal of Biological Chemisty, Jul. 2004, pp. 41377-41383, vol. 279, No. 40.
Zeng, Y. et al., "Recognition and Cleavage of Primary MicroRNA Precursors by the Nuclear Processing Enzyme Drosha," The EMBO Journal, 2005, pp. 138-148, vol. 24.
Zhang, L. et al., "Genomic and Epigenetic Alterations Deregulate MicroRNA Expression in Human Epithelial Ovarian Cancer," PNAS, May 2008, pp. 7004-7009, vol. 105, No. 19.
Zhang, L. et al., "MicroRNAs Exhibit High Frequency Genomic Alterations in Human Cancer," PNAS, Jun. 2006, pp. 9136-9141, vol. 103, No. 24.
Zhang, L. et al., Supporting Information, PNAS 2008, pp. 1-11.
Zhang, Z. et al., "Three Biomarkers Identified from Serum Proteomic Analysis for the Detection of Early Stage Ovarian Cancer," Cancer Research, Aug. 2004, pp. 5882-5890, vol. 64.
Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.
Calin, et al., MicroRNA profiling reveals distinct signatures in B cell chronic lymphocytic leukemias, PNAS, Aug. 10, 2004, pp. 11755-11760, vol. 101, No. 32.
Calin, et al., Frequent deletions and down-regulation of micro-RNA genes miR15 and miR16 at 13q14 in chronic lymphocytic leukemia, PNAS, Nov. 26, 2002, pp. 15524-15529, vol. 99, No. 24.
Cheng, et al., Antisense inhibition of human miRNAs and indications for an involvement of miRNA in cell growth and apoptosis, Nucleic Acids Research, 2005, pp. 1290-1297, vol. 33, No. 4.
Krek, et al., Combinatorial microRNA target predictions, Nature Genetics, May 2005, pp. 495-500, vol. 37, No. 5.
Lewis, et al., Prediction of Mammalian MicroRNA Targets, Cell, Dec. 26, 2003, pp. 787-798, vol. 115.
Liu, et al., An oligonucleotide microchip for genome-wide microRNA profiling in human and mouse tissues, PNAS, Jun. 29, 2004, pp. 9740-9744, vol. 101, No. 26.
Mcmanus, MicroRNAs and Cancer, Seminars in Cancer Biology, (2003), pp. 253-258, vol. 13.
PCT/US06/29889, Filed Jul. 31, 2006, Notification of Transmittal of the International Search Report and the Written Opinion of the International Searching Authority, or the Declaration, date of mailing Jul. 10, 2007.
PCT/US06/29889, Filed Jul. 31, 2006, Written Opinion of the International Searching Authority, date of mailing Jul. 10, 2007.
PCT/US2006/029889, European Search Report, date of mailing Oct. 19, 2009.
Ambros, V. et al., "A Uniform System for MicroRNA Annotation," RNA, 2003, pp. 277-279, vol. 9.
Baira, E. et al., "Ultraconserved Elements: Genomics, Function and Disease," RNA Biology, Jul. 2008, pp. 132-134, vol. 5, No. 3.
Bloomston, M. et al., "MicroRNA Expression Patterns to Differentiate Pancreatic Adenocarcinoma from Normal Pancreas and Chronic Pancreatitis," JAMA, May 2007, pp. 1901-1908 vol. 297, No. 1.
Blum, W. et al., "Clinical Response and miR-29b Predictive Significance in Older AML Patients Treated With a 10-Day Schedule of Decitabine," PNAS, Apr. 2010, pp. 7473-7478, vol. 107, No. 16.
Boland, C.R. et al., "Lynch Syndrome: Form, Function, Proteins, and Basketball," Gastroenterology, Aug. 2005, pp. 751-755, vol. 129, No. 2.
Caldas, C. et al., "Sizing Up miRNAs as Cancer Genes," Nature Medicine, Jul. 2005, pp. 712-714, vol. 11, No. 7.
Canadian Intellectual Property Office, Requisition by the Examiner, Application No. 2,635,616, Dated Feb. 21, 2011.
Canadian Office Action, Application No. 2,621,441, dated Feb. 1, 2011.
Castoldi, M. et al., "A Sensitive Array for MicroRNA Expression Profiling (miChip) Based on Locked Nucleic Acids (LNA)," RNA, 2006, pp. 913-920, vol. 12.
Chinese Office Action, Application No. 200680036598.3 dated Feb. 24, 2011.
Chinese Office Action, Application No. 200780040146.7 dated May 25, 2011.
Cui, S. et al., "MicroRNAs that Underlie Ovarian Cancer Development and Response to Chemotherapy," 98th AACR Annual Meeting, Apr. 14-18, 2007, Los Angeles, CA.
Davies, B.R. et al., "AZD6244 (ARRY-142886), a Potent Inhibitor of Mitogen-Activated Protein Kinase/Extracellular Signal-Regulated Kinase Kinase 1/2 Kinases: Mechanism of Action in vivo, Pharmacokinetic/Pharmacodynamic Relationship, and Potential for Combination in Preclinical Needs," Mol. Cancer Ther., Aug. 2007, vol. 6, No. 8, pp. 2209-2219.
EP Search Report, Application No. 08782609.5 dated Oct. 28, 2010, 57-29302.
Esquela-Kerscher, A. et al., "Oncomirs—MicroRNAs with a Role in Cancer," Nature Reviews:Cancer, Apr. 2006, pp. 259-269, vol. 6.
European Communication Pursuant to Article 94(3) EPC, Application No. 07810382.7, dated Dec. 8, 2010.
European Communication Pursuant to Article 94(3) EPC, Application No. 07867402.5, dated Jan. 5, 2011.
European Search Report, Application No. 08798444.9-2402, PCT/US2008/073964, dated Dec. 16, 2010.
European Search Report, Application No. 08799295.4-2402, PCT/US2008/075565, dated Nov. 9, 2010.
European Supplementary Search Report, Application No. 09715064.3 dated May 24, 2011.
Felli, N. et al., "MicroRNAs 221 and 222 Inhibit Normal Erythropoiesis and Erythroleukemic Cell Growth via Kit Receptor Down-Modulation," PNAS, Dec. 2005, pp. 18081-18086, vol. 102, No. 50.
Flavin, RJ et al., "MicroRNA Gene Expression Profiling in Human Ovarian and Primary Peritoneal Serous Carcinomas" USCAP 96th Annual Meeting, Abstract #897, San Diego, CA, Mar. 2007.
Ford, L.P., "A MicroRNA Expression Signature of Human Solid Tumors Defines Cancer Gene Targets," Leukemia Research, 2006, pp. 511-513, vol. 30.
Garofalo, M. et al., "miR-221&222 Regulate Trail Resistance and Enhance Tumorigenicity through PTEN and TIMP3 Downregulation," Cancer Cell, Dec. 2009, pp. 498-509, vol. 16.
Garzon, R. et al., "MicroRNA Expression and Function in Cancer," Trends in Molecular Medicine, Oct. 2006, pp. 580-587, vol. 12, No. 12.
Garzon, R. et al., "MicroRNA Signatures Associated with Cytogenetics and Outcome in Acute Myeloid Leukemia," ASH Annual Meeting Abstracts, Nov. 2006, Abstract #151, Part 1, p. 498, vol. 108, Issue 11.
Griffths-Jones, S. et al., "miRBase: Tools for MicroRNA Genomics," Nucleic Acids Research, 2008, pp. D154-D157, vol. 36.
Griffths-Jones, S., "The MicroRNA Registry," Nucleic Acids Research, 2004, pp. D109-D111, vol. 32.
He, X. et al., "MicroRNA and Esophageal Carcinoma," Journal of Nanjing Medical University, 2007, pp. 201206, vol. 21, No. 4.
Kelly, L.M. et al., "CT53518, A Novel Selective FLT3 Antagonist for the Treatment of Acute Myelogenous Leukemia (AML)," Cancer Cell, Jun. 2002,pp. 421-432, vol. 1.
Kozomara, A. et al., "miRBase: Integrating MicroRNA Annotation and Deep-Sequencing Data," Nucleic Acids Research, 2011, pp. D152-D157, vol. 39.
Lagos-Quintana, M. et al., "Identification of Tissue-Specific MicroRNAs from Mouse," Current Biology, Apr. 2002, pp. 735-739, vol. 12.
Landgraf, P. et al., "A Mammalian MicroRNA Expression Atlas Based on Small RNA Library Sequencing," Cell, Jun. 2007, pp. 1401-1414, vol. 129.

(56) References Cited

OTHER PUBLICATIONS

Lanza, G. et al., "mRNA/microRNA Gene Expression Profile in Microsatellite Unstable Colorectal Cancer," Molecular Cancer, 2007, pp. 1-11, vol. 6, No. 54.
Li, S.-C. et al., "Bioinformatic Discovery of MicroRNA Precursors from Human ESTs and Introns," BMC Genomics, 2006, vol. 7.
Lujambio, A. et al., "A MicroRNA DNA Methylation Signature for Human Cancer Metastasis," PNAS, Sep. 2008, pp. 13556-13561, vol. 105, No. 36.
Medina, P.P. et al., "OncomiR Addiction in an in Vivo Model of MicroRNA-21-Induced Pre-B-Cell Lymphoma," Nature Letters, Sep. 2010, pp. 86-91, vol. 467.
Medina, P.P., "OncomiR Addicton in an in vivo Model of Micro-RNA-21-Induced Pre-B-Cell Lymphoma," Supplementary Information, Sep. 2010, p. 1-22.
Naegeli, K. et al., "Novel Mechanisms of Ovarian Cancer Growth Inhibition, via MicroRNA Downregulation and Oxidative Damage, by a Ratioanlly Designed Histone Deacetylase Inhibitor," Abstract #2475, 98th ACCR Annual Meeting, Apr. 14-18, 2007, Los Angeles, CA.
Nicoloso, M.S. et al., "MicroRNAs—The Micro Steering Wheel of Tumour Metastases," Nature Reviews: Cancer, Apr. 2009, pp. 293-302, vol. 9.
Nurden, A.T., "Qualitative Disorders of Platelets and Megakaryocytes," Journal of Thrombosis and Haemostasis, 2005, vol. 3, pp. 1773-1782.
Pichiorri, F. et al., "MicroRNAs Regulate Critical Genes Associated with Multiple Myeloma Pathogenesis," PNAS, Sep. 2008, pp. 12885-12890, vol. 105, No. 35.
Pineau, P. et al., "miR-221 Overexpression Contributes to Liver Tumorigenesis," PNAS, Jan. 2010, pp. 264-269, vol. 107, No. 1.
Porkka, K.P. et al., "MicroRNA Expression Profiling in Prostate Cancer," Cancer Research, 2007, pp. 6130-6135, vol. 67, No. 13.
Pruitt, K.D. et al., "NCBI Reference Sequence (RefSeq): A Curated Non-Redundant Sequence Database of Genomes, Transcripts and Proteins," Nucleic Acids Research, 2005, pp. D501-D504, vol. 33.
Saini, H. K. et al., "Annotation of Mammalian Primary MicroRNAs," BMC Genomics, 2008, vol. 9.
Santanam, U. et al., "Chronic Lymphocytic Leukemia Modeled in Mouse by Targeted miR-29 Expression," PNAS, Jul. 2010, pp. 12210-12215, vol. 107, No. 27.
Sasaki, Y.T.F. et al., "Coordinated Expression of ncRNAs and HOX mRNAs in the Human HOXA Locus," Biochemical and Biophysical Communications, 2007, pp. 724-730, vol. 357.
Schetter, A.J. et al., "Association of Inflammation-Related and MicroRNA Gene Expression with Cancer Specific Mortality of Colon Adenocarcinoma," Clin. Cancer Res., Sep. 2009, pp. 5878-5887, vol. 15, No. 18.
Slack, F.J., "Big Roles for Small RNAs," Nature, Feb. 2010, p. 616, vol. 463.
State Intellectual Property Office of the People's Republic of China, Notification of the First Office Action, Application No. 200780005791.5, dated Mar. 24, 2011.
Suarez-Saiz, F.J. et al., "MicroRNA Expression Profiling in Acute Myelogenous Leukemia," Canada Blood, Nov. 2004, Abstract #1131, p. 320A.
Taccioli, C. et al., "Ucbase & miRfunc: A Database of Ultraconserved Sequences and MicroRNA Function," Nucleic Acids Research, 2009, pp. D41-D48, vol. 37.
Valeri, N. et al., "Modulation of Mismatch Repair and Genomic Stability by miR-155," PNAS, Apr. 2010, pp. 6982-6987, vol. 107, No. 15.
Wijermans, P.W., "Low Dose Azanucleosidesfor High Risk (s) MDS and AML," Haematologica Reports, Nov. 2006, pp. 74-76. vol. 2, Issue, 15.
Australian Office Action, Application No. 2007227423 dated Apr. 13. 2012.
Australian Office Action, Application No. 2007205257 dated Dec. 22, 2011.
Australian Office Action, Application No. 2006291165 dated Feb. 13, 2012.
Australian Office Action, Application No. 2006291165 dated Aug. 23, 2011.
Australian Office Action, Application No. 2007205234 dated Sep. 20, 2011.
Canadian Office Action, Application No. 2,617,581, dated Feb. 1, 2011.
Canadian Office Action, Application No. 2,635,616, dated Feb. 27, 20112.
Canadian Office Action, Application No. 2,617,581, dated Apr. 2, 2012.
Chinese Office Action, Application No. 200680039776.8 dated Jun. 30, 2011.
Chinese Office Action, Application No. 20088011920639 dated May 3, 2012.
Chinese Office Action, Application No. 200780005821.2 dated Jan. 26, 2011.
Communication Concerning Office Action Received from Japanese Patent Office dated Jan. 30, 2012, Japanese Patent Application No. 2008-531200.
EP Search Report, Application No. 11196261.9 dated Feb. 28, 2012.
EP Search Report, Application No. 11196264-3 dated Feb. 28, 2012.
EP Search Report, Application No. 11196253.6 dated Apr. 24, 2012.
EP Search Report, Application No. 11196190.0 dated Apr. 24, 2012.
EP Search Report, Application No. 11196250.2 dated Apr. 24, 2012.
EP Search Report, Application No. 11196254.4 dated Feb. 28, 2012.
EP Search Report, Application No. 11196256.9 dated Feb. 28, 2012.
EP Search Report, Application No. 11196262.7 dated Feb. 28, 2012.
EP Search Report, Application No. 11196265.0 dated Mar. 5, 2012.
European Communication Pursuant to Article 94(3) EPC, Application No. 06800599.0 dated Nov. 25, 2011.
European Communication Pursuant to Article 94(3) EPC, Application No. 08767439.6, dated Feb. 12, 2011.
European Communication Pursuant to Article 94(3) EPC, Application No. 08767439.9, dated Mar. 15, 2011.
European Communication Pursuant to Article 94(3) EPC, Application No. 08768266.2, dated Apr. 18, 2011.
European Communication Pursuant to Article 94(3) EPC, Application No. 08799295.4, dated Nov. 18, 2011.
European Communication Pursuant to Article 94(3)EPC, Application No. 06814375.9 dated Oct. 14, 2011.
European Communication Pursuant to Article 94(3) EPC, Application No. 07867402.5, dated Apr. 10, 2012.
European Communication Pursuant to Article 94(3) EPC, Application No. 07717903.4, dated Apr. 25, 2012.
European Communication Pursuant to Article 94(3) EPC, Application No. 07716208.9, dated Sep. 13, 2011.
European Seach Report, Application No. 11151749.6, dated Feb. 8, 2011.
European Seach Report, Application No. 09714868.8 dated Aug. 1, 2011.
European Search Reoprt, Application No. 08841700.1, dated Jan. 4, 2011.
European Search Report, Application No. 09713926.5 dated Jul. 21, 2011.
European Search Report, Application No. 11151771-0, dated Feb. 8, 2011.
European Search Report, Application No. 08713330.2, dated Jul. 22, 2011.
European Search Report, Application No. 11151772-8, dated Feb. 8, 2011.
European Search Report, Application No. 11151769-4, dated Feb. 8, 2011.
European Search Report, Application No. 08770974.4, dated Oct. 21, 2011.
Japanese Office Action dated Feb. 22, 2012, Japanese Patent Application No. 2008-549549.
Japanese Office Action dated Feb. 24, 2012, Japanese Patent Application No. 2008-549555.
Japanese Office Action dated Jan. 4, 2012, Japanese Patent Application No. 2008-5251070.

(56) References Cited

OTHER PUBLICATIONS

Japanese Office Action dated Feb. 24, 2012, Japanese Patent Application No. 2008-549532.
PCT International Preliminary Report on Patentability, PCT/US2009/038214 filed Mar. 25, 2009, dated Jun. 16, 2011.
PCT International Preliminary Report on Patentability, PCT/US2010/025173 filed Feb. 24, 2010, dated Sep. 9, 2011.
PCT International Preliminary Report on Patentability, PCT/US2009/065072 filed Nov. 19, 2009, dated Jun. 3, 2011.
PCT International Search Report and the Written Opinion, PCT/US2012/020911 filed Jan. 11, 2012, dated Apr. 25, 2012.
PCT Invitation to Pay Additional Fees, PCT/US2012/028016 filed Mar. 7, 2012, dated May 29, 2012.
Aiba, M. "Pathology of the Breast Carcinoma from the Viewpoint of the Proliferative Activity and Grade of Malignancy," JP J Cancer Clin, 2000, pp. 475-181, vol. 46, No. 5. Only Abstract considered.
Alvarez-Secord, A. et al., "Maspin Expression in Epithelial Ovarian Cancer and Associations with Poor Prognosis: A gynecologic Oncology Group Study," Gynecologic Oncology, 2006, pp. 390-397, vol. 101.
Braun et al., "p53-Responsive MicroRNAs 192 and 215 are Capable of Inducing Cell Cycle Arrest," Cancer Research, 2008, pp. 10094-10104, vol. 68.
Cannistra, S.A., "Cancer of the Ovary," The New England Journal of Medicine, 2004, pp. 2519-2529, vol. 351, No. 25.
Chim, S.S.C. et al., "Detection and Characterization of Placental MicroRNAs in Maternal Plasma," Clinical Chemistry, 2008, pp. 482-490, vol. 54, No. 3.
Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.
Feng, G. et al., "Elevated Serum-Circulating RNA in Patients with Conventional Renal Cell Cancer," Anticancer Research, 2008, pp. 321-326, vol. 28.
Fujuta, S. et al., "miR-21 Gene Expression Triggered by AP-1 is Sustained Through a Double-Negative Feedback Mechanism," J. Mol. Biol., Abstract, 2008, pp. 492-504, vol. 378.
Gang, M. et al., "Expression of Programmed Cell Death 4 and Its Clinicopathological Significance in Human Pancreatic Cancer," Abstract, 2005, pp. 597-600, vol. 27.
He, L. et al., "A MicroRNA Polycistron as a Potential Human Oncogene," Nature, Jun. 2005, pp. 828-833, vol. 435.
Ishii, H. et al., "Effect of Adenoviral Transduction of the Fragile Histidine Triad Gene into Esophageal Cancer Cells," Cancer Research, Feb. 2001, pp. 1578-1584, vol. 61.
Jacobs, I.J. et al., "Progress and Challenges in Screening for Early Detection of Ovarian Cancer," Molecular & Cellular Proteomics, 2004, pp. 355-366, vol. 3.
Jacobs, I.J. et al., "Prevalence Screening for Ovarian Cancer in Postmenopausal Women by CA 125 Measurement and Ultrasonography," BMJ, Apr. 1993, pp. 1030-1034, vol. 306.
Jazbutyte, V. et al., "MicroNRA-21: From Cancer to Cardiovascular Disease," Current Drug Targets, Abstract, 2010, pp. 926-935, vol. 11.
Jemal, A. et al., "Cancer Statistics, 2008," CA Cancer J. Clin., 2008, pp. 71-96, vol. 58, No. 2.
Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.
Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.
Mendell, J.T., "miRiad Roles for the miR-17-92 Cluster in Development and Disease," Cell, 2008, pp. 217-222.
Meng, F. et al., "MicroRNA-21 Regulates Expression of the Pten Tumor Suppressor Gene in Human Hepatocellular Cancer," Gastroenterology, 2007, pp. 647-658, vol. 133.

Nakajima, G. et al., "Non-Coding MicroRNAs HAS-LET-7G and HAS-MIR-181b are Associated with Chemoresponse to S-1 in Colon Cancer," Cancer Genomics & Proteomics, Sep. 2006, pp. 317-324, vol. 3, No. 5.
Nam, E.J. et al., "MicroRNA Expression Profiles in Serous Ovarian Carcinoma," Clinical Cancer Research, 2008, pp. 2690-2695, vol. 14, No. 9.
Okada, H. et al., "MicroRNAs in Immune Regulation—Opportunities for Cancer Immunotherapy," The International Journal of Biochemistry & Cell Biology, 2010, pp. 1256-1261, vol. 42.
Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.
Petrocca, F. et al., "MicroRNAs Deregulation in Gastric Cancer," PNAS, Apr. 2006, p. 1338, vol. 47, Abstract # 5690.
Pichiorri et al., "Downregulation of p53-Inducible MicroRNAs 192, 194 and 215 Impairs the p53/MDM2 Autoregulatory Loop in Multiple Myeloma Development," Cancer Cell, 2010, pp. 367-381, vol. 18.
Ribas, J. et al., "The Transcriptional Regulation of miR-21, Its Multiple Transcripts, and Their Implication in Prostate Cancer," Cell Cycle, 2010, pp. 923-929, vol. 9.
Rossi, S. et al., "MicroRNA Fingerprinting of CLL Patients with Chromosome 17p Deletion Identify a miR-21 Score that Stratifies Early Survival," Blood, Aug. 2010, pp. 945-952, vol. 116, No. 6.
Ryu, J.K. et al., "Aberrant MicroRNA-155 Expression is an Early Event in the Multistep Progression of Pancreatic Adenocarcinoma," Pancreatology, 2010, pp. 66-73, vol. 10.
Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.
Schagen, F. et al., "Genetic Targeting of Adenovirus Vectors Using a Reovirus Sigmal-Based Attachment Protein," Molecular Therapy, May 2006, pp. 997-1005, vol. 13, No. 5.
Stamatopoulos, B. et al., "MicroRNA-29c and MicroRNA-233 Down-Regulation has in Vivo Significance in Chronic Lymphocytic Leukemia and Improves Disease Risk Stratification," Blood, May 2009, pp. 5237-5245, vol. 113, No. 21.
Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.
Thomson, M., Supplementary data for "A Custon Microarray Platform for Analysis of MicroRNA Gene Expression," Nature Methods, Oct. 2004, pp. 47-53, vol. 1, No. 1.
Tilt, E. et al., "Expression and Function of Micro RNAs in Immune Cells During Normal or Disease State," International Journal of Medicine Sciences, 2008, pp. 73-79, vol. 5, No. 2.
Uil, T.G. et al., "Generation of an Adenoviral Vector Containing an Addition of a Heterologous Ligand to the Serotpe 3 Fiber Knob," Cancer Gene Therapy, Feb. 2003, pp. 121-124, vol. 10, No. 2.
Vassilev et al., "In Vivo Activation of the p53 Pathway by Small-Molecule Antagonists of MDM2," Science, 2004, pp. 844-848, vol. 303.
Verschuur, A.C., "Acute Megakaryoblastic Leukemia," May 2004, pp. 1-5, Retrieved from the Internet: URL: http://www.orpga.net/data/patho/GB/uk-AMLM7.pdf.
Watson, D.I. et al., "MicroRNA Expression Profiles in Barrett's Oesophagus," RACS Annual Scientific Congress, 2007, pp. A45, vol. 77.
Wiemer et al., "The Role of MicroRNAs in Cancer: No Small Matter," European Journal of Cancer, Jun. 12, 2007, vol. 43, No. 10, pp. 1529-1544.
Xi, Y. et al., "Prognostic Values of MicroRNAs in Colorectal Cancer," Biomarker Insights, Jan. 2006, pp. 113-121, vol. 1.
Zawacka-Pankau, J. et al., "Expression and Simple, One-Step Purification of Fragile Histidine Triad (Fhit) Tumor Suppressor Mutant Forms in *Escherichia coli* and their Interaction with Protoporphyrin IX," Biotechnology Letters, Jun. 2007, pp. 877-883, vol. 29, No. 6.
Zhao et al., "p53 Mediates the Negative Regulation of MDM2 by Orphan Receptor TR3," The EMBO Journal, 2006, pp. 5703-5715, vol. 25.

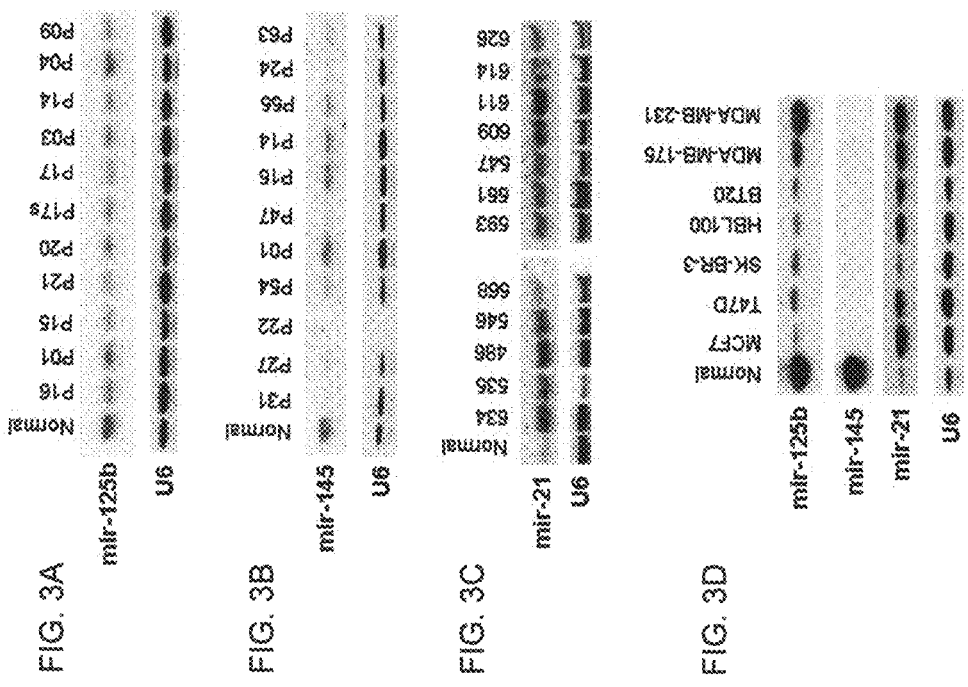

FIG. 4A

| N samples feature | 20 ER+ | 13 ER- | Probability |
|---|---|---|---|
| mir-26a | 2.473 | 1.483 | 0.0273 |
| mir-26b | 3.751 | 1.932 | 0.0273 |
| mir-29b | 1.280 | 0.935 | 0.0188 |
| mir-30a-5p | 1.779 | 1.202 | 0.0191 |
| mir-30b | 1.810 | 1.184 | 0.0250 |
| mir-30c | 1.587 | 1.040 | 0.0191 |
| mir-30d | 2.986 | 1.736 | 0.0273 |
| mir-185 | 1.568 | 2.296 | 0.0399 |
| mir-191 | 6.354 | 2.908 | 0.0273 |
| mir-206 | 1.811 | 2.373 | 0.0273 |
| mir-212 | 2.811 | 3.905 | 0.0403 |

FIG. 4B

| N samples feature | 18 PR+ | 14 PR- | Probability |
|---|---|---|---|
| let-7c | 1.445 | 1.129 | 0.0130 |
| mir-26a | 2.451 | 1.673 | 0.0474 |
| mir-29b | 1.283 | 0.997 | 0.0194 |
| mir-30a-5p | 1.679 | 1.219 | 0.0012 |
| mir-30b | 1.898 | 1.220 | 0.0044 |
| mir-30c | 1.643 | 1.089 | 0.0047 |
| mir-30d | 3.211 | 1.777 | 0.0055 |

FIG. 4C

| N samples feature | 9 pT1 | 22 pT2-3 | Probability |
|---|---|---|---|
| mir-9-2 | 0.894 | 0.840 | 0.0078 |
| mir-15-a | 0.905 | 0.830 | 0.0024 |
| mir-21 | 1.080 | 1.348 | 0.0040 |
| mir-30a-s | 0.944 | 0.875 | 0.0065 |
| mir-133a-1 | 0.928 | 0.843 | 0.0025 |
| mir-137 | 0.894 | 0.818 | 0.0100 |
| mir-153-2 | 0.896 | 0.833 | 0.0096 |
| mir-154 | 0.924 | 0.852 | 0.0062 |
| mir-181a | 1.024 | 1.225 | 0.0045 |
| mir-203 | 0.905 | 1.102 | 0.0011 |
| mir-213 | 1.915 | 3.197 | 0.0003 |

FIG. 4D

| N samples feature | 16 pN0 | 6 pN1b+ | Probability |
|---|---|---|---|
| let-7f-1 | 1.195 | 1.053 | 0.0378 |
| let-7a-3 | 1.191 | 1.039 | 0.0303 |
| let-7a-2 | 1.470 | 1.213 | 0.0300 |
| mir-9-3 | 1.634 | 1.344 | 0.0152 |

FIG. 4E

| N samples feature | 21 Vascular invasion absent | 11 Vascular invasion present | Probability |
|---|---|---|---|
| mir-9-3 | 1.059 | 0.988 | 0.0451 |
| mir-10b | 1.048 | 0.972 | 0.0210 |
| mir-27a | 1.104 | 0.992 | 0.0317 |
| mir-28a | 1.101 | 0.970 | 0.0346 |
| mir-123 | 1.125 | 0.852 | 0.0161 |
| mir-205 | 1.299 | 0.762 | 0.0451 |

FIG. 4F

| N samples feature | 26 Low PI | 23 High PI | Probability |
|---|---|---|---|
| let-7c | 1.817 | 1.361 | 0.0071 |
| let-7d | 1.594 | 1.310 | 0.0073 |
| mir-26a | 2.602 | 1.928 | 0.0492 |
| mir-26b | 4.039 | 2.685 | 0.0297 |
| mir-30a-5p | 1.783 | 1.394 | 0.0257 |
| mir-102 | 1.389 | 1.037 | 0.0017 |
| mir-145 | 1.557 | 1.281 | 0.0136 |

FIG. 4G

| N samples feature | 30 p53- | 14 p53+ | Probability |
|---|---|---|---|
| mir-16a | 0.895 | 1.030 | 0.0026 |
| mir-128b | 0.964 | 1.059 | 0.0096 |

FIG. 4

SEQUENCE LISTING

<160> NUMBER OF SEQ ID NOS: 290

<210> SEQ ID NO 1
<211> LENGTH: 90
<212> TYPE: DNA
<213> ORGANISM: Homo sapiens

<400> SEQUENCE: 1
cactgtggga tgaggtagta ggttgtatag ttttagggtc acacccacca ctgggagata    60
actatacaat ctactgtctt tcctaacgtg                                     90

<210> SEQ ID NO 2
<211> LENGTH: 72
<212> TYPE: DNA
<213> ORGANISM: Homo sapiens

<400> SEQUENCE: 2
aggttgaggt agtaggttgt atagtttaga attacatcaa gggagataac tgtacagcct    60
cctagctttc ct                                                        72

<210> SEQ ID NO 3
<211> LENGTH: 74
<212> TYPE: DNA
<213> ORGANISM: Homo sapiens

<400> SEQUENCE: 3
gggtgaggta gtaggttgta tagtttgggg ctctgccctg ctatgggata actatacaat    60

```
ctactgtctt tcct                                                      74
```

<210> SEQ ID NO 4
<211> LENGTH: 107
<212> TYPE: DNA
<213> ORGANISM: Homo sapiens

<400> SEQUENCE: 4

```
gtgactgcat gctcccaggt tgaggtagta ggttgtatag tttagaatta cacaagggag    60
ataactgtac agcctcctag ctttccttgg gtcttgcact aaacaac                 107
```

<210> SEQ ID NO 5
<211> LENGTH: 85
<212> TYPE: DNA
<213> ORGANISM: Homo sapiens

<400> SEQUENCE: 5

```
ggcggggtga ggtagtaggt tgtgtggttt cagggcagtg atgttgcccc tcggaagata    60
actatacaac ctactgcctt ccctg                                          85
```

<210> SEQ ID NO 6
<211> LENGTH: 84
<212> TYPE: DNA
<213> ORGANISM: Homo sapiens

<400> SEQUENCE: 6

```
gcatccgggt tgaggtagta ggttgtatgg tttagagtta caccctggga gttaactgta    60
caaccttcta gctttccttg gagc                                           84
```

<210> SEQ ID NO 7
<211> LENGTH: 87
<212> TYPE: DNA
<213> ORGANISM: Homo sapiens

<400> SEQUENCE: 7

```
cctaggaaga ggtagtaggt tgcatagttt tagggcaggg attttgccca caaggaggta    60
actatacgac ctgctgcctt tcttagg                                        87
```

<210> SEQ ID NO 8
<211> LENGTH: 85
<212> TYPE: DNA
<213> ORGANISM: Homo sapiens

<400> SEQUENCE: 8

```
ctaggaagag gtagtagttt gcatagtttt agggcaaaga ttttgcccac aagtagttag    60
ctatacgacc tgcagccttt tgtag                                          85
```

<210> SEQ ID NO 9
<211> LENGTH: 85
<212> TYPE: DNA
<213> ORGANISM: Homo sapiens

<400> SEQUENCE: 9

```
ctggctgagg tagtagtttg tgctgttggt cgggttgtga cattgcccgc tgtggagata    60
actgcgcaag ctactgcctt gctag                                          85
```

<210> SEQ ID NO 10
<211> LENGTH: 79
<212> TYPE: DNA
<213> ORGANISM: Homo sapiens

```
<400> SEQUENCE: 10
cccgggctga ggtaggaggt tgtatagttg aggaggacac ccaaggagat cactatacgg      60
cctcctagct ttccccagg                                                  79

<210> SEQ ID NO 11
<211> LENGTH: 87
<212> TYPE: DNA
<213> ORGANISM: Homo sapiens

<400> SEQUENCE: 11
tcagagtgag gtagtagatt gtatagttgt ggggtagtga ttttaccctg ttcaggagat      60
aactatacaa tctattgcct tccctga                                         87

<210> SEQ ID NO 12
<211> LENGTH: 89
<212> TYPE: DNA
<213> ORGANISM: Homo sapiens

<400> SEQUENCE: 12
ctgtgggatg aggtagtaga ttgtatagtt gtggggtagt gattttaccc tgttcaggag      60
ataactatac aatctattgc cttccctga                                       89

<210> SEQ ID NO 13
<211> LENGTH: 85
<212> TYPE: DNA
<213> ORGANISM: Homo sapiens

<400> SEQUENCE: 13
ctgtgggatg aggtagtaga ttgtatagtt ttagggtcat accccatctt ggagataact      60
atacagtcta ctgtctttcc cacgg                                           85

<210> SEQ ID NO 14
<211> LENGTH: 108
<212> TYPE: DNA
<213> ORGANISM: Homo sapiens

<400> SEQUENCE: 14
ttgcctgatt ccaggctgag gtagtagttt gtacagtttg agggtctatg ataccacccg      60
gtacaggaga taactgtaca ggccactgcc ttgccaggaa cagcgcgc                 108

<210> SEQ ID NO 15
<211> LENGTH: 85
<212> TYPE: DNA
<213> ORGANISM: Homo sapiens

<400> SEQUENCE: 15
ctggctgagg tagtagtttg tgctgttggt cgggttgtga cattgcccgc tgtggagata      60
actgcgcaag ctactgcctt gctag                                           85

<210> SEQ ID NO 16
<211> LENGTH: 85
<212> TYPE: DNA
<213> ORGANISM: Homo sapiens

<400> SEQUENCE: 16
acctactcag agtacatact tctttatgta cccatatgaa catacaatgc tatggaatgt      60
aaagaagtat gtattttggt aggc                                            85
```

```
<210> SEQ ID NO 17
<211> LENGTH: 108
<212> TYPE: DNA
<213> ORGANISM: Homo sapiens

<400> SEQUENCE: 17
cagctaacaa cttagtaata cctactcaga gtacatactt ctttatgtac ccatatgaac      60
atacaatgct atggaatgta aagaagtatg tattttggt aggcaata                   108

<210> SEQ ID NO 18
<211> LENGTH: 85
<212> TYPE: DNA
<213> ORGANISM: Homo sapiens

<400> SEQUENCE: 18
gcctgcttgg gaaacatact tctttatatg cccatatgga cctgctaagc tatggaatgt      60
aaagaagtat gtatctcagg ccggg                                            85

<210> SEQ ID NO 19
<211> LENGTH: 71
<212> TYPE: DNA
<213> ORGANISM: Homo sapiens

<400> SEQUENCE: 19
tgggaaacat acttctttat atgcccatat ggacctgcta agctatggaa tgtaaagaag      60
tatgtatctc a                                                           71

<210> SEQ ID NO 20
<211> LENGTH: 85
<212> TYPE: DNA
<213> ORGANISM: Homo sapiens

<400> SEQUENCE: 20
acctactcag agtacatact tctttatgta cccatatgaa catacaatgc tatggaatgt      60
aaagaagtat gtattttggg taggc                                            85

<210> SEQ ID NO 21
<211> LENGTH: 108
<212> TYPE: DNA
<213> ORGANISM: Homo sapiens

<400> SEQUENCE: 21
tggatgttgg cctagttctg tgtggaagac tagtgatttt gttgttttta gataactaaa      60
tcgacaacaa atcacagtct gccatatggc acaggccatg cctctaca                  108

<210> SEQ ID NO 22
<211> LENGTH: 110
<212> TYPE: DNA
<213> ORGANISM: Homo sapiens

<400> SEQUENCE: 22
ttggatgttg gcctagttct gtgtggaaga ctagtgattt tgttgttttt agataactaa      60
atcgacaaca aatcacagtc tgccatatgg cacaggccat gcctctacag                110

<210> SEQ ID NO 23
<211> LENGTH: 110
<212> TYPE: DNA
<213> ORGANISM: Homo sapiens

<400> SEQUENCE: 23
ctggatacag agtggaccgg ctggccccat ctggaagact agtgattttg ttgttgtctt      60
```

```
actgcgctca acaacaaatc ccagtctacc taatggtgcc agccatcgca           110

<210> SEQ ID NO 24
<211> LENGTH: 110
<212> TYPE: DNA
<213> ORGANISM: Homo sapiens

<400> SEQUENCE: 24
ctggatacag agtggaccgg ctggccccat ctggaagact agtgattttg ttgttgtctt   60
actgcgctca acaacaaatc ccagtctacc taatggtgcc agccatcgca           110

<210> SEQ ID NO 25
<211> LENGTH: 110
<212> TYPE: DNA
<213> ORGANISM: Homo sapiens

<400> SEQUENCE: 25
agattagagt ggctgtggtc tagtgctgtg tggaagacta gtgattttgt tgttctgatg   60
tactacgaca acaagtcaca gccggcctca tagcgcagac tcccttcgac           110

<210> SEQ ID NO 26
<211> LENGTH: 110
<212> TYPE: DNA
<213> ORGANISM: Homo sapiens

<400> SEQUENCE: 26
agattagagt ggctgtggtc tagtgctgtg tggaagacta gtgattttgt tgttctgatg   60
tactacgaca acaagtcaca gccggcctca tagcgcagac tcccttcgac           110

<210> SEQ ID NO 27
<211> LENGTH: 89
<212> TYPE: DNA
<213> ORGANISM: Homo sapiens

<400> SEQUENCE: 27
cggggttggt tgttatcttt ggttatctag ctgtatgagt ggtgtggagt cttcataaag   60
ctagataacc gaaagtaaaa ataccccca                                  89

<210> SEQ ID NO 28
<211> LENGTH: 87
<212> TYPE: DNA
<213> ORGANISM: Homo sapiens

<400> SEQUENCE: 28
ggaagcgagt tgttatcttt ggttatctag ctgtatgagt gtattggtct tcataaagct   60
agataaccga aagtaaaaac tccttca                                    87

<210> SEQ ID NO 29
<211> LENGTH: 90
<212> TYPE: DNA
<213> ORGANISM: Homo sapiens

<400> SEQUENCE: 29
ggaggcccgt ttctctcttt ggttatctag ctgtatgagt gccacagagc cgtcataaag   60
ctagataacc gaaagtagaa atgattctca                                 90

<210> SEQ ID NO 30
<211> LENGTH: 110
<212> TYPE: DNA
```

```
<400> SEQUENCE: 30
gatctgtctg tcttctgtat atacccgtgta gatccgaatt tgtgtaagga attttgtggt    60
cacaaattcg tatctagggg aatatgtagt tgacataaac actccgctct              110

<210> SEQ ID NO 31
<211> LENGTH: 110
<212> TYPE: DNA
<213> ORGANISM: Homo sapiens

<400> SEQUENCE: 31
ccagaggttg taacgttgtc tatatatacc ctgtagaacc gaatttgtgt ggtatccgta    60
tagtcacaga ttcgattcta ggggaatata tggtcgatgc aaaaacttca              110

<210> SEQ ID NO 32
<211> LENGTH: 108
<212> TYPE: DNA
<213> ORGANISM: Homo sapiens

<400> SEQUENCE: 32
gcgcgaatgt gtgtttaaaa aaataaaaac cttggagtaa agtagcagca cataatggtt    60
tgtggatttt gaaaaggtgc aggccatatt gtgctgcctc aaaaatac                108

<210> SEQ ID NO 33
<211> LENGTH: 83
<212> TYPE: DNA
<213> ORGANISM: Homo sapiens

<400> SEQUENCE: 33
ccttggagta agtagcagc acataatggt ttgtggattt tgaaaaggtg caggccatat     60
tgtgctgcct caaaaataca agg                                           83

<210> SEQ ID NO 34
<211> LENGTH: 64
<212> TYPE: DNA
<213> ORGANISM: Homo sapiens

<400> SEQUENCE: 34
ctgtagcagc acatcatggt ttacatgcta cagtcaagat gcgaatcatt atttgctgct    60
ctag                                                                64

<210> SEQ ID NO 35
<211> LENGTH: 98
<212> TYPE: DNA
<213> ORGANISM: Homo sapiens

<400> SEQUENCE: 35
ttgaggcctt aaagtactgt agcagcacat catggtttac atgctacagt caagatgcga    60
atcattattt gctgctctag aaatttaagg aaattcat                           98

<210> SEQ ID NO 36
<211> LENGTH: 89
<212> TYPE: DNA
<213> ORGANISM: Homo sapiens

<400> SEQUENCE: 36
gtcagcagtg ccttagcagc acgtaaatat tggcgttaag attctaaaat tatctccagt    60
attaactgtg ctgctgaagt aaggttgac                                     89
```

```
<210> SEQ ID NO 37
<211> LENGTH: 81
<212> TYPE: DNA
<213> ORGANISM: Homo sapiens

<400> SEQUENCE: 37
gttccactct agcagcacgt aaatattggc gtagtgaaat atatattaaa caccaatatt    60
actgtgctgc tttagtgtga c                                              81

<210> SEQ ID NO 38
<211> LENGTH: 81
<212> TYPE: DNA
<213> ORGANISM: Homo sapiens

<400> SEQUENCE: 38
gcagtgcctt agcagcacgt aaatattggc gttaagattc taaaattatc tccagtatta    60
actgtgctgc tgaagtaagg t                                              81

<210> SEQ ID NO 39
<211> LENGTH: 84
<212> TYPE: DNA
<213> ORGANISM: Homo sapiens

<400> SEQUENCE: 39
gtcagaataa tgtcaaagtg cttacagtgc aggtagtgat atgtgcatct actgcagtga    60
aggcacttgt agcattatgg tgac                                           84

<210> SEQ ID NO 40
<211> LENGTH: 71
<212> TYPE: DNA
<213> ORGANISM: Homo sapiens

<400> SEQUENCE: 40
tgttctaagg tgcatctagt gcagatagtg aagtagatta gcatctactg ccctaagtgc    60
tccttctggc a                                                         71

<210> SEQ ID NO 41
<211> LENGTH: 81
<212> TYPE: DNA
<213> ORGANISM: Homo sapiens

<400> SEQUENCE: 41
tttttgttct aaggtgcatc tagtgcagat agtgaagtag attagcatct actgccctaa    60
gtgctccttc tggcataaga a                                              81

<210> SEQ ID NO 42
<211> LENGTH: 82
<212> TYPE: DNA
<213> ORGANISM: Homo sapiens

<400> SEQUENCE: 42
gcagtcctct gttagttttg catagttgca ctacaagaag aatgtagttg tgcaaatcta    60
tgcaaaactg atggtggcct gc                                             82

<210> SEQ ID NO 43
<211> LENGTH: 80
<212> TYPE: DNA
<213> ORGANISM: Homo sapiens

<400> SEQUENCE: 43
cagtcctctg ttagttttgc atagttgcac tacaagaaga atgtagttgt gcaaatctat    60
```

```
gcaaaactga tggtggcctg                                            80

<210> SEQ ID NO 44
<211> LENGTH: 87
<212> TYPE: DNA
<213> ORGANISM: Homo sapiens

<400> SEQUENCE: 44
cactgttcta tggttagttt tgcaggtttg catccagctg tgtgatattc tgctgtgcaa   60
atccatgcaa aactgactgt ggtagtg                                      87

<210> SEQ ID NO 45
<211> LENGTH: 96
<212> TYPE: DNA
<213> ORGANISM: Homo sapiens

<400> SEQUENCE: 45
acattgctac ttacaattag ttttgcaggt ttgcatttca gcgtatatat gtatatgtgg   60
ctgtgcaaat ccatgcaaaa ctgattgtga taatgt                            96

<210> SEQ ID NO 46
<211> LENGTH: 80
<212> TYPE: DNA
<213> ORGANISM: Homo sapiens

<400> SEQUENCE: 46
ttctatggtt agttttgcag gtttgcatcc agctgtgtga tattctgctg tgcaaatcca   60
tgcaaaactg actgtggtag                                              80

<210> SEQ ID NO 47
<211> LENGTH: 81
<212> TYPE: DNA
<213> ORGANISM: Homo sapiens

<400> SEQUENCE: 47
ttacaattag ttttgcaggt ttgcatttca gcgtatatat gtatatgtgg ctgtgcaaat   60
ccatgcaaaa ctgattgtga t                                            81

<210> SEQ ID NO 48
<211> LENGTH: 71
<212> TYPE: DNA
<213> ORGANISM: Homo sapiens

<400> SEQUENCE: 48
gtagcactaa agtgcttata gtgcaggtag tgtttagtta tctactgcat tatgagcact   60
taaagtactg c                                                       71

<210> SEQ ID NO 49
<211> LENGTH: 72
<212> TYPE: DNA
<213> ORGANISM: Homo sapiens

<400> SEQUENCE: 49
tgtcgggtag cttatcagac tgatgttgac tgttgaatct catggcaaca ccagtcgatg   60
ggctgtctga ca                                                      72

<210> SEQ ID NO 50
<211> LENGTH: 81
<212> TYPE: DNA
<213> ORGANISM: Homo sapiens
```

```
<400> SEQUENCE: 50
accttgtcgg gtagcttatc agactgatgt tgactgttga atctcatggc aacaccagtc    60
gatgggctgt ctgacattt g                                               81

<210> SEQ ID NO 51
<211> LENGTH: 85
<212> TYPE: DNA
<213> ORGANISM: Homo sapiens

<400> SEQUENCE: 51
ggctgagccg cagtagttct tcagtggcaa gctttatgtc ctgacccagc taaagctgcc    60
agttgaagaa ctgttgccct ctgcc                                          85

<210> SEQ ID NO 52
<211> LENGTH: 73
<212> TYPE: DNA
<213> ORGANISM: Homo sapiens

<400> SEQUENCE: 52
ggccggctgg ggttcctggg gatgggattt gcttcctgtc acaaatcaca ttgccaggga    60
tttccaaccg acc                                                       73

<210> SEQ ID NO 53
<211> LENGTH: 97
<212> TYPE: DNA
<213> ORGANISM: Homo sapiens

<400> SEQUENCE: 53
ctcaggtgct ctggctgctt gggttcctgg catgctgatt tgtgacttaa gattaaaatc    60
acattgccag ggattaccac gcaaccacga ccttggc                             97

<210> SEQ ID NO 54
<211> LENGTH: 81
<212> TYPE: DNA
<213> ORGANISM: Homo sapiens

<400> SEQUENCE: 54
ccacggccgg ctggggttcc tggggatggg atttgcttcc tgtcacaaat cacattgcca    60
gggatttcca accgaccctg a                                              81

<210> SEQ ID NO 55
<211> LENGTH: 68
<212> TYPE: DNA
<213> ORGANISM: Homo sapiens

<400> SEQUENCE: 55
ctccggtgcc tactgagctg atatcagttc tcattttaca cactggctca gttcagcagg    60
aacaggag                                                             68

<210> SEQ ID NO 56
<211> LENGTH: 73
<212> TYPE: DNA
<213> ORGANISM: Homo sapiens

<400> SEQUENCE: 56
ctctgcctcc cgtgcctact gagctgaaac acagttggtt tgtgtacact ggctcagttc    60
agcaggaaca ggg                                                       73
```

```
<210> SEQ ID NO 57
<211> LENGTH: 81
<212> TYPE: DNA
<213> ORGANISM: Homo sapiens

<400> SEQUENCE: 57
ccctgggctc tgcctcccgt gcctactgag ctgaaacaca gttggtttgt gtacactggc      60
tcagttcagc aggaacaggg g                                                81

<210> SEQ ID NO 58
<211> LENGTH: 71
<212> TYPE: DNA
<213> ORGANISM: Homo sapiens

<400> SEQUENCE: 58
ccctccggtg cctactgagc tgatatcagt tctcatttta cacactggct cagttcagca      60
ggaacagcat c                                                           71

<210> SEQ ID NO 59
<211> LENGTH: 84
<212> TYPE: DNA
<213> ORGANISM: Homo sapiens

<400> SEQUENCE: 59
ggccagtgtt gagaggcgga gacttgggca attgctggac gctgccctgg gcattgcact      60
tgtctcggtc tgacagtgcc ggcc                                             84

<210> SEQ ID NO 60
<211> LENGTH: 86
<212> TYPE: DNA
<213> ORGANISM: Homo sapiens

<400> SEQUENCE: 60
aggccgtggc ctcgttcaag taatccagga taggctgtgc aggtcccaat ggcctatctt      60
ggttacttgc acggggacgc gggcct                                           86

<210> SEQ ID NO 61
<211> LENGTH: 77
<212> TYPE: DNA
<213> ORGANISM: Homo sapiens

<400> SEQUENCE: 61
ccgggaccca gttcaagtaa ttcaggatag gttgtgtgct gtccagcctg ttctccatta      60
cttggctcgg ggaccgg                                                     77

<210> SEQ ID NO 62
<211> LENGTH: 78
<212> TYPE: DNA
<213> ORGANISM: Homo sapiens

<400> SEQUENCE: 62
ctgaggagca gggcttagct gcttgtgagc agggtccaca ccaagtcgtg ttcacagtgg      60
ctaagttccg cccccccag                                                   78

<210> SEQ ID NO 63
<211> LENGTH: 73
<212> TYPE: DNA
<213> ORGANISM: Homo sapiens

<400> SEQUENCE: 63
aggtgcagag cttagctgat tggtgaacag tgattggttt ccgctttgtt cacagtggct      60
```

```
aagttctgca cct                                                           73

<210> SEQ ID NO 64
<211> LENGTH: 97
<212> TYPE: DNA
<213> ORGANISM: Homo sapiens

<400> SEQUENCE: 64
acctctctaa caaggtgcag agcttagctg attggtgaac agtgattggt ttccgctttg        60
ttcacagtgg ctaagttctg cacctgaaga gaaggtg                                 97

<210> SEQ ID NO 65
<211> LENGTH: 80
<212> TYPE: DNA
<213> ORGANISM: Homo sapiens

<400> SEQUENCE: 65
cctgaggagc agggcttagc tgcttgtgag cagggtccac accaagtcgt gttcacagtg        60
gctaagttcc gccccccagg                                                    80

<210> SEQ ID NO 66
<211> LENGTH: 86
<212> TYPE: DNA
<213> ORGANISM: Homo sapiens

<400> SEQUENCE: 66
ggtccttgcc ctcaaggagc tcacagtcta ttgagttacc tttctgactt tcccactaga        60
ttgtgagctc ctggagggca ggcact                                             86

<210> SEQ ID NO 67
<211> LENGTH: 108
<212> TYPE: DNA
<213> ORGANISM: Homo sapiens

<400> SEQUENCE: 67
ccttctgtga cccttagag gatgactgat ttcttttggt gttcagagtc aatataattt         60
tctagcacca tctgaaatcg gttataatga ttggggaaga gcaccatg                    108

<210> SEQ ID NO 68
<211> LENGTH: 64
<212> TYPE: DNA
<213> ORGANISM: Homo sapiens

<400> SEQUENCE: 68
atgactgatt tcttttggtg ttcagagtca atataatttt ctagcaccat ctgaaatcgg        60
ttat                                                                     64

<210> SEQ ID NO 69
<211> LENGTH: 110
<212> TYPE: DNA
<213> ORGANISM: Homo sapiens

<400> SEQUENCE: 69
accactggcc catctcttac acaggctgac cgatttctcc tggtgttcag agtctgtttt        60
tgtctagcac catttgaaat cggttatgat gtaggggggaa aagcagcagc                 110

<210> SEQ ID NO 70
<211> LENGTH: 71
<212> TYPE: DNA
<213> ORGANISM: Homo sapiens
```

```
<400> SEQUENCE: 70
gcgactgtaa acatcctcga ctggaagctg tgaagccaca gatgggcttt cagtcggatg        60
tttgcagctg c                                                              71

<210> SEQ ID NO 71
<211> LENGTH: 60
<212> TYPE: DNA
<213> ORGANISM: Homo sapiens

<400> SEQUENCE: 71
atgtaaacat cctacactca gctgtaatac atggattggc tgggaggtgg atgtttacgt        60

<210> SEQ ID NO 72
<211> LENGTH: 88
<212> TYPE: DNA
<213> ORGANISM: Homo sapiens

<400> SEQUENCE: 72
accaagtttc agttcatgta aacatcctac actcagctgt aatacatgga ttggctggga        60
ggtggatgtt tacttcagct gacttgga                                           88

<210> SEQ ID NO 73
<211> LENGTH: 72
<212> TYPE: DNA
<213> ORGANISM: Homo sapiens

<400> SEQUENCE: 73
agatactgta aacatcctac actctcagct gtggaaagta agaaagctgg gagaaggctg        60
tttactcttt ct                                                            72

<210> SEQ ID NO 74
<211> LENGTH: 70
<212> TYPE: DNA
<213> ORGANISM: Homo sapiens

<400> SEQUENCE: 74
gttgttgtaa acatccccga ctggaagctg taagacacag ctaagctttc agtcagatgt        60
ttgctgctac                                                               70

<210> SEQ ID NO 75
<211> LENGTH: 71
<212> TYPE: DNA
<213> ORGANISM: Homo sapiens

<400> SEQUENCE: 75
ggagaggagg caagatgctg gcatagctgt tgaactggga acctgctatg ccaacatatt        60
gccatctttc c                                                             71

<210> SEQ ID NO 76
<211> LENGTH: 70
<212> TYPE: DNA
<213> ORGANISM: Homo sapiens

<400> SEQUENCE: 76
ggagatattg cacattacta agttgcatgt tgtcacggcc tcaatgcaat ttagtgtgtg        60
tgatattttc                                                               70

<210> SEQ ID NO 77
<211> LENGTH: 110
```

```
<212> TYPE: DNA
<213> ORGANISM: Homo sapiens

<400> SEQUENCE: 77
gggggccgag agaggcgggc ggccccgcgg tgcattgctg ttgcattgca cgtgtgtgag    60
gcgggtgcag tgcctcggca gtgcagcccg gagccggccc ctggcaccac              110

<210> SEQ ID NO 78
<211> LENGTH: 69
<212> TYPE: DNA
<213> ORGANISM: Homo sapiens

<400> SEQUENCE: 78
ctgtggtgca ttgtagttgc attgcatgtt ctggtggtac ccatgcaatg tttccacagt    60
gcatcacag                                                            69

<210> SEQ ID NO 79
<211> LENGTH: 110
<212> TYPE: DNA
<213> ORGANISM: Homo sapiens

<400> SEQUENCE: 79
ggccagctgt gagtgtttct ttggcagtgt cttagctggt tgttgtgagc aatagtaagg    60
aagcaatcag caagtatact gccctagaag tgctgcacgt tgtggggccc               110

<210> SEQ ID NO 80
<211> LENGTH: 82
<212> TYPE: DNA
<213> ORGANISM: Homo sapiens

<400> SEQUENCE: 80
tcagaataat gtcaaagtgc ttacagtgca ggtagtgata tgtgcatcta ctgcagtgaa    60
ggcacttgta gcattatggt ga                                             82

<210> SEQ ID NO 81
<211> LENGTH: 78
<212> TYPE: DNA
<213> ORGANISM: Homo sapiens

<400> SEQUENCE: 81
ctttctacac aggttgggat cggttgcaat gctgtgtttc tgtatggtat tgcacttgtc    60
ccggcctgtt gagtttgg                                                  78

<210> SEQ ID NO 82
<211> LENGTH: 75
<212> TYPE: DNA
<213> ORGANISM: Homo sapiens

<400> SEQUENCE: 82
tcatccctgg gtgggatttt gttgcattac ttgtgttcta tataaagtat tgcacttgtc    60
ccggcctgtg gaaga                                                     75

<210> SEQ ID NO 83
<211> LENGTH: 80
<212> TYPE: DNA
<213> ORGANISM: Homo sapiens

<400> SEQUENCE: 83 ctggggctc caaagtgctg ttcgtgcagg tagtgtgatt acccaaccta ctgctgagct    60
agcacttccc gagcccccgg                                                80
```

<210> SEQ ID NO 84
<211> LENGTH: 80
<212> TYPE: DNA
<213> ORGANISM: Homo sapiens

<400> SEQUENCE: 84
ctgggggctc caaagtgctg ttcgtgcagg tagtgtgatt acccaaccta ctgctgagct    60
agcacttccc gagcccccgg                                                80

<210> SEQ ID NO 85
<211> LENGTH: 81
<212> TYPE: DNA
<213> ORGANISM: Homo sapiens

<400> SEQUENCE: 85
aacacagtgg gcactcaata aatgtctgtt gaattgaaat gcgttacatt caacgggtat    60
ttattgagca cccactctgt g                                              81

<210> SEQ ID NO 86
<211> LENGTH: 78
<212> TYPE: DNA
<213> ORGANISM: Homo sapiens

<400> SEQUENCE: 86
tggccgattt tggcactagc acattttgc ttgtgtctct ccgctctgag caatcatgtg     60
cagtgccaat atgggaaa                                                  78

<210> SEQ ID NO 87
<211> LENGTH: 80
<212> TYPE: DNA
<213> ORGANISM: Homo sapiens

<400> SEQUENCE: 87
gtgaggtagt aagttgtatt gttgtggggt agggatatta ggccccaatt agaagataac    60
tatacaactt actactttcc                                                80

<210> SEQ ID NO 88
<211> LENGTH: 70
<212> TYPE: DNA
<213> ORGANISM: Homo sapiens

<400> SEQUENCE: 88
ggcacccacc cgtagaaccg accttgcggg gccttcgccg cacacaagct cgtgtctgtg    60
ggtccgtgtc                                                           70

<210> SEQ ID NO 89
<211> LENGTH: 81
<212> TYPE: DNA
<213> ORGANISM: Homo sapiens

<400> SEQUENCE: 89
cccattggca taaacccgta gatccgatct tgtggtgaag tggaccgcac aagctcgctt    60
ctatgggtct gtgtcagtgt g                                              81

<210> SEQ ID NO 90
<211> LENGTH: 108
<212> TYPE: DNA
<213> ORGANISM: Homo sapiens

<400> SEQUENCE: 90

```
aagagagaag atattgaggc ctgttgccac aaacccgtag atccgaactt gtggtattag    60
tccgcacaag cttgtatcta taggtatgtg tctgttaggc aatctcac                108
```

<210> SEQ ID NO 91
<211> LENGTH: 80
<212> TYPE: DNA
<213> ORGANISM: Homo sapiens

<400> SEQUENCE: 91

```
cctgttgcca caaacccgta gatccgaact tgtggtatta gtccgcacaa gcttgtatct    60
ataggtatgt gtctgttagg                                                80
```

<210> SEQ ID NO 92
<211> LENGTH: 110
<212> TYPE: DNA
<213> ORGANISM: Homo sapiens

<400> SEQUENCE: 92

```
aggctgccct ggctcagtta tcacagtgct gatgctgtct attctaaagg tacagtactg    60
tgataactga aggatggcag ccatcttacc ttccatcaga ggagcctcac               110
```

<210> SEQ ID NO 93
<211> LENGTH: 57
<212> TYPE: DNA
<213> ORGANISM: Homo sapiens

<400> SEQUENCE: 93

```
tcagttatca cagtgctgat gctgtccatt ctaaaggtac agtactgtga taactga       57
```

<210> SEQ ID NO 94
<211> LENGTH: 75
<212> TYPE: DNA
<213> ORGANISM: Homo sapiens

<400> SEQUENCE: 94

```
tgccctggct cagttatcac agtgctgatg ctgtctattc taaaggtaca gtactgtgat    60
aactgaagga tggca                                                     75
```

<210> SEQ ID NO 95
<211> LENGTH: 75
<212> TYPE: DNA
<213> ORGANISM: Homo sapiens

<400> SEQUENCE: 95

```
tgtccttttt cggttatcat ggtaccgatg ctgtatatct gaaaggtaca gtactgtgat    60
aactgaagaa tggtg                                                     75
```

<210> SEQ ID NO 96
<211> LENGTH: 81
<212> TYPE: DNA
<213> ORGANISM: Homo sapiens

<400> SEQUENCE: 96

```
cttctggaag ctggtttcac atggtggctt agattttttcc atctttgtat ctagcaccat    60
ttgaaatcag tgttttagga g                                              81
```

<210> SEQ ID NO 97
<211> LENGTH: 81
<212> TYPE: DNA

```
<400> SEQUENCE: 97
cttcaggaag ctggtttcat atggtggttt agatttaaat agtgattgtc tagcaccatt    60
tgaaatcagt gttcttgggg g                                              81

<210> SEQ ID NO 98
<211> LENGTH: 81
<212> TYPE: DNA
<213> ORGANISM: Homo sapiens

<400> SEQUENCE: 98
cttcaggaag ctggtttcat atggtggttt agatttaaat agtgattgtc tagcaccatt    60
tgaaatcagt gttcttgggg g                                              81

<210> SEQ ID NO 99
<211> LENGTH: 78
<212> TYPE: DNA
<213> ORGANISM: Homo sapiens

<400> SEQUENCE: 99
ttgtgctttc agcttcttta cagtgctgcc ttgtagcatt caggtcaagc aacattgtac    60
agggctatga aagaacca                                                  78

<210> SEQ ID NO 100
<211> LENGTH: 78
<212> TYPE: DNA
<213> ORGANISM: Homo sapiens

<400> SEQUENCE: 100
ttgtgctttc agcttcttta cagtgctgcc ttgtagcatt caggtcaagc aacattgtac    60
agggctatga aagaacca                                                  78

<210> SEQ ID NO 101
<211> LENGTH: 78
<212> TYPE: DNA
<213> ORGANISM: Homo sapiens

<400> SEQUENCE: 101
tactgccctc ggcttcttta cagtgctgcc ttgttgcata tggatcaagc agcattgtac    60
agggctatga aggcattg                                                  78

<210> SEQ ID NO 102
<211> LENGTH: 78
<212> TYPE: DNA
<213> ORGANISM: Homo sapiens

<400> SEQUENCE: 102
aaatgtcaga cagcccatcg actggtgttg ccatgagatt caacagtcaa catcagtctg    60
ataagctacc cgacaagg                                                  78

<210> SEQ ID NO 103
<211> LENGTH: 81
<212> TYPE: DNA
<213> ORGANISM: Homo sapiens

<400> SEQUENCE: 103
tgtgcatcgt ggtcaaatgc tcagactcct gtggtggctg ctcatgcacc acggatgttt    60
gagcatgtgc tacggtgtct a                                              81
```

```
<210> SEQ ID NO 104
<211> LENGTH: 81
<212> TYPE: DNA
<213> ORGANISM: Homo sapiens

<400> SEQUENCE: 104
tgtgcatcgt ggtcaaatgc tcagactcct gtggtggctg ctcatgcacc acggatgttt      60
gagcatgtgc tacggtgtct a                                                81

<210> SEQ ID NO 105
<211> LENGTH: 81
<212> TYPE: DNA
<213> ORGANISM: Homo sapiens

<400> SEQUENCE: 105
ccttggccat gtaaaagtgc ttacagtgca ggtagctttt tgagatctac tgcaatgtaa      60
gcacttctta cattaccatg g                                                81

<210> SEQ ID NO 106
<211> LENGTH: 81
<212> TYPE: DNA
<213> ORGANISM: Homo sapiens

<400> SEQUENCE: 106
ctctctgctt tcagcttctt tacagtgttg ccttgtggca tggagttcaa gcagcattgt      60
acagggctat caaagcacag a                                                81

<210> SEQ ID NO 107
<211> LENGTH: 85
<212> TYPE: DNA
<213> ORGANISM: Homo sapiens

<400> SEQUENCE: 107
ccttagcaga gctgtggagt gtgacaatgg tgtttgtgtc taaactatca acgccatta       60 tcacactaaa tagctactgc taggc                                            85

<210> SEQ ID NO 108
<211> LENGTH: 66
<212> TYPE: DNA
<213> ORGANISM: Homo sapiens

<400> SEQUENCE: 108
agctgtggag tgtgacaatg gtgtttgtgt ccaaactatc aaacgccatt atcacactaa      60
atagct                                                                 66

<210> SEQ ID NO 109
<211> LENGTH: 61
<212> TYPE: DNA
<213> ORGANISM: Homo sapiens

<400> SEQUENCE: 109
acattattac ttttggtacg cgctgtgaca cttcaaactc gtaccgtgag taataatgcg      60
c                                                                      61

<210> SEQ ID NO 110
<211> LENGTH: 100
<212> TYPE: DNA
<213> ORGANISM: Homo sapiens

<400> SEQUENCE: 110
tccttcctca ggagaaaggc ctctctctcc gtgttcacag cggaccttga tttaaatgtc      60
```

```
catacaatta aggcacgcgg tgaatgccaa gaatggggct                           100
```

<210> SEQ ID NO 111
<211> LENGTH: 85
<212> TYPE: DNA
<213> ORGANISM: Homo sapiens

<400> SEQUENCE: 111

```
aggcctctct ctccgtgttc acagcggacc ttgatttaaa tgtccataca attaaggcac    60
gcggtgaatg ccaagaatgg ggctg                                          85
```

<210> SEQ ID NO 112
<211> LENGTH: 110
<212> TYPE: DNA
<213> ORGANISM: Homo sapiens

<400> SEQUENCE: 112

```
atcaagatta gaggctctgc tctccgtgtt cacagcggac cttgatttaa tgtcatacaa    60
ttaaggcacg cggtgaatgc caagagcgga gcctacggct gcacttgaag             110
```

<210> SEQ ID NO 113
<211> LENGTH: 110
<212> TYPE: DNA
<213> ORGANISM: Homo sapiens

<400> SEQUENCE: 113

```
cccgccccag ccctgagggc ccctctgcgt gttcacagcg gaccttgatt taatgtctat    60
acaattaagg cacgcggtga atgccaagag aggcgcctcc gccgctcctt             110
```

<210> SEQ ID NO 114
<211> LENGTH: 87
<212> TYPE: DNA
<213> ORGANISM: Homo sapiens

<400> SEQUENCE: 114

```
tgagggcccc tctgcgtgtt cacagcggac cttgatttaa tgtctataca attaaggcac    60
gcggtgaatg ccaagagagg cgcctcc                                        87
```

<210> SEQ ID NO 115
<211> LENGTH: 68
<212> TYPE: DNA
<213> ORGANISM: Homo sapiens

<400> SEQUENCE: 115

```
ctctgcgtgt tcacagcgga ccttgattta atgtctatac aattaaggca cgcggtgaat    60
gccaagag                                                             68
```

<210> SEQ ID NO 116
<211> LENGTH: 67
<212> TYPE: DNA
<213> ORGANISM: Homo sapiens

<400> SEQUENCE: 116

```
ctctccgtgt tcacagcgga ccttgattta atgtcataca attaaggcac gcggtgaatg    60
ccaagag                                                              67
```

<210> SEQ ID NO 117
<211> LENGTH: 86
<212> TYPE: DNA
<213> ORGANISM: Homo sapiens

```
<400> SEQUENCE: 117
tgccagtctc taggtccctg agacccttta acctgtgagg acatccaggg tcacaggtga    60
ggttcttggg agcctggcgt ctggcc                                         86

<210> SEQ ID NO 118
<211> LENGTH: 65
<212> TYPE: DNA
<213> ORGANISM: Homo sapiens

<400> SEQUENCE: 118
ggtccctgag acctttaac ctgtgaggac atccagggtc acaggtgagg ttcttgggag    60
cctgg                                                                65

<210> SEQ ID NO 119
<211> LENGTH: 108
<212> TYPE: DNA
<213> ORGANISM: Homo sapiens

<400> SEQUENCE: 119
acattgttgc gctcctctca gtccctgaga ccctaacttg tgatgtttac cgtttaaatc    60
cacgggttag gctcttggga gctgcgagtc gtgcttttgc atcctgga                108

<210> SEQ ID NO 120
<211> LENGTH: 88
<212> TYPE: DNA
<213> ORGANISM: Homo sapiens

<400> SEQUENCE: 120
tgcgctcctc tcagtccctg agaccctaac ttgtgatgtt taccgtttaa atccacgggt    60
taggctcttg ggagctgcga gtcgtgct                                       88

<210> SEQ ID NO 121
<211> LENGTH: 89
<212> TYPE: DNA
<213> ORGANISM: Homo sapiens

<400> SEQUENCE: 121
accagacttt tcctagtccc tgagacccta acttgtgagg tattttagta acatcacaag    60
tcaggctctt gggacctagg cggaggggga                                     89

<210> SEQ ID NO 122
<211> LENGTH: 70
<212> TYPE: DNA
<213> ORGANISM: Homo sapiens

<400> SEQUENCE: 122
cctagtccct gagaccctaa cttgtgaggt attttagtaa catcacaagt caggctcttg    60
ggacctaggc                                                           70

<210> SEQ ID NO 123
<211> LENGTH: 85
<212> TYPE: DNA
<213> ORGANISM: Homo sapiens

<400> SEQUENCE: 123
cgctggcgac gggacattat tactttggt acgcgctgtg acacttcaaa ctcgtaccgt    60
gagtaataat gcgccgtcca cggca                                          85
```

```
<210> SEQ ID NO 124
<211> LENGTH: 61
<212> TYPE: DNA
<213> ORGANISM: Homo sapiens

<400> SEQUENCE: 124
acattattac ttttggtacg cgctgtgaca cttcaaactc gtaccgtgag taataatgcg    60
c                                                                   61

<210> SEQ ID NO 125
<211> LENGTH: 97
<212> TYPE: DNA
<213> ORGANISM: Homo sapiens

<400> SEQUENCE: 125
tgtgatcact gtctccagcc tgctgaagct cagagggctc tgattcagaa agatcatcgg    60
atccgtctga gcttggctgg tcggaagtct catcatc                             97

<210> SEQ ID NO 126
<211> LENGTH: 70
<212> TYPE: DNA
<213> ORGANISM: Homo sapiens

<400> SEQUENCE: 126
ccagcctgct gaagctcaga gggctctgat tcagaaagat catcggatcc gtctgagctt    60
ggctggtcgg                                                           70

<210> SEQ ID NO 127
<211> LENGTH: 82
<212> TYPE: DNA
<213> ORGANISM: Homo sapiens

<400> SEQUENCE: 127
tgagctgttg gattcggggc cgtagcactg tctgagaggt ttacatttct cacagtgaac    60
cggtctcttt ttcagctgct tc                                             82

<210> SEQ ID NO 128
<211> LENGTH: 110
<212> TYPE: DNA
<213> ORGANISM: Homo sapiens

<400> SEQUENCE: 128
gcccggcagc cactgtgcag tgggaagggg ggccgataca ctgtacgaga gtgagtagca    60
ggtctcacag tgaaccggtc tctttcccta ctgtgtcaca ctcctaatgg              110

<210> SEQ ID NO 129
<211> LENGTH: 70
<212> TYPE: DNA
<213> ORGANISM: Homo sapiens

<400> SEQUENCE: 129
gttggattcg gggccgtagc actgtctgag aggtttacat ttctcacagt gaaccggtct    60 cttttttcagc                                                          70

<210> SEQ ID NO 130
<211> LENGTH: 74
<212> TYPE: DNA
<213> ORGANISM: Homo sapiens

<400> SEQUENCE: 130
tggatctttt tgcggtctgg gcttgctgtt cctctcaaca gtagtcagga agcccttacc    60
```

```
ccaaaaagta tcta                                              74

<210> SEQ ID NO 131
<211> LENGTH: 89
<212> TYPE: DNA
<213> ORGANISM: Homo sapiens

<400> SEQUENCE: 131
tgctgctggc cagagctctt ttcacattgt gctactgtct gcacctgtca ctagcagtgc    60
aatgttaaaa gggcattggc cgtgtagtg                                     89

<210> SEQ ID NO 132
<211> LENGTH: 110
<212> TYPE: DNA
<213> ORGANISM: Homo sapiens

<400> SEQUENCE: 132
gccaggaggc ggggttggtt gttatctttg gttatctagc tgtatgagtg gtgtggagtc   60
ttcataaagc tagataaccg aaagtaaaaa taaccccata cactgcgcag              110

<210> SEQ ID NO 133
<211> LENGTH: 110
<212> TYPE: DNA
<213> ORGANISM: Homo sapiens

<400> SEQUENCE: 133
cacggcgcgg cagcggcact ggctaaggga ggcccgtttc tctctttggt tatctagctg   60
tatgagtgcc acagagccgt cataaagcta gataaccgaa agtagaaatg              110

<210> SEQ ID NO 134
<211> LENGTH: 72
<212> TYPE: DNA
<213> ORGANISM: Homo sapiens

<400> SEQUENCE: 134
gttgttatct ttggttatct agctgtatga gtgtattggt cttcataaag ctagataacc   60
gaaagtaaaa ac                                                       72

<210> SEQ ID NO 135
<211> LENGTH: 101
<212> TYPE: DNA
<213> ORGANISM: Homo sapiens

<400> SEQUENCE: 135 ccgccccgc gtctccaggg caaccgtggc tttcgattgt tactgtggga actggaggta    60
acagtctaca gccatggtcg ccccgcagca cgcccacgcg c                       101

<210> SEQ ID NO 136
<211> LENGTH: 66
<212> TYPE: DNA
<213> ORGANISM: Homo sapiens

<400> SEQUENCE: 136
gggcaaccgt ggctttcgat tgttactgtg gaactggag gtaacagtct acagccatgg    60
tcgccc                                                              66

<210> SEQ ID NO 137
<211> LENGTH: 88
<212> TYPE: DNA
<213> ORGANISM: Homo sapiens
```

<400> SEQUENCE: 137
acaatgcttt gctagagctg gtaaaatgga accaaatcgc ctcttcaatg gatttggtcc   60
ccttcaacca gctgtagcta tgcattga                                      88

<210> SEQ ID NO 138
<211> LENGTH: 102
<212> TYPE: DNA
<213> ORGANISM: Homo sapiens

<400> SEQUENCE: 138
gggagccaaa tgctttgcta gagctggtaa aatggaacca aatcgactgt ccaatggatt   60
tggtcccctt caaccagctg tagctgtgca ttgatggcgc cg                     102

<210> SEQ ID NO 139
<211> LENGTH: 68
<212> TYPE: DNA
<213> ORGANISM: Homo sapiens

<400> SEQUENCE: 139
gctagagctg gtaaaatgga accaaatcgc ctcttcaatg gatttggtcc ccttcaacca   60
gctgtagc                                                            68

<210> SEQ ID NO 140
<211> LENGTH: 73
<212> TYPE: DNA
<213> ORGANISM: Homo sapiens

<400> SEQUENCE: 140
cagggtgtgt gactggttga ccagaggggc atgcactgtg ttcaccctgt gggccaccta   60
gtcaccaacc ctc                                                      73

<210> SEQ ID NO 141
<211> LENGTH: 71
<212> TYPE: DNA
<213> ORGANISM: Homo sapiens

<400> SEQUENCE: 141
agggtgtgtg actggttgac cagaggggca tgcactgtgt tcaccctgtg gccacctag   60 tcaccaaccc t                                                        71

<210> SEQ ID NO 142
<211> LENGTH: 90
<212> TYPE: DNA
<213> ORGANISM: Homo sapiens

<400> SEQUENCE: 142
aggcctcgct gttctctatg gcttttatt cctatgtgat tctactgctc actcatatag    60
ggattggagc cgtggcgcac ggcggggaca                                    90

<210> SEQ ID NO 143
<211> LENGTH: 100
<212> TYPE: DNA
<213> ORGANISM: Homo sapiens

<400> SEQUENCE: 143
agataaattc actctagtgc tttatggctt tttattccta tgtgatagta ataaagtctc   60
atgtagggat ggaagccatg aaatacattg tgaaaaatca                        100

<210> SEQ ID NO 144
<211> LENGTH: 60
<212> TYPE: DNA
<213> ORGANISM: Homo sapiens

<400> SEQUENCE: 144
ctatggcttt ttattcctat gtgattctac tgctcactca tatagggatt ggagccgtgg    60

<210> SEQ ID NO 145
<211> LENGTH: 82
<212> TYPE: DNA
<213> ORGANISM: Homo sapiens

<400> SEQUENCE: 145
tgagccctcg gaggactcca tttgttttga tgatggattc ttatgctcca tcatcgtctc    60
aaatgagtct tcagagggtt ct                                            82

<210> SEQ ID NO 146
<211> LENGTH: 62
<212> TYPE: DNA
<213> ORGANISM: Homo sapiens

<400> SEQUENCE: 146
gaggactcca tttgttttga tgatggattc ttatgctcca tcatcgtctc aaatgagtct    60
tc                                                                  62

<210> SEQ ID NO 147
<211> LENGTH: 73
<212> TYPE: DNA
<213> ORGANISM: Homo sapiens

<400> SEQUENCE: 147
cttcggtgac gggtattctt gggtggataa tacggattac gttgttattg cttaagaata    60
cgcgtagtcg agg                                                      73

<210> SEQ ID NO 148
<211> LENGTH: 99
<212> TYPE: DNA
<213> ORGANISM: Homo sapiens

<400> SEQUENCE: 148
ccctggcatg gtgtggtggg gcagctggtg ttgtgaatca ggccgttgcc aatcagagaa    60
cggctacttc acaacaccag ggccacacca cactacagg                          99

<210> SEQ ID NO 149
<211> LENGTH: 84
<212> TYPE: DNA
<213> ORGANISM: Homo sapiens

<400> SEQUENCE: 149
cgttgctgca gctggtgttg tgaatcaggc cgacgagcag cgcatcctct acccggcta    60 tttcacgaca ccagggttgc atca                                          84

<210> SEQ ID NO 150
<211> LENGTH: 71
<212> TYPE: DNA
<213> ORGANISM: Homo sapiens

<400> SEQUENCE: 150
cagctggtgt tgtgaatcag gccgacgagc agcgcatcct cttacccggc tatttcacga    60
caccagggtt g                                                        71

<210> SEQ ID NO 151
<211> LENGTH: 68
<212> TYPE: DNA
<213> ORGANISM: Homo sapiens

<400> SEQUENCE: 151
gtgtattcta cagtgcacgt gtctccagtg tggctcggag gctggagacg cggccctgtt    60
ggagtaac                                                             68

<210> SEQ ID NO 152
<211> LENGTH: 100
<212> TYPE: DNA
<213> ORGANISM: Homo sapiens

<400> SEQUENCE: 152
tgtgtctctc tctgtgtcct gccagtggtt tnaccctatg gtaggttacg tcatgctgtt    60
ctaccacagg gtagaaccac ggacaggata ccggggcacc                         100

<210> SEQ ID NO 153
<211> LENGTH: 72
<212> TYPE: DNA
<213> ORGANISM: Homo sapiens

<400> SEQUENCE: 153
tcctgccagt ggttttaccc tatggtaggt tacgtcatgc tgttctacca cagggtagaa    60
ccacggacag ga                                                        72

<210> SEQ ID NO 154
<211> LENGTH: 70
<212> TYPE: DNA
<213> ORGANISM: Homo sapiens

<400> SEQUENCE: 154
cctgccagtg gttttaccct atggtaggtt acgtcatgct gttctaccac agggtagaac    60
cacggacagg                                                           70

<210> SEQ ID NO 155
<211> LENGTH: 95
<212> TYPE: DNA
<213> ORGANISM: Homo sapiens

<400> SEQUENCE: 155
cggccggccc tgggtccatc ttccagtaca gtgttggatg gtctaattgt gaagctccta    60
acactgtctg gtaaagatgg ctcccgggtg ggttc                               95

<210> SEQ ID NO 156
<211> LENGTH: 72
<212> TYPE: DNA
<213> ORGANISM: Homo sapiens

<400> SEQUENCE: 156
gggtccatct tccagtacag tgttggatgg tctaattgtg aagctcctaa cactgtctgg    60
taaagatggc cc                                                        72

<210> SEQ ID NO 157
<211> LENGTH: 64
<212> TYPE: DNA
<213> ORGANISM: Homo sapiens

<400> SEQUENCE: 157

```
acccataaag tagaaagcac tactaacagc actggagggt gtagtgtttc ctactttatg    60
gatg                                                                 64

<210> SEQ ID NO 158
<211> LENGTH: 87
<212> TYPE: DNA
<213> ORGANISM: Homo sapiens

<400> SEQUENCE: 158
gacagtgcag tcacccataa agtagaaagc actactaaca gcactggagg gtgtagtgtt    60 tcctactttta tggatgagtg tactgtg                                      87

<210> SEQ ID NO 159
<211> LENGTH: 64
<212> TYPE: DNA
<213> ORGANISM: Homo sapiens

<400> SEQUENCE: 159
acccataaag tagaaagcac tactaacagc actggagggt gtagtgtttc ctactttatg    60
gatg                                                                 64

<210> SEQ ID NO 160
<211> LENGTH: 106
<212> TYPE: DNA
<213> ORGANISM: Homo sapiens

<400> SEQUENCE: 160
gcgcagcgcc ctgtctccca gcctgaggtg cagtgctgca tctctggtca gttgggagtc    60
tgagatgaag cactgtagct caggaagaga gaagttgttc tgcagc                  106

<210> SEQ ID NO 161
<211> LENGTH: 63
<212> TYPE: DNA
<213> ORGANISM: Homo sapiens

<400> SEQUENCE: 161
cctgaggtgc agtgctgcat ctctggtcag ttgggagtct gagatgaagc actgtagctc    60
agg                                                                  63

<210> SEQ ID NO 162
<211> LENGTH: 86
<212> TYPE: DNA
<213> ORGANISM: Homo sapiens

<400> SEQUENCE: 162
tggggccctg gctgggatat catcatatac tgtaagtttg cgatgagaca ctacagtata    60
gatgatgtac tagtccgggc acccc                                          86

<210> SEQ ID NO 163
<211> LENGTH: 66
<212> TYPE: DNA
<213> ORGANISM: Homo sapiens

<400> SEQUENCE: 163
ggctgggata tcatcatata ctgtaagttt gcgatgagac actacagtat agatgatgta    60
ctagtc                                                               66

<210> SEQ ID NO 164
<211> LENGTH: 88
```

```
<212> TYPE: DNA
<213> ORGANISM: Homo sapiens

<400> SEQUENCE: 164
caccttgtcc tcacggtcca gttttcccag gaatccctta gatgctaaga tgggattcc      60 tggaaatact gttcttgagg tcatggtt                                        88

<210> SEQ ID NO 165
<211> LENGTH: 70
<212> TYPE: DNA
<213> ORGANISM: Homo sapiens

<400> SEQUENCE: 165
ctcacggtcc agttttccca ggaatccctt agatgctaag atggggattc ctggaaatac      60
tgttcttgag                                                             70

<210> SEQ ID NO 166
<211> LENGTH: 99
<212> TYPE: DNA
<213> ORGANISM: Homo sapiens

<400> SEQUENCE: 166
ccgatgtgta tcctcagctt tgagaactga attccatggg ttgtgtcagt gtcagacctc      60
tgaaattcag ttcttcagct gggatatctc tgtcatcgt                             99

<210> SEQ ID NO 167
<211> LENGTH: 65
<212> TYPE: DNA
<213> ORGANISM: Homo sapiens

<400> SEQUENCE: 167
agctttgaga actgaattcc atgggttgtg tcagtgtcag acctgtgaaa ttcagttctt      60
cagct                                                                  65

<210> SEQ ID NO 168
<211> LENGTH: 72
<212> TYPE: DNA
<213> ORGANISM: Homo sapiens

<400> SEQUENCE: 168
aatctaaaga caacatttct gcacacacac cagactatgg aagccagtgt gtggaaatgc      60
ttctgctaga tt                                                          72

<210> SEQ ID NO 169
<211> LENGTH: 68
<212> TYPE: DNA
<213> ORGANISM: Homo sapiens

<400> SEQUENCE: 169
gaggcaaagt tctgagacac tccgactctg agtatgatag aagtcagtgc actacagaac      60
tttgtctc                                                               68

<210> SEQ ID NO 170
<211> LENGTH: 89
<212> TYPE: DNA
<213> ORGANISM: Homo sapiens

<400> SEQUENCE: 170
gccggcgccc gagctctggc tccgtgtctt cactcccgtg cttgtccgag gagggaggga      60
gggacggggg ctgtgctggg gcagctgga                                        89
```

```
<210> SEQ ID NO 171
<211> LENGTH: 53
<212> TYPE: DNA
<213> ORGANISM: Homo sapiens

<400> SEQUENCE: 171
gctctggctc cgtgtcttca ctcccgtgct tgtccgagga gggagggagg gac        53

<210> SEQ ID NO 172
<211> LENGTH: 84
<212> TYPE: DNA
<213> ORGANISM: Homo sapiens

<400> SEQUENCE: 172
ctccccatgg ccctgtctcc caaccttgt accagtgctg ggctcagacc ctggtacagg   60 cctggggac agggacctgg ggac                                         84

<210> SEQ ID NO 173
<211> LENGTH: 64
<212> TYPE: DNA
<213> ORGANISM: Homo sapiens

<400> SEQUENCE: 173
ccctgtctcc caaccttgt accagtgctg ggctcagacc ctggtacagg cctggggac    60 aggg                                                              64

<210> SEQ ID NO 174
<211> LENGTH: 69
<212> TYPE: DNA
<213> ORGANISM: Homo sapiens

<400> SEQUENCE: 174
cctgccctcg aggagctcac agtctagtat gtctcatccc ctactagact gaagctcctt  60
gaggacagg                                                         69

<210> SEQ ID NO 175
<211> LENGTH: 87
<212> TYPE: DNA
<213> ORGANISM: Homo sapiens

<400> SEQUENCE: 175
tgtccccccc ggcccaggtt ctgtgataca ctccgactcg ggctctggag cagtcagtgc  60
atgacagaac ttgggcccgg aaggacc                                     87

<210> SEQ ID NO 176
<211> LENGTH: 71
<212> TYPE: DNA
<213> ORGANISM: Homo sapiens

<400> SEQUENCE: 176
ggcccaggtt ctgtgataca ctccgactcg ggctctggag cagtcagtgc atgacagaac  60
ttgggccccg g                                                      71

<210> SEQ ID NO 177
<211> LENGTH: 90
<212> TYPE: DNA
<213> ORGANISM: Homo sapiens

<400> SEQUENCE: 177
ctcacagctg ccagtgtcat ttttgtgatc tgcagctagt attctcactc cagttgcata  60
```

```
gtcacaaaag tgatcattgg caggtgtggc                                       90

<210> SEQ ID NO 178
<211> LENGTH: 71
<212> TYPE: DNA
<213> ORGANISM: Homo sapiens

<400> SEQUENCE: 178
tctctctctc cctcacagct gccagtgtca ttgtcacaaa agtgatcatt ggcaggtgtg      60
gctgctgcat g                                                          71

<210> SEQ ID NO 179
<211> LENGTH: 87
<212> TYPE: DNA
<213> ORGANISM: Homo sapiens

<400> SEQUENCE: 179
agcggtggcc agtgtcattt ttgtgatgtt gcagctagta atatgagccc agttgcatag      60
tcacaaaagt gatcattgga aactgtg                                         87

<210> SEQ ID NO 180
<211> LENGTH: 69
<212> TYPE: DNA
<213> ORGANISM: Homo sapiens

<400> SEQUENCE: 180
cagtgtcatt tttgtgatgt tgcagctagt aatatgagcc cagttgcata gtcacaaaag      60
tgatcattg                                                             69

<210> SEQ ID NO 181
<211> LENGTH: 84
<212> TYPE: DNA
<213> ORGANISM: Homo sapiens

<400> SEQUENCE: 181
gtggtacttg aagataggtt atccgtgttg ccttcgcttt atttgtgacg aatcatacac      60
ggttgaccta tttttcagta ccaa                                            84

<210> SEQ ID NO 182
<211> LENGTH: 66
<212> TYPE: DNA
<213> ORGANISM: Homo sapiens

<400> SEQUENCE: 182
gaagataggt tatccgtgtt gccttcgctt tatttgtgac gaatcataca cggttgacct      60
attttt                                                                66

<210> SEQ ID NO 183
<211> LENGTH: 65
<212> TYPE: DNA
<213> ORGANISM: Homo sapiens

<400> SEQUENCE: 183
ctgttaatgc taatcgtgat aggggttttt gcctccaact gactcctaca tattagcatt      60
aacag                                                                 65

<210> SEQ ID NO 184
<211> LENGTH: 108
<212> TYPE: DNA
<213> ORGANISM: Homo sapiens
```

```
<400> SEQUENCE: 184
caatgtcagc agtgccttag cagcacgtaa atattggcgt taagattcta aaattatctc    60
cagtattaac tgtgctgctg aagtaaggtt gaccatactc tacagttg                108

<210> SEQ ID NO 185
<211> LENGTH: 110
<212> TYPE: DNA
<213> ORGANISM: Homo sapiens

<400> SEQUENCE: 185
agaagggcta tcaggccagc cttcagagga ctccaaggaa cattcaacgc tgtcggtgag    60
tttgggattt gaaaaaacca ctgaccgttg actgtacctt ggggtcctta              110

<210> SEQ ID NO 186
<211> LENGTH: 110
<212> TYPE: DNA
<213> ORGANISM: Homo sapiens

<400> SEQUENCE: 186
tgagttttga ggttgcttca gtgaacattc aacgctgtcg gtgagtttgg aattaaaatc    60
aaaaccatcg accgttgatt gtaccctatg gctaaccatc atctactcca              110

<210> SEQ ID NO 187
<211> LENGTH: 110
<212> TYPE: DNA
<213> ORGANISM: Homo sapiens

<400> SEQUENCE: 187
cggaaaattt gccaagggtt tgggggaaca ttcaacctgt cggtgagttt ggcagctca    60 ggcaaaccat cgaccgttga gtggaccctg aggcctggaa ttgccatcct              110

<210> SEQ ID NO 188
<211> LENGTH: 110
<212> TYPE: DNA
<213> ORGANISM: Homo sapiens

<400> SEQUENCE: 188
gagctgcttg cctccccccg tttttggcaa tggtagaact cacactggtg aggtaacagg    60
atccggtggt tctagacttg ccaactatgg ggcgaggact cagccggcac              110

<210> SEQ ID NO 189
<211> LENGTH: 70
<212> TYPE: DNA
<213> ORGANISM: Homo sapiens

<400> SEQUENCE: 189
tttttggcaa tggtagaact cacactggtg aggtaacagg atccggtggt tctagacttg    60
ccaactatgg                                                          70

<210> SEQ ID NO 190
<211> LENGTH: 110
<212> TYPE: DNA
<213> ORGANISM: Homo sapiens

<400> SEQUENCE: 190
ccgcagagtg tgactcctgt tctgtgtatg gcactggtag aattcactgt gaacagtctc    60
agtcagtgaa ttaccgaagg gccataaaca gagcagagac agatccacga              110
```

```
<210> SEQ ID NO 191
<211> LENGTH: 84
<212> TYPE: DNA
<213> ORGANISM: Homo sapiens

<400> SEQUENCE: 191
ccagtcacgt cccctta tca cttttccagc ccagctttgt gactgtaagt gttggacgga      60
gaactgataa gggtaggtga ttga                                             84

<210> SEQ ID NO 192
<211> LENGTH: 65
<212> TYPE: DNA
<213> ORGANISM: Homo sapiens

<400> SEQUENCE: 192
ccttatcact ttt ccagccc agctttgtga ctgtaagtgt tggacggaga actgataagg      60
gtagg                                                                  65

<210> SEQ ID NO 193
<211> LENGTH: 82
<212> TYPE: DNA
<213> ORGANISM: Homo sapiens

<400> SEQUENCE: 193 aggggcgag ggattggaga gaaaggcagt tcctgatggt cccctcccca ggggctggct       60
ttcctctggt ccttccctcc ca                                               82

<210> SEQ ID NO 194
<211> LENGTH: 66
<212> TYPE: DNA
<213> ORGANISM: Homo sapiens

<400> SEQUENCE: 194
agggattgga gagaaaggca gttcctgatg gtcccctccc cagggctgg ctttcctctg       60 gtcctt                                                                 66

<210> SEQ ID NO 195
<211> LENGTH: 86
<212> TYPE: DNA
<213> ORGANISM: Homo sapiens

<400> SEQUENCE: 195
tgcttgtaac tttccaaaga attctccttt tgggctttct ggttttattt taagcccaaa      60 ggtgaattt t ttgggaagtt tgagct                                          86

<210> SEQ ID NO 196
<211> LENGTH: 71
<212> TYPE: DNA
<213> ORGANISM: Homo sapiens

<400> SEQUENCE: 196
actttccaaa gaattctcct tttgggcttt ctggttttat tttaagccca aaggtgaatt      60
ttttgggaag t                                                           71

<210> SEQ ID NO 197
<211> LENGTH: 109
<212> TYPE: DNA
<213> ORGANISM: Homo sapiens

<400> SEQUENCE: 197
ggtcgggctc accatgacac agtgtgagac tcgggctaca acacaggacc cggggcgctg      60
```

```
ctctgacccc tcgtgtcttg tgttgcagcc ggagggacgc aggtccgca                  109
```

<210> SEQ ID NO 198
<211> LENGTH: 86
<212> TYPE: DNA
<213> ORGANISM: Homo sapiens

<400> SEQUENCE: 198

```
tgctccctct ctcacatccc ttgcatggtg gagggtgagc tttctgaaaa cccctcccac      60
atgcagggtt tgcaggatgg cgagcc                                          86
```

<210> SEQ ID NO 199
<211> LENGTH: 68
<212> TYPE: DNA
<213> ORGANISM: Homo sapiens

<400> SEQUENCE: 199

```
tctcacatcc cttgcatggt ggagggtgag ctttctgaaa acccctccca catgcagggt      60
ttgcagga                                                              68
```

<210> SEQ ID NO 200
<211> LENGTH: 102
<212> TYPE: DNA
<213> ORGANISM: Homo sapiens

<400> SEQUENCE: 200

```
ctgtcgattg gacccgccct ccggtgccta ctgagctgat atcagttctc attttacaca     60
ctggctcagt tcagcaggaa caggagtcga gcccttgagc aa                        102
```

<210> SEQ ID NO 201
<211> LENGTH: 68
<212> TYPE: DNA
<213> ORGANISM: Homo sapiens

<400> SEQUENCE: 201

```
ctccggtgcc tactgagctg atatcagttc tcattttaca cactggctca gttcagcagg     60
aacaggag                                                              68
```

<210> SEQ ID NO 202
<211> LENGTH: 85
<212> TYPE: DNA
<213> ORGANISM: Homo sapiens

<400> SEQUENCE: 202

```
tgcaggcctc tgtgtgatat gtttgatata ttaggttgtt atttaatcca actatatatc     60
aaacatattc ctacagtgtc ttgcc                                           85
```

<210> SEQ ID NO 203
<211> LENGTH: 67
<212> TYPE: DNA
<213> ORGANISM: Homo sapiens

<400> SEQUENCE: 203

```
ctgtgtgata tgtttgatat attaggttgt tatttaatcc aactatatat caaacatatt     60
cctacag                                                               67
```

<210> SEQ ID NO 204
<211> LENGTH: 92
<212> TYPE: DNA
<213> ORGANISM: Homo sapiens

```
<400> SEQUENCE: 204
cggctggaca gcgggcaacg gaatcccaaa agcagctgtt gtctccagag cattccagct    60
gcgcttggat ttcgtcccct gctctcctgc ct                                  92

<210> SEQ ID NO 205
<211> LENGTH: 74
<212> TYPE: DNA
<213> ORGANISM: Homo sapiens

<400> SEQUENCE: 205
agcgggcaac ggaatcccaa aagcagctgt tgtctccaga gcattccagc tgcgcttgga    60
tttcgtcccc tgct                                                      74

<210> SEQ ID NO 206
<211> LENGTH: 108
<212> TYPE: DNA
<213> ORGANISM: Homo sapiens

<400> SEQUENCE: 206
ccgagaccga gtgcacaggg ctctgaccta tgaattgaca gccagtgctc tcgtctcccc    60
tctggctgcc aattccatag gtcacaggta tgttcgcctc aatgccag                108

<210> SEQ ID NO 207
<211> LENGTH: 110
<212> TYPE: DNA
<213> ORGANISM: Homo sapiens

<400> SEQUENCE: 207
gccgagaccg agtgcacagg gctctgacct atgaattgac agccagtgct ctcgtctccc    60
ctctggctgc caattccata ggtcacaggt atgttcgcct caatgccagc              110

<210> SEQ ID NO 208
<211> LENGTH: 88
<212> TYPE: DNA
<213> ORGANISM: Homo sapiens

<400> SEQUENCE: 208
cgaggatggg agctgagggc tgggtctttg cgggcgagat gagggtgtcg gatcaactgg    60
cctacaaagt cccagttctc ggcccccg                                       88

<210> SEQ ID NO 209
<211> LENGTH: 58
<212> TYPE: DNA
<213> ORGANISM: Homo sapiens

<400> SEQUENCE: 209
gctgggtctt tgcgggcgag atgagggtgt cggatcaact ggcctacaaa gtcccagt      58

<210> SEQ ID NO 210
<211> LENGTH: 85
<212> TYPE: DNA
<213> ORGANISM: Homo sapiens

<400> SEQUENCE: 210
atggtgttat caagtgtaac agcaactcca tgtggactgt gtaccaattt ccagtggaga    60
tgctgttact tttgatggtt accaa                                          85

<210> SEQ ID NO 211
<211> LENGTH: 63
```

```
<212> TYPE: DNA
<213> ORGANISM: Homo sapiens

<400> SEQUENCE: 211
gtgtaacagc aactccatgt ggactgtgta ccaatttcca gtggagatgc tgttactttt    60
gat                                                                  63

<210> SEQ ID NO 212
<211> LENGTH: 87
<212> TYPE: DNA
<213> ORGANISM: Homo sapiens

<400> SEQUENCE: 212
agcttccctg gctctagcag cacagaaata ttggcacagg gaagcgagtc tgccaatatt    60
ggctgtgctg ctccaggcag ggtggtg                                        87

<210> SEQ ID NO 213
<211> LENGTH: 58
<212> TYPE: DNA
<213> ORGANISM: Homo sapiens

<400> SEQUENCE: 213
tagcagcaca gaaatattgg cacagggaag cgagtctgcc aatattggct gtgctgct      58

<210> SEQ ID NO 214
<211> LENGTH: 110
<212> TYPE: DNA
<213> ORGANISM: Homo sapiens

<400> SEQUENCE: 214
ctagagcttg aattggaact gctgagtgaa ttaggtagtt tcatgttgtt gggcctgggt    60
ttctgaacac aacaacatta aaccacccga ttcacggcag ttactgctcc               110

<210> SEQ ID NO 215
<211> LENGTH: 70
<212> TYPE: DNA
<213> ORGANISM: Homo sapiens

<400> SEQUENCE: 215
gtgaattagg tagtttcatg ttgttgggcc tgggtttctg aacacaacaa cattaaacca    60
cccgattcac                                                           70

<210> SEQ ID NO 216
<211> LENGTH: 110
<212> TYPE: DNA
<213> ORGANISM: Homo sapiens

<400> SEQUENCE: 216
tgctcgctca gctgatctgt ggcttaggta gtttcatgtt gttgggattg agttttgaac    60
tcggcaacaa gaaactgcct gagttacatc agtcggtttt cgtcgagggc               110

<210> SEQ ID NO 217
<211> LENGTH: 70
<212> TYPE: DNA
<213> ORGANISM: Homo sapiens

<400> SEQUENCE: 217
gtgaattagg tagtttcatg ttgttgggcc tgggtttctg aacacaacaa cattaaacca    60
cccgattcac                                                           70
```

```
<210> SEQ ID NO 218
<211> LENGTH: 75
<212> TYPE: DNA
<213> ORGANISM: Homo sapiens

<400> SEQUENCE: 218
ggctgtgccg ggtagagagg gcagtgggag gtaagagctc ttcacccttc accaccttct    60
ccacccagca tggcc                                                    75

<210> SEQ ID NO 219
<211> LENGTH: 62
<212> TYPE: DNA
<213> ORGANISM: Homo sapiens

<400> SEQUENCE: 219
tcattggtcc agaggggaga taggttcctg tgattttcc ttcttctcta tagaataaat     60
ga                                                                   62

<210> SEQ ID NO 220
<211> LENGTH: 71
<212> TYPE: DNA
<213> ORGANISM: Homo sapiens

<400> SEQUENCE: 220
gccaacccag tgttcagact acctgttcag gaggctctca atgtgtacag tagtctgcac    60
attggttagg c                                                        71

<210> SEQ ID NO 221
<211> LENGTH: 110
<212> TYPE: DNA
<213> ORGANISM: Homo sapiens

<400> SEQUENCE: 221
aggaagcttc tggagatcct gctccgtcgc cccagtgttc agactacctg ttcaggacaa    60
tgccgttgta cagtagtctg cacattggtt agactgggca agggagagca              110

<210> SEQ ID NO 222
<211> LENGTH: 110
<212> TYPE: DNA
<213> ORGANISM: Homo sapiens

<400> SEQUENCE: 222
ccagaggaca cctccactcc gtctacccag tgtttagact atctgttcag gactcccaaa    60
ttgtacagta gtctgcacat tggttaggct gggctgggtt agaccctcgg              110

<210> SEQ ID NO 223
<211> LENGTH: 71
<212> TYPE: DNA
<213> ORGANISM: Homo sapiens

<400> SEQUENCE: 223
gccaacccag tgttcagact acctgttcag gaggctctca atgtgtacag tagtctgcac    60
attggttagg c                                                        71

<210> SEQ ID NO 224
<211> LENGTH: 70
<212> TYPE: DNA
<213> ORGANISM: Homo sapiens

<400> SEQUENCE: 224
gccgtggcca tcttactggg cagcattgga tggagtcagg tctctaatac tgcctggtaa    60
```

```
tgatgacggc                                                            70

<210> SEQ ID NO 225
<211> LENGTH: 95
<212> TYPE: DNA
<213> ORGANISM: Homo sapiens

<400> SEQUENCE: 225
ccagctcggg cagccgtggc catcttactg ggcagcattg gatggagtca ggtctctaat     60
actgcctggt aatgatgacg gcggagccct gcacg                                95

<210> SEQ ID NO 226
<211> LENGTH: 72
<212> TYPE: DNA
<213> ORGANISM: Homo sapiens

<400> SEQUENCE: 226
gttccttttt cctatgcata tacttctttg aggatctggc ctaaagaggt atagggcatg     60
ggaagatgga gc                                                         72

<210> SEQ ID NO 227
<211> LENGTH: 110
<212> TYPE: DNA
<213> ORGANISM: Homo sapiens

<400> SEQUENCE: 227
gtgttgggga ctcgcgcgct gggtccagtg gttcttaaca gttcaacagt tctgtagcgc     60
aattgtgaaa tgtttaggac cactagaccc ggcgggcgcg gcgacagcga               110

<210> SEQ ID NO 228
<211> LENGTH: 110
<212> TYPE: DNA
<213> ORGANISM: Homo sapiens

<400> SEQUENCE: 228
ggctacagtc tttcttcatg tgactcgtgg acttcccttt gtcatcctat gcctgagaat     60
atatgaagga ggctgggaag gcaaagggac gttcaattgt catcactggc               110

<210> SEQ ID NO 229
<211> LENGTH: 110
<212> TYPE: DNA
<213> ORGANISM: Homo sapiens

<400> SEQUENCE: 229
aaagatcctc agacaatcca tgtgcttctc ttgtccttca ttccaccgga gtctgtctca     60
tacccaacca gatttcagtg gagtgaagtt caggaggcat ggagctgaca               110

<210> SEQ ID NO 230
<211> LENGTH: 86
<212> TYPE: DNA
<213> ORGANISM: Homo sapiens

<400> SEQUENCE: 230
tgcttcccga ggccacatgc ttctttatat ccccatatgg attactttgc tatggaatgt     60
aaggaagtgt gtggtttcgg caagtg                                          86

<210> SEQ ID NO 231
<211> LENGTH: 69
<212> TYPE: DNA
<213> ORGANISM: Homo sapiens
```

<400> SEQUENCE: 231
aggccacatg cttctttata tccccatatg gattactttg ctatggaatg taaggaagtg    60
tgtggtttt                                                            69

<210> SEQ ID NO 232
<211> LENGTH: 71
<212> TYPE: DNA
<213> ORGANISM: Homo sapiens

<400> SEQUENCE: 232
tgacgggcga gcttttggcc cgggttatac ctgatgctca cgtataagac gagcaaaaag    60
cttgttggtc a                                                         71

<210> SEQ ID NO 233
<211> LENGTH: 110
<212> TYPE: DNA
<213> ORGANISM: Homo sapiens

<400> SEQUENCE: 233
acccggcagt gcctccaggc gcagggcagc ccctgcccac cgcacactgc gctgccccag    60
acccactgtg cgtgtgacag cggctgatct gtgcctgggc agcgcgaccc               110

<210> SEQ ID NO 234
<211> LENGTH: 110
<212> TYPE: DNA
<213> ORGANISM: Homo sapiens

<400> SEQUENCE: 234
tcacctggcc atgtgacttg tgggcttccc tttgtcatcc ttcgcctagg gctctgagca    60
gggcagggac agcaaagggg tgctcagttg tcacttccca cagcacggag               110

<210> SEQ ID NO 235
<211> LENGTH: 110
<212> TYPE: DNA
<213> ORGANISM: Homo sapiens

<400> SEQUENCE: 235
cggggcaccc cgcccggaca gcgcgccggc accttggctc tagactgctt actgcccggg    60 ccgcccctcag taacagtctc cagtcacggc caccgacgcc tggccccgcc              110

<210> SEQ ID NO 236
<211> LENGTH: 110
<212> TYPE: DNA
<213> ORGANISM: Homo sapiens

<400> SEQUENCE: 236
cctgtgcaga gattattttt taaaaggtca caatcaacat tcattgctgt cggtgggttg    60
aactgtgtgg acaagctcac tgaacaatga atgcaactgt ggccccgctt               110

<210> SEQ ID NO 237
<211> LENGTH: 108
<212> TYPE: DNA
<213> ORGANISM: Homo sapiens

<400> SEQUENCE: 237
gagttttgag gttgcttcag tgaacattca acgctgtcgg tgagtttgga attaaaatca    60
aaaccatcga ccgttgattg taccctatgg ctaaccatca tctactcc                 108

```
<210> SEQ ID NO 238
<211> LENGTH: 110
<212> TYPE: DNA
<213> ORGANISM: Homo sapiens

<400> SEQUENCE: 238
ggcctggctg acagagttg tcatgtgtct gcctgtctac acttgctgtg cagaacatcc      60
gctcacctgt acagcaggca cagacaggca gtcacatgac aacccagcct              110

<210> SEQ ID NO 239
<211> LENGTH: 110
<212> TYPE: DNA
<213> ORGANISM: Homo sapiens

<400> SEQUENCE: 239
atcattcaga aatggtatac aggaaaatga cctatgaatt gacagacaat atagctgagt      60
ttgtctgtca tttctttagg ccaatattct gtatgactgt gctacttcaa              110

<210> SEQ ID NO 240
<211> LENGTH: 110
<212> TYPE: DNA
<213> ORGANISM: Homo sapiens

<400> SEQUENCE: 240
gatggctgtg agttggctta atctcagctg gcaactgtga gatgttcata caatccctca      60
cagtggtctc tgggattatg ctaaacagag caatttccta gccctcacga              110

<210> SEQ ID NO 241
<211> LENGTH: 110
<212> TYPE: DNA
<213> ORGANISM: Homo sapiens

<400> SEQUENCE: 241
agtataatta ttacatagtt tttgatgtcg cagatactgc atcaggaact gattggataa      60
gaatcagtca ccatcagttc ctaatgcatt gccttcagca tctaaacaag              110

<210> SEQ ID NO 242
<211> LENGTH: 110
<212> TYPE: DNA
<213> ORGANISM: Homo sapiens

<400> SEQUENCE: 242
gtgataatgt agcgagattt tctgttgtgc ttgatctaac catgtggttg cgaggtatga      60
gtaaaacatg gttccgtcaa gcaccatgga acgtcacgca gctttctaca              110

<210> SEQ ID NO 243
<211> LENGTH: 110
<212> TYPE: DNA
<213> ORGANISM: Homo sapiens

<400> SEQUENCE: 243
gaccagtcgc tgcggggctt tcctttgtgc ttgatctaac catgtggtgg aacgatggaa      60
acggaacatg gttctgtcaa gcaccgcgga aagcaccgtg ctctcctgca              110

<210> SEQ ID NO 244
<211> LENGTH: 110
<212> TYPE: DNA
<213> ORGANISM: Homo sapiens

<400> SEQUENCE: 244
ccgccccggg ccgcggctcc tgattgtcca aacgcaattc tcgagtctat ggctccggcc      60
```

```
gagagttgag tctggacgtc ccgagccgcc gcccccaaac ctcgagcggg        110
```

<210> SEQ ID NO 245
<211> LENGTH: 110
<212> TYPE: DNA
<213> ORGANISM: Homo sapiens

<400> SEQUENCE: 245

```
gacagtgtgg cattgtaggg ctccacaccg tatctgacac tttgggcgag ggcaccatgc     60
tgaaggtgtt catgatgcgg tctgggaact cctcacggat cttactgatg               110
```

<210> SEQ ID NO 246
<211> LENGTH: 110
<212> TYPE: DNA
<213> ORGANISM: Homo sapiens

<400> SEQUENCE: 246

```
tgaacatcca ggtctggggc atgaacctgg catacaatgt agatttctgt gttcgttagg     60
caacagctac attgtctgct gggtttcagg ctacctggaa acatgttctc               110
```

<210> SEQ ID NO 247
<211> LENGTH: 110
<212> TYPE: DNA
<213> ORGANISM: Homo sapiens

<400> SEQUENCE: 247

```
gctgctggaa ggtgtaggta ccctcaatgg ctcagtagcc agtgtagatc ctgtctttcg     60
taatcagcag ctacatctgg ctactgggtc tctgatggca tcttctagct               110
```

<210> SEQ ID NO 248
<211> LENGTH: 110
<212> TYPE: DNA
<213> ORGANISM: Homo sapiens

<400> SEQUENCE: 248

```
cctggcctcc tgcagtgcca cgctccgtgt atttgacaag ctgagttgga cactccatgt     60
ggtagagtgt cagtttgtca aatacccccaa gtgcggcaca tgcttaccag              110
```

<210> SEQ ID NO 249
<211> LENGTH: 81
<212> TYPE: DNA
<213> ORGANISM: Homo sapiens

<400> SEQUENCE: 249

```
gggcttttcaa gtcactagtg gttccgttta gtagatgatt gtgcattgtt tcaaaatggt    60
gccctagtga ctacaaagcc c                                               81
```

<210> SEQ ID NO 250
<211> LENGTH: 81
<212> TYPE: DNA
<213> ORGANISM: Homo sapiens

<400> SEQUENCE: 250

```
cttctggaag ctggtttcac atggtggctt agattttttcc atctttgtat ctagcaccat    60
ttgaaatcag tgttttagga g                                               81
```

<210> SEQ ID NO 251
<211> LENGTH: 81
<212> TYPE: DNA
<213> ORGANISM: Homo sapiens

<400> SEQUENCE: 251
cttcaggaag ctggtttcat atggtggttt agatttaaat agtgattgtc tagcaccatt    60
tgaaatcagt gttcttgggg g                                              81

<210> SEQ ID NO 252
<211> LENGTH: 81
<212> TYPE: DNA
<213> ORGANISM: Homo sapiens

<400> SEQUENCE: 252
cttcaggaag ctggtttcat atggtggttt agatttaaat agtgattgtc tagcaccatt    60
tgaaatcagt gttcttgggg g                                              81

<210> SEQ ID NO 253
<211> LENGTH: 80
<212> TYPE: DNA
<213> ORGANISM: Homo sapiens

<400> SEQUENCE: 253
gtgagcgact gtaaacatcc tcgactggaa gctgtgaagc cacagatggg ctttcagtcg    60
gatgtttgca gctgcctact                                                80

<210> SEQ ID NO 254
<211> LENGTH: 88
<212> TYPE: DNA
<213> ORGANISM: Homo sapiens

<400> SEQUENCE: 254
accaagtttc agttcatgta aacatcctac actcagctgt aatacatgga ttggctggga    60
ggtggatgtt tacttcagct gacttgga                                       88

<210> SEQ ID NO 255
<211> LENGTH: 75
<212> TYPE: DNA
<213> ORGANISM: Homo sapiens

<400> SEQUENCE: 255
tgccctggct cagttatcac agtgctgatg ctgtctattc taaaggtaca gtactgtgat    60
aactgaagga tggca                                                     75

<210> SEQ ID NO 256
<211> LENGTH: 90
<212> TYPE: DNA
<213> ORGANISM: Homo sapiens

<400> SEQUENCE: 256
acactgcaag aacaataagg attttaggg gcattatgac tgagtcagaa aacacagctg    60
cccctgaaag tccctcattt ttcttgctgt                                     90

<210> SEQ ID NO 257
<211> LENGTH: 80
<212> TYPE: DNA
<213> ORGANISM: Homo sapiens

<400> SEQUENCE: 257
actgcaagag caataaggat ttttaggggc attatgatag tggaatggaa acacatctgc    60
ccccaaaagt ccctcatttt                                                80

```
<210> SEQ ID NO 258
<211> LENGTH: 85
<212> TYPE: DNA
<213> ORGANISM: Homo sapiens

<400> SEQUENCE: 258
cgctggcgac gggacattat tacttttggt acgcgctgtg acacttcaaa ctcgtaccgt       60
gagtaataat gcgccgtcca cggca                                            85

<210> SEQ ID NO 259
<211> LENGTH: 61
<212> TYPE: DNA
<213> ORGANISM: Homo sapiens

<400> SEQUENCE: 259
acattattac ttttggtacg cgctgtgaca cttcaaactc gtaccgtgag taataatgcg       60
c                                                                      61

<210> SEQ ID NO 260
<211> LENGTH: 74
<212> TYPE: DNA
<213> ORGANISM: Homo sapiens

<400> SEQUENCE: 260
tggatctttt tgcggtctgg gcttgctgtt cctctcaaca gtagtcagga agcccttacc       60
ccaaaaagta tcta                                                        74

<210> SEQ ID NO 261
<211> LENGTH: 90
<212> TYPE: DNA
<213> ORGANISM: Homo sapiens

<400> SEQUENCE: 261
tgcccttcgc gaatcttttt gcggtctggg cttgctgtac ataactcaat agccggaagc       60
ccttacccca aaagcatttt gcggagggcg                                       90

<210> SEQ ID NO 262
<211> LENGTH: 80
<212> TYPE: DNA
<213> ORGANISM: Homo sapiens

<400> SEQUENCE: 262 gcccctgct ctggctggtc aaacggaacc aagtccgtct tcctgagagg tttggtcccc       60
ttcaaccagc tacagcaggg                                                  80

<210> SEQ ID NO 263
<211> LENGTH: 100
<212> TYPE: DNA
<213> ORGANISM: Homo sapiens

<400> SEQUENCE: 263
agataaattc actctagtgc tttatggctt tttattccta tgtgatagta ataaagtctc       60
atgtagggat ggaagccatg aaatacattg tgaaaaatca                            100

<210> SEQ ID NO 264
<211> LENGTH: 70
<212> TYPE: DNA
<213> ORGANISM: Homo sapiens

<400> SEQUENCE: 264
aagcacgatt agcatttgag gtgaagttct gttatacact caggctgtgg ctctctgaaa       60
```

```
gtcagtgcat                                                              70

<210> SEQ ID NO 265
<211> LENGTH: 69
<212> TYPE: DNA
<213> ORGANISM: Homo sapiens

<400> SEQUENCE: 265
cctgtcctca aggagcttca gtctagtagg ggatgagaca tactagactg tgagctcctc      60
gagggcagg                                                              69

<210> SEQ ID NO 266
<211> LENGTH: 65
<212> TYPE: DNA
<213> ORGANISM: Homo sapiens

<400> SEQUENCE: 266
ctgttaatgc taatcgtgat aggggttttt gcctccaact gactcctaca tattagcatt      60
aacag                                                                  65

<210> SEQ ID NO 267
<211> LENGTH: 82
<212> TYPE: DNA
<213> ORGANISM: Homo sapiens

<400> SEQUENCE: 267
cctaacactg tctggtaaag atggctcccg ggtgggttct ctcggcagta accttcaggg      60
agccctgaag accatggagg ac                                               82

<210> SEQ ID NO 268
<211> LENGTH: 110
<212> TYPE: DNA
<213> ORGANISM: Homo sapiens

<400> SEQUENCE: 268
gccgagaccg agtgcacagg gctctgacct atgaattgac agccagtgct ctcgtctccc      60
ctctggctgc caattccata ggtcacaggt atgttcgcct caatgccagc                110

<210> SEQ ID NO 269
<211> LENGTH: 80
<212> TYPE: DNA
<213> ORGANISM: Homo sapiens

<400> SEQUENCE: 269
tcccgccccc tgtaacagca actccatgtg gaagtgccca ctggttccag tggggctgct      60
gttatctggg gcgagggcca                                                  80

<210> SEQ ID NO 270
<211> LENGTH: 70
<212> TYPE: DNA
<213> ORGANISM: Homo sapiens

<400> SEQUENCE: 270
aaagctgggt tgagagggcg aaaaaggatg aggtgactgg tctgggctac gctatgctgc      60
ggcgctcggg                                                             70

<210> SEQ ID NO 271
<211> LENGTH: 64
<212> TYPE: DNA
<213> ORGANISM: Homo sapiens
```

```
<400> SEQUENCE: 271
cattggcctc ctaagccagg gattgtgggt tcgagtccca cccggggtaa agaaaggccg    60
aatt                                                                64

<210> SEQ ID NO 272
<211> LENGTH: 70
<212> TYPE: DNA
<213> ORGANISM: Homo sapiens

<400> SEQUENCE: 272
cctaagccag ggattgtggg ttcgagtccc acctggggta gaggtgaaag ttccttttac    60 ggaattttttt                                                         70

<210> SEQ ID NO 273
<211> LENGTH: 81
<212> TYPE: DNA
<213> ORGANISM: Homo sapiens

<400> SEQUENCE: 273 gggcttttcaa gtcactagtg gttccgttta gtagatgatt gtgcattgtt tcaaaatggt   60
gccctagtga ctacaaagcc c                                             81

<210> SEQ ID NO 274
<211> LENGTH: 70
<212> TYPE: DNA
<213> ORGANISM: Homo sapiens

<400> SEQUENCE: 274
acgcaagtgt cctaaggtga gctcagggag cacagaaacc tccagtggaa cagaagggca    60
aaagctcatt                                                          70

<210> SEQ ID NO 275
<211> LENGTH: 70
<212> TYPE: DNA
<213> ORGANISM: Homo sapiens

<400> SEQUENCE: 275
catgtgtcac tttcaggtgg agtttcaaga gtcccttcct ggttcaccgt ctcctttgct    60
cttccacaac                                                          70

<210> SEQ ID NO 276
<211> LENGTH: 109
<212> TYPE: DNA
<213> ORGANISM: Homo sapiens

<400> SEQUENCE: 276
ggtcgggctc accatgacac agtgtgagac tcgggctaca acacaggacc cggggcgctg    60
ctctgacccc tcgtgtcttg tgttgcagcc ggagggacgc aggtccgca              109

<210> SEQ ID NO 277
<211> LENGTH: 86
<212> TYPE: DNA
<213> ORGANISM: Homo sapiens

<400> SEQUENCE: 277
tgctccctct ctcacatccc ttgcatggtg gagggtgagc tttctgaaaa cccctcccac    60
atgcagggtt tgcaggatgg cgagcc                                        86
```

<210> SEQ ID NO 278
<211> LENGTH: 85
<212> TYPE: DNA
<213> ORGANISM: Homo sapiens

<400> SEQUENCE: 278
tgcaggcctc tgtgtgatat gtttgatata ttaggttgtt atttaatcca actatatatc    60
aaacatattc ctacagtgtc ttgcc                                         85

<210> SEQ ID NO 279
<211> LENGTH: 60
<212> TYPE: DNA
<213> ORGANISM: Homo sapiens

<400> SEQUENCE: 279
gtgcatgtgt atgtatgtgt gcatgtgcat gtgtatgtgt atgagtgcat gcgtgtgtgc    60

<210> SEQ ID NO 280
<211> LENGTH: 75
<212> TYPE: DNA
<213> ORGANISM: Homo sapiens

<400> SEQUENCE: 280
ggctgtgccg ggtagagagg gcagtgggag gtaagagctc ttcacccttc accaccttct    60
ccacccagca tggcc                                                    75

<210> SEQ ID NO 281
<211> LENGTH: 72
<212> TYPE: DNA
<213> ORGANISM: Homo sapiens

<400> SEQUENCE: 281
gttccttttt cctatgcata tacttctttg aggatctggc ctaaagaggt atagggcatg    60
ggaagatgga gc                                                       72

<210> SEQ ID NO 282
<211> LENGTH: 60
<212> TYPE: DNA
<213> ORGANISM: Homo sapiens

<400> SEQUENCE: 282
caatcttcct ttatcatggt attgattttt cagtgcttcc cttttgtgtg agagaagata    60

<210> SEQ ID NO 283
<211> LENGTH: 102
<212> TYPE: DNA
<213> ORGANISM: Homo sapiens

<400> SEQUENCE: 283
atggagctgc tcaccctgtg ggcctcaaat gtggaggaac tattctgatg tccaagtgga    60
aagtgctgcg acatttgagc gtcaccggtg acgcccatat ca                      102

<210> SEQ ID NO 284
<211> LENGTH: 101
<212> TYPE: DNA
<213> ORGANISM: Homo sapiens

<400> SEQUENCE: 284
gcatcccctc agcctgtggc actcaaactg tgggggcact ttctgctctc tggtgaaagt    60
gccgccatct tttgagtgtt accgcttgag aagactcaac c                       101

```
<210> SEQ ID NO 285
<211> LENGTH: 102
<212> TYPE: DNA
<213> ORGANISM: Homo sapiens

<400> SEQUENCE: 285
cgaggagctc atactgggat actcaaaatg ggggcgcttt ccttttttgtc tgttactggg    60 aagtgcttcg attttggggt gtccctgttt gagtagggca tc                      102

<210> SEQ ID NO 286
<211> LENGTH: 81
<212> TYPE: DNA
<213> ORGANISM: Homo sapiens

<400> SEQUENCE: 286
cttcaggaag ctggtttcat atggtggttt agatttaaat agtgattgtc tagcaccatt    60
tgaaatcagt gttcttgggg g                                              81

<210> SEQ ID NO 287
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
tcaacatcag tctgataagc ta                                             22

<210> SEQ ID NO 288
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
tcacaagtta gggtctcagg ga                                             22

<210> SEQ ID NO 289
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
aagggattcc tgggaaaact ggac                                           24

<210> SEQ ID NO 290
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290 gcagggcca tgctaatctt ctctgtatcg                                      30
```

MICRORNA-BASED METHODS AND COMPOSITIONS FOR THE DIAGNOSIS, PROGNOSIS AND TREATMENT OF BREAST CANCER

GOVERNMENT SUPPORT

This invention was supported, in whole or in part, by a grant under Program Project Grant P01CA76259, P01CA81534, and P30CA56036 from the National Cancer Institute. The Government has certain rights in this invention.

CROSS-REFERENCE TO RELATED APPLICATIONS

This application claims the benefit of U.S. Provisional Application No. 60/704,464, filed Aug. 1, 2005, and PCT US06/029889 filed Jul. 31, 2006, the disclosures of which are expressly incorporated herein by reference.

BACKGROUND OF THE INVENTION

Breast cancer is a significant health problem for women in the United States and throughout the world. Although advances have been made in the detection and treatment of the disease, breast cancer remains the second leading cause of cancer-related deaths in women, affecting more than 180,000 women in the United States each year. For women in North America, the life-time odds of getting breast cancer are now one in eight.

No universally successful method for the treatment or prevention of breast cancer is currently available. Management of breast cancer currently relies on a combination of early diagnosis (e.g., through routine breast screening procedures) and aggressive treatment, which may include one or more of a variety of treatments, such as surgery, radiotherapy, chemotherapy and hormone therapy. The course of treatment for a particular breast cancer is often selected based on a variety of prognostic parameters including an analysis of specific tumor markers. See, e.g., Porter-Jordan and Lippman, *Breast Cancer* 8:73-100 (1994).

Although the discovery of BRCA1 and BRCA2 were important steps in identifying key genetic factors involved in breast cancer, it has become clear that mutations in BRCA1 and BRCA2 account for only a fraction of inherited susceptibility to breast cancer (Nathanson, K. L. et al., *Human Mol. Gen.* 10(7):715-720 (2001); Anglican Breast Cancer Study Group. *Br. J. Cancer* 83(10):1301-08 (2000); and Sydjakoski K., et al., *J. Natl. Cancer Inst.* 92:1529-31 (2000)). In spite of considerable research into therapies for breast cancer, breast cancer remains difficult to diagnose and treat effectively, and the high mortality observed in breast cancer patients indicates that improvements are needed in the diagnosis, treatment and prevention of the disease.

MicroRNAs are a class of small, non-coding RNAs that control gene expression by hybridizing to and triggering either translational repression or, less frequently, degradation of a messenger RNA (mRNA) target. The discovery and study of mRNAs has revealed miRNA-mediated gene regulatory mechanisms that play important roles in organismal development and various cellular processes, such as cell differentiation, cell growth and cell death (Cheng, A. M., et al., *Nucleic Acids Res.* 33:1290-1297 (2005)). Recent studies suggest that aberrant expression of particular miRNAs may be involved in human diseases, such as neurological disorders (Ishizuka, A., et al., *Genes Dev.* 16:2497-2508 (2002)) and cancer. In particular, misexpression of miR-16-1 and/or miR-15a has been found in human chronic lymphocytic leukemias (Calin, G. A., et al., *Proc. Natl. Acad. Sci. U.S.A.* 99:15524-15529 (2002)).

The development and use of microarrays containing all known human microRNAs has permitted a simultaneous analysis of the expression of every miRNA in a sample (Liu, C. G., et al., *Proc Natl. Acad. Sci U.S.A.* 101:9740-9744 (2004)). These microRNA microarrays have not only been used to confirm that miR-16-1 is deregulated in human CLL cells, but also to generate miRNA expression signatures that are associated with well-defined clinico-pathological features of human CLL (Calin, G. A., et al., *Proc. Natl. Acad. Sci. U.S.A.* 101:1175-11760 (2004)).

The use of microRNA microarrays to identify a group of microRNAs, which are differentially-expressed between normal cells and breast cancer cells (i.e., an expression signature or expression profile), may help pinpoint specific miRNAs that are involved in breast cancer. Furthermore, the identification of putative targets of these miRNAs may help to unravel their pathogenic role. The present invention provides novel methods and compositions for the diagnosis, prognosis and treatment of breast cancer.

SUMMARY OF THE INVENTION

The present invention is based, in part, on the identification of a breast cancer-specific signature of miRNAs that are differentially-expressed in breast cancer cells, relative to normal control cells.

Accordingly, the invention encompasses methods of diagnosing whether a subject has, or is at risk for developing, breast-cancer, comprising measuring the level of at least one miR gene product in a test sample from the subject and comparing the level of the miR gene product in the test sample to the level of a corresponding miR gene product in a control sample. An alteration (e.g., an increase, a decrease) in the level of the miR gene product in the test sample, relative to the level of a corresponding miR gene product in a control sample, is indicative of the subject either having, or being at risk for developing, breast cancer. In certain embodiments, the at least one miR gene product is selected from the group consisting of miR-125b-1, miR125b-2, miR-145, miR-21, miR-155, miR-10b and combinations thereof.

The level of the at least one miR gene product can be measured using a variety of techniques that are well known to those of skill in the art. In one embodiment, the level of the at least one miR gene product is measured using Northern blot analysis. In another embodiment, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample. An alteration in the signal of at least one miRNA in the test sample relative to the control sample is indicative of the subject either having, or being at risk for developing, breast cancer. In a particular embodiment, the microarray comprises miRNA-specific probe oligonucleotides for a substantial portion of the human miRNome. In a further embodiment, the microarray comprises miRNA-specific probe oligonucleotides for one or more miRNAs selected from the group consisting of miR-145, miR-21, miR-155, miR-10b, miR-009-1 (miR131-1), miR-34 (miR-170), miR-102 (miR-29b), miR-123 (miR-126), miR-140-as, miR-125a, miR-125b-1, miR-125b-2, miR-194, miR-204, miR-213 let-7a-2, let-7a-3, let-7d (let-7d-v1), let-7f-2, let-71 (let- 7d-v2), miR-101-1, miR-122a, miR-128b, miR-136, miR-143, miR-149, miR-191, miR-196-1, miR-196-2, miR-202, miR-203, miR-205, miR-206, miR-210 and combinations thereof.

The invention also provides methods of diagnosing a breast cancer associated with one or more prognostic markers, comprising measuring the level of at least one miR gene product in a breast cancer test sample from a subject and comparing the level of the at least one miR gene product in the breast cancer test sample to the level of a corresponding miR gene product in a control sample. The breast cancer can be associated with one or more adverse prognostic markers associated with breast cancer, such as, but not limited to, estrogen receptor expression, progesterone receptor expression, positive lymph node metastasis, high proliferative index, detectable p53 expression, advanced tumor stage, and high vascular invasion. In one embodiment, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample. An alteration in the signal of at least one miRNA in the test sample relative to the control sample is indicative of the subject either having, or being at risk for developing, a breast cancer associated with the one or more prognostic markers. In a particular embodiment, the microarray comprises at least one miRNA-specific probe oligonucleotide for a miRNA selected from the group consisting of miR-26a, miR-26b, miR-102 (miR-29b), miR-30a-5p, miR-30b, miR-30c, miR-30d, miR-185, miR-191, miR-206, miR-212, let-7c, miR-9-2, miR-15-a, miR-21, miR-30a-s, miR-133a-1, miR-137, miR-153-2, miR-154, miR-181a, miR-203, miR-213, let-7f-1, let-7a-3, let-7a-2, miR-9-3, miR-10b, miR-27a, miR-29a, miR-123, miR-205, let-7d, miR-145, miR-16a, miR-128b and combinations thereof.

The invention also encompasses methods of treating breast cancer in a subject, wherein at least one miR gene product is de-regulated (e.g., down-regulated, up-regulated) in the cancer cells of the subject. When the at least one isolated miR gene product is down-regulated in the breast cancer cells, the method comprises administering an effective amount of the at least one isolated miR gene product, such that proliferation of cancer cells in the subject is inhibited. In one embodiment, the method comprises administering an effective amount of the at least one isolated miR gene product, provided that the miR gene is not miR-15a or miR-16-1, such that proliferation of cancer cells in the subject is inhibited. When the at least one isolated miR gene product is up-regulated in the cancer cells, the method comprises administering to the subject an effective amount of at least one compound for inhibiting expression of the at least one miR gene, such that proliferation of breast cancer cells is inhibited.

In related embodiments, the invention provides methods of treating breast cancer in a subject, comprising determining the amount of at least one miR gene product in breast cancer cells from the subject, relative to control cells. If expression of the miR gene product is deregulated in breast cancer cells, the methods further comprise altering the amount of the at least one miR gene product expressed in the breast cancer cells. If the amount of the miR gene product expressed in the cancer cells is less than the amount of the miR gene product expressed in control cells, the method comprises administering an effective amount of at least one isolated miR gene product. In one embodiment, the miR gene product is not miR15a or miR-16-1. If the amount of the miR gene product expressed in the cancer cells is greater than the amount of the miR gene product expressed in control cells, the method comprises administering to the subject an effective amount of at least one compound for inhibiting expression of the at least one miR gene. In one embodiment, the miR gene product is not miR-15a or miR-16-1.

The invention further provides pharmaceutical compositions for treating breast cancer. In one embodiment, the pharmaceutical compositions comprise at least one isolated miR gene product and a pharmaceutically-acceptable carrier. In a particular embodiment, the at least one miR gene product corresponds to a miR gene product that has a decreased level of expression in breast cancer cells relative to suitable control cells. In certain embodiments the isolated miR gene product is selected from the group consisting of miR-145, miR-10b, miR-123 (miR-126), miR-140-as, miR-125a, miR-125b-1, miR-125b-2, miR-194, miR-204, let-7a-2, let-7a-3, let-7d (let-7d-v1), let-7f-2, miR-101-1, miR-143 and combinations thereof.

In another embodiment, the pharmaceutical compositions of the invention comprise at least one miR expression inhibition compound. In a particular embodiment, the at least one miR expression inhibition compound is specific for a miR gene whose expression is greater in breast cancer cells than control cells. In certain embodiments, the miR expression inhibition compound is specific for one or more miR gene products selected from the group consisting of miR-21, miR-155, miR-009-1 (miR131-1), miR-34 (miR-170), miR-102 (miR-29b), miR-213, let-71 (let-7d-v2), miR-122a, miR-128b, miR-136, miR-149, miR-191, miR-196-1, miR-196-2, miR-202, miR-203, miR-206, miR-210, miR-213 and combinations thereof.

The invention also encompasses methods of identifying an anti-breast cancer agent, comprising providing a test agent to a cell and measuring the level of at least one miR gene product in the cell. In one embodiment, the method comprises providing a test agent to a cell and measuring the level of at least one miR gene product associated with decreased expression levels in breast cancer cells. An increase in the level of the miR gene product in the cell, relative to a suitable control cell, is indicative of the test agent being an anti-breast cancer agent. In a particular embodiment, the at least one miR gene product associated with decreased expression levels in breast cancer cells is selected from the group consisting of miR-145, miR-10b, miR-123 (miR-126), miR-140-as, miR-125a, miR-125b-1, miR-125b-2, miR-194, miR-204, let-7a-2, let-7a-3, let-7d (let-7d-v1), let-7f-2, miR-101-1, miR-143 and combinations thereof.

In other embodiments the method comprises providing a test agent to a cell and measuring the level of at least one miR gene product associated with increased expression levels in breast cancer cells. A decrease in the level of the miR gene product in the cell, relative to a suitable control cell, is indicative of the test agent being an anti-breast cancer agent. In a particular embodiment, at least one miR gene product associated with increased expression levels in breast cancer cells is selected from the group consisting of miR-21, miR-155, miR-009-1 (miR131-1), miR-34 (miR-170), miR-102 (miR-29b), miR-213, let-71 (let-7d-v2), miR-122a, miR-128b, miR-136, miR-149, miR-191, miR-196-1, miR-196-2, miR-202, miR-203, miR-206, miR-210, miR-213 and combinations thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A is a Northern blot depicting the expression level of miR-125b, using a miR-125b complementary probe, in a normal sample, as well as several tumor samples from breast cancer patients (P). The U6 probe was used for normalization of expression levels for each sample.

FIG. 3B is a Northern blot depicting the expression level of miR-145, using a miR-145 complementary probe, in a normal sample, as well as several tumor samples from breast cancer patients (P). The U6 probe was used for normalization of expression levels for each sample.

FIG. 3C is a Northern blot depicting the expression level of miR-21, using a miR-21 complementary probe, in a normal sample, as well as several tumor samples from breast cancer patients (labeled as numbered patients). The U6 probe was used for normalization of expression levels for each sample.

FIG. 3D is a Northern blot depicting the expression levels of microRNAs miR-125b, miR-145 and miR-21 in various breast cancer cell lines. The expression level of each microRNA was also determined in a sample from normal tissues. The U6 probe was used for normalization of expression levels for each sample.

FIG. 4A is a table listing miRNAs that are differentially-expressed in breast cancer samples associated with the presence (ER+) or absence (ER−) of estrogen receptor.

FIG. 4B is a table listing miRNAs that are differentially-expressed in breast cancer samples associated with the presence (PR+) or absence (PR−) of progesterone receptor.

FIG. 4C is a table listing miRNAs that are differentially-expressed in breast cancer samples associated with stage 1 (pT1) or stage 2 or 3 (pT2-3) tumors.

FIG. 4D is a table listing miRNAs that are differentially-expressed in breast cancer samples associated with the presence (pN0) or absence (pN10+) of lymph node metastasis.

FIG. 4E is a table listing miRNAs that are differentially-expressed in breast cancer samples associated with the presence or absence of vascular invasion.

FIG. 4F is a table listing miRNAs that are differentially-expressed in breast cancer samples associated with a high (MIB-1>30) or low (MIB-1<20) proliferative index (PI).

FIG. 4G is a table listing miRNAs that are differentially-expressed in breast cancer samples associated with positive (p53+) or negative (p53−) immunostaining of p53.

DETAILED DESCRIPTION OF THE INVENTION

Figure 1:
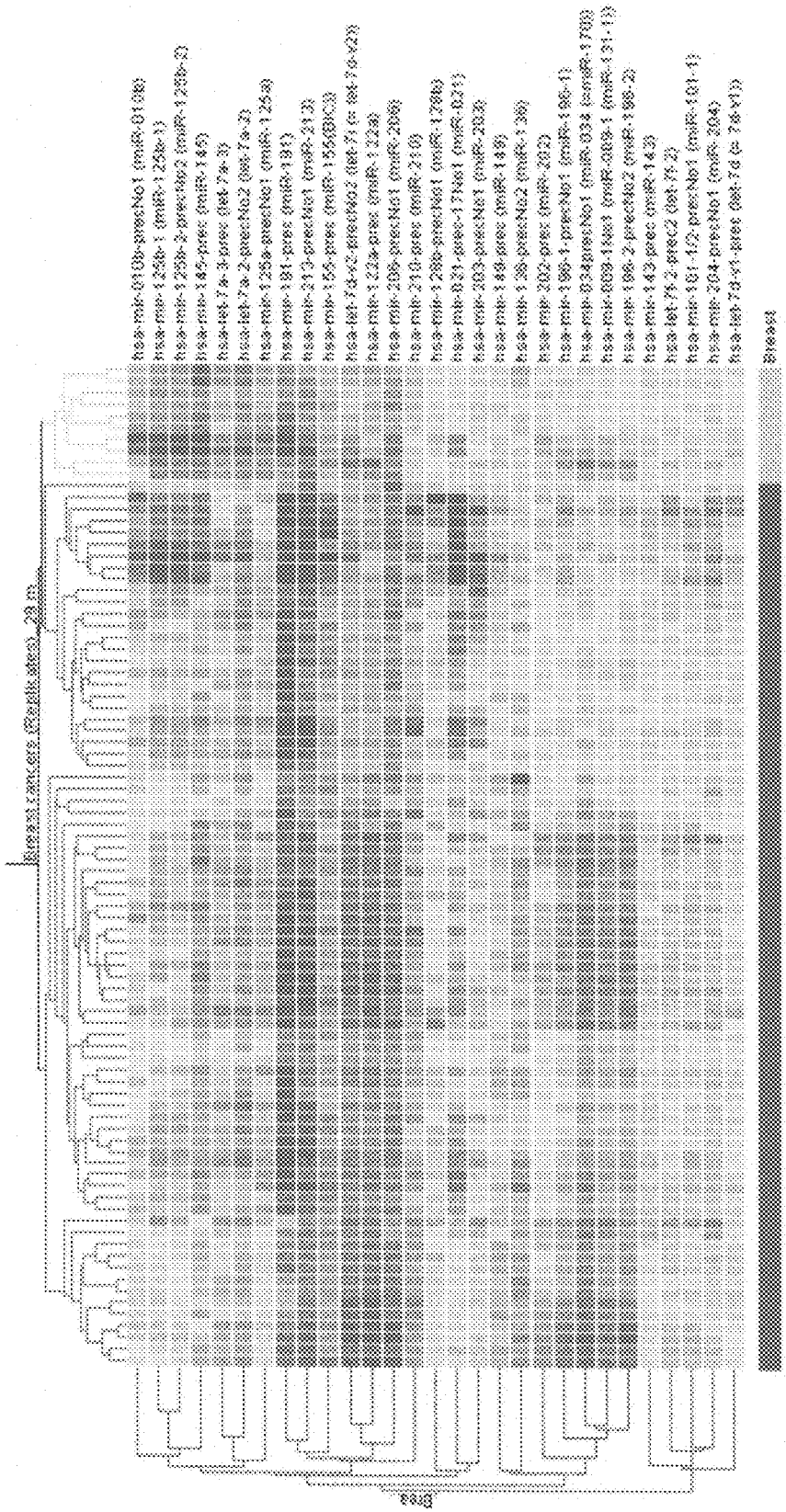
FIG. 1 depicts a tree generated by cluster analysis showing a separation of breast cancer from normal tissues on the basis of differential microRNA expression (P<0.05). The bar at the bottom of the figure indicates the group of cancer (red) or normal breast tissues (yellow).
Figure 2:
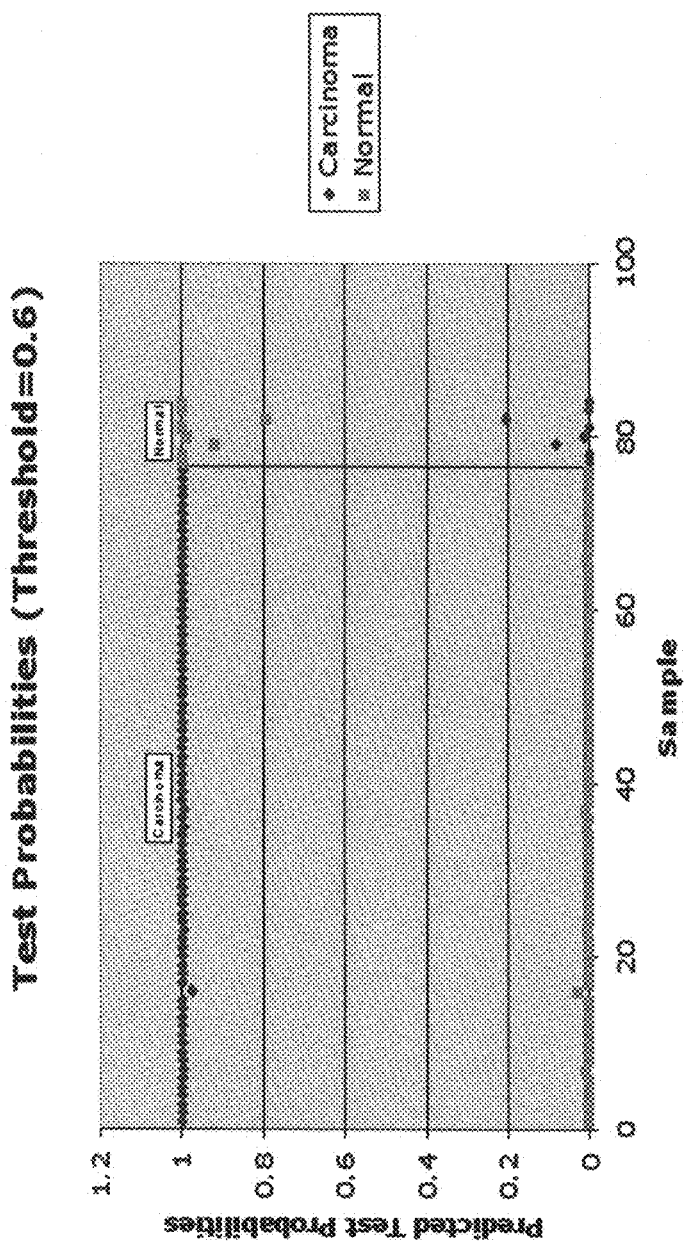
FIG. 2 is a graph depicting the probability (0.0 to 1.0) of each sample being a cancerous or normal tissue based on PAM analysis. All breast cancer and normal tissues were correctly predicted by the miR signature shown in Table 2.

The present invention is based, in part, on the identification of particular miRNAs whose expression is altered in breast cancer cells relative to normal control cells, and microRNAs whose expression is altered in breast cancer cells associated with particular prognostic features, relative to breast cancer cells lacking such features.

As used herein interchangeably, a "miR gene product," "microRNA," "miR," or "miRNA" refers to the unprocessed or processed RNA transcript from an miR gene. As the miR gene products are not translated into protein, the term "miR gene products" does not include proteins. The unprocessed miR gene transcript is also called an "miR precursor," and typically comprises an RNA transcript of about 70-100 nucleotides in length. The miR precursor can be processed by digestion with an RNAse (for example, Dicer, Argonaut, or RNAse III, e.g., *E. coli* RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAase III). It is understood that the active 19-25 nucleotide RNA molecule can also be produced directly by biological or chemical synthesis, without having been processed from the miR precursor.

The sequences of 187 miR gene products are provided in Table 1. All nucleic acid sequences herein are given in the 5' to 3' direction. In addition, genes are represented by italics, and gene products are represented by normal type; e.g. mir-17 is the gene and miR-17 is the gene product.

The present invention encompasses methods of diagnosing whether a subject has, or is at risk for developing, breast cancer, comprising measuring the level of at least one miR gene product in a test sample from the subject and comparing the level of the miR gene product in the test sample to the level of a corresponding miR gene product in a control sample. As used herein, a "subject" can be any mammal that has, or is suspected of having, breast cancer. In a particular embodiment, the subject is a human who has, or is suspected of having, breast cancer.

The breast cancer can be any form of breast cancer and may be associated with one or more prognostic markers or features, including, but not limited to, estrogen receptor expression, progesterone receptor expression, lymph node metastasis, high proliferative index, detectable p53 expression, advanced tumor stage, and high vascular invasion. The prognostic marker can be associated with an adverse or negative prognosis, or it may be associated with a good or positive prognosis.

TABLE 1

Human miR Gene Product Sequences

| Name | Precursor Sequence (5' to 3')* | SEQ ID NO. |
|---|---|---|
| hsa-let-7a-1-prec | CACTGTGGGATGAGGTAGTAGGTTGTATAGTTTTAGG GTCACACCCACCACTGGGAGATAACTATACAATCTAC TGTCTTTCCTAACGTG | 1 |
| hsa-let-7a-2-prec | AGGTTGAGGTAGTAGGTTGTATAGTTTAGAATTACAT CAAGGGAGATAACTGTACAGCCTCCTAGCTTTCCT | 2 |

TABLE 1-continued

Human miR Gene Product Sequences

| Name | Precursor Sequence (5' to 3')* | SEQ ID NO. |
|---|---|---|
| hsa-let-7a-3-prec | GGGTGAGGTAGTAGGTTGTATAGTTTGGGGCTCTGCCCTGCTATGGGATAACTATACAATCTACTGTCTTTCCT | 3 |
| hsa-let-7a-4-prec | GTGACTGCATGCTCCCAGGTTGAGGTAGTAGGTTGTATAGTTTAGAATTACACAAGGGAGATAACTGTACAGCCTCCTAGCTTTCCTTGGGTCTTGCACTAAACAAC | 4 |
| hsa-let-7b-prec | GGCGGGGTGAGGTAGTAGGTTGTGTGGTTTCAGGGCAGTGATGTTGCCCCTCGGAAGATAACTATACAACCTACTGCCTTCCCTG | 5 |
| hsa-let-7c-prec | GCATCCGGGTTGAGGTAGTAGGTTGTATGGTTTAGAGTTACACCCTGGGAGTTAACTGTACAACCTTCTAGCTTTCCTTGGAGC | 6 |
| hsa-let-7d-prec | CCTAGGAAGAGGTAGTAGGTTGCATAGTTTTAGGGCAGGGATTTTGCCCACAAGGAGGTAACTATACGACCTGCTGCCTTTCTTAGG | 7 |
| hsa-let-7d-v1-prec | CTAGGAAGAGGTAGTAGTTTGCATAGTTTTAGGGCAAAGATTTTGCCCACAAGTAGTTAGCTATACGACCTGCAGCCTTTTGTAG | 8 |
| hsa-let-7d-v2-prec | CTGGCTGAGGTAGTAGTTTGTGCTGTTGGTCGGGTTGTGACATTGCCCGCTGTGGAGATAACTGCGCAAGCTACTGCCTTGCTAG | 9 |
| hsa-let-7e-prec | CCCGGGCTGAGGTAGGAGGTTGTATAGTTGAGGAGGACACCCAAGGAGATCACTATACGGCCTCCTAGCTTTCCCCAGG | 10 |
| hsa-let-7f-1-prec | TCAGAGTGAGGTAGTAGATTGTATAGTTGTGGGGTAGTGATTTTACCCTGTTCAGGAGATAACTATACAATCTATTGCCTTCCCTGA | 11 |
| hsa-let-7f-2-prec | CTGTGGGATGAGGTAGTAGATTGTATAGTTGTGGGGTAGTGATTTTACCCTGTTCAGGAGATAACTATACAATCTATTGCCTTCCCTGA | 12 |
| hsa-let-7f-2-prec | CTGTGGGATGAGGTAGTAGATTGTATAGTTTTAGGGTCATACCCCATCTTGGAGATAACTATACAGTCTACTGTCTTTCCCACGG | 13 |
| hsa-let-7g-prec | TTGCCTGATTCCAGGCTGAGGTAGTAGTTTGTACAGTTTGAGGGTCTATGATACCACCCGGTACAGGAGATAACTGTACAGGCCACTGCCTTGCCAGGAACAGCGCGC | 14 |
| hsa-let-7i-prec | CTGGCTGAGGTAGTAGTTTGTGCTGTTGGTCGGGTTGTGACATTGCCCGCTGTGGAGATAACTGCGCAAGCTACTGCCTTGCTAG | 15 |
| hsa-mir-001b-1-prec | ACCTACTCAGAGTACATACTTCTTTATGTACCCATATGAACATACAATGCTATGGAATGTAAAGAAGTATGTATTTTTGGTAGGC | 16 |
| hsa-mir-001b-1-prec | CAGCTAACAACTTAGTAATACCTACTCAGAGTACATACTTCTTTATGTACCCATATGAACATACAATGCTATGGAATGTAAAGAAGTATGTATTTTTGGTAGGCAATA | 17 |
| hsa-mir-001b-2-prec | GCCTGCTTGGGAAACATACTTCTTTATATGCCCATATGGACCTGCTAAGCTATGGAATGTAAAGAAGTATGTATCTCAGGCCGGG | 18 |
| hsa-mir-001b-prec | TGGGAAACATACTTCTTTATATGCCCATATGGACCTGCTAAGCTATGGAATGTAAAGAAGTATGTATCTCA | 19 |
| hsa-mir-001d-prec | ACCTACTCAGAGTACATACTTCTTTATGTACCCATATGAACATACAATGCTATGGAATGTAAAGAAGTATGTATTTTTGGTAGGC | 20 |
| hsa-mir-007-1 | TGGATGTTGGCCTAGTTCTGTGTGGAAGACTAGTGATTTTGTTGTTTTTAGATAACTAAATCGACAACAAATCACAGTCTGCCATATGGCACAGGCCATGCCTCTACA | 21 |

TABLE 1-continued

Human miR Gene Product Sequences

| Name | Precursor Sequence (5' to 3')* | SEQ ID NO. |
|---|---|---|
| hsa-mir-007-1-prec | TTGGATGTTGGCCTAGTTCTGTG<u>TGGAAGACTAGTGA</u><br><u>TTTTGTT</u>GTTTTTAGATAACTAAATCGACAACAAATC<br>ACAGTCTGCCATATGGCACAGGCCATGCCTCTACAG | 22 |
| hsa-mir-007-2 | CTGGATACAGAGTGGACCGGCTGGCCCCATC<u>TGGAAG</u><br><u>ACTAGTGATTTTGTT</u>GTTGTCTTACTGCGCTCAACAA<br>CAAATCCCAGTCTACCTAATGGTGCCAGCCATCGCA | 23 |
| hsa-mir-007-2-prec | CTGGATACAGAGTGGACCGGCTGGCCCCATC<u>TGGAAG</u><br><u>ACTAGTGATTTTGTT</u>GTTGTCTTACTGCGCTCAACAA<br>CAAATCCCAGTCTACCTAATGGTGCCAGCCATCGCA | 24 |
| hsa-mir-007-3 | AGATTAGAGTGGCTGTGGTCTAGTGCTGTG<u>TGGAAGA</u><br><u>CTAGTGATTTTGTT</u>GTTCTGATGTACTACGACAACAA<br>GTCACAGCCGGCCTCATAGCGCAGACTCCCTTCGAC | 25 |
| hsa-mir-007-3-prec | AGATTAGAGTGGCTGTGGTCTAGTGCTGTG<u>TGGAAGA</u><br><u>CTAGTGATTTTGTT</u>GTTCTGATGTACTACGACAACAA<br>GTCACAGCCGGCCTCATAGCGCAGACTCCCTTCGAC | 26 |
| hsa-mir-009-1 | CGGGGTTGGTTGTTA<u>TCTTTGGTTATCTAGCTGTATG</u><br><u>A</u>GTGGTGTGGAGTCTTCATAAAGCTAGATAACCGAAA<br>GTAAAAATAACCCCA | 27 |
| hsa-mir-009-2 | GGAAGCGAGTTGTTA<u>TCTTTGGTTATCTAGCTGTATG</u><br><u>A</u>GTGTATTGGTCTTCATAAAGCTAGATAACCGAAAGT<br>AAAAACTCCTTCA | 28 |
| hsa-mir-009-3 | GGAGGCCCGTTTCT<u>CTCTTTGGTTATCTAGCTGTATG</u><br><u>A</u>GTGCCACAGAGCCGTCATAAAGCTAGATAACCGAAA<br>GTAGAAATGATTCTCA | 29 |
| hsa-mir-010a-prec | GATCTGTCTGTCTTCTGTATA<u>TACCCTGTAGATCCGA</u><br><u>ATTTGTG</u>TAAGGAATTTTGTGGTCACAAATTCGTATC<br>TAGGGGAATATGTAGTTGACATAAACACTCCGCTCT | 30 |
| hsa-mir-010b-prec | CCAGAGGTTGTAACGTTGTCTATATA<u>TACCCTGTAGA</u><br><u>ACCGAATTTGT</u>GTGGTATCCGTATAGTCACAGATTCG<br>ATTCTAGGGGAATATATGGTCGATGCAAAAACTTCA | 31 |
| hsa-mir-015a-2-prec | GCGCGAATGTGTGTTTAAAAAAAATAAAACCTTGGAG<br>TAAAGT<u>AGCAGCACATAATGGTTTGTG</u>GATTTTGAAA<br>AGGTGCAGGCCATATTGTGCTGCCTCAAAAATAC | 32 |
| hsa-mir-015a-prec | CCTTGGAGTAAAG<u>TAGCAGCACATAATGGTTTGTGGA</u><br>TTTTGAAAAGGTGCAGGCCATATTGTGCTGCCTCAAA<br>AATACAAGG | 33 |
| hsa-mir-015b-prec | CTG<u>TAGCAGCACATCATGGTTTACATGCTACA</u>GTCAA<br>GATGCGAATCATTATTTGCTGCTCTAG | 34 |
| hsa-mir-015b-prec | TTGAGGCCTTAAAGTACTGT<u>AGCAGCACATCATGGTT</u><br><u>TACA</u>TGCTACAGTCAAGATGCGAATCATTATTTGCTG<br>CTCTAGAAATTTAAGGAAATTCAT | 35 |
| hsa-mir-016a-chr13 | GTCAGCAGTGCCT<u>TAGCAGCACGTAAATATTGGCG</u>TT<br>AAGATTCTAAAATTATCTCCAGTATTAACTGTGCTGC<br>TGAAGTAAGGTTGAC | 36 |
| hsa-mir-016b-chr3 | GTTCCACTC<u>TAGCAGCACGTAAATATTGGCG</u>TAGTGA<br>AATATATATTAAACACCAATATTACTGTGCTGCTTTA<br>GTGTGAC | 37 |
| hsa-mir-016-prec-13 | GCAGTGCCT<u>TAGCAGCACGTAAATATTGGCG</u>TTAAGA<br>TTCTAAAATTATCTCCAGTATTAACTGTGCTGCTGAA<br>GTAAGGT | 38 |
| hsa-mir-017-prec | GTCAGAATAATGTCAAAGTGCTTACAGTGCAGGTAGT<br>GATATGTGCATCT<u>ACTGCAGTGAAGGCACTTGTAGCA</u><br>TTATGGTGAC | 39 |
| hsa-mir-018-prec | TGTTC<u>TAAGGTGCATCTAGTGCAGATA</u>GTGAAGTAGA<br>TTAGCATCTACTGCCCTAAGTGCTCCTTCTGGCA | 40 |

TABLE 1-continued

Human miR Gene Product Sequences

| Name | Precursor Sequence (5' to 3')* | SEQ ID NO. |
|---|---|---|
| hsa-mir-018-prec-13 | TTTTTGTTC<u>TAAGGTGCATCTAGTGCAGATAG</u>TGAAG TAGATTAGCATCTACTGCCCTAAGTGCTCCTTCTGGC ATAAGAA | 41 |
| hsa-mir-019a-prec | GCAGTCCTCTGTTAGTTTTGCATAGTTGCACTACAAG AAGAATGTAGT<u>TGTGCAAATCTATGCAAAACTGATGG</u> TGGCCTGC | 42 |
| hsa-mir-019a-prec-13 | CAGTCCTCTGTTAGTTTTGCATAGTTGCACTACAAGA AGAATGTAGT<u>TGTGCAAATCTATGCAAAACTGAT</u>GGT GGCCTG | 43 |
| hsa-mir-019b-1-prec | CACTGTTCTATGGTTAGTTTTGCAGGTTTGCATCCAG CTGTGTGATATTCTGC<u>TGTGCAAATCCATGCAAAACT GA</u>CTGTGGTAGTG | 44 |
| hsa-mir-019b-2-prec | ACATTGCTACTTACAATTAGTTTTGCAGGTTTGCATT TCAGCGTATATATGTATATGTGGC<u>TGTGCAAATCCAT GCAAAACTGA</u>TTGTGATAATGT | 45 |
| hsa-mir-019b-prec-13 | TTCTATGGTTAGTTTTGCAGGTTTGCATCCAGCTGTG TGATATTC<u>TGCTGTGCAAATCCATGCAAAACTGA</u>CTG TGGTAG | 46 |
| hsa-mir-019b-prec-X | TTACAATTAGTTTTGCAGGTTTGCATTTCAGCGTATA TATGTATATG<u>TGGCTGTGCAAATCCATGCAAAACTGA</u> TTGTGAT | 47 |
| hsa-mir-020-prec | GTAGCAC<u>TAAAGTGCTTATAGTGCAGGTAG</u>TGTTTAG TTATCTACTGCATTATGAGCACTTAAAGTACTGC | 48 |
| hsa-mir-021-prec | TGTCGGG<u>TAGCTTATCAGACTGATGTTGA</u>CTGTTGAA TCTCATGGCAACACCAGTCGATGGGCTGTCTGACA | 49 |
| hsa-mir-021-prec-17 | ACCTTGTCGGG<u>TAGCTTATCAGACTGATGTTGA</u>CTGT TGAATCTCATGGCAACACCAGTCGATGGGCTGTCTGA CATTTTG | 50 |
| hsa-mir-022-prec | GGCTGAGCCGCAGTAGTTCTTCAGTGGCAAGCTTTAT GTCCTGACCCAGCTA<u>AAGCTGCCAGTTGAAGAACTGT</u> TGCCCTCTGCC | 51 |
| hsa-mir-023a-prec | GGCCGGCTGGGGTTCCTGGGGATGGGATTTGCTTCCT GTCACAA<u>ATCACATTGCCAGGGATTTCC</u>AACCGACC | 52 |
| hsa-mir-023b-prec | CTCAGGTGCTCTGGCTGCTTGGGTTCCTGGCATGCTG ATTTGTGACTTAAGATTAAA<u>ATCACATTGCCAGGGAT TAC</u>CACGCAACCACGACCTTGGC | 53 |
| hsa-mir-023-prec-19 | CCACGGCCGGCTGGGGTTCCTGGGGATGGGATTTGCT TCCTGTCACAA<u>ATCACATTGCCAGGGATTTCC</u>AACCG ACCCTGA | 54 |
| hsa-mir-024-1-prec | CTCCGGTGCCTACTGAGCTGATATCAGTTCTCATTTT ACACAC<u>TGGCTCAGTTCAGCAGGAACAG</u>GAG | 55 |
| hsa-mir-024-2-prec | CTCTGCCTCCCGTGCCTACTGAGCTGAAACACAGTTG GTTTGTGTACAC<u>TGGCTCAGTTCAGCAGGAACAG</u>GG | 56 |
| hsa-mir-024-prec-19 | CCCTGGGCTCTGCCTCCCGTGCCTACTGAGCTGAAAC ACAGTTGGTTTGTGTACAC<u>TGGCTCAGTTCAGCAGGA ACAG</u>GGG | 57 |
| hsa-mir-024-prec-9 | CCCTCCGGTGCCTACTGAGCTGATATCAGTTCTCATT TTACACAC<u>TGGCTCAGTTCAGCAGGAACAG</u>CATC | 58 |
| hsa-mir-025-prec | GGCCAGTGTTGAGAGGCGGAGACTTGGGCAATTGCTG GACGCTGCCCTGGG<u>CATTGCACTTGTCTCGGTCTGAC</u> AGTGCCGGCC | 59 |
| hsa-mir-026a-prec | AGGCCGTGGCCTCGTT<u>CAAGTAATCCAGGATAGGCTG</u> TGCAGGTCCCAATGGCCTATCTTGGTTACTTGCACGG GGACGCGGGCCT | 60 |

TABLE 1-continued

Human miR Gene Product Sequences

| Name | Precursor Sequence (5' to 3')* | SEQ ID NO. |
|---|---|---|
| hsa-mir-026b-prec | CCGGGACCCAGTTCAAGTAATTCAGGATAGGTTGTGT GCTGTCCAGCCTGTTCTCCATTACTTGGCTCGGGGAC CGG | 61 |
| hsa-mir-027a-prec | CTGAGGAGCAGGGCTTAGCTGCTTGTGAGCAGGGTCC ACACCAAGTCGTGTTCACAGTGGCTAAGTTCCGCCCC CCAG | 62 |
| hsa-mir-027b-prec | AGGTGCAGAGCTTAGCTGATTGGTGAACAGTGATTGG TTTCCGCTTTGTTCACAGTGGCTAAGTTCTGCACCT | 63 |
| hsa-mir-027b-prec | ACCTCTCTAACAAGGTGCAGAGCTTAGCTGATTGGTG AACAGTGATTGGTTTCCGCTTTGTTCACAGTGGCTAA GTTCTGCACCTGAAGAGAAGGTG | 64 |
| hsa-mir-027-prec-19 | CCTGAGGAGCAGGGCTTAGCTGCTTGTGAGCAGGGTC CACACCAAGTCGTGTTCACAGTGGCTAAGTTCCGCCC CCAGG | 65 |
| hsa-mir-028-prec | GGTCCTTGCCCTCAAGGAGCTCACAGTCTATTGAGTT ACCTTTCTGACTTTCCCACTAGATTGTGAGCTCCTGG AGGGCAGGCACT | 66 |
| hsa-mir-029a-2 | CCTTCTGTGACCCCTTAGAGGATGACTGATTTCTTTT GGTGTTCAGAGTCAATATAATTTTCTAGCACCATCTG AAATCGGTTATAATGATTGGGGAAGAGCACCATG | 67 |
| hsa-mir-029a-prec | ATGACTGATTTCTTTTGGTGTTCAGAGTCAATATAAT TTTCTAGCACCATCTGAAATCGGTTAT | 68 |
| hsa-mir-029c-prec | ACCACTGGCCCATCTCTTACACAGGCTGACCGATTTC TCCTGGTGTTCAGAGTCTGTTTTTGTCTAGCACCATT TGAAATCGGTTATGATGTAGGGGGAAAAGCAGCAGC | 69 |
| hsa-mir-030a-prec | GCGACTGTAAACATCCTCGACTGGAAGCTGTGAAGCC ACAGATGGGCTTTCAGTCGGATGTTTGCAGCTGC | 70 |
| hsa-mir-030b-prec | ATGTAAACATCCTACACTCAGCTGTAATACATGGATT GGCTGGGAGGTGGATGTTTACGT | 71 |
| hsa-mir-030b-prec | ACCAAGTTTCAGTTCATGTAAACATCCTACACTCAGC TGTAATACATGGATTGGCTGGGAGGTGGATGTTTACT TCAGCTGACTTGGA | 72 |
| hsa-mir-030c-prec | AGATACTGTAAACATCCTACACTCTCAGCTGTGGAAA GTAAGAAAGCTGGGAGAAGGCTGTTTACTCTTTCT | 73 |
| hsa-mir-030d-prec | GTTGTTGTAAACATCCCCGACTGGAAGCTGTAAGACA CAGCTAAGCTTTCAGTCAGATGTTTGCTGCTAC | 74 |
| hsa-mir-031-prec | GGAGAGGAGGCAAGATGCTGGCATAGCTGTTGAACTG GGAACCTGCTATGCCAACATATTGCCATCTTTCC | 75 |
| hsa-mir-032-prec | GGAGATATTGCACATTACTAAGTTGCATGTTGTCACG GCCTCAATGCAATTTAGTGTGTGTGATATTTTC | 76 |
| hsa-mir-033b-prec | GGGGGCCGAGAGAGGCGGGCGGCCCCGCGGTGCATTG CTGTTGCATTGCACGTGTGTGAGGCGGGTGCAGTGCC TCGGCAGTGCAGCCCGGAGCCGGCCCCTGGCACCAC | 77 |
| hsa-mir-033-prec | CTGTGGTGCATTGTAGTTGCATTGCATGTTCTGGTGG TACCCATGCAATGTTTCCACAGTGCATCACAG | 78 |
| hsa-mir-034-prec | GGCCAGCTGTGAGTGTTTCTTTGGCAGTGTCTTAGCT GGTTGTTGTGAGCAATAGTAAGGAAGCAATCAGCAAG TATACTGCCCTAGAAGTGCTGCACGTTGTGGGGCCC | 79 |
| hsa-mir-091-prec-13 | TCAGAATAATGTCAAAGTGCTTACAGTGCAGGTAGTG ATATGTGCATCTACTGCAGTGAAGGCACTTGTAGCAT TATGGTGA | 80 |
| hsa-mir-092-prec prec-13 = 092-1 | CTTTCTACACAGGTTGGGATCGGTTGCAATGCTGTGT TTCTGTATGGTATTGCACTTGTCCCGGCCTGTTGAGT TTGG | 81 |

TABLE 1-continued

Human miR Gene Product Sequences

| Name | Precursor Sequence (5' to 3')* | SEQ ID NO. |
| --- | --- | --- |
| hsa-mir-092-prec prec-X = 092-2 | TCATCCCTGGGTGGGGATTTGTTGCATTACTTGTGTT CTATATAAAGTATTGCACTTGTCCCGGCCTGTGGAAG A | 82 |
| hsa-mir-093-prec prec-7.1 = 093-1 | CTGGGGGCTCCAAAGTGCTGTTCGTGCAGGTAGTGTG ATTACCCAACCTACTGCTGAGCTAGCACTTCCCGAGC CCCCGG | 83 |
| hsa-mir-093- prec-7.2 = 093-2 | CTGGGGGCTCCAAAGTGCTGTTCGTGCAGGTAGTGTG ATTACCCAACCTACTGCTGAGCTAGCACTTCCCGAGC CCCCGG | 84 |
| hsa-mir-095- prec-4 | AACACAGTGGGCACTCAATAAATGTCTGTTGAATTGA AATGCGTTACATTCAACGGGTATTTATTGAGCACCCA CTCTGTG | 85 |
| hsa-mir-096- prec-7 | TGGCCGATTTTGGCACTAGCACATTTTTGCTTGTGTC TCTCCGCTCTGAGCAATCATGTGCAGTGCCAATATGG GAAA | 86 |
| hsa-mir-098- prec-X | GTGAGGTAGTAAGTTGTATTGTTGTGGGGTAGGGATA TTAGGCCCCAATTAGAAGATAACTATACAACTTACTA CTTTCC | 87 |
| hsa-mir-099b- prec-19 | GGCACCCACCCGTAGAACCGACCTTGCGGGGCCTTCG CCGCACACAAGCTCGTGTCTGTGGGTCCGTGTC | 88 |
| hsa-mir-099- prec-21 | CCCATTGGCATAAACCCGTAGATCCGATCTTGTGGTG AAGTGGACCGCACAAGCTCGCTTCTATGGGTCTGTGT CAGTGTG | 89 |
| hsa-mir-100-1/2- prec | AAGAGAGAAGATATTGAGGCCTGTTGCCACAAACCCG TAGATCCGAACTTGTGGTATTAGTCCGCACAAGCTTG TATCTATAGGTATGTGTCTGTTAGGCAATCTCAC | 90 |
| hsa-mir-100- prec-11 | CCTGTTGCCACAAACCCGTAGATCCGAACTTGTGGTA TTAGTCCGCACAAGCTTGTATCTATAGGTATGTGTCT GTTAGG | 91 |
| hsa-mir-101-1/2- prec | AGGCTGCCCTGGCTCAGTTATCACAGTGCTGATGCTG TCTATTCTAAAGGTACAGTACTGTGATAACTGAAGGA TGGCAGCCATCTTACCTTCCATCAGAGGAGCCTCAC | 92 |
| hsa-mir-101-prec | TCAGTTATCACAGTGCTGATGCTGTCCATTCTAAAGG TACAGTACTGTGATAACTGA | 93 |
| hsa-mir-101- prec-1 | TGCCCTGGCTCAGTTATCACAGTGCTGATGCTGTCTA TTCTAAAGGTACAGTACTGTGATAACTGAAGGATGGC A | 94 |
| hsa-mir-101- prec-9 | TGTCCTTTTTCGGTTATCATGGTACCGATGCTGTATA TCTGAAAGGTACAGTACTGTGATAACTGAAGAATGGT G | 95 |
| hsa-mir-102- prec-1 | CTTCTGGAAGCTGGTTTCACATGGTGGCTTAGATTTT TCCATCTTTGTATCTAGCACCATTTGAAATCAGTGTT TTAGGAG | 96 |
| hsa-mir-102- prec-7.1 | CTTCAGGAAGCTGGTTTCATATGGTGGTTTAGATTTA AATAGTGATTGTCTAGCACCATTTGAAATCAGTGTTC TTGGGGG | 97 |
| hsa-mir-102- prec-7.2 | CTTCAGGAAGCTGGTTTCATATGGTGGTTTAGATTTA AATAGTGATTGTCTAGCACCATTTGAAATCAGTGTTC TTGGGGG | 98 |
| hsa-mir-103-2- prec | TTGTGCTTTCAGCTTCTTTACAGTGCTGCCTTGTAGC ATTCAGGTCAAGCAACATTGTACAGGGCTATGAAAGA ACCA | 99 |
| hsa-mir-103- prec-20 | TTGTGCTTTCAGCTTCTTTACAGTGCTGCCTTGTAGC ATTCAGGTCAAGCAACATTGTACAGGGCTATGAAAGA ACCA | 100 |

TABLE 1-continued

Human miR Gene Product Sequences

| Name | Precursor Sequence (5' to 3')* | SEQ ID NO. |
|---|---|---|
| hsa-mir-103-prec-5 = 103-1 | TACTGCCCTCGGCTTCTTTACAGTGCTGCCTTGTTGC ATATGGATCAAGCAGCATTGTACAGGGCTATGAAGGC ATTG | 101 |
| hsa-mir-104-prec-17 | AAATGTCAGACAGCCCATCGACTGGTGTTGCCATGAG ATTCAACAGTCAACATCAGTCTGATAAGCTACCCGAC AAGG | 102 |
| hsa-mir-105-prec-X.1 = 105-1 | TGTGCATCGTGGTCAAATGCTCAGACTCCTGTGGTGG CTGCTCATGCACCACGGATGTTTGAGCATGTGCTACG GTGTCTA | 103 |
| hsa-mir-105-prec-X.2 = 105-2 | TGTGCATCGTGGTCAAATGCTCAGACTCCTGTGGTGG CTGCTCATGCACCACGGATGTTTGAGCATGTGCTACG GTGTCTA | 104 |
| hsa-mir-106-prec-X | CCTTGGCCATGTAAAAGTGCTTACAGTGCAGGTAGCT TTTGAGATCTACTGCAATGTAAGCACTTCTTACATT ACCATGG | 105 |
| hsa-mir-107-prec-10 | CTCTCTGCTTTCAGCTTCTTTACAGTGTTGCCTTGTG GCATGGAGTTCAAGCAGCATTGTACAGGGCTATCAAA GCACAGA | 106 |
| hsa-mir-122a-prec | CCTTAGCAGAGCTGTGGAGTGTGACAATGGTGTTTGT GTCTAAACTATCAAACGCCATTATCACACTAAATAGC TACTGCTAGGC | 107 |
| hsa-mir-122a-prec | AGCTGTGGAGTGTGACAATGGTGTTTGTGTCCAAACT ATCAAACGCCATTATCACACTAAATAGCT | 108 |
| hsa-mir-123-prec | ACATTATTACTTTTGGTACGCGCTGTGACACTTCAAA CTCGTACCGTGAGTAATAATGCGC | 109 |
| hsa-mir-124a-1-prec | tccttcctCAGGAGAAAGGCCTCTCTCTCCGTGTTCA CAGCGGACCTTGATTTAAATGTCCATACAATTAAGGC ACGCGGTGAATGCCAAGAATGGGGCT | 110 |
| hsa-mir-124a-1-prec | AGGCCTCTCTCTCCGTGTTCACAGCGGACCTTGATTT AAATGTCCATACAATTAAGGCACGCGGTGAATGCCAA GAATGGGGCTG | 111 |
| hsa-mir-124a-2-prec | ATCAAGATTAGAGGCTCTGCTCTCCGTGTTCACAGCG GACCTTGATTTAATGTCATACAATTAAGGCACGCGGT GAATGCCAAGAGCGGAGCCTACGGCTGCACTTGAAG | 112 |
| hsa-mir-124a-3-prec | CCCGCCCCAGCCCTGAGGGCCCCTCTGCGTGTTCACA GCGGACCTTGATTTAATGTCTATACAATTAAGGCACG CGGTGAATGCCAAGAGAGGCGCCTCCGCCGCTCCTT | 113 |
| hsa-mir-124a-3-prec | TGAGGGCCCCTCTGCGTGTTCACAGCGGACCTTGATT TAATGTCTATACAATTAAGGCACGCGGTGAATGCCAA GAGAGGCGCCTCC | 114 |
| hsa-mir-124a-prec | CTCTGCGTGTTCACAGCGGACCTTGATTTAATGTCTA TACAATTAAGGCACGCGGTGAATGCCAAGAG | 115 |
| hsa-mir-124b-prec | CTCTCCGTGTTCACAGCGGACCTTGATTTAATGTCAT ACAATTAAGGCACGCGGTGAATGCCAAGAG | 116 |
| hsa-mir-125a-prec | TGCCAGTCTCTAGGTCCCTGAGACCCTTTAACCTGTG AGGACATCCAGGGTCACAGGTGAGGTTCTTGGGAGCC TGGCGTCTGGCC | 117 |
| hsa-mir-125a-prec | GGTCCCTGAGACCCTTTAACCTGTGAGGACATCCAGG GTCACAGGTGAGGTTCTTGGGAGCCTGG | 118 |
| hsa-mir-125b-1 | ACATTGTTGCGCTCCTCTCAGTCCCTGAGACCCTAAC TTGTGATGTTTACCGTTTAAATCCACGGGTTAGGCTC TTGGGAGCTGCGAGTCGTGCTTTTGCATCCTGGA | 119 |

TABLE 1-continued

Human miR Gene Product Sequences

| Name | Precursor Sequence (5' to 3')* | SEQ ID NO. |
|---|---|---|
| hsa-mir-125b-1 | TGCGCTCCTCTCAGTCCCTGAGACCCTAACTTGTGAT GTTTACCGTTTAAATCCACGGGTTAGGCTCTTGGGAG CTGCGAGTCGTGCT | 120 |
| hsa-mir-125b-2-prec | ACCAGACTTTTCCTAGTCCCTGAGACCCTAACTTGTG AGGTATTTTAGTAACATCACAAGTCAGGCTCTTGGGA CCTAGGCGGAGGGGA | 121 |
| hsa-mir-125b-2-prec | CCTAGTCCCTGAGACCCTAACTTGTGAGGTATTTTAG TAACATCACAAGTCAGGCTCTTGGGACCTAGGC | 122 |
| hsa-mir-126-prec | CGCTGGCGACGGGACATTATTACTTTTGGTACGCGCT GTGACACTTCAAACTCGTACCGTGAGTAATAATGCGC CGTCCACGGCA | 123 |
| hsa-mir-126-prec | ACATTATTACTTTTGGTACGCGCTGTGACACTTCAAA CTCGTACCGTGAGTAATAATGCGC | 124 |
| hsa-mir-127-prec | TGTGATCACTGTCTCCAGCCTGCTGAAGCTCAGAGGG CTCTGATTCAGAAAGATCATCGGATCCGTCTGAGCTT GGCTGGTCGGAAGTCTCATCATC | 125 |
| hsa-mir-127-prec | CCAGCCTGCTGAAGCTCAGAGGGCTCTGATTCAGAAA GATCATCGGATCCGTCTGAGCTTGGCTGGTCGG | 126 |
| hsa-mir-128a-prec | TGAGCTGTTGGATTCGGGGCCGTAGCACTGTCTGAGA GGTTTACATTTCTCACAGTGAACCGGTCTCTTTTTCA GCTGCTTC | 127 |
| hsa-mir-128b-prec | GCCCGGCAGCCACTGTGCAGTGGGAAGGGGGGCCGAT ACACTGTACGAGAGTGAGTAGCAGGTCTCACAGTGAA CCGGTCTCTTTCCCTACTGTGTCACACTCCTAATGG | 128 |
| hsa-mir-128-prec | GTTGGATTCGGGGCCGTAGCACTGTCTGAGAGGTTTA CATTTCTCACAGTGAACCGGTCTCTTTTTCAGC | 129 |
| hsa-mir-129-prec | TGGATCTTTTTGCGGTCTGGGCTTGCTGTTCCTCTCA ACAGTAGTCAGGAAGCCCTTACCCCAAAAAGTATCTA | 130 |
| hsa-mir-130a-prec | TGCTGCTGGCCAGAGCTCTTTTCACATTGTGCTACTG TCTGCACCTGTCACTAGCAGTGCAATGTTAAAAGGGC ATTGGCCGTGTAGTG | 131 |
| hsa-mir-131-1-prec | gccaggaggcggGGTTGGTTGTTATCTTTGGTTATCT AGCTGTATGAGTGGTGTGGAGTCTTCATAAAGCTAGA TAACCGAAAGTAAAAATAACCCCATACACTGCGCAG | 132 |
| hsa-mir-131-3-prec | CACGGCGCGGCAGCGGCACTGGCTAAGGGAGGCCCGT TTCTCTCTTTGGTTATCTAGCTGTATGAGTGCCACAG AGCCGTCATAAAGCTAGATAACCGAAAGTAGAAATG | 133 |
| hsa-mir-131-prec | GTTGTTATCTTTGGTTATCTAGCTGTATGAGTGTATT GGTCTTCATAAAGCTAGATAACCGAAAGTAAAAAC | 134 |
| hsa-mir-132-prec | CCGCCCCCGCGTCTCCAGGGCAACCGTGGCTTTCGAT TGTTACTGTGGGAACTGGAGGTAACAGTCTACAGCCA TGGTCGCCCCGCAGCACGCCCACGCGC | 135 |
| hsa-mir-132-prec | GGGCAACCGTGGCTTTCGATTGTTACTGTGGGAACTG GAGGTAACAGTCTACAGCCATGGTCGCCC | 136 |
| hsa-mir-133a-1 | ACAATGCTTTGCTAGAGCTGGTAAAATGGAACCAAAT CGCCTCTTCAATGGATTTGGTCCCCTTCAACCAGCTG TAGCTATGCATTGA | 137 |
| hsa-mir-133a-2 | GGGAGCCAAATGCTTTGCTAGAGCTGGTAAAATGGAA CCAAATCGACTGTCCAATGGATTTGGTCCCCTTCAAC CAGCTGTAGCTGTGCATTGATGGCGCCG | 138 |
| hsa-mir-133-prec | GCTAGAGCTGGTAAAATGGAACCAAATCGCCTCTTCA ATGGATTTGGTCCCCTTCAACCAGCTGTAGC | 139 |
| hsa-mir-134-prec | CAGGGTGTGTGACTGGTTGACCAGAGGGGCATGCACT GTGTTCACCCTGTGGGCCACCTAGTCACCAACCCTC | 140 |

TABLE 1-continued

Human miR Gene Product Sequences

| Name | Precursor Sequence (5' to 3')* | SEQ ID NO. |
|---|---|---|
| hsa-mir-134-prec | AGGGTGTGTGACTGGTTGACCAGAGGGGCATGCACTG TGTTCACCCTGTGGGCCACCTAGTCACCAACCCT | 141 |
| hsa-mir-135-1-prec | AGGCCTCGCTGTTCTCTATGGCTTTTTATTCCTATGT GATTCTACTGCTCACTCATATAGGGATTGGAGCCGTG GCGCACGGCGGGGACA | 142 |
| hsa-mir-135-2-prec | AGATAAATTCACTCTAGTGCTTTATGGCTTTTTATTC CTATGTGATAGTAATAAAGTCTCATGTAGGGATGGAA GCCATGAAATACATTGTGAAAAATCA | 143 |
| hsa-mir-135-prec | CTATGGCTTTTTATTCCTATGTGATTCTACTGCTCAC TCATATAGGGATTGGAGCCGTGG | 144 |
| hsa-mir-136-prec | TGAGCCCTCGGAGGACTCCATTTGTTTTGATGATGGA TTCTTATGCTCCATCATCGTCTCAAATGAGTCTTCAG AGGGTTCT | 145 |
| hsa-mir-136-prec | GAGGACTCCATTTGTTTTGATGATGGATTCTTATGCT CCATCATCGTCTCAAATGAGTCTTC | 146 |
| hsa-mir-137-prec | CTTCGGTGACGGGTATTCTTGGGTGGATAATACGGAT TACGTTGTTATTGCTTAAGAATACGCGTAGTCGAGG | 147 |
| hsa-mir-138-1-prec | CCCTGGCATGGTGTGGTGGGGCAGCTGGTGTTGTGAA TCAGGCCGTTGCCAATCAGAGAACGGCTACTTCACAA CACCAGGGCCACACCACACTACAGG | 148 |
| hsa-mir-138-2-prec | CGTTGCTGCAGCTGGTGTTGTGAATCAGGCCGACGAG CAGCGCATCCTCTTACCCGGCTATTTCACGACACCAG GGTTGCATCA | 149 |
| hsa-mir-138-prec | CAGCTGGTGTTGTGAATCAGGCCGACGAGCAGCGCAT CCTCTTACCCGGCTATTTCACGACACCAGGGTTG | 150 |
| hsa-mir-139-prec | GTGTATTCTACAGTGCACGTGTCTCCAGTGTGGCTCG GAGGCTGGAGACGCGGCCCTGTTGGAGTAAC | 151 |
| hsa-mir-140 | TGTGTCTCTCTCTGTGTCCTGCCAGTGGTTTTACCCT ATGGTAGGTTACGTCATGCTGTTCTACCACAGGGTAG AACCACGGACAGGATACCGGGGCACC | 152 |
| hsa-mir-140as-prec | TCCTGCCAGTGGTTTTACCCTATGGTAGGTTACGTCA TGCTGTTCTACCACAGGGTAGAACCACGGACAGGA | 153 |
| hsa-mir-140s-prec | CCTGCCAGTGGTTTTACCCTATGGTAGGTTACGTCAT GCTGTTCTACCACAGGGTAGAACCACGGACAGG | 154 |
| hsa-mir-141-prec | CGGCCGGCCCTGGGTCCATCTTCCAGTACAGTGTTGG ATGGTCTAATTGTGAAGCTCCTAACACTGTCTGGTAA AGATGGCTCCCGGGTGGGTTC | 155 |
| hsa-mir-141-prec | GGGTCCATCTTCCAGTACAGTGTTGGATGGTCTAATT GTGAAGCTCCTAACACTGTCTGGTAAAGATGGCCC | 156 |
| hsa-mir-142as-prec | ACCCATAAAGTAGAAAGCACTACTAACAGCACTGGAG GGTGTAGTGTTTCCTACTTTATGGATG | 157 |
| hsa-mir-142-prec | GACAGTGCAGTCACCCATAAAGTAGAAAGCACTACTA ACAGCACTGGAGGGTGTAGTGTTTCCTACTTTATGGA TGAGTGTACTGTG | 158 |
| hsa-mir-142s-pres | ACCCATAAAGTAGAAAGCACTACTAACAGCACTGGAG GGTGTAGTGTTTCCTACTTTATGGATG | 159 |
| hsa-mir-143-prec | GCGCAGCGCCCTGTCTCCCAGCCTGAGGTGCAGTGCT GCATCTCTGGTCAGTTGGGAGTCTGAGATGAAGCACT GTAGCTCAGGAAGAGAGAAGTTGTTCTGCAGC | 160 |
| hsa-mir-143-prec | CCTGAGGTGCAGTGCTGCATCTCTGGTCAGTTGGGAG TCTGAGATGAAGCACTGTAGCTCAGG | 161 |

TABLE 1-continued

Human miR Gene Product Sequences

| Name | Precursor Sequence (5' to 3')* | SEQ ID NO. |
|---|---|---|
| hsa-mir-144-prec | TGGGGCCCTGGCTGGGATATCATCATATACTGTAAGT TTGCGATGAGACACTACAGTATAGATGATGTACTAGT CCGGGCACCCCC | 162 |
| hsa-mir-144-prec | GGCTGGGATATCATCATATACTGTAAGTTTGCGATGA GACACTACAGTATAGATGATGTACTAGTC | 163 |
| hsa-mir-145-prec | CACCTTGTCCTCACGGTCCAGTTTTCCCAGGAATCCC TTAGATGCTAAGATGGGGATTCCTGGAAATACTGTTC TTGAGGTCATGGTT | 164 |
| hsa-mir-145-prec | CTCACGGTCCAGTTTTCCCAGGAATCCCTTAGATGCT AAGATGGGGATTCCTGGAAATACTGTTCTTGAG | 165 |
| hsa-mir-146-prec | CCGATGTGTATCCTCAGCTTTGAGAACTGAATTCCAT GGGTTGTGTCAGTGTCAGACCTCTGAAATTCAGTTCT TCAGCTGGGATATCTCTGTCATCGT | 166 |
| hsa-mir-146-prec | AGCTTTGAGAACTGAATTCCATGGGTTGTGTCAGTGT CAGACCTGTGAAATTCAGTTCTTCAGCT | 167 |
| hsa-mir-147-prec | AATCTAAAGACAACATTTCTGCACACACACCAGACTA TGGAAGCCAGTGTGTGGAAATGCTTCTGCTAGATT | 168 |
| hsa-mir-148-prec | GAGGCAAAGTTCTGAGACACTCCGACTCTGAGTATGA TAGAAGTCAGTGCACTACAGAACTTTGTCTC | 169 |
| hsa-mir-149-prec | GCCGGCGCCCGAGCTCTGGCTCCGTGTCTTCACTCCC GTGCTTGTCCGAGGAGGGAGGGAGGGACGGGGCTG TGCTGGGGCAGCTGGA | 170 |
| hsa-mir-149-prec | GCTCTGGCTCCGTGTCTTCACTCCCGTGCTTGTCCGA GGAGGGAGGGAGGGAC | 171 |
| hsa-mir-150-prec | CTCCCCATGGCCCTGTCTCCCAACCCTTGTACCAGTG CTGGGCTCAGACCCTGGTACAGGCCTGGGGACAGG GACCTGGGGAC | 172 |
| hsa-mir-150-prec | CCCTGTCTCCCAACCCTTGTACCAGTGCTGGGCTCAG ACCCTGGTACAGGCCTGGGGACAGGG | 173 |
| hsa-mir-151-prec | CCTGCCCTCGAGGAGCTCACAGTCTAGTATGTCTCAT CCCCTACTAGACTGAAGCTCCTTGAGGACAGG | 174 |
| hsa-mir-152-prec | TGTCCCCCCCGGCCCAGGTTCTGTGATACACTCCGAC TCGGGCTCTGGAGCAGTCAGTGCATGACAGAACTTGG GCCCGGAAGGACC | 175 |
| hsa-mir-152-prec | GGCCCAGGTTCTGTGATACACTCCGACTCGGGCTCTG GAGCAGTCAGTGCATGACAGAACTTGGGCCCCGG | 176 |
| hsa-mir-153-1-prec | CTCACAGCTGCCAGTGTCATTTTTGTGATCTGCAGCT AGTATTCTCACTCCAGTTGCATAGTCACAAAAGTGAT CATTGGCAGGTGTGGC | 177 |
| hsa-mir-153-1-prec | tctctctctccctcACAGCTGCCAGTGTCATTGTCAA AACGTGATCATTGGCAGGTGTGGCTGCTGCATG | 178 |
| hsa-mir-153-2-prec | AGCGGTGGCCAGTGTCATTTTTGTGATGTTGCAGCTA GTAATATGAGCCCAGTTGCATAGTCACAAAAGTGATC ATTGGAAACTGTG | 179 |
| hsa-mir-153-2-rec | CAGTGTCATTTTTGTGATGTTGCAGCTAGTAATATGA GCCCAGTTGCATAGTCACAAAAGTGATCATTG | 180 |
| hsa-mir-154-prec | GTGGTACTTGAAGATAGGTTATCCGTGTTGCCTTCGC TTTATTTGTGACGAATCATACACGGTTGACCTATTTT TCAGTACCAA | 181 |
| hsa-mir-154-prec | GAAGATAGGTTATCCGTGTTGCCTTCGCTTTATTTGT GACGAATCATACACGGTTGACCTATTTTT | 182 |
| hsa-mir-155-prec | CTGTTAATGCTAATCGTGATAGGGGTTTTTGCCTCCA ACTGACTCCTACATATTAGCATTAACAG | 183 |

TABLE 1-continued

Human miR Gene Product Sequences

| Name | Precursor Sequence (5' to 3')* | SEQ ID NO. |
|---|---|---|
| hsa-mir-16-2-prec | CAATGTCAGCAGTGCCTTAGCAGCACGTAAATATTGG CGTTAAGATTCTAAAATTATCTCCAGTATTAACTGTG CTGCTGAAGTAAGGTTGACCATACTCTACAGTTG | 184 |
| hsa-mir-181a-prec | AGAAGGGCTATCAGGCCAGCCTTCAGAGGACTCCAAG GAACATTCAACGCTGTCGGTGAGTTTGGGATTTGAAA AAACCACTGACCGTTGACTGTACCTTGGGGTCCTTA | 185 |
| hsa-mir-181b-prec | TGAGTTTTGAGGTTGCTTCAGTGAACATTCAACGCTG TCGGTGAGTTTGGAATTAAAATCAAAACCATCGACCG TTGATTGTACCCTATGGCTAACCATCATCTACTCCA | 186 |
| hsa-mir-181c-prec | CGGAAAATTTGCCAAGGGTTTGGGGAACATTCAACC TGTCGGTGAGTTTGGGCAGCTCAGGCAAACCATCGAC CGTTGAGTGGACCCTGAGGCCTGGAATTGCCATCCT | 187 |
| hsa-mir-182-as-prec | GAGCTGCTTGCCTCCCCCCGTTTTTGGCAATGGTAGA ACTCACACTGGTGAGGTAACAGGATCCGGTGGTTCTA GACTTGCCAACTATGGGGCGAGGACTCAGCCGGCAC | 188 |
| hsa-mir-182-prec | TTTTTGGCAATGGTAGAACTCACACTGGTGAGGTAAC AGGATCCGGTGGTTCTAGACTTGCCAACTATGG | 189 |
| hsa-mir-183-prec | CCGCAGAGTGTGACTCCTGTTCTGTGTATGGCACTGG TAGAATTCACTGTGAACAGTCTCAGTCAGTGAATTAC CGAAGGGCCATAAACAGAGCAGAGACAGATCCACGA | 190 |
| hsa-mir-184-prec | CCAGTCACGTCCCCTTATCACTTTTCCAGCCCAGCTT TGTGACTGTAAGTGTTGGACGGAGAACTGATAAGGGT AGGTGATTGA | 191 |
| hsa-mir-184-prec | CCTTATCACTTTTCCAGCCCAGCTTTGTGACTGTAAG TGTTGGACGGAGAACTGATAAGGGTAGG | 192 |
| hsa-mir-185-prec | AGGGGGCGAGGGATTGGAGAGAAAGGCAGTTCCTGAT GGTCCCCTCCCCAGGGGCTGGCTTTCCTCTGGTCCTT CCCTCCCA | 193 |
| hsa-mir-185-prec | AGGGATTGGAGAGAAAGGCAGTTCCTGATGGTCCCCT CCCCAGGGGCTGGCTTTCCTCTGGTCCTT | 194 |
| hsa-mir-186-prec | TGCTTGTAACTTTCCAAAGAATTCTCCTTTTGGGCTT TCTGGTTTTATTTTAAGCCCAAAGGTGAATTTTTTGG GAAGTTTGAGCT | 195 |
| hsa-mir-186-prec | ACTTTCCAAAGAATTCTCCTTTTGGGCTTTCTGGTTT TATTTTAAGCCCAAAGGTGAATTTTTTGGGAAGT | 196 |
| hsa-mir-187-prec | GGTCGGGCTCACCATGACACAGTGTGAGACTCGGGCT ACAACACAGGACCCGGGGCGCTGCTCTGACCCCTCGT GTCTTGTGTTGCAGCCGGAGGGACGCAGGTCCGCA | 197 |
| hsa-mir-188-prec | TGCTCCCTCTCTCACATCCCTTGCATGGTGGAGGGTG AGCTTTCTGAAAACCCCTCCCACATGCAGGGTTTGCA GGATGGCGAGCC | 198 |
| hsa-mir-188-prec | TCTCACATCCCTTGCATGGTGGAGGGTGAGCTTTCTG AAAACCCCTCCCACATGCAGGGTTTGCAGGA | 199 |
| hsa-mir-189-prec | CTGTCGATTGGACCCGCCCTCCGGTGCCTACTGAGCT GATATCAGTTCTCATTTTACACACTGGCTCAGTTCAG CAGGAACAGGAGTCGAGCCCTTGAGCAA | 200 |
| hsa-mir-189-prec | CTCCGGTGCCTACTGAGCTGATATCAGTTCTCATTTT ACACACTGGCTCAGTTCAGCAGGAACAGGAG | 201 |
| hsa-mir-190-prec | TGCAGGCCTCTGTGTGATATGTTTGATATATTAGGTT GTTATTTAATCCAACTATATATCAAACATATTCCTAC AGTGTCTTGCC | 202 |
| hsa-mir-190-prec | CTGTGTGATATGTTTGATATATTAGGTTGTTATTTAA TCCAACTATATATCAAACATATTCCTACAG | 203 |

TABLE 1-continued

Human miR Gene Product Sequences

| Name | Precursor Sequence (5' to 3')* | SEQ ID NO. |
| --- | --- | --- |
| hsa-mir-191-prec | CGGCTGGACAGCGGGCAACGGAATCCCAAAAGCAGCTGTTGTCTCCAGAGCATTCCAGCTGCGCTTGGATTTCGTCCCCTGCTCTCCTGCCT | 204 |
| hsa-mir-191-prec | AGCGGGCAACGGAATCCCAAAAGCAGCTGTTGTCTCCAGAGCATTCCAGCTGCGCTTGGATTTCGTCCCCTGCT | 205 |
| hsa-mir-192-²/₃ | CCGAGACCGAGTGCACAGGGCTCTGACCTATGAATTGACAGCCAGTGCTCTCGTCTCCCCTCTGGCTGCCAATTCCATAGGTCACAGGTATGTTCGCCTCAATGCCAG | 206 |
| hsa-mir-192-prec | GCCGAGACCGAGTGCACAGGGCTCTGACCTATGAATTGACAGCCAGTGCTCTCGTCTCCCCTCTGGCTGCCAATTCCATAGGTCACAGGTATGTTCGCCTCAATGCCAGC | 207 |
| hsa-mir-193-prec | CGAGGATGGGAGCTGAGGGCTGGGTCTTTGCGGGCGAGATGAGGGTGTCGGATCAACTGGCCTACAAAGTCCCAGTTCTCGGCCCCCG | 208 |
| hsa-mir-193-prec | GCTGGGTCTTTGCGGGCGAGATGAGGGTGTCGGATCAACTGGCCTACAAAGTCCCAGT | 209 |
| hsa-mir-194-prec | ATGGTGTTATCAAGTGTAACAGCAACTCCATGTGGACTGTGTACCAATTTCCAGTGGAGATGCTGTTACTTTTGATGGTTACCAA | 210 |
| hsa-mir-194-prec | GTGTAACAGCAACTCCATGTGGACTGTGTACCAATTTCCAGTGGAGATGCTGTTACTTTTGAT | 211 |
| hsa-mir-195-prec | AGCTTCCCTGGCTCTAGCAGCACAGAAATATTGGCACAGGGAAGCGAGTCTGCCAATATTGGCTGTGCTGCTCCAGGCAGGGTGGTG | 212 |
| hsa-mir-195-prec | TAGCAGCACAGAAATATTGGCACAGGGAAGCGAGTCTGCCAATATTGGCTGTGCTGCT | 213 |
| hsa-mir-196-1-prec | CTAGAGCTTGAATTGGAACTGCTGAGTGAATTAGGTAGTTTCATGTTGTTGGGCCTGGGTTTCTGAACACAACAACATTAAACCACCCGATTCACGGCAGTTACTGCTCC | 214 |
| hsa-mir-196-1-prec | GTGAATTAGGTAGTTTCATGTTGTTGGGCCTGGGTTTCTGAACACAACAACATTAAACCACCCGATTCAC | 215 |
| hsa-mir-196-2-prec | TGCTCGCTCAGCTGATCTGTGGCTTAGGTAGTTTCATGTTGTTGGGATTGAGTTTTGAACTCGGCAACAAGAAACTGCCTGAGTTACATCAGTCGGTTTTCGTCGAGGGC | 216 |
| hsa-mir-196-prec | GTGAATTAGGTAGTTTCATGTTGTTGGGCCTGGGTTTCTGAACACAACAACATTAAACCACCCGATTCAC | 217 |
| hsa-mir-197-prec | GGCTGTGCCGGGTAGAGAGGGCAGTGGGAGGTAAGAGCTCTTCACCCTTCACCACCTTCTCCACCCAGCATGGCC | 218 |
| hsa-mir-198-prec | TCATTGGTCCAGAGGGGAGATAGGTTCCTGTGATTTTCCTTCTTCTCTATAGAATAAATGA | 219 |
| hsa-mir-199a-1-prec | GCCAACCCAGTGTTCAGACTACCTGTTCAGGAGGCTCTCAATGTGTACAGTAGTCTGCACATTGGTTAGGC | 220 |
| hsa-mir-199a-2-prec | AGGAAGCTTCTGGAGATCCTGCTCCGTCGCCCCAGTGTTCAGACTACCTGTTCAGGACAATGCCGTTGTACAGTAGTCTGCACATTGGTTAGACTGGGCAAGGGAGAGCA | 221 |
| hsa-mir-199b-prec | CCAGAGGACACCTCCACTCCGTCTACCCAGTGTTTAGACTATCTGTTCAGGACTCCCAAATTGTACAGTAGTCTGCACATTGGTTAGGCTGGGCTGGGTAGACCCTCGG | 222 |
| hsa-mir-199s-prec | GCCAACCCAGTGTTCAGACTACCTGTTCAGGAGGCTCTCAATGTGTACAGTAGTCTGCACATTGGTTAGGC | 223 |
| hsa-mir-200a-prec | GCCGTGGCCATCTTACTGGGCAGCATTGGATGGAGTCAGGTCTCTAATACTGCCTGGTAATGATGACGGC | 224 |

TABLE 1-continued

Human miR Gene Product Sequences

| Name | Precursor Sequence (5' to 3')* | SEQ ID NO. |
|---|---|---|
| hsa-mir-200b-prec | CCAGCTCGGGCAGCCGTGGCCATCTTACTGGGCAGCA TTGGATGGAGTCAGGT<u>CTCTAATACTGCCTGGTAATG ATG</u>ACGGCGGAGCCCTGCACG | 225 |
| hsa-mir-202-prec | GTTCCTTTTTCCTATGCATATACTTCTTTGAGGATCT GGCCTAA<u>AGAGGTATAGGGCATGGGAAGATGGAGC</u> | 226 |
| hsa-mir-203-prec | GTGTTGGGGACTCGCGCGCTGGGTCCAGTGGTTCTTA ACAGTTCAACAGTTCTGTAGCGCAATT<u>GTGAAATGTT TAGGACCACTAG</u>ACCCGGCGGGCGCGGCGACAGCGA | 227 |
| hsa-mir-204-prec | GGCTACAGTCTTTCTTCATGTGACTCGTGGAC<u>TTCCC TTTGTCATCCTATGCCTGAGAATATATGAAGGAGGCT GGGAAGG</u>CAAAGGGACGTTCAATTGTCATCACTGGC | 228 |
| hsa-mir-205-prec | AAAGATCCTCAGACAATCCATGTGCTTCTCTTG<u>TCCT TCATTCCACCGGAGTCTGTCTCATACCCAACCAGATT</u> TCAGTGGAGTGAAGTTCAGGAGGCATGGAGCTGACA | 229 |
| hsa-mir-206-prec | TGCTTCCCGAGGCCACATGCTTCTTTATATCCCCATA TGGATTACTTTGCTA<u>TGGAATGTAAGGAAGTGTGTGG</u> TTTCGGCAAGTG | 230 |
| hsa-mir-206-prec | AGGCCACATGCTTCTTTATATCCCCATATGGATTACT TTGCTA<u>TGGAATGTAAGGAAGTGTGTGG</u>TTTT | 231 |
| hsa-mir-208-prec | TGACGGGCGAGCTTTTGGCCCGGGTTATACCTGATGC TCACGT<u>ATAAGACGAGCAAAAAGCTTGTTGGTCA</u> | 232 |
| hsa-mir-210-prec | ACCCGGCAGTGCCTCCAGGCGCAGGGCAGCCCCTGCC CACCGCACACTGCGCTGCCCCAGACCCA<u>CTGTGCGTG TGACAGCGGCTG</u>ATCTGTGCCTGGGCAGCGCGACCC | 233 |
| hsa-mir-211-prec | TCACCTGGCCATGTGACTTGTGGGC<u>TTCCCTTTGTCA TCCTTCGCC</u>TAGGGCTCTGAGCAGGGCAGGGACAGCA AAGGGGTGCTCAGTTGTCACTTCCCACAGCACGGAG | 234 |
| hsa-mir-212-prec | CGGGGCACCCCGCCCGGACAGCGCGCCGGCACCTTGG CTCTAGACTGCTTACTGCCCGGGCCGCCCTCAGT<u>AAC AGTCTCCAGTCACGGCC</u>ACCGACGCCTGGCCCCGCC | 235 |
| hsa-mir-213-prec | CCTGTGCAGAGATTATTTTTTAAAAGGTCACAATC<u>AA CATTCATTGCTGTCGGTGGGTT</u>GAACTGTGTGGACAA GCTCACTGAACAATGAATGCAACTGTGGCCCCGCTT | 236 |
| hsa-mir-213-prec-LIM | GAGTTTTGAGGTTGCTTCAGTGAACATTCAACGCTGT CGGTGAGTTTGGAATTAAAATCAAA<u>ACCATCGACCGT TGATTGTACC</u>CTATGGCTAACCATCATCTACTCC | 237 |
| hsa-mir-214-prec | GGCCTGGCTGGACAGAGTTGTCATGTGTCTGCCTGTC TACACTTGCTGTGCAGAACATCCGCTCACCTGT<u>ACAG CAGGCACAGACAGGCAGT</u>CACATGACAACCCAGCCT | 238 |
| hsa-mir-215-prec | ATCATTCAGAAATGGTATACAGGAAA<u>ATGACCTATGA ATTGACAGAC</u>AATATAGCTGAGTTTGTCTGTCATTTC TTTAGGCCAATATTCTGTATGACTGTGCTACTTCAA | 239 |
| hsa-mir-216-prec | GATGGCTGTGAGTTGGCT<u>TAATCTCAGCTGGCAACTG TG</u>AGATGTTCATACAATCCCTCACAGTGGTCTCTGGG ATTATGCTAAACAGAGCAATTTCCTAGCCCTCACGA | 240 |
| hsa-mir-217-prec | AGTATAATTATTACATAGTTTTTGATGTCGCAGA<u>TAC TGCATCAGGAACTGATTGGATA</u>AGAATCAGTCACCAT CAGTTCCTAATGCATTGCCTTCAGCATCTAAACAAG | 241 |
| hsa-mir-218-1-prec | GTGATAATGTAGCGAGATTTTCT<u>GTTGTGCTTGATCT AACCATGTGG</u>TTGCGAGGTATGAGTAAAACATGGTTC CGTCAAGCACCATGGAACGTCACGCAGCTTTCTACA | 242 |
| hsa-mir-218-2-prec | GACCAGTCGCTGCGGGGCTTTCCT<u>TTGTGCTTGATCT AACCATGTGG</u>TGGAACGATGGAAACGGAACATGGTTC TGTCAAGCACCGCGGAAAGCACCGTGCTCTCCTGCA | 243 |

TABLE 1-continued

Human miR Gene Product Sequences

| Name | Precursor Sequence (5' to 3')* | SEQ ID NO. |
|---|---|---|
| hsa-mir-219-prec | CCGCCCCGGGCCGCGGCTCCTGATTGTCCAAACGCAATTCTCGAGTCTATGGCTCCGGCCGAGAGTTGAGTCTGGACGTCCCGAGCCGCCGCCCCCAAACCTCGAGCGGG | 244 |
| hsa-mir-220-prec | GACAGTGTGGCATTGTAGGGCTCCACACCGTATCTGACACTTTGGGCGAGGGCACCATGCTGAAGGTGTTCATGATGCGGTCTGGGAACTCCTCACGGATCYITACTGATG | 245 |
| hsa-mir-221-prec | TGAACATCCAGGTCTGGGGCATGAACCTGGCATACAATGTAGATTTCTGTGTTCGTTAGGCAACAGCTACATTGTCTGCTGGGTTTCAGGCTACCTGGAAACATGTTCTC | 246 |
| hsa-mir-222-prec | GCTGCTGGAAGGTGTAGGTACCCTCAATGGCTCAGTAGCCAGTGTAGATCCTGTCTTTCGTAATCAGCAGCTACATCTGGCTACTGGGTCTCTGATGGCATCTTCTAGCT | 247 |
| hsa-mir-223-prec | CCTGGCCTCCTGCAGTGCCACGCTCCGTGTATTTGACAAGCTGAGTTGGACACTCCATGTGGTAGAGTGTCAGTTGTCAAATACCCCAAGTGCGGCACATGCTTACCAG | 248 |
| hsa-mir-224-prec | GGGCTTTCAAGTCACTAGTGGTTCCGTTTAGTAGATGATTGTGCATTGTTTCAAAATGGTGCCCTAGTGACTACAAAGCCC | 249 |
| hsA-mir-29b-1 = 102-prec1 | CTTCTGGAAGCTGGTTTCACATGGTGGCTTAGATTTTTCCATCTTTGTATCTAGCACCATTTGAAATCAGTGTTTTAGGAG | 250 |
| hsA-mir-29b-2 = 102prec7.1 = 7.2 | CTTCAGGAAGCTGGTTTCATATGGTGGTTTAGATTTAAATAGTGATTGTCTAGCACCATTTGAAATCAGTGTTCTTGGGGG | 251 |
| hsA-mir-29b-3 = 102prec7.1 = 7.2 | CTTCAGGAAGCTGGTTTCATATGGTGGTTTAGATTTAAATAGTGATTGTCTAGCACCATTTGAAATCAGTGTTCTTGGGGG | 252 |
| hsa-mir-30* = mir-097-prec-6 | GTGAGCGACTGTAAACATCCTCGACTGGAAGCTGTGAAGCCACAGATGGGCTTTCAGTCGGATGTTTGCAGCTGCCTACT | 253 |
| mir-033b | ACCAAGTTTCAGTTCATGTAAACATCCTACACTCAGCTGTAATACATGGATTGGCTGGGAGGTGGATGTTTACTTCAGCTGACTTGGA | 254 |
| mir-101-precursor-9 = mir-101-3 | TGCCCTGGCTCAGTTATCACAGTGCTGATGCTGTCTATTCTAAAGGTACAGTACTGTGATAACTGAAGGATGGCA | 255 |
| mir-108-1-small | ACACTGCAAGAACAATAAGGATTTTTAGGGGCATTATGACTGAGTCAGAAAACACAGCTGCCCCTGAAAGTCCCTCATTTTTCTTGCTGT | 256 |
| mir-108-2-small | ACTGCAAGAGCAATAAGGATTTTTAGGGGCATTATGATAGTGGAATGGAAACACATCTGCCCCCAAAAGTCCCTCATTTT | 257 |
| mir-123-prec = mir-126-prec | CGCTGGCGACGGGACATTATTACTTTTGGTACGCGCTGTGACACTTCAAACTCGTACCGTGAGTAATAATGCGCCGTCCACGGCA | 258 |
| mir-123-prec = mir-126-prec | ACATTATTACTTTTGGTACGCGCTGTGACACTTCAAACTCGTACCGTGAGTAATAATGCGC | 259 |
| mir-129-1-prec | TGGATCTTTTTGCGGTCTGGGCTTGCTGTTCCTCTCAACAGTAGTCAGGAAGCCCTTACCCCAAAAAGTATCTA | 260 |
| mir-129-small-2 = 129b? | TGCCCTTCGCGAATCTTTTTGCGGTCTGGGCTTGCTGTACATAACTCAATAGCCGGAAGCCCTTACCCCAAAAAGCATTTGCGGAGGGCG | 261 |
| mir-133b-small | GCCCCTGCTCTGGCTGGTCAAACGGAACCAAGTCCGTCTTCCTGAGAGGTTTGGTCCCCTTCAACCAGCTACAGCAGGG | 262 |

TABLE 1-continued

Human miR Gene Product Sequences

| Name | Precursor Sequence (5' to 3')* | SEQ ID NO. |
| --- | --- | --- |
| mir-135-small-2 | AGATAAATTCACTCTAGTGCTTTATGGCTTTTTATTCCTATGTGATAGTAATAAAGTCTCATGTAGGGATGGAAGCCATGAAATACATTGTGAAAAATCA | 263 |
| mir-148b-small | AAGCACGATTAGCATTTGAGGTGAAGTTCTGTTATACACTCAGGCTGTGGCTCTCTGAAAGTCAGTGCAT | 264 |
| mir-151-prec | CCTGTCCTCAAGGAGCTTCAGTCTAGTAGGGGATGAGACATACTAGACTGTGAGCTCCTCGAGGGCAGG | 265 |
| mir-155-prec(BIC) | CTGTTAATGCTAATCGTGATAGGGGTTTTTGCCTCCAACTGACTCCTACATATTAGCATTAACAG | 266 |
| mir-156 = mir-157 = overlap mir-141 | CCTAACACTGTCTGGTAAAGATGGCTCCCGGGTGGGTTCTCTCGGCAGTAACCTTCAGGGAGCCCTGAAGACCATGGAGGAC | 267 |
| mir-158-small = mir-192 | GCCGAGACCGAGTGCACAGGGCTCTGACCTATGAATTGACAGCCAGTGCTCTCGTCTCCCCTCTGGCTGCCAATTCCATAGGTCACAGGTATGTTCGCCTCAATGCCAGC | 268 |
| mir-159-1-small | TCCCGCCCCCTGTAACAGCAACTCCATGTGGAAGTGCCCACTGGTTCCAGTGGGGCTGCTGTTATCTGGGGCGAGGGCCA | 269 |
| mir-161-small | AAAGCTGGGTTGAGAGGGCGAAAAAGGATGAGGTGACTGGTCTGGGCTACGCTATGCTGCGGCGCTCGGG | 270 |
| mir-163-1b-small | CATTGGCCTCCTAAGCCAGGGATTGTGGGTTCGAGTCCCACCCGGGGTAAAGAAAGGCCGAATT | 271 |
| mir-163-3-small | CCTAAGCCAGGGATTGTGGGTTCGAGTCCCACCTGGGGTAGAGGTGAAAGTTCCTTTTACGGAATTTTTT | 272 |
| mir-175-small = mir-224 | GGGCTTTCAAGTCACTAGTGGTTCCGTTTAGTAGATGATTGTGCATTGTTTCAAAATGGTGCCCTAGTGACTACAAAGCCC | 273 |
| mir-177-small | ACGCAAGTGTCCTAAGGTGAGCTCAGGGAGCACAGAAACCTCCAGTGGAACAGAAGGGCAAAAGCTCATT | 274 |
| mir-180-small | CATGTGTCACTTTCAGGTGGAGTTTCAAGAGTCCCTTCCTGGTTCACCGTCTCCTTTGCTCTTCCACAAC | 275 |
| mir-187-prec | GGTCGGGCTCACCATGACACAGTGTGAGACTCGGGCTACAACACAGGACCCGGGGCGCTGCTCTGACCCCTCGTGTCTTGTGTTGCAGCCGGAGGGACGCAGGTCCGCA | 276 |
| mir-188-prec | TGCTCCCTCTCTCACATCCCTTGCATGGTGGAGGGTGAGCTTTCTGAAAACCCCTCCCACATGCAGGGTTTGCAGGATGGCGAGCC | 277 |
| mir-190-prec | TGCAGGCCTCTGTGTGATATGTTTGATATATTAGGTTGTTATTTAATCCAACTATATATCAAACATATTCCTACAGTGTCTTGCC | 278 |
| mir-197-2 | GTGCATGTGTATGTATGTGTGCATGTGCATGTGTATGTGTATGAGTGCATGCGTGTGTGC | 279 |
| mir-197-prec | GGCTGTGCCGGGTAGAGAGGGCAGTGGGAGGTAAGAGCTCTTCACCCTTCACCACCTTCTCCACCCAGCATGGCC | 280 |
| mir-202-prec | GTTCCTTTTTCCTATGCATATACTTCTTTGAGGATCTGGCCTAAAGAGGTATAGGGCATGGGAAGATGGAGC | 281 |
| mir-294-1 (chr16) | CAATCTTCCTTTATCATGGTATTGATTTTTCAGTGCTTCCCTTTTGTGTGAGAGAAGATA | 282 |
| mir-hes1 | ATGGAGCTGCTCACCCTGTGGGCCTCAAATGTGGAGGAACTATTCTGATGTCCAAGTGGAAAGTGCTGCGACATTTGAGCGTCACCGGTGACGCCCATATCA | 283 |

TABLE 1-continued

Human miR Gene Product Sequences

| Name | Precursor Sequence (5' to 3')* | SEQ ID NO. |
|---|---|---|
| mir-hes2 | GCATCCCCTCAGCCTGTGGCACTCAAACTGTGGGGGC ACTTTCTGCTCTCTGGTGAAAGTGCCGCCATCTTTTG AGTGTTACCGCTTGAGAAGACTCAACC | 284 |
| mir-hes3 | CGAGGAGCTCATACTGGGATACTCAAAATGGGGCGC TTTCCTTTTTGTCTGTTACTGGGAAGTGCTTCGATTT TGGGGTGTCCCTGTTTGAGTAGGGCATC | 285 |
| hsa-mir-29b-1 | CTTCAGGAAGCTGGTTTCATATGGTGGTTTAGATTTA AATAGTGATTGTCTAGCACCATTTGAAATCAGTGTTC TTGGGGG | 286 |

*An underlined sequence within a precursor sequence represents a processed miR transcript. All sequences are human.

The level of at least one miR gene product can be measured in cells of a biological sample obtained from the subject. For example, a tissue sample can be removed from a subject suspected of having breast cancer associated with by conventional biopsy techniques. In another example, a blood sample can be removed from the subject, and white blood cells can be isolated for DNA extraction by standard techniques. The blood or tissue sample is preferably obtained from the subject prior to initiation of radiotherapy, chemotherapy or other therapeutic treatment. A corresponding control tissue or blood sample can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR gene product produced from a given miR gene in cells from the subject's sample can be compared to the corresponding miR gene product levels from cells of the control sample.

An alteration (i.e., an increase or decrease) in the level of a miR gene product in the sample obtained from the subject, relative to the level of a corresponding miR gene product in a control sample, is indicative of the presence of breast cancer in the subject. In one embodiment, the level of the at least one miR gene product in the test sample is greater than the level of the corresponding miR gene product in the control sample (i.e., expression of the miR gene product is "up-regulated"). As used herein, expression of an miR gene product is "up-regulated" when the amount of miR gene product in a cell or tissue sample from a subject is greater than the amount the same gene product in a control cell or tissue sample. In another embodiment, the level of the at least one miR gene product in the test sample is less than the level of the corresponding miR gene product in the control sample (i.e., expression of the miR gene product is "down-regulated"). As used herein, expression of an miR gene is "down-regulated" when the amount of miR gene product produced from that gene in a cell or tissue sample from a subject is less than the amount produced from the same gene in a control cell or tissue sample. The relative miR gene expression in the control and normal samples can be determined with respect to one or more RNA expression standards. The standards can comprise, for example, a zero miR gene expression level, the miR gene expression level in a standard cell line, or the average level of miR gene expression previously obtained for a population of normal human controls.

The level of a miR gene product in a sample can be measured using any technique that is suitable for detecting RNA expression levels in a biological sample. Suitable techniques for determining RNA expression levels in cells from a biological sample (e.g., Northern blot analysis, RT-PCR, in situ hybridization) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, *Molecular Cloning: A Laboratory Manual*, J. Sambrook et al., eds., 2nd edition, Cold Spring Harbor Laboratory Press, 1989, Chapter 7, the entire disclosure of which is incorporated by reference.

Suitable probes for Northern blot hybridization of a given miR gene product can be produced from the nucleic acid sequences provided in Table 1. Methods for preparation of labeled DNA and RNA probes, and the conditions for hybridization thereof to target nucleotide sequences, are described in *Molecular Cloning: A Laboratory Manual*, J. Sambrook et al., eds., 2nd edition, Cold Spring Harbor Laboratory Press, 1989, Chapters 10 and 11 the disclosures of which are incorporated herein by reference.

For example, the nucleic acid probe can be labeled with, e.g., a radionuclide, such as $^{3}$H, $^{32}$P, $^{33}$P, $^{14}$C, or $^{35}$S; a heavy metal; or a ligand capable of functioning as a specific binding pair member for a labeled ligand (e.g., biotin, avidin or an antibody), a fluorescent molecule, a chemiluminescent molecule, an enzyme or the like.

Probes can be labeled to high specific activity by either the nick translation method of Rigby et al. (1977). *J. Mol. Biol.* 113:237-251 or by the random priming method of Fienberg et al. (1983), *Anal. Biochem.* 132:6-13, the entire disclosures of which are incorporated herein by reference. The latter is the method of choice for synthesizing $^{32}$P-labeled probes of high specific activity from single-stranded DNA or from RNA templates. For example, by replacing preexisting nucleotides with highly radioactive nucleotides according to the nick translation method, it is possible to prepare $^{32}$P-labeled nucleic acid probes with a specific activity well in excess of $10^{8}$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR gene product can be produced from the nucleic acid sequences provided in Table 1, as described above.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). The methods for quantitative RT-PCR and variations thereof are within the skill in the art.

In some instances, it may be desirable to simultaneously determine the expression level of a plurality of different miR gene products in a sample. In other instances, it may be desirable to determine the expression level of the transcripts of all known miR genes correlated with a cancer. Assessing cancer-specific expression levels for hundreds of miR genes is time consuming and requires a large amount of total RNA (at least 20 μg for each Northern blot) and autoradiographic techniques that require radioactive isotopes.

To overcome these limitations, an oligolibrary, in microchip format (i.e., a microarray), may be constructed containing a set of probe oligodeoxynucleotides that are specific for a set of miR genes. Using such a microarray, the expression level of multiple microRNAs in a biological sample can be determined by reverse transcribing the RNAs to generate a set of target oligodeoxynucleotides, and hybridizing them to probe oligodeoxynucleotides on the microarray to generate a hybridization, or expression, profile. The hybridization profile of the test sample can then be compared to that of a control sample to determine which microRNAs have an altered expression level in breast cancer cells. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for an miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from breast cancer tissue, and within breast cancer tissue, different prognosis states (good or poor long term survival prospects, for example) may be determined. By comparing expression profiles of breast cancer tissue in different states, information regarding which genes are important (including both up- and down-regulation of genes) in each of these states is obtained. The identification of sequences that are differentially expressed in breast cancer tissue or normal breast tissue, as well as differential expression resulting in different prognostic outcomes, allows the use of this information in a number of ways. For example, a particular treatment regime may be evaluated (e.g., to determine whether a chemotherapeutic drug act to improve the long-term prognosis in a particular patient). Similarly, diagnosis may be done or confirmed by comparing patient samples with the known expression profiles. Furthermore, these gene expression profiles (or individual genes) allow screening of drug candidates that suppress the breast cancer expression profile or convert a poor prognosis profile to a better prognosis profile.

Accordingly, the invention provides methods of diagnosing whether a subject has, or is at risk for developing, breast cancer, comprising reverse transcribing RNA from a test sample obtained from the subject to provide a set of target oligo-deoxynucleotides, hybridizing the target oligo-deoxynucleotides to a microarray comprising miRNA-specific probe oligonucleotides to provide a hybridization profile for the test sample, and comparing the test sample hybridization profile to a hybridization profile generated from a control sample, wherein an alteration in the signal of at least one miRNA is indicative of the subject either having, or being at risk for developing, breast cancer. In one embodiment, the microarray comprises miRNA-specific probe oligonucleotides for a substantial portion of the human miRNome. In a particular embodiment, the microarray comprises miRNA-specific probe oligo-nucleotides for one or more miRNAs selected from the group consisting of miR-125b, miR-145, miR-21, miR-155, miR-10b, miR-009-1 (miR131-1), miR-34 (miR-170), miR-102 (miR-29b), miR-123 (miR-126), miR-140-as, miR-125a, miR-125b-1, miR-125b-2, miR-194, miR-204, miR-213, let-7a-2, let-7a-3, let-7d (let-7d-v1), let-7f-2, let-71 (let-7d-v2), miR-101-1, miR-122a, miR-128b, miR-136, miR-143, miR-149, miR-191, miR-196-1, miR-196-2, miR-202, miR-203, miR-206, miR-210 and combinations thereof. In a further embodiment, the at least one miR gene product is selected from the group consisting of miR-125b, miR-145, miR-21, miR-155, miR-10b and combinations thereof.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miR5, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 µg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

In addition to use for quantitative expression level assays of specific miR5, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a cancer (e.g., breast cancer) is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal, i.e., noncancerous, control sample. An alteration in the signal is indicative of the presence of the cancer in the subject.

Other techniques for measuring miR gene expression are also within the skill in the art, and include various techniques for measuring rates of RNA transcription and degradation.

The invention also provides methods of diagnosing a breast cancer associated with one or more prognostic markers, comprising measuring the level of at least one miR gene product in a breast cancer test sample from a subject and comparing the level of the at least one miR gene product in the breast cancer test sample to the level of a corresponding miR gene product in a control sample. An alteration (e.g., an increase, a decrease) in the signal of at least one miRNA in the test sample relative to the control sample is indicative of the subject either having, or being at risk for developing, breast cancer associated with the one or more prognostic markers.

The breast cancer can be associated with one or more prognostic markers or features, including, a marker associated with an adverse (i.e., negative) prognosis, or a marker associated with a good (i.e., positive) prognosis. In certain embodiments, the breast cancer that is diagnosed using the methods described herein is associated with one or more adverse prognostic features selected from the group consisting of estrogen receptor expression, progesterone receptor expression, positive lymph node metastasis, high proliferative index, detectable p53 expression, advanced tumor stage, and high vascular invasion. Particular microRNAs whose expression is altered in breast cancer cells associated with each of these prognostic markers are described herein (see, for example, Example 3 and FIG. 4). In one embodiment, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Without wishing to be bound by any one theory, it is believed that alterations in the level of one or more miR gene products in cells can result in the deregulation of one or more intended targets for these miR5, which can lead to the formation of breast cancer. Therefore, altering the level of the miR gene product (e.g., by decreasing the level of a miR that is up-regulated in breast cancer cells, by increasing the level of a miR that is don-regulated in cancer cells) may successfully treat the breast cancer. Examples of putative gene targets for miRNAs that are deregulated in breast cancer tissues are described herein (see, e.g., Example 2 and Table 4).

Accordingly, the present invention encompasses methods of treating breast cancer in a subject, wherein at least one miR gene product is de-regulated (e.g., down-regulated, up-regulated) in the cancer cells of the subject. When the at least one isolated miR gene product is down-regulated in the breast cancer cells, the method comprises administering an effective amount of the at least one isolated miR gene product, provided that the miR gene is not miR15 or miR16, such that proliferation of cancer cells in the subject is inhibited. When the at least one isolated miR gene product is up-regulated in the cancer cells, the method comprises administering to the subject an effective amount of at least one compound for inhibiting expression of the at least one miR gene, referred to herein as miR gene expression inhibition compounds, such that proliferation of breast cancer cells is inhibited.

The terms "treat", "treating" and "treatment", as used herein, refer to ameliorating symptoms associated with a disease or condition, for example, breast cancer, including preventing or delaying the onset of the disease symptoms, and/or lessening the severity or frequency of symptoms of the disease or condition. The terms "subject" and "individual" are defined herein to include animals, such as mammals, including but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR gene product is an amount sufficient to inhibit proliferation of a cancer cell in a subject suffering from breast cancer. One skilled in the art can readily determine an effective amount of an miR gene product to be administered to a given subject, by taking into account factors, such as the size and weight of the subject; the extent of disease penetration; the age, health and sex of the subject; the route of administration; and whether the administration is regional or systemic.

For example, an effective amount of an isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of an isolated miR gene product can also be based on the approximate or estimated body weight of a subject to be treated. Preferably, such effective amounts are administered parenterally or enterally, as described herein. For example, an effective amount of the isolated miR gene product is administered to a subject can range from about 5-3000 micrograms/kg of body weight, from about 700-1,000 micrograms/kg of body weight, or greater than about 1000 micrograms/kg of body weight.

One skilled in the art can also readily determine an appropriate dosage regimen for the administration of an isolated miR gene product to a given subject. For example, an miR gene product can be administered to the subject once (e.g., as a single injection or deposition). Alternatively, an miR gene product can be administered once or twice daily to a subject for a period of from about three to about twenty-eight days, more particularly from about seven to about ten days. In a particular dosage regimen, an miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one which is synthesized, or altered or removed from the natural state through human intervention. For example, a synthetic miR gene product, or an miR gene product partially or completely separated from the coexisting materials of its natural state, is considered to be "isolated." An isolated miR gene product can exist in substantially-purified form, or can exist in a cell into which the miR gene product has been delivered. Thus, an miR gene product which is deliberately delivered to, or expressed in, a cell is considered an "isolated" miR gene product. An miR gene product produced inside a cell from an miR precursor molecule is also considered to be "isolated" molecule.

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cancer cells.

The miR gene products that are expressed from recombinant plasmids can be isolated from cultured cell expression systems by standard techniques. The miR gene products which are expressed from recombinant plasmids can also be delivered to, and expressed directly in, the cancer cells. The use of recombinant plasmids to deliver the miR gene products to cancer cells is discussed in more detail below.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which are incorporated herein by reference) and the *E. coli* RNAse III system (e.g., as described in U.S. Published Patent Application No. 2004/0014113 to Yang et al., the entire disclosure of which are incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol,* 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein. "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the miR gene products to cancer cells is discussed in more detail below.

The recombinant viral vectors of the invention comprise sequences encoding the miR gene products and any suitable promoter for expressing the RNA sequences. Suitable promoters include, for example, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), *J. Virol.* 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), *Gene Therap.* 2:301-310; Eglitis (1988), *Biotechniques* 6:608-614; Miller (1990), *Hum. Gene Therap.* 1:5-14; and Anderson (1998), *Nature* 392:25-30, the entire disclosures of which are incorporated herein by reference.

Particularly suitable viral vectors are those derived from AV and AAV. A suitable AV vector for expressing the miR gene products, a method for constructing the recombinant AV vector, and a method for delivering the vector into target cells, are described in Xia et al. (2002), *Nat. Biotech.* 20:1006-1010, the entire disclosure of which is incorporated herein by reference. Suitable AAV vectors for expressing the miR gene products, methods for constructing the recombinant AAV vector, and methods for delivering the vectors into target cells are described in Samulski et al. (1987), *J. Virol.* 61:3096-3101; Fisher et al. (1996), *J. Virol.*, 70:520-532; Samulski et al. (1989), *J. Virol.* 63:3822-3826; U.S. Pat. Nos. 5,252,479; 5,139,941; International Patent Application No. WO 94/13788; and International Patent Application No. WO 93/24641, the entire disclosures of which are incorporated herein by reference. In one embodiment, the miR gene products are expressed from a single recombinant AAV vector comprising the CMV intermediate early promoter.

In a certain embodiment, a recombinant AAV viral vector of the invention comprises a nucleic acid sequence encoding an miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In other embodiments of the treatment methods of the invention, an effective amount of at least one compound which inhibits miR expression can also be administered to the subject. As used herein, "inhibiting miR expression" means that the production of the active, mature form of miR gene product after treatment is less than the amount produced prior to treatment. One skilled in the art can readily determine whether miR expression has been inhibited in a cancer cell, using for example the techniques for determining miR transcript level discussed above for the diagnostic method. Inhibition can occur at the level of gene expression (i.e., by inhibiting transcription of a miR gene encoding the miR gene product) or at the level of processing (e.g., by inhibiting processing of a miR precursor into a mature, active miR).

As used herein, an "effective amount" of a compound that inhibits miR expression is an amount sufficient to inhibit proliferation of a cancer cell in a subject suffering from a cancer associated with a cancer-associated chromosomal feature. One skilled in the art can readily determine an effective amount of an miR expression-inhibiting compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibiting compound can be based on the approximate weight of a tumor mass to be treated. The approximate weight of a tumor mass can be determined by calculating the approximate volume of the mass, wherein one cubic centimeter of volume is roughly equivalent to one gram. An effective amount based on the weight of a tumor mass can be between about 10-500 micrograms/gram of tumor mass, at least about 10 micrograms/gram of tumor mass, at least about 60 micrograms/gram of tumor mass, and at least about 100 micrograms/gram of tumor mass.

An effective amount of a compound that inhibits miR expression can also be based on the approximate or estimated body weight of a subject to be treated. Such effective amounts are administered parenterally or enterally, among others, as described herein. For example, an effective amount of the expression-inhibiting compound administered to a subject can range from about 5-3000 micrograms/kg of body weight, from about 700-1000 micrograms/kg of body weight, or it can be greater than about 1000 micrograms/kg of body weight.

One skilled in the art can also readily determine an appropriate dosage regimen for administering a compound that inhibits miR expression to a given subject. For example, an expression-inhibiting compound can be administered to the subject once (e.g., as a single injection or deposition). Alternatively, an expression-inhibiting compound can be administered once or twice-daily to a subject for a period of from about three to about twenty-eight days, more preferably from about seven to about ten days. In a particular dosage regimen, an expression-inhibiting compound is administered once a day for seven days. Where a dosage regimen comprises multiple administrations, it is understood that the effective amount of the expression-inhibiting compound administered to the subject can comprise the total amount of compound administered over the entire dosage regimen.

Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR gene product and destroy or induce the destruction of the target miR gene product.

For example, expression of a given miR gene can be inhibited by inducing RNA interference of the miR gene with an isolated double-stranded RNA ("dsRNA") molecule which has at least 90%, for example at least 95%, at least 98%, at least 99% or 100%, sequence homology with at least a portion of the miR gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence which is substantially identical to a nucleic acid sequence contained within the target miR gene product.

As used herein, a nucleic acid sequence in an siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3%-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA or RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, PNA) that generally comprise a nucleic acid sequence complementary to a contiguous nucleic acid sequence in an miR gene product. The antisense nucleic acid can comprise a nucleic acid sequence that is 50-100% complementary, 75-100% complementary, or 95-100% complementary to a contiguous nucleic acid sequence in an miR gene product. Nucleic acid sequences for the miR gene products are provided in Table 1. Without wishing to be bound by any theory, it is believed that the antisense nucleic acids activate RNase H or another cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated miR gene products. Exemplary methods for producing and testing are within the skill in the art; see, e.g., Stein and Cheng (1993), *Science* 261:1004 and U.S. Pat. No. 5,849,902 to Woolf et al., the entire disclosures of which are incorporated herein by reference.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of an miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in an miR gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), *Nucl. Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are incorporated herein by reference.

Administration of at least one miR gene product, or at least one compound for inhibiting miR expression, will inhibit the proliferation of cancer cells in a subject who has a cancer associated with a cancer-associated chromosomal feature. As used herein, to "inhibit the proliferation of a cancer cell" means to kill the cell, or permanently or temporarily arrest or slow the growth of the cell. Inhibition of cancer cell proliferation can be inferred if the number of such cells in the subject remains constant or decreases after administration of the miR gene products or miR gene expression-inhibiting compounds. An inhibition of cancer cell proliferation can also be inferred if the absolute number of such cells increases, but the rate of tumor growth decreases.

The number of cancer cells in a subject's body can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The size of a tumor mass can be ascertained by direct visual observation, or by diagnostic imaging methods, such as X-ray, magnetic resonance imaging, ultrasound, and scintigraphy. Diagnostic imaging methods used to ascertain size of the tumor mass can be employed with or without contrast agents, as is known in the art. The size of a tumor mass can also be ascertained by physical means, such as palpation of the tissue mass or measurement of the tissue mass with a measuring instrument, such as a caliper.

The miR gene products or miR gene expression-inhibiting compounds can be administered to a subject by any means suitable for delivering these compounds to cancer cells of the subject. For example, the miR gene products or miR expression inhibiting compounds can be administered by methods suitable to transfect cells of the subject with these compounds, or with nucleic acids comprising sequences encoding these compounds. In one embodiment, the cells are transfected with a plasmid or viral vector comprising sequences encoding at least one miR gene product or miR gene expression inhibiting compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per 1 cells can be used.

An miR gene product or miR gene expression inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable-administration routes are injection, infusion and direct injection into the tumor.

In the present methods, an miR gene product or miR gene product expression inhibiting compound can be administered to the subject either as naked RNA, in combination with a delivery reagent, or as a nucleic acid (e.g., a recombinant plasmid or viral vector) comprising sequences that express the miR gene product or expression inhibiting compound. Suitable delivery reagents include, e.g., the Mirus Transit TKO lipophilic reagent; lipofectin; lipofectamine; cellfectin; polycations (e.g., polylysine), and liposomes.

Recombinant plasmids and viral vectors comprising sequences that express the miR gene products or miR gene expression inhibiting compounds, and techniques for delivering such plasmids and vectors to cancer cells, are discussed herein.

In a particular embodiment, liposomes are used to deliver an miR gene product or miR gene expression-inhibiting compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands which bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiet is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers, such as polyacrylamide or poly N-vinyl pyrrolidone;

linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH$_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example solid tumors, will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression inhibition compounds (or nucleic acids comprising sequences encoding them) to tumor cells.

The miR gene products or miR gene expression inhibition compounds can be formulated as pharmaceutical compositions, sometimes called "medicaments," prior to administering them to a subject, according to techniques known in the art. Accordingly, the invention encompasses pharmaceutical compositions for treating breast cancer. In one embodiment, the pharmaceutical compositions comprise at least one isolated miR gene product and a pharmaceutically-acceptable carrier. In a particular embodiment, the at least one miR gene product corresponds to a miR gene product that has a decreased level of expression in breast cancer cells relative to suitable control cells. In certain embodiments the isolated miR gene product is selected from the group consisting of miR-145, miR-10b, miR-123 (miR-126), miR-140-as, miR-125a, miR-125b-1, miR-125b-2, miR-194, miR-204, let-7a-2, let-7a-3, let-7d (let-7d-v1), let-7f-2, miR-101-1, miR-143 and combinations thereof.

In other embodiments, the pharmaceutical compositions of the invention comprise at least one miR expression inhibition compound. In a particular embodiment, the at least one miR gene expression inhibition compound is specific for a miR gene whose expression is greater in breast cancer cells than control cells. In certain embodiments, the miR gene expression inhibition compound is specific for one or more miR gene products selected from the group consisting of miR-21, miR-155, miR-009-1 (miR131-1), miR-34 (miR-170), miR-102 (miR-29b), miR-213, let-71 (let-7d-v2), miR-122a, miR-128b, miR-136, miR-149, miR-191, miR-196-1, miR-196-2, miR-202, miR-203, miR-206, miR-210, miR-213 and combinations thereof.

Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is incorporated herein by reference.

The present pharmaceutical formulations comprise at least one miR gene product or miR gene expression inhibition compound (or at least one nucleic acid comprising sequences encoding them) (e.g., 0.1 to 90% by weight), or a physiologically acceptable salt thereof, mixed with a pharmaceutically-acceptable carrier. The pharmaceutical formulations of the invention can also comprise at least one miR gene product or miR gene expression inhibition compound (or at least one nucleic acid comprising sequences encoding them) which are encapsulated by liposomes and a pharmaceutically-acceptable carrier. In one embodiment, the pharmaceutical compositions comprise an miR gene or gene product that is not miR-15, miR-16, miR-143 and/or miR-145.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR gene product or miR gene expression inhibition compound (or at least one nucleic acid comprising sequences encoding them) which is resistant to degradation by nucleases. One skilled in the art can readily synthesize nucleic acids which are nuclease resistant, for example by incorporating one or more ribonucleotides that are modified at the 2'-position into the miR gene products. Suitable 2'-modified ribonucleotides include those modified at the 2'-position with fluoro, amino, alkyl, alkoxy, and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression inhibition compound (or at least one nucleic acid comprising sequences encoding them) encapsulated in a liposome as described above, and a propellant. A carrier can also be included as desired; e.g., lecithin for intranasal delivery.

The invention also encompasses methods of identifying an anti-breast cancer agent, comprising providing a test agent to a cell and measuring the level of at least one miR gene product in the cell. In one embodiment, the method comprises providing a test agent to a cell and measuring the level of at least one miR gene product associated with decreased expression levels in breast cancer cells. An increase in the level of the miR gene product in the cell, relative to a suitable control cell, is indicative of the test agent being an anti-breast cancer agent. In a particular embodiment, at least one miR gene product associated with decreased expression levels in breast cancer cells is selected from the group consisting of miR-145, miR-10b, miR-123 (miR-126), miR-140-as, miR-125a, miR-125b-1, miR-125b-2, miR-194, miR-204, let-7a-2, let-7a-3, let-7d (let-7d-v1), let-7f-2, miR-101-1, miR-143 and combinations thereof.

In other embodiments the method comprises providing a test agent to a cell and measuring the level of at least one miR gene product associated with increased expression levels in breast cancer cells. A decrease in the level of the miR gene product in the cell, relative to a suitable control cell, is indicative of the test agent being an anti-breast cancer agent. In a particular embodiment, at least one miR gene product associated with increased expression levels in breast cancer cells is selected from the group consisting of miR-21, miR-155, miR-009-1 (miR131-1), miR-34 (miR-170), miR-102 (miR-29b), miR-213, let-71 (let-7d-v2), miR-122a, miR-128b, miR-136, miR-149, miR-191, miR-196-1, miR-196-2, miR-202, miR-203, miR-206, miR-210, miR-213 and combinations thereof.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR gene product (e.g., Northern blotting, in situ hybridization, RT-PCR, expression profiling) are also well known in the art. Several of these methods are also described hereinabove.

The invention will now be illustrated by the following non-limiting examples.

EXAMPLE 1

Identification of a microRNA Expression Signature that Discriminates Breast Cancer Tissues from Normal Tissues Materials and Methods Breast cancer samples and cell lines. RNAs from primary tumors were obtained from 76 samples collected at the University of Ferrara (Italy), Istituto Nazionale dei Tumori, Milano (Italy) and Thomas Jefferson University (Philadelphia, Pa.). Clinico-pathological information was available for 58 tumor samples. RNA from normal samples consisted of 6 pools of RNA from 5 normal breast tissues each, as well as RNTA from 4 additional single breast tissues. Breast cancer RNAs were also obtained from the following cell lines: Hs578-T, MCF7, T47D, BT20, SK-BR-3, HBL100, HCC2218, MDA-MB-175, MDA-MB-231, MDA-MB-361, MDA-MB-435, MDA-MB-436, MDA-MB-453 and MDAMB-468.

miRNA microarray. Total RNA isolation was performed with Trizol Reagent (Invitrogen) according to the manufacturer's instructions. RNA labeling and hybridization on microRNA microarray chips was performed as previously described (Liu, C.-G., et al., *Proc. Natl. Acad. Sci. U.S.A.* 101:9740-9744 (2004)). Briefly, 5 µg of RNA from each sample was labeled with biotin during reverse transcription using random hexamers. Hybridization was carried out on a miRNA microarray chip (KCl version 1.0) (Liu, C.-G., et al., *Proc. Natl. Acad. Sci. U.S.A.* 101:9740-9744 (2004)), which contains 368 probes, including 245 human and mouse miRNA genes, in triplicate. Hybridization signals were detected by binding of biotin to a Streptavidin-Alexa647 conjugate using a Perkin-Elmer. ScanArray XL5K. Scanner images were quantified by the Quantarray software (Perkin Elmer).

Statistical and bioinformatic analysis of microarray data. Raw data were normalized and analyzed using the GeneSpring® software, version 7.2 (SiliconGenetics, Redwood City, Calif.). Expression data were median centered. Statistical comparisons were performed by ANOVA (Analysis of Variance), using the Benjamini and Hochberg correction for reduction of false positives. Prognostic miRNAs for tumor or normal class prediction were determined using both the PAM software (Prediction Analysis of Microarrays, available at http://www.stat.stanford.edu/~tibs/PAM/index.html) (Tibshirani, R., et al. *Proc. Natl. Acad. Sci. U.S.A.* 99:6567-6572 (2002)) and the Support Vector Machine (Furey, T. S., et al. *Bioinformatics* 16: 906-914 (2000)) software. Both algorithms were used for Cross-validation and Test-set prediction. All data were submitted using MIAMExpress to the Array Express database (accession numbers to be received upon revision).

Northern Blotting. Northern blot analysis was performed as previously described (Calin, G. A., et al., *Proc. Natl. Acad. Sci. U.S.A.* 99:15524-29 (2002)). RNA samples (10 µg each) were electrophoresed on 15% acrylamide, 7 M urea Criterion pre-casted gels (Bio-Rad) and transferred onto Hybond-N+ membrane (Amersham Pharmacia Biotech). The hybridization was performed at 37° C. in 7% sodium dodecyl sulfate (SDS)/0.2M $Na_2PO_4$ (pH 7.0) for 16 hours. Membranes were washed twice at 42° C. with 2× standard saline phosphate (0.18 M NaCl/10 mM phosphate, pH 7.4), supplemented with 1 mM EDTA (SSPE) and 0.1% SDS, and twice with 0.5× SSPE/0.1% SDS. Oligonucleotide probes were complementary to the sequence of the corresponding mature microRNA (see miR Registry at http://www.sanger.ac.uk/Software/Rfam/mirna/): miR-215'-TCA ACA TCA GTC TGA TAA GCT A-3 (SEQ ID NO:287); miR-125b1: 5'-TCA CAA GTT AGG GTC TCA GGG A-3 (SEQ ID NO:288); miR-145: 5'-AAG GGA TTC CTG GGA AAA CTG GAC-3' (SEQ ID NO:289). An oligonucleotide that was complementary to the U6 RNA (5'-GCA GGG GCC ATG CTA ATC TTC TCT GTA TCG-3' (SEQ ID NO:290)) was used for normalizing expression levels. 200 ng of each probe was end labeled with 100 mCi [gamma-$^{32}$P]-ATP using a polynucleotide kinase (Roche). Northern Blots were stripped in a boiling 0.1% SDS solution for 10 minutes before re-hybridization.

Results

A microRNA microarray (Liu, C.-G., et al., *Proc. Natl. Acad. Sci. U.S.A.* 101:9740-9744 (2004)) was used to generate microRNA expression profiles for 10 normal and 76 neoplastic breast tissues. Each tumor sample was derived from a single specimen, while 6 of the 10 normal samples consisted of pools of RNA made from five different normal breast tissues. Hence, 34 normal breast samples were actually examined in the study.

To identify miRNAs that were differentially-expressed between normal and tumor samples, and, therefore, can be used to distinguish normal from cancerous breast tissues, analyses of variance and class prediction statistical tools were utilized. Results of the ANOVA analysis on normalized data generated a profile of differentially-expressed miRNAs ($p<0.05$) between normal and cancerous breast tissues (Table 2). Cluster analysis, based on differentially-expressed-miRNA, generated a tree having a clear distinction between normal and cancer tissues (FIG. 1A).

To accurately identify a set of predictive miRNAs capable of differentiating normal from breast cancer tissues, we used Support Vector Machine (GeneSpring software) and PAM (Prediction Analysis of Microarrays) (http://wwwstat.stanford.edu/~tibs/). Results from the two class prediction analyses largely overlapped (Table 3 and FIG. 1B). Among the miRNAs listed in Table 3, 11 of 15 have an ANOVA p-value of less than 0.05. To confirm the results obtained by microarray analysis, we performed Northern blot analysis to assess expression levels for a subset of microRNAs, namely, mir-125b, mir-145 and mir-21, that were differentially-expressed in normal and cancerous breast tissues. Northern blot analysis confirmed results obtained by microarray analysis. In many cases, expression differences appeared stronger than those anticipated by the microarray studies (FIG. 1C).

TABLE 2 miRNAs differentially-expressed between breast carcinoma and normal breast tissue.

| | | Breast Cancer | | | Normal Breast | | |
|---|---|---|---|---|---|---|---|
| | | Median | Range | | Median | Range | |
| | P-value | Normalized | Min | Max | Normalized | Min | Max |
| let-7a-2 | 1.94E-02 | 1.67 | 0.96-6.21 | | 2.30 | 1.34-5.00 | |
| let-7a-3 | 4.19E-02 | 1.26 | 0.81-3.79 | | 1.58 | 1.02-2.91 | |
| let-7d (= 7d-v1) | 4.61E-03 | 0.90 | 0.59-1.54 | | 1.01 | 0.63-1.25 | |
| let-7f-2 | 6.57E-03 | 0.84 | 0.51-1.58 | | 0.92 | 0.76-1.03 | |
| let-7i (= let-7d-v2) | 3.38E-02 | 2.05 | 1.02-7.49 | | 1.53 | 1.01-3.47 | |
| mir-009-1 (mir-131-1) | 9.12E-03 | 1.36 | 0.69-4.16 | | 1.01 | 0.61-2.44 | |
| mir-010b | 4.49E-02 | 1.11 | 0.69-4.79 | | 1.70 | 0.96-6.32 | |
| mir-021 | 4.67E-03 | 1.67 | 0.66-28.43 | | 1.08 | 0.80-2.31 | |
| mir-034 (=mir-170) | 1.06E-02 | 1.67 | 0.70-6.40 | | 1.09 | 0.65-3.17 | |
| mir-101-1 | 4.15E-03 | 0.83 | 0.52-1.26 | | 0.90 | 0.77-1.05 | |
| mir-122a | 3.43E-03 | 2.21 | 0.93-8.08 | | 1.48 | 1.06-3.67 | |
| mir-125a | 3.28E-03 | 1.20 | 0.69-2.36 | | 1.73 | 1.21-3.34 | |
| mir-125b-1 | 2.65E-02 | 1.30 | 0.55-8.85 | | 2.87 | 1.45-18.38 | |
| mir-125b-2 | 2.33E-02 | 1.26 | 0.69-6.29 | | 2.63 | 1.40-16.78 | |
| mir-128b | 1.60E-02 | 1.12 | 0.68-7.34 | | 1.02 | 0.89-1.27 | |
| mir-136 | 2.42E-03 | 1.32 | 0.74-10.26 | | 1.08 | 0.76-1.47 | |
| mir-143 | 7.11E-03 | 0.87 | 0.68-1.33 | | 0.96 | 0.81-1.17 | |
| mir-145 | 4.02E-03 | 1.52 | 0.92-8.46 | | 3.61 | 1.65-14.45 | |
| mir-149 | 2.75E-02 | 1.11 | 0.53-1.73 | | 1.03 | 0.63-1.22 | |
| mir-155(BIC) | 1.24E-03 | 1.75 | 0.95-11.45 | | 1.37 | 1.11-1.88 | |
| mir-191 | 4.26E-02 | 5.17 | 1.03-37.81 | | 3.12 | 1.45-14.56 | |
| mir-196-1 | 1.07E-02 | 1.20 | 0.57-3.95 | | 0.95 | 0.66-1.75 | |
| mir-196-2 | 1.16E-03 | 1.46 | 0.57-5.55 | | 1.04 | 0.79-1.80 | |
| mir-202 | 1.25E-02 | 1.05 | 0.71-2.03 | | 0.89 | 0.65-1.20 | |
| mir-203 | 4.06E-07 | 1.12 | 0.50-5.69 | | 0.86 | 0.71-1.04 | |
| mir-204 | 2.15E-03 | 0.78 | 0.48-1.04 | | 0.89 | 0.72-1.08 | |
| mir-206 | 1.42E-02 | 2.55 | 1.22-6.42 | | 1.95 | 1.34-3.22 | |
| mir-210 | 6.40E-13 | 1.60 | 0.98-12.13 | | 1.12 | 0.97-1.29 | |
| mir-213 | 1.08E-02 | 3.72 | 1.42-40.83 | | 2.47 | 1.35-5.91 | |

TABLE 3

Normal and tumor breast tissues class predictor microRNAs

| miRNA name | Median expression | | ANOVA[a] Probability | SVM prediction strength[b] | PAM score[c] | | Chromos map |
|---|---|---|---|---|---|---|---|
| | Cancer | Normal | | | Cancer | Normal | |
| mir-009-1 | 1.36 | 1.01 | 0.0091 | 8.05 | 0.011 | −0.102 | 1q22 |
| mir-010b | 1.11 | 1.70 | 0.0449 | 8.70 | −0.032 | 0.299 | 2q31 |
| mir-021 | 1.67 | 1.08 | 0.0047 | 10.20 | 0.025 | −0.235 | 17q23.2 |
| mir-034 | 1.67 | 1.09 | 0.0106 | 8.05 | 0.011 | −0.106 | 1p36.22 |
| mir-102 (mir-29b) | 1.36 | 1.14 | >0.10 | 8.92 | 0.000 | −0.004 | 1q32.2-32.3 |
| mir-123 (mir-126) | 0.92 | 1.13 | 0.0940 | 9.13 | −0.015 | 0.138 | 9q34 |
| mir-125a | 1.20 | 1.73 | 0.0033 | 8.99 | −0.040 | 0.381 | 19q13.4 |
| mir-125b-1 | 1.30 | 2.87 | 0.0265 | 14.78 | −0.096 | 0.915 | 11q24.1 |

TABLE 3-continued

Normal and tumor breast tissues class predictor microRNAs

| miRNA name | Median expression | | ANOVA[a] Probability | SVM prediction strength[b] | PAM score[c] | | Chromos map |
|---|---|---|---|---|---|---|---|
| | Cancer | Normal | | | Cancer | Normal | |
| mir-125b-2 | 1.26 | 2.63 | 0.0233 | 17.62 | −0.106 | 1.006 | 21q11.2 |
| mir-140-as | 0.93 | 1.10 | 0.0695 | 11.01 | −0.005 | 0.050 | 16q22.1 |
| mir-145 | 1.52 | 3.61 | 0.0040 | 12.93 | −0.158 | 1.502 | 5q32-33 |
| mir-155(BIC) | 1.75 | 1.37 | 0.0012 | 10.92 | 0.003 | −0.030 | 21q21 |
| mir-194 | 0.96 | 1.09 | >0.10 | 11.12 | −0.025 | 0.234 | 1q41 |
| mir-204 | 0.78 | 0.89 | 0.0022 | 8.10 | −0.015 | 0.144 | 9q21.1 |
| mir-213 | 3.72 | 2.47 | 0.0108 | 9.44 | 0.023 | −0.220 | 1q31.3-q32.1 |

[a]Analysis of Variance (Welch t-test in Genespring software package) as calculated in Table 2.
[b]Support Vector Machine prediction analysis tool (from Genespring 7.2 software package). Prediction strengths are calculated as negative natural log of the probability to predict the observed number of samples, in one of the two classes, by chance. The higher is the score, the best is the prediction strength.
[c]Centroid scores for the two classes of the Prediction Analysis of Microarrays (Tibshirani, R., et al. Proc. Natl. Acad Sci. U.S.A. 99: 6567-6572 (2002)).

Of the 29 miRNAs whose expression is significantly ($p<0.05$) deregulated according to the microarray analysis, a set of 15 miRNAs were able to correctly predict the nature of the sample analyzed (i.e., normal vs. tumor) with 100% accuracy. Among the differentially-expressed miRNAs, miR-10b, miR-125b, miR145, miR-21 and miR-155 were the most consistently deregulated miRNAs in breast cancer samples. Three of these, namely, miR-10b, miR-125b and miR-145, were down-regulated, while the remaining two, miR-21 and miR-155, were up-regulated, suggesting that they might act as tumor suppressor genes or oncogenes, respectively.

EXAMPLE 2

Determination of Putative Gene Targets of miRNAs that are Deregulated in Breast Cancer Tissues At present, the lack of knowledge about bona fide miRNA gene targets hampers a full understanding of which biological functions are deregulated in cancers characterized by aberrant miRNA expression. To identify putative targets of the most significantly de-regulated miRNAs from our study: miR-10b, miR125b, miR-145, miR-21 and miR-155 (see Example 1), we utilized multiple computational approaches. In particular, the analysis was performed using three algorithms, miRanda, TargetScan and PicTar, which are commonly used to predict human miRNA gene targets (Enright, A. J., et al. *Genome Biol.* 5:R1 (2003); Lewis, B. P. et al., *Cell* 115:787-798 (2003); Krek, A., et al., *Nat. Genet.* 37:495-500 (2005)). The results obtained using each of the three algorithms were cross-referenced with one another to validate putative targets and only targets that were identified by at least 2 of the 3 algorithms were considered. Results of this analysis are presented in Table 4.

Several genes with potential oncogenic functions were identified as putative targets of miRNAs that are down-regulated in breast cancer samples. Notably, oncogenes were identified as targets of miR-10b (e.g., FLT1, the v-crk homolog, the growth factor BDNF and the transducing factor SHC1), miR-125b (e.g., YES, ETS1, TEL, AKT3, the growth factor receptor FGFR2 and members of the mitogen-activated signal transduction pathway VTS58635, MAP3K10, MAP3K11, MAPK14), and miR-145 (e.g., MYCN, FOS, YES and FLI1, integration site of Friend leukemia virus, cell cycle promoters, such as cyclins D2 and L1, MAPK transduction proteins, such as MAP3K3 and MAP4K4). The proto-oncogene, YES, and the core-binding transcription factor, CBFB, were determined to be potential targets of both miR-125 and miR-145.

Consistent with these findings, multiple tumor suppressor genes were identified as targets of miR-21 and miR-155, miRNAs that are up-regulated in breast cancer cells. For miR-21, the TGFB gene was predicted as target by all three methods. For miR-155, potential targets included the tumor suppressor genes, SOCS1 and APC, and the kinase, WEE1, which blocks the activity of Cdc2 and prevents entry into mitosis. The hypoxia inducible factor, HIF1A, was also a predicted target of miR-155. Notably, the tripartite motif-containing protein TRIM2, the proto-oncogene, SKI, and the RAS homologs, RAB6A and RAB6C, were found as potential targets of both miR-21 and miR-155.

TABLE 4

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-10b | AL117516 | 38596 | strand-exchange protein 1 | P + T | exonuclease activity\|nucleus |
| miR-10b | NM_004915 | ABCG1 | ATP-binding cassette, sub-family G (WHITE), member 1 | P + T | ATP binding\|ATPase activity\|ATPase activity, coupled to transmembrane movement of substances\|L-tryptophan transporter activity\|cholesterol homeostasis\|cholesterol metabolism\|detection of hormone stimulus\|integral to plasma membrane\|lipid |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| | | | | | transport\|membrane\|membrane fraction\|permease activity\|protein dimerization activity\|purine nucleotide transporter activity\|response to organic substance |
| miR-10b | NM_001148 | ANK2 | ankyrin 2, neuronal | P + T | actin cytoskeleton\|membrane\|metabolism\|oxidoreductase activity\|protein binding\|signal transduction\|structural constituent of cytoskeleton |
| miR-10b | NM_020987 | ANK3 | ankyrin 3, node of Ranvier (ankyrin G) | P + T | Golgi apparatus\|cytoskeletal anchoring\|cytoskeleton\|cytoskeleton\|endoplasmic reticulum\|protein binding\|protein targeting\|signal transduction\|structural constituent of cytoskeleton |
| miR-10b | NM_016376 | ANKHZN | ANKHZN protein | P + T | endocytosis\|endosome membrane\|membrane\|protein binding\|zinc ion binding |
| miR-10b | NM_006380 | APPBP2 | amyloid beta precursor protein (cytoplasmic tail) binding protein 2 | P + T | binding\|cytoplasm\|intracellular protein transport\|membrane\|microtubule associated complex\|microtubule motor activity\|nucleus |
| miR-10b | NM_006321 | ARIH2 | ariadne homolog 2 (*Drosophila*) | P + T | development\|nucleic acid binding\|nucleus\|protein ubiquitination\|ubiquitin ligase complex\|ubiquitin-protein ligase activity\|zinc ion binding |
| miR-10b | NM_001668 | ARNT | aryl hydrocarbon receptor nuclear translocator | P + T | aryl hydrocarbon receptor nuclear translocator activity\|nucleus\|nucleus\|protein-nucleus import, translocation\|receptor activity\|regulation of transcription, DNA-dependent\|signal transducer activity\|signal transduction\|transcription coactivator activity\|transcription factor activity\|transcription factor activity |
| miR-10b | AI829840 | ASXL1 | ESTs, Weakly similar to SFRB_HUMAN Splicing factor arginine/serine-rich 11 (Arginine-rich 54 kDa nuclear protein) (P54) [*H. sapiens*] | P + T | nucleus\|regulation of transcription, DNA-dependent\|transcription |
| miR-10b | NM_021813 | BACH2 | BTB and CNC homology 1, basic leucine zipper transcription factor 2 | P + T | DNA binding\|nucleus\|protein binding\|regulation of transcription, DNA-dependent\|transcription |
| miR-10b | NM_013450 | BAZ2B | bromodomain adjacent to zinc finger domain, 2B | P + T | DNA binding\|nucleus\|regulation of transcription, DNA-dependent\|transcription |
| miR-10b | NM_001706 | BCL6 | B-cell CLL/lymphoma 6 (zinc finger protein 51) | P + T | inflammatory response\|mediator complex\|negative regulation of transcription from RNA polymerase II promoter\|nucleus\|positive regulation of cell proliferation\|protein binding\|regulation of transcription, DNA-dependent\|transcription\|transcription factor activity\|zinc ion binding |
| miR-10b | NM_001709 | BDNF | brain-derived neurotrophic factor | P + T | growth factor activity\|growth factor activity\|neurogenesis |
| miR-10b | NM_006624 | BS69 | adenovirus 5 E1A binding protein | P + T | DNA binding\|cell cycle\|cell proliferation\|negative regulation of cell cycle\|negative regulation of transcription from RNA polymerase II promoter\|nucleus\|regulation of transcription, DNA-dependent\|transcription |
| miR-10b | AF101784 | BTRC | beta-transducin repeat containing | P + T | Wnt receptor signaling pathway\|endoplasmic reticulum\|ligase activity\|signal |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| | | | | | transduction|ubiquitin conjugating enzyme activity|ubiquitin cycle|ubiquitin-dependent protein catabolism |
| miR-10b | NM_005808 | C3orf8 | HYA22 protein | P + T | biological_process unknown|molecular_function unknown|nucleus |
| miR-10b | BF111268 | CAMK2G | calcium/calmodulin-dependent protein kinase (CaM kinase) II gamma | P + T | ATP binding|ATP binding|calcium- and calmodulin-dependent protein kinase activity|calcium-dependent protein serine/threonine phosphatase activity|calmodulin binding|cellular_component unknown|insulin secretion|kinase activity|protein amino acid phosphorylation|protein amino acid phosphorylation|protein serine/threonine kinase activity|protein-tyrosine kinase activity|signal transduction|transferase activity |
| miR-10b | NM_020184 | CNNM4 | cyclin M4 | P + T | |
| miR-10b | NM_022730 | COPS7B | COP9 constitutive photomorphogenic homolog subunit 7B (*Arabidopsis*) | P + T | signalosome complex |
| miR-10b | NM_016823 | CRK | v-crk sarcoma virus CT10 oncogene homolog (avian) | P + T | SH3/SH2 adaptor activity|actin cytoskeleton organization and biogenesis|cell motility|cytoplasm|intracellular signaling cascade|nucleus|regulation of transcription from RNA polymerase II promoter |
| miR-10b | NM_020248 | CTNNBIP1 | catenin, beta interacting protein 1 | P + T | Wnt receptor signaling pathway|beta-catenin binding|cell proliferation|development|nucleus|regulation of transcription, DNA-dependent|signal transduction |
| miR-10b | NM_018959 | DAZAP1 | DAZ associated protein 1 | P + T | RNA binding|cell differentiation|nucleotide binding|nucleus|spermatogenesis |
| miR-10b | AL136828 | DKFZP434K0427 | hypothetical protein DKFZp434K0427 | P + T | cation transport|cation transporter activity |
| miR-10b | R20763 | DKFZp547J036 | ELAV (embryonic lethal, abnormal vision, *Drosophila*)-like 3 (Hu antigen C) | P + T | |
| miR-10b | AF009204 | DLGAP2 | discs, large (*Drosophila*) homolog-associated protein 2 | P + T | cell-cell signaling|membrane|nerve-nerve synaptic transmission|neurofilament|protein binding |
| miR-10b | NM_001949 | E2F3 | E2F transcription factor 3 | P + T | nucleus|protein binding|regulation of cell cycle|regulation of transcription, DNA-dependent|transcription|transcription factor activity|transcription factor complex|transcription initiation from RNA polymerase II promoter |
| miR-10b | NM_022659 | EBF2 | early B-cell factor 2 | P + T | DNA binding|development|nucleus|regulation of transcription, DNA-dependent|transcription |
| miR-10b | NM_004432 | ELAVL2 | ELAV (embryonic lethal, abnormal vision, *Drosophila*)-like 2 (Hu antigen B) | P + T | RNA binding|mRNA 3'-UTR binding|nucleotide binding|regulation of transcription, DNA-dependent |
| miR-10b | NM_001420 | ELAVL3 | ELAV (embryonic lethal, abnormal vision, *Drosophila*)-like 3 (Hu antigen C) | P + T | RNA binding|cell differentiation|mRNA 3'-UTR binding|neurogenesis|nucleotide binding |
| miR-10b | NM_004438 | EPHA4 | EphA4 | P + T | ATP binding|ephrin receptor activity|integral to plasma membrane|membrane|protein amino acid phosphorylation|receptor activity|signal |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| | | | | | transduction\|transferase activity\|transmembrane receptor protein tyrosine kinase signaling pathway |
| miR-10b | AL035703 | EPHA8; EEK; HEK3; Hek3; KIAA1459 | EphA8 | P + T | |
| miR-10b | NM_004468 | FHL3 | four and a half LIM domains 3 | P + T | muscle development\|zinc ion binding |
| miR-10b | NM_024679 | FLJ11939 | hypothetical protein FLJ11939 | P + T | |
| miR-10b | AI742838 | FLJ32122 | hypothetical protein FLJ32122 | P + T | GTP binding\|GTPase binding\|guanyl-nucleotide exchange factor activity |
| miR-10b | AL040935 | FLJ33957 | hypothetical protein FLJ33957 | P + T | protein binding |
| miR-10b | AA058828 | FLT1 | ESTs | P + T | ATP binding\|angiogenesis\|cell differentiation\|extracellular space\|integral to plasma membrane\|membrane\|positive regulation of cell proliferation\|pregnancy\|protein amino acid phosphorylation\|receptor activity\|transferase activity\|transmembrane receptor protein tyrosine kinase signaling pathway\|vascular endothelial growth factor receptor activity |
| miR-10b | NM_004860 | FXR2 | fragile X mental retardation, autosomal homolog 2 | P + T | RNA binding\|cytoplasm\|cytosolic large ribosomal subunit (sensu Eukaryota)\|nucleus |
| miR-10b | NM_020474 | GALNT1 | UDP-N-acetyl-alpha-D-galactosamine:polypeptide N-acetylgalactosaminyl-transferase 1 (GalNAc-T1) | P + T | Golgi apparatus\|O-linked glycosylation\|integral to membrane\|manganese ion binding\|polypeptide N-acetylgalactosaminyltransferase activity\|sugar binding\|transferase activity, transferring glycosyl groups |
| miR-10b | D87811 | GATA6 | GATA binding protein 6 | P + T | muscle development\|nucleus\|positive regulation of transcription\|regulation of transcription, DNA-dependent\|transcription\|transcription factor activity\|transcriptional activator activity\|zinc ion binding |
| miR-10b | NM_000840 | GRM3 | glutamate receptor, metabotropic 3 | P + T | G-protein coupled receptor protein signaling pathway\|integral to plasma membrane\|membrane\|metabotropic glutamate, GABA-B-like receptor activity\|negative regulation of adenylate cyclase activity\|receptor activity\|signal transduction\|synaptic transmission |
| miR-10b | NM_005316 | GTF2H1 | general transcription factor IIH, polypeptide 1, 62 kDa | P + T | DNA repair\|[RNA-polymerase]-subunit kinase activity\|general RNA polymerase II transcription factor activity\|nucleus\|regulation of cyclin dependent protein kinase activity\|regulation of transcription, DNA-dependent\|transcription\|transcription factor TFIIH complex\|transcription from RNA polymerase II promoter |
| miR-10b | AF232772 | HAS3 | hyaluronan synthase 3 | P + T | carbohydrate metabolism\|hyaluronan synthase activity\|integral to plasma membrane\|transferase activity, transferring glycosyl groups |
| miR-10b | AL023584 | HIVEP2 | human immunodeficiency virus type I enhancer binding protein 2 | P + T | |
| miR-10b | S79910 | HOXA1 | homeo box A1 | P + T | RNA polymerase II transcription factor activity\|development\|nucleus\|regulation of transcription, DNA-dependent\|transcription factor activity |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-10b | NM_030661 | HOXA3 | homeo box A3 | P + T | development\|nucleus\|regulation of transcription, DNA-dependent\|transcription factor activity |
| miR-10b | AW299531 | HOXD10 | homeo box D10 | P + T | RNA polymerase II transcription factor activity\|development\|nucleus\|regulation of transcription, DNA-dependent\|transcription factor activity |
| miR-10b | BF031714 | HYA22 | HYA22 protein | P + T | |
| miR-10b | NM_001546 | ID4 | inhibitor of DNA binding 4, dominant negative helix-loop-helix protein | P + T | nucleus\|regulation of transcription from RNA polymerase II promoter\|transcription corepressor activity |
| miR-10b | NM_014333 | IGSF4 | immunoglobulin superfamily, member 4 | P + T | |
| miR-10b | NM_014271 | IL1RAPL1 | interleukin 1 receptor accessory protein-like 1 | P + T | integral to membrane\|learning and/or memory\|membrane\|signal transduction\|transmembrane receptor activity |
| miR-10b | D87450 | KIAA0261 | KIAA0261 protein | P + T | |
| miR-10b | AL117518 | KIAA0978 | KIAA0978 protein | P + T | nucleus\|regulation of transcription, DNA-dependent\|transcription |
| miR-10b | AK025960 | KIAA1255 | KIAA1255 protein | P + T | endocytosis\|endosome membrane\|membrane\|protein binding\|zinc ion binding |
| miR-10b | AB037797 | KIAA1376 | KIAA1376 protein | P + T | |
| miR-10b | NM_004795 | KL | klotho | P + T | beta-glucosidase activity\|carbohydrate metabolism\|extracellular space\|glucosidase activity\|integral to membrane\|integral to plasma membrane\|membrane fraction\|signal transducer activity\|soluble fraction |
| miR-10b | NM_015995 | KLF13 | Kruppel-like factor 13 | P + T | DNA binding\|RNA polymerase II transcription factor activity\|nucleus\|regulation of transcription, DNA-dependent\|transcription\|transcription from RNA polymerase II promoter\|zinc ion binding |
| miR-10b | NM_004235 | KLF4 | Kruppel-like factor 4 (gut) | P + T | mesodermal cell fate determination\|negative regulation of cell proliferation\|negative regulation of transcription, DNA-dependent\|negative regulation of transcription, DNA-dependent\|nucleic acid binding\|nucleus\|transcription factor activity\|transcription factor activity\|transcriptional activator activity\|transcriptional activator activity\|transcriptional repressor activity\|transcriptional repressor activity\|zinc ion binding\|zinc ion binding |
| miR-10b | AW511293 | LOC144455 | hypothetical protein BC016658 | P + T | regulation of cell cycle\|regulation of transcription, DNA-dependent\|transcription factor activity\|transcription factor complex |
| miR-10b | NM_014921 | LPHN1 | lectomedin-2 | P + T | G-protein coupled receptor activity\|integral to membrane\|latrotoxin receptor activity\|membrane\|neuropeptide signaling pathway\|receptor activity\|signal transduction\|sugar binding |
| miR-10b | NM_012325 | MAPRE1 | microtubule-associated protein, RP/EB family, member 1 | P + T | cell proliferation\|cytokinesis\|microtubule binding\|mitosis\|protein C-terminus binding\|regulation of cell cycle |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-10b | AA824369 | MGC4643 | hypothetical protein MGC4643 | P + T | Wnt receptor signaling pathway\|endoplasmic reticulum\|ligase activity\|signal transduction\|ubiquitin conjugating enzyme activity\|ubiquitin cycle\|ubiquitin-dependent protein catabolism |
| miR-10b | NM_021090 | MTMR3 | myotubularin related protein 3 | P + T | cytoplasm\|hydrolase activity\|inositol or phosphatidylinositol phosphatase activity\|membrane\|membrane fraction\|phospholipid dephosphorylation\|protein amino acid dephosphorylation\|protein serine/threonine phosphatase activity\|protein tyrosine phosphatase activity\|protein tyrosine/serine/threonine phosphatase activity\|zinc ion binding |
| miR-10b | AI498126 | NAC1 | transcriptional repressor NAC1 | P + T | protein binding |
| miR-10b | AF128458 | NCOA6 | nuclear receptor coactivator 6 | P + T | DNA recombination\|DNA repair\|DNA replication\|brain development\|chromatin binding\|embryonic development (sensu Mammalia)\|estrogen receptor binding\|estrogen receptor signaling pathway\|glucocorticoid receptor signaling pathway\|heart development\|ligand-dependent nuclear receptor transcription coactivator activity\|myeloid blood cell differentiation\|nucleus\|nucleus\|positive regulation of transcription from RNA polymerase II promoter\|protein binding\|regulation of transcription, DNA-dependent\|response to hormone stimulus\|retinoid X receptor binding\|thyroid hormone receptor binding\|transcription\|transcription factor complex\|transcription initiation from RNA polymerase II promoter\|transcriptional activator activity |
| miR-10b | NM_006312 | NCOR2 | nuclear receptor corepressor 2 | P + T | DNA binding\|nucleus\|regulation of transcription, DNA-dependent\|transcription corepressor activity |
| miR-10b | NM_006599 | NFAT5 | nuclear factor of activated T-cells 5, tonicity-responsive | P + T | RNA polymerase II transcription factor activity\|excretion\|nucleus\|regulation of transcription, DNA-dependent\|signal transduction\|transcription factor activity\|transcription from RNA polymerase II promoter |
| miR-10b | NM_006981 | NR4A3 | nuclear receptor subfamily 4, group A, member 3 | M + P + T | binding\|nucleus\|nucleus\|regulation of transcription, DNA-dependent\|steroid hormone receptor activity\|steroid hormone receptor activity\|thyroid hormone receptor activity\|transcription\|transcription factor activity |
| miR-10b | NM_003822 | NR5A2 | nuclear receptor subfamily 5, group A, member 2 | P + T | RNA polymerase II transcription factor activity, enhancer binding\|morphogenesis\|nucleus\|nucleus\|regulation of transcription, DNA-dependent\|steroid hormone receptor activity\|transcription\|transcription factor activity\|transcription from RNA polymerase II promoter |
| miR-10b | AA295257 | NRP2 | neuropilin 2 | P + T | angiogenesis\|axon guidance\|cell adhesion\|cell adhesion\|cell differentiation\|electron transport\|electron transporter |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| | | | | | activity\|integral to membrane\|integral to membrane\|membrane fraction\|neurogenesis\|receptor activity\|semaphorin receptor activity\|vascular endothelial growth factor receptor activity\|vascular endothelial growth factor receptor activity |
| miR-10b | NM_000430 | PAFAH1B1 | platelet-activating factor acetylhydrolase, isoform Ib, alpha subunit 45 kDa | P + T | astral microtubule\|cell cortex\|cell cycle\|cell differentiation\|cell motility\|cytokinesis\|cytoskeleton\|dynein binding\|establishment of mitotic spindle orientation\|kinetochore\|lipid metabolism\|microtubule associated complex\|microtubule-based process\|mitosis\|neurogenesis\|nuclear membrane\|signal transduction |
| miR-10b | NM_013382 | POMT2 | putative protein O-mannosyltransferase | P + T | O-linked glycosylation\|dolichyl-phosphate-mannose-protein mannosyltransferase activity\|endoplasmic reticulum\|integral to membrane\|magnesium ion binding\|membrane\|transferase activity, transferring glycosyl groups |
| miR-10b | BF337790 | PURB | purine-rich element binding protein B | P + T | |
| miR-10b | AI302106 | RAP2A | RAP2A, member of RAS oncogene family | P + T | GTP binding\|GTPase activity\|membrane\|signal transduction\|small GTPase mediated signal transduction |
| miR-10b | NM_002886 | RAP2B | RAP2B, member of RAS oncogene family | P + T | GTP binding\|protein transport\|small GTPase mediated signal transduction |
| miR-10b | NM_014781 | RB1CC1 | RB1-inducible coiled-coil 1 | P + T | kinase activity |
| miR-10b | NM_012234 | RYBP | RING1 and YY1 binding protein | P + T | development\|negative regulation of transcription from RNA polymerase II promoter\|nucleus\|transcription corepressor activity |
| miR-10b | NM_005506 | SCARB2 | scavenger receptor class B, member 2 | P + T | cell adhesion\|integral to plasma membrane\|lysosomal membrane\|membrane fraction\|receptor activity |
| miR-10b | AF225986 | SCN3A | sodium channel, voltage-gated, type III, alpha polypeptide | P + T | cation channel activity\|cation transport\|integral to membrane\|membrane\|sodium ion transport\|voltage-gated sodium channel activity\|voltage-gated sodium channel complex |
| miR-10b | NM_002997 | SDC1 | syndecan 1 | P + T | cytoskeletal protein binding\|integral to plasma membrane\|membrane |
| miR-10b | NM_006924 | SFRS1 | splicing factor, arginine/serine-rich 1 (splicing factor 2, alternate splicing factor) | P + T | RNA binding\|mRNA splice site selection\|nuclear mRNA splicing, via spliceosome\|nucleotide binding\|nucleus |
| miR-10b | AI809967 | SHC1 | SHC (Src homology 2 domain containing) transforming protein 1 | P + T | activation of MAPK\|activation of MAPK\|intracellular signaling cascade\|phospholipid binding\|phospholipid binding\|plasma membrane\|plasma membrane\|positive regulation of cell proliferation\|positive regulation of cell proliferation\|positive regulation of mitosis\|positive regulation of mitosis\|regulation of cell growth\|regulation of epidermal growth factor receptor activity\|transmembrane receptor protein tyrosine kinase adaptor protein activity\|transmembrane receptor protein tyrosine kinase adaptor protein activity |
| miR-10b | NM_018976 | SLC38A2 | solute carrier family 38, member 2 | P + T | amino acid transport\|amino acid-polyamine transporter activity\|integral to |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-10b | NM_003794 | SNX4 | sorting nexin 4 | P + T | membrane\|membrane\|oxygen transport\|oxygen transporter activity\|transport endocytosis\|intracellular signaling cascade\|protein transport |
| miR-10b | NM_003103 | SON | SON DNA binding protein | P + T | DNA binding\|DNA binding\|anti-apoptosis\|double-stranded RNA binding\|intracellular\|nucleic acid binding\|nucleus |
| miR-10b | Z48199 | | syndecan-1 | P + T | |
| miR-10b | NM_003222 | TFAP2C | transcription factor AP-2 gamma (activating enhancer binding protein 2 gamma) | P + T | cell-cell signaling\|nucleus\|regulation of transcription from RNA polymerase II promoter\|transcription\|transcription factor activity |
| miR-10b | NM_003275 | TMOD1 | tropomodulin | P + T | actin binding\|cytoskeleton\|cytoskeleton organization and biogenesis\|tropomyosin binding |
| miR-10b | NM_003367 | USF2 | upstream transcription factor 2, c-fos interacting | P + T | RNA polymerase II transcription factor activity\|nucleus\|regulation of transcription, DNA-dependent\|transcription\|transcription factor activity |
| miR-10b | N62196 | ZNF367 | zinc finger protein 367 | P + T | nucleic acid binding\|nucleus\|zinc ion binding |
| miR-125b | AI948503 | ABCC4 | ATP-binding cassette, sub-family C (CFTR/MRP), member 4 | P + T | 15-hydroxyprostaglandin dehydrogenase (NAD+) activity\|ATP binding\|ATPase activity\|ATPase activity, coupled to transmembrane movement of substances\|chloride channel activity\|integral to membrane\|ion transport\|membrane |
| miR-125b | AL534702 | ABHD3 | abhydrolase domain containing 3 | M + P + T | |
| miR-125b | AL527773 | ABR | active BCR-related gene | P + T | GTPase activator activity\|guanyl-nucleotide exchange factor activity\|small GTPase mediated signal transduction |
| miR-125b | NM_020039 | ACCN2 | amiloride-sensitive cation channel 2, neuronal | P + T | amiloride-sensitive sodium channel activity\|integral to plasma membrane\|ion channel activity\|ion transport\|membrane\|response to pH\|signal transduction\|sodium ion transport |
| miR-125b | NM_003816 | ADAM9 | a disintegrin and metalloproteinase domain 9 (meltrin gamma) | P + T | SH3 domain binding\|integral to plasma membrane\|integrin binding\|metalloendopeptidase activity\|protein binding\|protein kinase binding\|protein kinase cascade\|proteolysis and peptidolysis\|zinc ion binding |
| miR-125b | L05500 | ADCY1 | adenylate cyclase 1 (brain) | P + T | cAMP biosynthesis\|calcium- and calmodulin-responsive adenylate cyclase activity\|calmodulin binding\|integral to membrane\|intracellular signaling cascade\|magnesium ion binding |
| miR-125b | NM_017488 | ADD2 | adducin 2 (beta) | P + T | actin binding\|actin cytoskeleton\|calmodulin binding\|membrane |
| miR-125b | NM_003488 | AKAP1 | A kinase (PRKA) anchor protein 1 | P + T | RNA binding\|integral to membrane\|mitochondrion\|outer membrane |
| miR-125b | NM_005465 | AKT3 | v-akt murine thymoma viral oncogene homolog 3 (protein kinase B, gamma) | P + T | ATP binding\|protein amino acid phosphorylation\|protein serine/threonine kinase activity\|signal transduction\|transferase activity |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-125b | NM_001150 | ANPEP | alanyl (membrane) aminopeptidase (aminopeptidase N, aminopeptidase M, microsomal aminopeptidase, CD13, p150) | P + T | aminopeptidase activity\|angiogenesis\|cell differentiation\|integral to plasma membrane\|membrane alanyl aminopeptidase activity\|metallopeptidase activity\|proteolysis and peptidolysis\|receptor activity\|zinc ion binding |
| miR-125b | AF193759 | APBA2BP | amyloid beta (A4) precursor protein-binding, family A, member 2 binding protein | M + P + T | Golgi cis cisterna\|Golgi cis cisterna\|antibiotic biosynthesis\|calcium ion binding\|cytoplasm\|cytoplasm\|endoplasmic reticulum membrane\|endoplasmic reticulum membrane\|nucleus\|oxidoreductase activity\|protein binding\|protein binding\|protein binding\|protein metabolism\|protein metabolism\|protein secretion\|protein secretion\|regulation of amyloid precursor protein biosynthesis |
| miR-125b | NM_000038 | APC | adenomatosis polyposis coli | P + T | Wnt receptor signaling pathway\|beta-catenin binding\|cell adhesion\|microtubule binding\|negative regulation of cell cycle\|protein complex assembly\|signal transduction |
| miR-125b | NM_001655 | ARCN1 | archain 1 | P + T | COPI vesicle coat\|Golgi apparatus\|clathrin vesicle coat\|intra-Golgi transport\|intracellular protein transport\|intracellular protein transport\|membrane\|retrograde transport, Golgi to ER\|transport |
| miR-125b | BC001719 | ASB6 | ankyrin repeat and SOCS box-containing 6 | M + P | intracellular signaling cascade |
| miR-125b | AI478147 | ATP10D | ATPase, Class V, type 10D | P + T | ATP binding\|ATPase activity\|cation transport\|hydrolase activity\|integral to membrane\|magnesium ion binding\|membrane\|phospholipid-translocating ATPase activity |
| miR-125b | NM_012069 | ATP1B4 | ATPase, (Na+)/K+ transporting, beta 4 polypeptide | P + T | hydrogen ion transporter activity\|integral to plasma membrane\|ion transport\|membrane\|potassium ion transport\|proton transport\|sodium ion transport\|sodium:potassium-exchanging ATPase activity |
| miR-125b | NM_005176 | ATP5G2 | ATP synthase, H + transporting, mitochondrial F0 complex, subunit c (subunit 9), isoform 2 | M + P + T | ATP synthesis coupled proton transport\|hydrogen-transporting ATP synthase activity, rotational mechanism\|hydrogen-transporting ATPase activity, rotational mechanism\|ion transport\|lipid binding\|membrane\|membrane fraction\|mitochondrion\|proton transport\|proton-transporting ATP synthase complex (sensu Eukaryota)\|proton-transporting two-sector ATPase complex\|transporter activity |
| miR-125b | NM_001702 | BAI1 | brain-specific angiogenesis inhibitor 1 | M + P + T | G-protein coupled receptor activity\|axonogenesis\|brain-specific angiogenesis inhibitor activity\|cell adhesion\|integral to plasma membrane\|intercellular junction\|negative regulation of cell proliferation\|neuropeptide signaling pathway\|peripheral nervous system development\|plasma membrane\|protein binding\|receptor activity\|signal transduction |
| miR-125b | NM_001188 | BAK1 | BCL2-antagonist/killer 1 | M + T | apoptotic mitochondrial changes\|induction of apoptosis\|integral to |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-125b | NM_013449 | BAZ2A | bromodomain adjacent to zinc finger domain, 2A | P + T | membrane\|protein heterodimerization activity\|regulation of apoptosis DNA binding\|chromatin remodeling\|nucleolus organizer complex\|nucleus\|regulation of transcription, DNA-dependent\|transcription\|transcription regulator activity |
| miR-125b | NM_004634 | BRPF1 | bromodomain and PHD finger containing, 1 | M + P + T | DNA binding\|nucleus\|nucleus\|regulation of transcription, DNA-dependent\|transcription\|zinc ion binding |
| miR-125b | NM_003458 | BSN | bassoon (presynaptic cytomatrix protein) | P + T | cytoskeleton\|metal ion binding\|nucleus\|structural constituent of cytoskeleton\|synapse\|synaptic transmission\|synaptosome |
| miR-125b | NM_018108 | C14orf130 | hypothetical protein FLJ10483 | P + T | ubiquitin cycle\|ubiquitin-protein ligase activity |
| miR-125b | AA025877 | C20orf136 | chromosome 20 open reading frame 136 | P + T | |
| miR-125b | AB054985 | CACNB1 | calcium channel, voltage-dependent, beta 1 subunit | M + P + T | calcium ion transport\|ion transport\|membrane fraction\|muscle contraction\|voltage-gated calcium channel activity\|voltage-gated calcium channel complex |
| miR-125b | NM_001224 | CASP2 | caspase 2, apoptosis-related cysteine protease (neural precursor cell expressed, developmentally down-regulated 2) | P + T | anti-apoptosis\|apoptotic program\|caspase activity\|caspase activity\|caspase activity\|cysteine-type peptidase activity\|enzyme binding\|intracellular\|protein binding\|proteolysis and peptidolysis\|proteolysis and peptidolysis\|regulation of apoptosis |
| miR-125b | NM_001755 | CBFB | core-binding factor, beta subunit | M + P + T | RNA polymerase II transcription factor activity\|nucleus\|transcription coactivator activity\|transcription factor activity\|transcription from RNA polymerase II promoter |
| miR-125b | AV648364 | CBX7 | ESTs, Highly similar to potassium voltage-gated channel, Isk-related subfamily, gene 4; potassium voltage-gated channel-like protein, Isk-related subfamily [*Homo sapiens*] [*H. sapiens*] | P + T | chromatin\|chromatin assembly or disassembly\|chromatin binding\|chromatin modification\|nucleus\|regulation of transcription, DNA-dependent\|transcription |
| miR-125b | NM_001408 | CELSR2 | cadherin, EGF LAG seven-pass G-type receptor 2 (flamingo homolog, *Drosophila*) | M + P + T | G-protein coupled receptor activity\|calcium ion binding\|cell adhesion\|development\|homophilic-cell adhesion\|integral to membrane\|membrane\|neuropeptide signaling pathway\|receptor activity\|signal transduction\|structural molecule activity |
| miR-125b | NM_015955 | CGI-27 | C21orf19-like protein | P + T | |
| miR-125b | AF263462 | CGN | cingulin | P + T | actin binding\|biological_process unknown\|motor activity\|myosin\|protein binding\|tight junction |
| miR-125b | AF064491 | CLIM2 | LIM domain binding 1 | P + T | LIM domain binding\|development\|development\|negative regulation of transcription, DNA-dependent\|nucleus\|transcription cofactor activity\|transcriptional repressor activity |
| miR-125b | AU152178 | CMG2 | capillary morphogenesis protein 2 | P + T | integral to membrane\|receptor activity |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-125b | NM_004073 | CNK | cytokine-inducible kinase | P + T | ATP binding\|protein amino acid phosphorylation\|protein binding\|protein serine/threonine kinase activity\|regulation of cell cycle\|transferase activity |
| miR-125b | NM_020348 | CNNM1 | cyclin M1 | M + P + T | fatty acid biosynthesis |
| miR-125b | NM_022730 | COPS7B | COP9 constitutive photomorphogenic homolog subunit 7B (*Arabidopsis*) | M + P + T | signalosome complex |
| miR-125b | NM_003389 | CORO2A | coronin, actin binding protein, 2A | P + T | actin binding\|glutamate-ammonia ligase activity\|glutamine biosynthesis\|intracellular signaling cascade\|nitrogen compound metabolism\|protein binding |
| miR-125b | BF939649 | CORO2B | coronin, actin binding protein, 2B | P + T | actin binding\|actin cytoskeleton\|actin cytoskeleton organization and biogenesis\|membrane |
| miR-125b | NM_007007 | CPSF6 | cleavage and polyadenylation specific factor 6, 68 kDa | P + T | RNA binding\|mRNA processing\|nucleic acid binding\|nucleotide binding\|nucleus |
| miR-125b | NM_004386 | CSPG3 | chondroitin sulfate proteoglycan 3 (neurocan) | P + T | calcium ion binding\|cell adhesion\|cell motility\|hyaluronic acid binding\|sugar binding |
| miR-125b | NM_004393 | DAG1 | dystroglycan 1 (dystrophin-associated glycoprotein 1) | M + P + T | actin cytoskeleton\|calcium ion binding\|extracellular matrix (sensu Metazoa)\|integral to plasma membrane\|laminin receptor activity\|membrane fraction\|muscle contraction\|plasma membrane\|protein binding\|protein complex assembly |
| miR-125b | NM_014764 | DAZAP2 | DAZ associated protein 2 | P + T | |
| miR-125b | NM_030927 | DC-TM4F2 | tetraspanin similar to TM4SF9 | P + T | integral to membrane |
| miR-125b | NM_004082 | DCTN1 | dynactin 1 (p150, glued homolog, *Drosophila*) | M + P + T | cytoplasm\|cytoskeleton\|dynein complex\|mitosis\|motor activity\|neurogenesis |
| miR-125b | NM_030621 | DICER1 | Dicer1, Dcr-1 homolog (*Drosophila*) | P + T | ATP binding\|ATP-dependent helicase activity\|RNA interference, targeting of mRNA for destruction\|RNA processing\|double-stranded RNA binding\|endonuclease activity\|hydrolase activity\|intracellular\|ribonuclease III activity |
| miR-125b | U53506 | DIO2 | deiodinase, iodothyronine, type II | P + T | integral to membrane\|membrane\|selenium binding\|selenocysteine incorporation\|thyroid hormone generation\|thyroxine 5'-deiodinase activity\|thyroxine 5'-deiodinase activity |
| miR-125b | AL136139 | dJ761I2.1 | | P + T | |
| miR-125b | AL357503 | dJ899C14.1 | Q9H4T4 like | P + T | |
| miR-125b | AL117482 | DKFZP434C131 | DKFZP434C131 protein | P + T | ATP binding\|protein amino acid phosphorylation\|protein serine/threonine kinase activity\|protein-tyrosine kinase activity\|transferase activity |
| miR-125b | AK023580 | DKFZP434H0820 | hypothetical protein DKFZp434H0820 | P + T | |
| miR-125b | T16388 | DKFZp564A176 | hypothetical protein DKFZp564A176 | P + T | development\|integral to membrane\|membrane\|receptor activity\|semaphorin receptor activity |
| miR-125b | AL137517 | DKFZp564O1278 | hypothetical protein DKFZp564O1278 | P + T | integral to membrane |
| miR-125b | BE781961 | DKFZp762A2013 | hypothetical protein DKFZp762A2013 | P + T | electron transport\|electron transporter activity |
| miR-125b | AB036931 | DLL4 | delta-like 4 (*Drosophila*) | M + P + T | Notch binding\|Notch signaling pathway\|cell differentiation\|circulation\|integral to |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| | | | | | membrane\|membrane\|signal transduction |
| miR-125b | NM_012266 | DNAJB5 | DnaJ (Hsp40) homolog, subfamily B, member 5 | P + T | heat shock protein binding\|protein folding\|response to unfolded protein\|unfolded protein binding |
| miR-125b | NM_005740 | DNAL4 | dynein, axonemal, light polypeptide 4 | P + T | ATPase activity, coupled\|axonemal dynein complex\|microtubule motor activity\|microtubule-based movement |
| miR-125b | BF593175 | DOCK3 | dedicator of cyto-kinesis 3 | P + T | GTP binding\|GTPase binding\|guanyl-nucleotide exchange factor activity |
| miR-125b | NM_006426 | DPYSL4 | dihydropyrimidinase-like 4 | P + T | hydrolase activity\|neurogenesis |
| miR-125b | NM_006465 | DRIL2 | dead ringer (*Drosophila*)-like 2 (bright and dead ringer) | P + T | DNA binding\|biological_process unknown\|nucleus |
| miR-125b | BC005047 | DUSP6 | dual specificity phosphatase 6 | P + T | MAP kinase phosphatase activity\|cytoplasm\|hydrolase activity\|inactivation of MAPK\|protein amino acid dephosphorylation\|protein serine/threonine phosphatase activity\|protein tyrosine phosphatase activity\|regulation of cell cycle\|soluble fraction |
| miR-125b | NM_004423 | DVL3 | dishevelled, dsh homolog 3 (*Drosophila*) | P + T | development\|frizzled signaling pathway\|heart development\|intracellular\|intracellular signaling cascade\|kinase activity\|neurogenesis\|protein binding\|signal transducer activity |
| miR-125b | NM_001949 | E2F3 | E2F transcription factor 3 | P + T | nucleus\|protein binding\|regulation of cell cycle\|regulation of transcription, DNA-dependent\|transcription\|transcription factor activity\|transcription factor complex\|transcription initiation from RNA polymerase II promoter |
| miR-125b | AU149385 | EAF1 | *Homo sapiens* cDNA FLJ13155 fis, clone NT2RP3003433, mRNA sequence | P + T | |
| miR-125b | NM_014674 | EDEM | KIAA0212 gene product | P + T | ER-associated protein catabolism\|GTP binding\|N-linked glycosylation\|calcium ion binding\|endoplasmic reticulum\|integral to endoplasmic reticulum membrane\|integral to membrane\|mannosyl-oligosaccharide 1,2-alpha-mannosidase activity\|membrane\|protein binding\|response to unfolded protein |
| miR-125b | NM_001955 | EDN1 | endothelin 1 | M + P + T | cell-cell signaling\|extracellular space\|hormone activity\|pathogenesis\|positive regulation of cell proliferation\|regulation of blood pressure\|regulation of vasoconstriction\|signal transduction\|soluble fraction |
| miR-125b | AI832074 | EIF2C2 | eukaryotic translation initiation factor 2C, 2 | M + P | cellular_component unknown\|protein biosynthesis\|translation initiation factor activity |
| miR-125b | AB044548 | EIF4EBP1 | eukaryotic translation initiation factor 4E binding protein 1 | P + T | eukaryotic initiation factor 4E binding\|negative regulation of protein biosynthesis\|negative regulation of translational initiation\|regulation of translation |
| miR-125b | NM_020390 | EIF5A2 | eukaryotic translation initiation factor 5A2 | P + T | DNA binding\|protein biosynthesis\|translation initiation factor activity\|translational initiation |
| miR-125b | NM_004438 | EPHA4 | EphA4 | P + T | ATP binding\|ephrin receptor activity\|integral to plasma membrane\|membrane\|protein amino |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| | | | | | acid phosphorylation\|receptor activity\|signal transduction\|transferase activity\|transmembrane receptor protein tyrosine kinase signaling pathway |
| miR-125b | NM_004451 | ESRRA | estrogen-related receptor alpha | P + T | nucleus\|regulation of transcription, DNA-dependent\|steroid binding\|steroid hormone receptor activity\|transcription\|transcription factor activity |
| miR-125b | NM_004907 | ETR101 | immediate early protein | P + T | |
| miR-125b | NM_005238 | ETS1 | v-ets erythroblastosis virus E26 oncogene homolog 1 (avian) | P + T | RNA polymerase II transcription factor activity\|immune response\|negative regulation of cell proliferation\|nucleus\|regulation of transcription, DNA-dependent\|transcription\|transcription factor activity\|transcription from RNA polymerase II promoter |
| miR-125b | NM_001987 | ETV6 | ets variant gene 6 (TEL oncogene) | P + T | nucleus\|regulation of transcription, DNA-dependent\|transcription\|transcription factor activity |
| miR-125b | NM_022763 | FAD104 | FAD104 | P + T | |
| miR-125b | AF308300 | FAPP2 | phosphoinositol 4-phosphate adaptor protein-2 | P + T | |
| miR-125b | NM_022976 | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) | M + P + T | ATP binding\|cell growth\|fibroblast growth factor receptor activity\|heparin binding\|integral to membrane\|membrane\|protein amino acid phosphorylation\|protein amino acid phosphorylation\|protein serine/threonine kinase activity\|protein-tyrosine kinase activity\|protein-tyrosine kinase activity\|receptor activity\|transferase activity |
| miR-125b | NM_004470 | FKBP2 | FK506 binding protein 2, 13 kDa | P + T | FK506 binding\|endoplasmic reticulum\|isomerase activity\|peptidyl-prolyl cis-trans isomerase activity\|protein folding |
| miR-125b | AL160175 | FKHL18 | forkhead-like 18 (*Drosophila*) | P + T | |
| miR-125b | BF515132 | FLJ00024 | hypothetical protein FLJ00024 | P + T | |
| miR-125b | BC002945 | FLJ10101 | hypothetical protein FLJ10101 | M + P | GTP binding\|protein transport\|small GTPase mediated signal transduction |
| miR-125b | NM_018243 | FLJ10849 | hypothetical protein FLJ10849 | P + T | GTP binding\|cell cycle\|cytokinesis |
| miR-125b | NM_019084 | FLJ10895 | hypothetical protein FLJ10895 | P + T | nucleus\|regulation of cell cycle |
| miR-125b | NM_018320 | FLJ11099 | hypothetical protein FLJ11099 | P + T | protein ubiquitination\|ubiquitin ligase complex\|ubiquitin-protein ligase activity\|zinc ion binding |
| miR-125b | NM_018375 | FLJ11274 | hypothetical protein FLJ11274 | M + P + T | membrane\|metal ion transport\|metal ion transporter activity |
| miR-125b | NM_024954 | FLJ11807 | hypothetical protein FLJ11807 | P + T | protein modification |
| miR-125b | BF434995 | FLJ14708 | hypothetical protein FLJ14708 | P + T | |
| miR-125b | NM_018992 | FLJ20040 | hypothetical protein FLJ20040 | P + T | membrane\|potassium ion transport\|protein binding\|voltage-gated potassium channel activity\|voltage-gated potassium channel complex |
| miR-125b | NM_017911 | FLJ20635 | hypothetical protein FLJ20635 | P + T | |
| miR-125b | NM_017936 | FLJ20707 | hypothetical protein FLJ20707 | M + P + T | ATP synthesis coupled proton transport\|cytoplasm\|hydrogen-transporting ATP synthase activity, rotational mechanism\|hydrogen-transporting ATPase activity, |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| | | | | | rotational mechanism\|membrane\|phosphate transport\|proton-transporting two-sector ATPase complex |
| miR-125b | NM_024789 | FLJ22529 | hypothetical protein FLJ22529 | P + T | |
| miR-125b | AA721230 | FLJ25604 | hypothetical protein FLJ25604 | P + T | guanyl-nucleotide exchange factor activity\|small GTPase mediated signal transduction |
| miR-125b | AI677701 | FLJ30829 | hypothetical protein FLJ30829 | P + T | nucleic acid binding\|nucleotide binding |
| miR-125b | NM_004475 | FLOT2 | flotillin 2 | M + P + T | cell adhesion\|epidermis development\|flotillin complex\|integral to membrane\|plasma membrane\|protein binding |
| miR-125b | AA830884 | FMR1 | fragile X mental retardation 1 | M + T | mRNA binding\|mRNA processing\|mRNA-nucleus export\|nucleoplasm\|polysome\|ribosome\|soluble fraction\|transport |
| miR-125b | AF305083 | FUT4 | fucosyltransferase 4 (alpha (1,3) fucosyltransferase, myeloid-specific) | P + T | Golgi apparatus\|L-fucose catabolism\|alpha(1,3)-fucosyltransferase activity\|carbohydrate metabolism\|integral to membrane\|membrane\|membrane fraction\|protein amino acid glycosylation\|transferase activity, transferring glycosyl groups |
| miR-125b | X92762 | G4.5 | tafazzin (cardiomyopathy, dilated 3A (X-linked); endocardial fibroelastosis 2; Barth syndrome) | M + P + T | acyltransferase activity\|heart development\|integral to membrane\|metabolism\|muscle contraction\|muscle development |
| miR-125b | NM_012296 | GAB2 | GRB2-associated binding protein 2 | P + T | |
| miR-125b | NM_015044 | GGA2 | golgi associated, gamma adaptin ear containing, ARF binding protein 2 | M + T | ADP-ribosylation factor binding\|Golgi stack\|Golgi transface\|clathrin coat of trans-Golgi network vesicle\|intra-Golgi transport\|intracellular protein transport\|intracellular protein transport\|membrane\|protein complex assembly\|protein transporter activity |
| miR-125b | AL049709 | GGTL3 | gamma-glutamyltransferase-like 3 | M + P + T | |
| miR-125b | NM_000165 | GJA1 | gap junction protein, alpha 1, 43 kDa (connexin 43) | P + T | cell-cell signaling\|connexon channel activity\|connexon complex\|gap junction assembly\|heart development\|integral to plasma membrane\|ion transporter activity\|muscle contraction\|perception of sound\|positive regulation of I-kappaB kinase/NF-kappaB cascade\|protein binding\|signal transducer activity\|transport |
| miR-125b | NM_014905 | GLS | glutaminase | P + T | glutaminase activity\|glutamine catabolism\|hydrolase activity\|mitochondrion |
| miR-125b | NM_005113 | GOLGA5 | golgi autoantigen, golgin subfamily a, 5 | P + T | ATP binding\|Golgi membrane\|cell surface receptor linked signal transduction\|integral to plasma membrane\|protein amino acid phosphorylation\|protein-tyrosine kinase activity |
| miR-125b | NM_001448 | GPC4 | glypican 4 | M + P + T | cell proliferation\|extracellular matrix (sensu Metazoa)\|integral to plasma membrane\|membrane\|morphogenesis |
| miR-125b | NM_005296 | GPR23 | G protein-coupled receptor 23 | M + T | G-protein coupled receptor protein signaling pathway\|integral to plasma membrane\|purinergic nucleotide receptor activity, G-protein coupled\|receptor activity\|rhodopsin-like receptor activity\|signal transduction |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-125b | U66065 | GRB10 | growth factor receptor-bound protein 10 | M + T | SH3/SH2 adaptor activity\|cell-cell signaling\|cytoplasm\|insulin receptor signaling pathway\|intracellular signaling cascade\|plasma membrane |
| miR-125b | NM_021643 | GS3955 | GS3955 protein | P + T | ATP binding\|protein amino acid phosphorylation\|protein kinase activity\|transferase activity |
| miR-125b | NM_019096 | GTPBP2 | GTP binding protein 2 | M + T | GTP binding\|GTPase activity\|protein biosynthesis\|small GTPase mediated signal transduction |
| miR-125b | U78181 | hBNaC2 | amiloride-sensitive cation channel 2, neuronal | P + T | amiloride-sensitive sodium channel activity\|integral to plasma membrane\|ion channel activity\|ion transport\|membrane\|response to pH\|signal transduction\|sodium ion transport |
| miR-125b | NM_005477 | HCN4 | hyperpolarization activated cyclic nucleotide-gated potassium channel 4 | P + T | 3',5'-cAMP binding\|cation channel activity\|cation transport\|circulation\|integral to plasma membrane\|membrane\|membrane fraction\|muscle contraction\|nucleotide binding\|potassium ion transport\|sodium ion transport\|voltage-gated potassium channel activity |
| miR-125b | NM_002112 | HDC | histidine decarboxylase | P + T | amino acid metabolism\|catecholamine biosynthesis\|histidine decarboxylase activity\|histidine metabolism\|lyase activity |
| miR-125b | U64317 | HEF1 | enhancer of filamentation 1 (cas-like docking; Crk-associated substrate related) | P + T | actin filament bundle formation\|cell adhesion\|cytokinesis\|cytoplasm\|cytoskeleton\|cytoskeleton organization and biogenesis\|integrin-mediated signaling pathway\|mitosis\|nucleus\|protein binding\|regulation of cell cycle\|regulation of cell growth\|signal transduction\|spindle |
| miR-125b | L38487 | hERRa | estrogen-related receptor alpha | P + T | nucleus\|regulation of transcription, DNA-dependent\|steroid binding\|steroid hormone receptor activity\|transcription\|transcription factor activity |
| miR-125b | AB028943 | HIC2 | hypermethylated in cancer 2 | P + T | DNA binding\|negative regulation of transcription, DNA-dependent\|nucleus\|protein C-terminus binding\|transcription\|zinc ion binding |
| miR-125b | AL023584 | HIVEP2 | human immunodeficiency virus type I enhancer binding protein 2 | P + T | |
| miR-125b | AL023584 | HIVEP2 | human immunodeficiency virus type I enhancer binding protein 2 | P + T | |
| miR-125b | NM_005342 | HMGB3 | high-mobility group box 3 | P + T | DNA bending activity\|DNA binding\|chromatin\|development\|nucleus\|regulation of transcription, DNA-dependent |
| miR-125b | AL031295 | HMGCL; HL | lysophospholipase II | M + P + T | |
| miR-125b | NM_004503 | HOXC6 | homeo box C6 | P + T | development\|development\|nucleus\|regulation of transcription from RNA polymerase II promoter\|regulation of transcription, DNA-dependent\|transcription corepressor activity\|transcription factor activity |
| miR-125b | AA844682 | HRD1 | HRD1 protein | P + T | protein ubiquitination\|ubiquitin ligase complex\|ubiquitin-protein ligase activity\|zinc ion binding |
| miR-125b | AL136667 | HSPC039 | HSPC039 protein | P + T | integral to membrane |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-125b | AF245044 | HT023 | hypothetical protein HT023 | P + T | |
| miR-125b | U13022 | Ich-1 | caspase 2, apoptosis-related cysteine protease (neural precursor cell expressed, developmentally down-regulated 2) | P + T | anti-apoptosis\|apoptotic program\|caspase activity\|caspase activity\|caspase activity\|cysteine-type peptidase activity\|enzyme binding\|intracellular\|protein binding\|proteolysis and peptidolysis\|proteolysis and peptidolysis\|regulation of apoptosis |
| miR-125b | NM_004513 | IL16 | interleukin 16 (lymphocyte chemoattractant factor) | M + P + T | chemotaxis\|cytokine activity\|extracellular space\|immune response\|protein binding\|sensory perception |
| miR-125b | NM_002460 | IRF4 | interferon regulatory factor 4 | P + T | RNA polymerase II transcription factor activity\|T-cell activation\|T-cell activation\|nucleus\|nucleus\|nucleus\|positive regulation of interleukin-10 biosynthesis\|positive regulation of interleukin-10 biosynthesis\|positive regulation of interleukin-13 biosynthesis\|positive regulation of interleukin-13 biosynthesis\|positive regulation of interleukin-2 biosynthesis\|positive regulation of interleukin-2 biosynthesis\|positive regulation of interleukin-4 biosynthesis\|positive regulation of interleukin-4 biosynthesis\|positive regulation of transcription\|positive regulation of transcription\|regulation of T-helper cell differentiation\|regulation of T-helper cell differentiation\|regulation of transcription, DNA-dependent\|regulation of transcription, DNA-dependent\|transcription\|transcription factor activity\|transcription factor activity\|transcription factor binding\|transcription factor binding\|transcriptional activator activity\|transcriptional activator activity |
| miR-125b | NM_002207 | ITGA9 | integrin, alpha 9 | P + T | cell-matrix adhesion\|integral to membrane\|integrin complex\|integrin-mediated signaling pathway\|protein binding\|receptor activity |
| miR-125b | NM_000212 | ITGB3 | integrin, beta 3 (platelet glycoprotein IIIa, antigen CD61) | P + T | blood coagulation\|cell-matrix adhesion\|integrin complex\|integrin-mediated signaling pathway\|protein binding\|receptor activity |
| miR-125b | NM_021991 | JUP | junction plakoglobin | P + T | cell adhesion\|cell adhesion\|cytoplasm\|cytoskeletal protein binding\|cytoskeleton\|cytoskeleton\|membrane fraction\|mitotic chromosome condensation\|protein binding\|soluble fraction\|structural molecule activity |
| miR-125b | AF032897 | KCNH7 | potassium voltage-gated channel, subfamily H (eag-related), member 7 | P + T | cation transport\|integral to membrane\|membrane\|potassium ion transport\|regulation of transcription, DNA-dependent\|signal transducer activity\|signal transduction\|voltage-gated potassium channel activity |
| miR-125b | NM_002252 | KCNS3 | potassium voltage-gated channel, delayed-rectifier, subfamily S, member 3 | M + P + T | cation transport\|delayed rectifier potassium channel activity\|membrane\|membrane fraction\|potassium channel regulator activity\|potassium ion transport\|protein binding\|voltage-gated potassium channel complex |
| miR-125b | NM_014735 | KIAA0215 | KIAA0215 gene product | P + T | DNA binding\|regulation of transcription, DNA-dependent |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-125b | NM_015288 | KIAA0239 | KIAA0239 protein | P + T | DNA binding\|regulation of transcription, DNA-dependent |
| miR-125b | D87469 | KIAA0279 | cadherin, EGF LAG seven-pass G-type receptor 2 (flamingo homolog, *Drosophila*) | M + P + T | G-protein coupled receptor activity\|calcium ion binding\|cell adhesion\|development\|homophilic cell adhesion\|integral to membrane\|membrane\|neuropeptide signaling pathway\|receptor activity\|signal transduction\|structural molecule activity |
| miR-125b | AB002356 | KIAA0358 | MAP-kinase activating death domain | P + T | cell surface receptor linked signal transduction\|cytoplasm\|death receptor binding\|kinase activity\|plasma membrane\|protein kinase activator activity |
| miR-125b | NM_014871 | KIAA0710 | KIAA0710 gene product | P + T | cysteine-type endopeptidase activity\|exonuclease activity\|nucleus\|ubiquitin cycle\|ubiquitin thiolesterase activity\|ubiquitin-dependent protein catabolism |
| miR-125b | AB018333 | KIAA0790 | KIAA0790 protein | P + T | cell cycle\|negative regulation of cell cycle |
| miR-125b | NM_014912 | KIAA0940 | KIAA0940 protein | P + T | nucleic acid binding |
| miR-125b | AB028957 | KIAA1034 | KIAA1034 protein | P + T | DNA binding\|nucleus\|regulation of transcription, DNA-dependent\|transcription factor activity |
| miR-125b | NM_014901 | KIAA1100 | KIAA1100 protein | M + P + T | protein ubiquitination\|ubiquitin ligase complex\|ubiquitin-protein ligase activity\|zinc ion binding |
| miR-125b | AB033016 | KIAA1190 | hypothetical protein KIAA1190 | P + T | DNA binding\|nucleic acid binding\|nucleus\|protein binding\|regulation of transcription, DNA-dependent\|zinc ion binding |
| miR-125b | AA056548 | KIAA1268 | KIAA1268 protein | P + T | NAD + ADP-ribosyltransferase activity\|nucleus\|protein amino acid ADP-ribosylation |
| miR-125b | BE670098 | KIAA1594 | KIAA1594 protein | M + P + T | cysteine-type endopeptidase activity\|ubiquitin cycle\|ubiquitin thiolesterase activity\|ubiquitin-dependent protein catabolism |
| miR-125b | AU157109 | KIAA1598 | KIAA1598 protein | P + T | |
| miR-125b | AA772278 | KIAA1673 | KIAA1673 | P + T | |
| miR-125b | NM_015995 | KLF13 | Kruppel-like factor 13 | P + T | DNA binding\|RNA polymerase II transcription factor activity\|nucleus\|regulation of transcription, DNA-dependent\|transcription\|transcription from RNA polymerase II promoter\|zinc ion binding |
| miR-125b | NM_016531 | KLF3 | Kruppel-like factor 3 (basic) | P + T | development\|negative regulation of transcription from RNA polymerase II promoter\|nucleus\|regulation of transcription, DNA-dependent\|transcription\|transcription factor activity\|zinc ion binding |
| miR-125b | BE892574 | LACTB | lactamase, beta | P + T | hydrolase activity\|integral to membrane\|response to antibiotic |
| miR-125b | BE566136 | LBP-32 | LBP protein 32 | P + T | |
| miR-125b | NM_024090 | LCE | long-chain fatty-acyl elongase | P + T | integral to membrane |
| miR-125b | NM_003893 | LDB1 | LIM domain binding 1 | P + T | LIM domain binding\|development\|development\|negative regulation of transcription, DNA-dependent\|nucleus\|transcription cofactor activity\|transcriptional repressor activity |
| miR-125b | U94354 | LFNG | lunatic fringe homolog (*Drosophila*) | M + T | Golgi apparatus\|development\|extracellular |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-125b | NM_002310 | LIFR | leukemia inhibitory factor receptor | M + P + T | region|integral to membrane|membrane|organogenesis|transferase activity, transferring glycosyl groups cell surface receptor linked signal transduction|integral to plasma membrane|leukemia inhibitory factor receptor activity|membrane|receptor activity |
| miR-125b | NM_016339 | Link-GEFII | Link guanine nucleotide exchange factor II | P + T | G-protein coupled receptor protein signaling pathway|guanyl-nucleotide exchange factor activity|membrane fraction|neurogenesis|small GTPase mediated signal transduction |
| miR-125b | NM_005575 | LNPEP | leucyl/cystinyl aminopeptidase | P + T | aminopeptidase activity|cell-cell signaling|integral to plasma membrane|membrane alanyl aminopeptidase activity|metallopeptidase activity|plasma membrane|pregnancy|proteolysis and peptidolysis|zinc ion binding |
| miR-125b | AL031186 | LOC129080 | putative emu1 | P + T | |
| miR-125b | AI884701 | LOC221002 | CG4853 gene product | M + P | guanyl-nucleotide exchange factor activity|small GTPase mediated signal transduction |
| miR-125b | AI953847 | LOC255488 | Homo sapiens mRNA full length insert cDNA clone EUROIMAGE 186647, mRNA sequence | P + T | electron transport|electron transporter activity|integral to membrane|iron ion binding|ligase activity|protein binding|protein ubiquitination during ubiquitin-dependent protein catabolism|ubiquitin ligase complex|ubiquitin-protein ligase activity|zinc ion binding |
| miR-125b | NM_015899 | LOC51054 | putative glycolipid transfer protein | P + T | |
| miR-125b | AA209239 | LOC57406 | lipase protein | P + T | aromatic compound metabolism|hydrolase activity|response to toxin|xenobiotic metabolism |
| miR-125b | NM_005576 | LOXL1 | lysyl oxidase-like 1 | M + P + T | copper ion binding|electron transporter activity|extracellular region|oxidoreductase activity|protein modification|protein-lysine 6-oxidase activity |
| miR-125b | AA584297 | LRP4 | low density lipoprotein receptor-related protein 4 | M + T | calcium ion binding|endocytosis|integral to membrane|membrane|receptor activity |
| miR-125b | NM_007260 | LYPLA2 | lysophospholipase II | M + P + T | fatty acid metabolism|hydrolase activity|lipid metabolism |
| miR-125b | NM_004901 | LYSAL1 | lysosomal apyrase-like 1 | P + T | Golgi apparatus|UDP catabolism|apyrase activity|hydrolase activity|integral to Golgi membrane|integral to membrane|lysosome|magnesium ion binding|nucleobase, nucleoside, nucleotide and nucleic acid metabolism|uridine-diphosphatase activity|vacuolar membrane |
| miR-125b | NM_002355 | M6PR | mannose-6-phosphate receptor (cation dependent) | M + P + T | endosome to lysosome transport|integral to plasma membrane|lysosome|receptor mediated endocytosis|transmembrane receptor activity|transport|transporter activity |
| miR-125b | AB002356 | MADD | MAP-kinase activating death domain | P + T | cell surface receptor linked signal transduction|cytoplasm|death receptor binding|kinase activity|plasma membrane|protein kinase activator activity |
| miR-125b | NM_016219 | MAN1B1 | mannosidase, alpha, class 1B, member 1 | P + T | N-linked glycosylation|N-linked glycosylation|calcium ion |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| | | | | | binding|calcium ion binding|carbohydrate metabolism|endoplasmic reticulum|hydrolase activity, acting on glycosyl bonds|integral to membrane|mannosyl-oligosaccharide 1,2-alpha-mannosidase activity|mannosyl-oligosaccharide 1,2-alpha-mannosidase activity|membrane|membrane fraction|oligosaccharide metabolism |
| miR-125b | NM_002446 | MAP3K10 | mitogen-activated protein kinase kinase kinase 10 | P + T | ATP binding|JUN kinase kinase kinase activity|activation of JNK|autophosphorylation|induction of apoptosis|protein homodimerization activity|protein serine/threonine kinase activity|protein-tyrosine kinase activity|signal transduction|transferase activity |
| miR-125b | NM_002419 | MAP3K11 | mitogen-activated protein kinase kinase kinase 11 | M + P + T | ATP binding|G1 phase of mitotic cell cycle|JUN kinase kinase kinase activity|activation of JNK|autophosphorylation|cell proliferation|centrosome|microtubule|microtubule-based process|protein homodimerization activity|protein oligomerization|protein serine/threonine kinase activity|protein-tyrosine kinase activity|transferase activity |
| miR-125b | Z25432 | MAPK14 | mitogen-activated protein kinase 14 | P + T | ATP binding|MAP kinase activity|MAP kinase kinase activity|MP kinase activity|antimicrobial humoral response (sensu Vertebrata)|cell motility|cell surface receptor linked signal transduction|chemotaxis|cytoplasm|nucleus|protein amino acid phosphorylation|protein kinase cascade|protein serine/threonine kinase activity|protein-tyrosine kinase activity|response to stress|transferase activity |
| miR-125b | NM_018650 | MARK1 | MAP/microtubule affinity-regulating kinase 1 | P + T | ATP binding|cytoplasm|cytoskeleton|cytoskeleton organization and biogenesis|magnesium ion binding|microtubule cytoskeleton|protein amino acid phosphorylation|protein amino acid phosphorylation|protein kinase cascade|protein serine/threonine kinase activity|protein serine/threonine kinase activity|transferase activity |
| miR-125b | NM_001879 | MASP1 | mannan-binding lectin serine protease 1 (C4/C2 activating component of Ra-reactive factor) | P + T | calcium ion binding|chymotrypsin activity|complement activation|complement activation, classical pathway|extracellular region|immune response|peptidase activity|proteolysis and peptidolysis|trypsin activity |
| miR-125b | NM_005911 | MAT2A | methionine adenosyltransferase II, alpha | P + T | ATP binding|magnesium ion binding|methionine adenosyltransferase activity|one-carbon compound metabolism|transferase activity |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-125b | NM_005920 | MEF2D | MADS box transcription enhancer factor 2, polypeptide D (myocyte enhancer factor 2D) | P + T | muscle development\|nucleus\|regulation of transcription, DNA-dependent\|transcription\|transcription coactivator activity\|transcription factor activity\|transcription from RNA polymerase II promoter |
| miR-125b | NM_020149 | MEIS2 | Meis1, myeloid ecotropic viral integration site 1 homolog 2 (mouse) | M + P | negative regulation of transcription from RNA polymerase II promoter\|nucleus\|regulation of transcription, DNA-dependent\|specific RNA polymerase II transcription factor activity\|transcription corepressor activity\|transcription factor activity\|transcription factor activity |
| miR-125b | NM_017927 | MFN1 | mitofusin 1 | P + T | GTP binding\|GTPase activity\|hydrolase activity\|integral to membrane\|mitochondrial fusion\|mitochondrial outer membrane\|mitochondrion |
| miR-125b | AI139252 | MGC16063 | ribosomal protein L35a | P + T | JAK-STAT cascade\|acute-phase response\|calcium ion binding\|cell motility\|cytoplasm\|hematopoietin/interferon-class (D200-domain) cytokine receptor signal transducer activity\|intracellular signaling cascade\|negative regulation of transcription from RNA polymerase II promoter\|neurogenesis\|nucleus\|nucleus\|regulation of transcription, DNA-dependent\|signal transducer activity\|transcription\|transcription factor activity\|transcription factor activity |
| miR-125b | AI862120 | MGC21981 | hypothetical protein MGC21981 | P + T | membrane |
| miR-125b | AL515061 | MGC24302 | hypothetical protein MGC24302 | P + T | |
| miR-125b | BE618656 | MGC2541 | similar to RIKEN cDNA 2610030J16 gene | M + P + T | |
| miR-125b | BC005842 | MGC2705 | hypothetical protein MGC2705 | P + T | |
| miR-125b | NM_024293 | MGC3035 | hypothetical protein MGC3035 | M + P | |
| miR-125b | NM_017572 | MKNK2 | MAP kinase-interacting serine/threonine kinase 2 | P + T | ATP binding\|ATP binding\|cell surface receptor linked signal transduction\|protein amino acid phosphorylation\|protein amino acid phosphorylation\|protein kinase cascade\|protein serine/threonine kinase activity\|protein serine/threonine kinase activity\|protein-tyrosine kinase activity\|regulation of translation\|response to stress\|transferase activity |
| miR-125b | NM_005439 | MLF2 | myeloid leukemia factor 2 | P + T | defense response\|nucleus |
| miR-125b | NM_007359 | MLN51 | MLN51 protein | P + T | mRNA processing\|mRNA-nucleus export\|molecular_function unknown\|nucleus\|transport |
| miR-125b | NM_002442 | MSI1 | musashi homolog 1 (*Drosophila*) | M + P + T | RNA binding\|neurogenesis\|nucleotide binding\|nucleus |
| miR-125b | NM_021090 | MTMR3 | myotubularin related protein 3 | M + P + T | cytoplasm\|hydrolase activity\|inositol or phosphatidylinositol phosphatase activity\|membrane\|membrane fraction\|phospholipid dephosphorylation\|protein amino acid dephosphorylation\|protein serine/threonine phosphatase activity\|protein tyrosine phosphatase activity\|protein |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-125b | AK024501 | MXD4 | MAX dimerization protein 4 | M + P + T | tyrosine/serine/threonine phosphatase activity\|zinc ion binding DNA binding\|negative regulation of cell proliferation\|negative regulation of transcription from RNA polymerase II promoter\|nucleus\|protein binding\|regulation of transcription, DNA-dependent\|transcription\|transcription corepressor activity |
| miR-125b | AB020642 | MYT1 | myelin transcription factor 1 | M + P + T | nucleus\|regulation of transcription, DNA-dependent\|transcription\|transcription factor activity\|zinc ion binding |
| miR-125b | NM_004540 | NCAM2 | neural cell adhesion molecule 2 | P + T | cell adhesion\|integral to membrane\|membrane\|neuron adhesion\|plasma membrane\|protein binding |
| miR-125b | NM_012338 | NET-2 | transmembrane 4 superfamily member tetraspan NET-2 | P + T | integral to membrane\|membrane fraction |
| miR-125b | U84246 | NEU1 | sialidase 1 (lysosomal sialidase) | P + T | carbohydrate metabolism\|exo-alpha-sialidase activity\|hydrolase activity, acting on glycosyl bonds\|lysosome |
| miR-125b | AI824012 | NRIP1 | nuclear receptor interacting protein 1 | P + T | nucleus\|regulation of transcription, DNA-dependent\|transcription coactivator activity |
| miR-125b | D81048 | NRM | nurim (nuclear envelope membrane protein) | P + T | |
| miR-125b | BC001794 | NUMBL | numb homolog (*Drosophila*)-like | P + T | neurogenesis |
| miR-125b | AB020713 | NUP210 | nucleoporin 210 | P + T | development\|nucleus |
| miR-125b | NM_002537 | OAZ2 | ornithine decarboxylase antizyme 2 | M + P + T | ornithine decarboxylase inhibitor activity\|polyamine metabolism |
| miR-125b | NM_024586 | OSBPL9 | oxysterol binding protein-like 9 | P + T | lipid transport\|steroid metabolism |
| miR-125b | U64661 | PABP | ESTs, Highly similar to PAB1_HUMAN Polyadenylate-binding protein 1 (Poly(A)-binding protein 1) (PABP 1) (PABP1) [*H. sapiens*] | P + T | |
| miR-125b | AK000003 | PCQAP | PC2 (positive cofactor 2, multiprotein complex) glutamine/Q-rich-associated protein | P + T | |
| miR-125b | NM_004716 | PCSK7 | proprotein convertase subtilisin/kexin type 7 | M + P + T | integral to Golgi membrane\|integral to membrane\|peptidase activity\|peptidase activity\|peptide hormone processing\|proteolysis and peptidolysis\|subtilase activity |
| miR-125b | NM_006201 | PCTK1 | PCTAIRE protein kinase 1 | M + P + T | ATP binding\|protein amino acid phosphorylation\|protein amino acid phosphorylation\|protein serine/threonine kinase activity\|protein serine/threonine kinase activity\|regulation of cell cycle\|transferase activity |
| miR-125b | NM_021213 | PCTP | phosphatidylcholine transfer protein | M + P + T | cytosol\|lipid binding\|lipid transport\|phosphatidylcholine transporter activity |
| miR-125b | NM_021255 | PELI2 | pellino homolog 2 (*Drosophila*) | M + P + T | |
| miR-125b | NM_002646 | PIK3C2B | phosphoinositide-3-kinase, class 2, beta polypeptide | P + T | inositol or phosphatidylinositol kinase activity\|intracellular signaling cascade\|microsome\|phosphatidylinositol 3-kinase activity\|phosphatidylinositol-4-phosphate 3-kinase activity\|phosphoinositide 3-kinase complex\|plasma membrane\|transferase activity |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-125b | NM_003628 | PKP4 | plakophilin 4 | P + T | cell adhesion\|cytoskeleton\|intercellular junction\|protein binding\|structural molecule activity |
| miR-125b | NM_006718 | PLAGL1 | pleiomorphic adenoma gene-like 1 | P + T | DNA binding\|cell cycle arrest\|induction of apoptosis\|nucleic acid binding\|nucleus\|regulation of transcription, DNA-dependent\|transcription\|zinc ion binding |
| miR-125b | AI457120 | PPAT | phosphoribosyl pyrophosphate amidotransferase | P + T | amidophosphoribosyltransferase activity\|glutamine metabolism\|magnesium ion binding\|metabolism\|nucleoside metabolism\|purine base biosynthesis\|purine nucleotide biosynthesis\|transferase activity, transferring glycosyl groups |
| miR-125b | NM_002719 | PPP2R5C | protein phosphatase 2, regulatory subunit B (B56), gamma isoform | P + T | hydrolase activity\|nucleus\|phosphoprotein phosphatase activity\|protein phosphatase type 2A complex\|protein phosphatase type 2A complex\|protein phosphatase type 2A regulator activity\|protein phosphatase type 2A regulator activity\|signal transduction\|signal transduction |
| miR-125b | AL022067 | PRDM1 | PR domain containing 1, with ZNF domain | P + T | |
| miR-125b | U23736 | PRDM2 | PR domain containing 2, with ZNF domain | P + T | DNA binding\|metal ion binding\|nucleus\|nucleus\|regulation of transcription\|regulation of transcription, DNA-dependent\|transcription factor activity\|transcription regulator activity\|zinc ion binding\|zinc ion binding |
| miR-125b | AF083033 | PRKRA | protein kinase, interferon-inducible double stranded RNA dependent activator | P + T | double-stranded RNA binding\|enzyme activator activity\|immune response\|intracellular\|kinase activity\|negative regulation of cell proliferation\|response to virus\|signal transducer activity\|signal transduction |
| miR-125b | NM_014369 | PTPN18 | protein tyrosine phosphatase, non-receptor type 18 (brain-derived) | P + T | hydrolase activity\|non-membrane spanning protein tyrosine phosphatase activity\|protein amino acid dephosphorylation\|protein amino acid dephosphorylation\|protein tyrosine phosphatase activity |
| miR-125b | AI762627 | PTPRF | protein tyrosine phosphatase, receptor type, F | P + T | cell adhesion\|hydrolase activity\|integral to membrane\|integral to plasma membrane\|protein amino acid dephosphorylation\|protein binding\|protein tyrosine phosphatase activity\|receptor activity\|transmembrane receptor protein tyrosine phosphatase activity\|transmembrane receptor protein tyrosine phosphatase signaling pathway |
| miR-125b | NM_002840 | PTPRF | protein tyrosine phosphatase, receptor type, F | P + T | cell adhesion\|hydrolase activity\|integral to membrane\|integral to plasma membrane\|protein amino acid dephosphorylation\|protein binding\|protein tyrosine phosphatase activity\|receptor activity\|transmembrane receptor protein tyrosine phosphatase activity\|transmembrane receptor protein tyrosine phosphatase signaling pathway |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-125b | AF142419 | QKI | homolog of mouse quaking QKI (KH domain RNA binding protein) | P + T | |
| miR-125b | NM_004283 | RAB3D | RAB3D, member RAS oncogene family | P + T | GTP binding\|GTPase activity\|exocytosis\|hemocyte development\|protein transport\|small GTPase mediated signal transduction |
| miR-125b | BC002510 | RAB6B | RAB6B, member RAS oncogene family | P + T | GTP binding\|GTPase activity\|Golgi apparatus\|intracellular protein transport\|retrograde transport, Golgi to ER\|small GTPase mediated signal transduction |
| miR-125b | AK022662 | RASAL2 | RAS protein activator like 2 | P + T | GTPase activator activity\|Ras GTPase activator activity\|signal transduction |
| miR-125b | NM_004841 | RASAL2 | RAS protein activator like 2 | P + T | GTPase activator activity\|Ras GTPase activator activity\|signal transduction |
| miR-125b | NM_016090 | RBM7 | RNA binding motif protein 7 | P + T | RNA binding\|meiosis\|nucleic acid binding\|nucleotide binding |
| miR-125b | NM_006268 | REQ | requiem, apoptosis response zinc finger gene | M + P + T | DNA binding\|apoptosis\|induction of apoptosis by extracellular signals\|nucleus\|protein ubiquitination\|regulation of transcription, DNA-dependent\|transcription\|ubiquitin ligase complex\|ubiquitin-protein ligase activity\|zinc ion binding |
| miR-125b | NM_000449 | RFX5 | regulatory factor X, 5 (influences HLA class II expression) | P + T | nucleus\|regulation of transcription, DNA-dependent\|transcription\|transcription coactivator activity\|transcription factor activity\|transcription from RNA polymerase II promoter |
| miR-125b | NM_003721 | RFXANK | regulatory factor X-associated ankyrin-containing protein | P + T | humoral immune response\|nucleus\|regulation of transcription, DNA-dependent\|transcription\|transcription coactivator activity\|transcription factor activity\|transcription from RNA polymerase II promoter |
| miR-125b | NM_014746 | RNF144 | likely ortholog of mouse ubiquitin conjugating enzyme 7 interacting protein 4 | P + T | nucleus\|protein ubiquitination\|ubiquitin ligase complex\|ubiquitin-protein ligase activity\|zinc ion binding |
| miR-125b | NM_014771 | RNF40 | ring finger protein 40 | M + P + T | protein ubiquitination\|ubiquitin ligase complex\|ubiquitin-protein ligase activity\|zinc ion binding |
| miR-125b | AL109955 | RNPC1 | RNA-binding region (RNP1, RRM) containing 1 | P + T | |
| miR-125b | AF116627 | RPL29 | ribosomal protein L29 | M + T | |
| miR-125b | NM_002953 | RPS6KA1 | ribosomal protein S6 kinase, 90 kDa, polypeptide 1 | M + P + T | ATP binding\|protein amino acid phosphorylation\|protein serine/threonine kinase activity\|protein serine/threonine kinase activity\|protein-tyrosine kinase activity\|signal transduction\|transferase activity |
| miR-125b | NM_000332 | SCA1 | spinocerebellar ataxia 1 (olivopontocerebellar ataxia 1, autosomal dominant, ataxin 1) | P + T | RNA binding\|cytoplasm\|nucleus |
| miR-125b | NM_012429 | SEC14L2 | SEC14-like 2 (S. cerevisiae) | P + T | cytoplasm\|intracellular protein transport\|membrane\|nucleus\|phospholipid binding\|positive regulation of transcription, DNA-dependent\|protein carrier activity\|regulation of cholesterol biosynthesis\|transcription\|transcriptional activator activity\|transport\|vitamin E binding |
| miR-125b | NM_005065 | SEL1L | sel-1 suppressor of lin-12-like (C. elegans) | P + T | catalytic activity\|integral to membrane |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-125b | NM_017789 | SEMA4C | sema domain, immunoglobulin domain (Ig), transmembrane domain (TM) and short cytoplasmic domain, (semaphorin) 4C | M + P + T | cell differentiation|integral to membrane|membrane|neurogenesis|receptor activity |
| miR-125b | NM_006378 | SEMA4D | sema domain, immunoglobulin domain (Ig), transmembrane domain (TM) and short cytoplasmic domain, (semaphorin) 4D | P + T | anti-apoptosis|cell adhesion|cell differentiation|immune response|integral to membrane|membrane|neurogenesis|receptor activity |
| miR-125b | BE622841 | SENP2 | sentrin-specific protease | M + P | |
| miR-125b | NM_003011 | SET | SET translocation (myeloid leukemia-associated) | M + T | DNA replication|endoplasmic reticulum|histone binding|negative regulation of histone acetylation|nucleocytoplasmic transport|nucleosome assembly|nucleosome disassembly|nucleus|perinuclear region|protein phosphatase inhibitor activity|protein phosphatase type 2A regulator activity |
| miR-125b | NM_006275 | SFRS6 | splicing factor, arginine/serine-rich 6 | P + T | RNA binding|mRNA splice site selection|nuclear mRNA splicing, via spliceosome|nucleotide binding|nucleus |
| miR-125b | AF015043 | SH3BP4 | SH3-domain binding protein 4 | P + T | cell cycle|endocytosis|nucleus|signal transducer activity |
| miR-125b | NM_016538 | SIRT7 | sirtuin silent mating type information regulation 2 homolog 7 (S. cerevisiae) | P + T | DNA binding|chromatin silencing|chromatin silencing complex|hydrolase activity|regulation of transcription, DNA-dependent |
| miR-125b | NM_020309 | SLC17A7 | solute carrier family 17 (sodium-dependent inorganic phosphate cotransporter), member 7 | P + T | integral to membrane|phosphate transport|sodium-dependent phosphate transporter activity|transport|transporter activity |
| miR-125b | NM_013272 | SLC21A11 | solute carrier family 21 (organic anion transporter), member 11 | P + T | integral to membrane|ion transport|membrane|transporter activity |
| miR-125b | AK000722 | SLC27A4 | solute carrier family 27 (fatty acid transporter), member 4 | P + T | catalytic activity|fatty acid transport|fatty acid transporter activity|ligase activity|lipid metabolism|lipid transport|metabolism |
| miR-125b | NM_003759 | SLC4A4 | solute carrier family 4, sodium bicarbonate cotransporter, member 4 | P + T | anion transport|inorganic anion exchanger activity|integral to membrane|integral to plasma membrane|membrane|sodium:bicarbonate symporter activity|transport |
| miR-125b | NM_003045 | SLC7A1 | solute carrier family 7 (cationic amino acid transporter, y + system), member 1 | P + T | amino acid metabolism|amino acid permease activity|amino acid transport|basic amino acid transporter activity|integral to plasma membrane|membrane|receptor activity|transport |
| miR-125b | NM_003983 | SLC7A6 | solute carrier family 7 (cationic amino acid transporter, y + system), member 6 | P + T | amino acid metabolism|amino acid transport|amino acid-polyamine transporter activity|integral to plasma membrane|plasma membrane|protein complex assembly|transport |
| miR-125b | AF113019 | SMARCD2 | SWI/SNF related, matrix associated, actin dependent regulator of chromatin, subfamily d, member 2 | M + P + T | chromatin remodeling|nucleoplasm|regulation of transcription from RNA polymerase II promoter|transcription|transcription coactivator activity |
| miR-125b | NM_005985 | SNAI1 | snail homolog 1 (Drosophila) | P + T | DNA binding|cartilage condensation|development|neurogenesis|nucleus|zinc ion binding |
| miR-125b | AB037750 | SORCS2 | VPS10 domain receptor protein | P + T | integral to membrane|intracellular protein transport|membrane|membrane|neuropeptide receptor activity|neuropeptide signaling |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-125b | BE742268 | SORT1 | sortilin 1 | P + T | pathway\|protein binding\|protein transporter activity\|sugar binding endocytosis\|endosome\|integral to membrane\|integral to membrane\|intracellular protein transport\|membrane\|neurotensin receptor activity, G-protein coupled\|protein transporter activity\|receptor activity |
| miR-125b | AI360875 | SOX11 | SRY (sex determining region Y)-box 11 | M + T | DNA binding\|neurogenesis\|nucleus\|regulation of transcription, DNA-dependent\|transcription |
| miR-125b | AU121035 | SP1 | Sp1 transcription factor | P + T | DNA binding\|RNA polymerase II transcription factor activity\|nucleus\|regulation of transcription, DNA-dependent\|transcription\|transcriptional activator activity\|zinc ion binding |
| miR-125b | NM_003131 | SRF | serum response factor (c-fos serum response element binding transcription factor) | M + T | RNA polymerase II transcription factor activity\|nucleus\|regulation of transcription from RNA polymerase II promoter\|signal transduction\|transcription\|transcription factor activity |
| miR-125b | NM_005637 | SS18 | synovial sarcoma translocation, chromosome 18 | P + T | nucleus |
| miR-125b | AF343880 | SSX2 | synovial sarcoma, X breakpoint 2 | P + T | nucleus |
| miR-125b | NM_014682 | ST18 | suppression of tumorigenicity 18 (breast carcinoma) (zinc finger protein) | P + T | nucleus\|regulation of transcription, DNA-dependent\|transcription factor activity |
| miR-125b | AA128023 | STARD13 | START domain containing 13 | P + T | |
| miR-125b | BC000627 | STAT3 | signal transducer and activator of transcription 3 (acute-phase response factor) | P + T | JAK-STAT cascade\|acute-phase response\|calcium ion binding\|cell motility\|cytoplasm\|hematopoietin\|interferon-class (D200-domain) cytokine receptor signal transducer activity\|intracellular signaling cascade\|negative regulation of transcription from RNA polymerase II promoter\|neurogenesis\|nucleus\|nucleus\|regulation of transcription, DNA-dependent\|signal transducer activity\|transcription\|transcription factor activity\|transcription factor activity |
| miR-125b | NM_003155 | STC1 | stanniocalcin 1 | P + T | calcium ion homeostasis\|cell surface receptor linked signal transduction\|cell-cell signaling\|extracellular region\|hormone activity\|response to nutrients |
| miR-125b | NM_003173 | SUV39H1 | suppressor of variegation 3-9 homolog 1 (*Drosophila*) | P + T | DNA replication and chromosome cycle\|S-adenosylmethionine-dependent methyltransferase activity\|chromatin\|chromatin assembly or disassembly\|chromatin binding\|chromatin modification\|condensed nuclear chromosome\|histone lysine N-methyltransferase activity (H3-K9 specific)\|histone-lysine N-methyltransferase activity\|methyltransferase activity\|nucleus\|nucleus\|protein binding\|transferase activity\|zinc ion binding |
| miR-125b | AW139618 | SYN2 | synapsin II | P + T | neurotransmitter secretion\|synapse\|synaptic transmission\|synaptic vesicle |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-125b | R60550 | TAF5L | TAF5-like RNA polymerase II, p300/CBP-associated factor (PCAF)-associated factor, 65 kDa | M + P + T | nucleus\|regulation of transcription, DNA-dependent\|transcription factor activity\|transcription from RNA polymerase II promoter |
| miR-125b | AF220509 | TAF9L | TAF9-like RNA polymerase II, TATA box binding protein (TBP)-associated factor, 31 kDa | P + T | DNA binding\|nucleus\|regulation of transcription, DNA-dependent\|transcription factor TFIID complex\|transcription initiation |
| miR-125b | NM_000116 | TAZ | tafazzin (cardiomyopathy, dilated 3A (X-linked); endocardial fibroelastosis 2; Barth syndrome) | M + P + T | acyltransferase activity\|heart development\|integral to membrane\|metabolism\|muscle contraction\|muscle development |
| miR-125b | NM_018488 | TBX4 | T-box 4 | P + T | development\|nucleus\|regulation of transcription, DNA-dependent\|transcription\|transcription factor activity |
| miR-125b | NM_012249 | TC10 | ras-like protein TC10 | M + T | GTP binding\|GTPase activity\|plasma membrane\|small GTPase mediated signal transduction |
| miR-125b | BG387172 | TEAD2 | TEA domain family member 2 | P + T | nucleus\|nucleus\|regulation of transcription, DNA-dependent\|regulation of transcription, DNA-dependent\|transcription\|transcription factor activity\|transcription factor activity |
| miR-125b | U06935 | TEF | thyrotrophic embryonic factor | P + T | RNA polymerase II transcription factor activity\|nucleus\|regulation of transcription from RNA polymerase II promoter\|rhythmic process\|transcription\|transcription factor activity |
| miR-125b | NM_006464 | TGOLN2 | trans-golgi network protein 2 | P + T | Golgi trans face\|integral to membrane\|transport vesicle |
| miR-125b | BE219311 | TIMM22 | translocase of inner mitochondrial membrane 22 homolog (yeast) | P + T | integral to membrane\|mitochondrial inner membrane\|mitochondrion\|protein transport\|protein transporter activity |
| miR-125b | NM_003326 | TNFSF4 | tumor necrosis factor (ligand) superfamily, member 4 (tax-transcriptionally activated glycoprotein 1, 34 kDa) | P + T | cell-cell signaling\|immune response\|integral to plasma membrane\|membrane\|positive regulation of cell proliferation\|signal transduction\|tumor necrosis factor receptor binding |
| miR-125b | AA873275 | TOR2A | torsin family 2, member A | P + T | ATP binding\|GTP cyclohydrolase I activity\|biosynthesis\|chaperone cofactor dependent protein folding\|endoplasmic reticulum\|nucleoside-triphosphatase activity\|nucleotide binding |
| miR-125b | AW341649 | TP53INP1 | tumor protein p53 inducible nuclear protein 1 | M + P + T | apoptosis\|nucleus |
| miR-125b | NM_014112 | TRPS1 | trichorhinophalangeal syndrome I | P + T | NLS-bearing substrate-nucleus import\|nucleus\|regulation of transcription, DNA-dependent\|skeletal development\|transcription\|transcription factor activity\|transcription from RNA polymerase II promoter\|zinc ion binding |
| miR-125b | NM_001070 | TUBG1 | tubulin, gamma 1 | P + T | GTP binding\|GTPase activity\|centrosome\|condensed nuclear chromosome\|gamma-tubulin complex\|meiotic spindle organization and biogenesis\|microtubule\|microtubule nucleation\|microtubule-based movement\|mitotic spindle organization and biogenesis\|polar microtubule\|protein binding\|protein polymerization\|spindle pole body\|structural constituent of cytoskeleton |
| miR-125b | NM_003330 | TXNRD1 | thioredoxin reductase 1 | P + T | FAD binding\|cell redox homeostasis\|cytoplasm\|disulfide |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| | | | | | oxidoreductase activity|electron transport|electron transporter activity|oxidoreductase activity, acting on NADH or NADPH, disulfide as acceptor|signal transduction|thioredoxin-disulfide reductase activity |
| miR-125b | BC004862 | UBE2R2 | ubiquitin-conjugating enzyme E2R 2 | P + T | ligase activity|ubiquitin conjugating enzyme activity|ubiquitin cycle|ubiquitin-protein ligase activity |
| miR-125b | NM_003728 | UNC5C | unc-5 homolog B (C. elegans) | P + T | apoptosis|axon guidance|brain development|development|integral to membrane|netrin receptor activity|protein binding|receptor activity|signal transduction |
| miR-125b | NM_003369 | UVRAG | UV radiation resistance associated gene | P + T | DNA repair|cytoplasm |
| miR-125b | AF195514 | VPS4B | vacuolar protein sorting 4B (yeast) | M + P + T | ATP binding|ATPase activity, coupled|membrane|membrane fusion|nucleoside-triphosphatase activity|nucleotide binding|peroxisome organization and biogenesis|protein binding|regulation of transcription, DNA-dependent |
| miR-125b | R51061 | VTS58635 | mitogen-activated protein kinase kinase kinase kinase 1 | P + T | GTP binding|small GTPase mediated signal transduction |
| miR-125b | NM_004184 | WARS | tryptophanyl-tRNA synthetase | M + T | ATP binding|cytoplasm|ligase activity|negative regulation of cell proliferation|protein biosynthesis|soluble fraction|tryptophan-tRNA ligase activity|tryptophanyl-tRNA aminoacylation|tryptophanyl-tRNA aminoacylation |
| miR-125b | NM_005433 | YES1 | v-yes-1 Yamaguchi sarcoma viral oncogene homolog 1 | P + T | ATP binding|intracellular signaling cascade|protein amino acid phosphorylation|protein-tyrosine kinase activity|transferase activity |
| miR-125b | NM_017740 | ZDHHC7 | zinc finger, DHHC domain containing 7 | P + T | integral to membrane|metal ion binding |
| miR-125b | BF525395 | ZFP385 | likely ortholog of mouse zinc finger protein 385 | M + P + T | DNA binding|nucleic acid binding|nucleus|regulation of transcription, DNA-dependent|transcription|zinc ion binding |
| miR-125b | NM_007345 | ZNF236 | zinc finger protein 236 | P + T | nucleus|regulation of transcription, DNA-dependent|transcription|transcription factor activity|zinc ion binding |
| miR-125b | NM_012482 | ZNF281 | zinc finger protein 281 | M + P + T | DNA binding|DNA-directed RNA polymerase II, core complex|negative regulation of transcription from RNA polymerase II promoter|nucleus|regulation of transcription, DNA-dependent|specific RNA polymerase II transcription factor activity|transcription|zinc ion binding |
| miR-125b | NM_003427 | ZNF76 | zinc finger protein 76 (expressed in testis) | P + T | DNA binding|nucleus|regulation of transcription from RNA polymerase II promoter|regulation of transcription from RNA polymerase III promoter|transcription|zinc ion binding |
| miR-125b | NM_022465 | ZNFN1A4 | zinc finger protein, subfamily 1A, 4 (Eos) | M + P + T | nucleic acid binding|nucleus|transcription factor activity|transcriptional repressor activity|zinc ion binding |
| miR-145 | NM_005502 | ABCA1 | ATP-binding cassette, sub-family A (ABC1), member 1 | P + T | ATP binding|ATP binding|ATPase activity|anion transporter activity|cholesterol metabolism|integral to plasma membrane|lipid metabolism|membrane fraction|nucleotide binding|steroid |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-145 | AL527773 | ABR | active BCR-related gene | M + P + T | metabolism\|sterol transporter activity\|transport\|transport GTPase activator activity\|guanyl-nucleotide exchange factor activity\|small GTPase mediated signal transduction |
| miR-145 | NM_001616 | ACVR2 | activin A receptor, type II | M + P + T | ATP binding\|integral to plasma membrane\|membrane\|protein amino acid phosphorylation\|receptor activity\|transferase activity\|transforming growth factor beta receptor activity\|transmembrane receptor protein serine/threonine kinase signaling pathway |
| miR-145 | NM_003183 | ADAM17 | a disintegrin and metalloproteinase domain 17 (tumor necrosis factor, alpha, converting enzyme) | P + T | cell-cell signaling\|integral to plasma membrane\|metalloendopeptidase activity\|proteolysis and peptidolysis\|zinc ion binding |
| miR-145 | NM_019903 | ADD3 | adducin 3 (gamma) | M + P + T | calmodulin binding\|cytoskeleton\|membrane\|structural constituent of cytoskeleton |
| miR-145 | AB003476 | AKAP12 | A kinase (PRKA) anchor protein (gravin) 12 | P + T | G-protein coupled receptor protein signaling pathway\|cytoplasm\|protein binding\|protein kinase A binding\|protein targeting\|signal transduction |
| miR-145 | NM_016201 | AMOTL2 | angiomotin like 2 | M + P + T | |
| miR-145 | NM_001128 | AP1G1 | adaptor-related protein complex 1, gamma 1 subunit | M + P + T | Golgi apparatus\|binding\|clathrin coat of trans-Golgi network vesicle\|coated pit\|endocytosis\|intracellular protein transport\|intracellular protein transport\|membrane coat adaptor complex\|protein complex assembly\|transporter activity |
| miR-145 | NM_001284 | AP3S1 | adaptor-related protein complex 3, sigma 1 subunit | M + P + T | Golgi apparatus\|clathrin vesicle coat\|insulin receptor signaling pathway\|intracellular protein transport\|membrane coat adaptor complex\|transport\|transport vesicle\|transporter activity |
| miR-145 | NM_006380 | APPBP2 | amyloid beta precursor protein (cytoplasmic tail) binding protein 2 | M + P + T | binding\|cytoplasm\|intracellular protein transport\|membrane\|microtubule associated complex\|microtubule motor activity\|nucleus |
| miR-145 | AB037845 | ARHGAP10 | Rho-GTPase activating protein 10 | M + T | protein binding |
| miR-145 | AL516350 | ARPC5 | actin related protein 2/3 complex, subunit 5, 16 kDa | P + T | Arp2/3 protein complex\|actin cytoskeleton organization and biogenesis\|cell motility\|cytoplasm\|cytoskeleton\|regulation of actin filament polymerization\|structural constituent of cytoskeleton |
| miR-145 | U72937 | ATRX | alpha thalassemia/mental retardation syndrome X-linked (RAD54 homolog, S. cerevisiae) | M + T | ATP binding\|DNA binding\|DNA helicase activity\|DNA methylation\|DNA recombination\|DNA repair\|chromosome organization and biogenesis (sensu Eukaryota)\|helicase activity\|hydrolase activity\|nuclear heterochromatin\|nucleus\|perception of sound\|regulation of transcription, DNA-dependent\|transcription factor activity |
| miR-145 | NM_021813 | BACH2 | BTB and CNC homology 1, basic leucine zipper transcription factor 2 | P + T | DNA binding\|nucleus\|protein binding\|regulation of transcription, DNA-dependent\|transcription |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-145 | NM_013449 | BAZ2A | bromodomain adjacent to zinc finger domain, 2A | P + T | DNA binding\|chromatin remodeling\|nucleolus organizer complex\|nucleus\|regulation of transcription, DNA-dependent\|transcription\|transcription regulator activity |
| miR-145 | NM_007005 | BCE-1 | BCE-1 protein | M + P | frizzled signaling pathway\|molecular_function unknown\|nucleus\|nucleus\|regulation of transcription\|regulation of transcription, DNA-dependent |
| miR-145 | NM_003458 | BSN | bassoon (presynaptic cytomatrix protein) | P + T | cytoskeleton\|metal ion binding\|nucleus\|structural constituent of cytoskeleton\|synapse\|synaptic transmission\|synaptosome |
| miR-145 | NM_013279 | C11orf9 | chromosome 11 open reading frame 9 | M + P + T | |
| miR-145 | NM_024643 | C14orf140 | hypothetical protein FLJ23093 | P + T | |
| miR-145 | NM_018270 | C20orf20 | chromosome 20 open reading frame 20 | P + T | chromatin modification\|nucleus\|regulation of cell growth\|regulation of transcription, DNA-dependent\|transcription |
| miR-145 | NM_004276 | CABP1 | calcium binding protein 1 (calbrain) | P + T | calcium ion binding\|calcium ion binding\|enzyme inhibitor activity |
| miR-145 | NM_001755 | CBFB | core-binding factor, beta subunit | M + P + T | RNA polymerase II transcription factor activity\|nucleus\|transcription coactivator activity\|transcription factor activity\|transcription from RNA polymerase II promoter |
| miR-145 | NM_001759 | CCND2 | cyclin D2 | P + T | cytokinesis\|nucleus\|regulation of cell cycle |
| miR-145 | NM_020307 | CCNL1 | cyclin L ania-6a | M + P + T | cell cycle\|regulation of cell cycle |
| miR-145 | AL118798 | CD47 | CD47 antigen (Rh-related antigen, integrin-associated signal transducer) | P + T | cell-matrix adhesion\|integral to plasma membrane\|integrin-mediated signaling pathway\|plasma membrane\|protein binding |
| miR-145 | BF576053 | CFL2 | cofilin 2 (muscle) | M + P + T | actin binding\|cytoskeleton\|nucleus |
| miR-145 | AA835485 | CKLiK | CamKI-like protein kinase | P + T | ATP binding\|calcium- and calmodulin-dependent protein kinase activity\|calmodulin binding\|nucleus\|protein amino acid phosphorylation\|protein serine/threonine kinase activity\|transferase activity |
| miR-145 | NM_004921 | CLCA3 | chloride channel, calcium activated, family member 3 | P + T | extracellular space\|transport\|transporter activity |
| miR-145 | NM_001326 | CSTF3 | cleavage stimulation factor, 3' pre-RNA, subunit 3, 77 kDa | M + P + T | RNA binding\|binding\|mRNA cleavage\|mRNA polyadenylylation\|nucleus |
| miR-145 | NM_020248 | CTNNBIP1 | catenin, beta interacting protein 1 | P + T | Wnt receptor signaling pathway\|beta-catenin binding\|cell proliferation\|development\|nucleus\|regulation of transcription, DNA-dependent\|signal transduction |
| miR-145 | AW772082 | DACH | dachshund homolog (*Drosophila*) | P + T | DNA binding\|development\|eye morphogenesis (sensu Endopterygota)\|nucleus\|regulation of transcription, DNA-dependent\|transcription |
| miR-145 | NM_004393 | DAG1 | dystroglycan 1 (dystrophin-associated glycoprotein 1) | M + P + T | actin cytoskeleton\|calcium ion binding\|extracellular matrix (sensu Metazoa)\|integral to plasma membrane\|laminin receptor activity\|membrane fraction\|muscle contraction\|plasma membrane\|protein binding\|protein complex assembly |
| miR-145 | NM_003887 | DDEF2 | development and differentiation enhancing factor 2 | P + T | GTPase activator activity\|Golgi apparatus\|regulation of GTPase activity |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-145 | AL080239 | DKFZp547M2010 | hypothetical protein DKFZp547M2010 | M + P + T | |
| miR-145 | AL137517 | DKFZp564O1278 | hypothetical protein DKFZp564O1278 | P + T | integral to membrane |
| miR-145 | NM_001386 | DPYSL2 | dihydropyrimidinase-like 2 | P + T | dihydropyrimidinase activity\|hydrolase activity\|neurogenesis\|nucleobase, nucleoside, nucleotide and nucleic acid metabolism\|signal transduction |
| miR-145 | BC003143 | DUSP6 | dual specificity phosphatase 6 | P + T | MAP kinase phosphatase activity\|cytoplasm\|hydrolase activity\|inactivation of MAPK\|protein amino acid dephosphorylation\|protein serine/threonine phosphatase activity\|protein tyrosine phosphatase activity\|regulation of cell cycle\|soluble fraction |
| miR-145 | D86550 | DYRK1A | dual-specificity tyrosine-(Y)-phosphorylation regulated kinase 1A | P + T | ATP binding\|neurogenesis\|nucleus\|protein amino acid phosphorylation\|protein serine/threonine kinase activity\|protein-tyrosine kinase activity\|transferase activity |
| miR-145 | NM_001967 | EIF4A2 | eukaryotic translation initiation factor 4A, isoform 2 | M + P + T | ATP binding\|ATP-dependent helicase activity\|DNA binding\|RNA binding\|eukaryotic translation initiation factor 4F complex\|hydrolase activity\|protein biosynthesis\|regulation of translational initiation\|translation initiation factor activity |
| miR-145 | NM_001417 | EIF4B | eukaryotic translation initiation factor 4B | M + T | RNA binding\|eukaryotic translation initiation factor 4F complex\|nucleic acid binding\|nucleotide binding\|protein biosynthesis\|regulation of translational initiation\|translation initiation factor activity\|translation initiation factor activity |
| miR-145 | BC005057 | EIF4EBP2 | eukaryotic translation initiation factor 4E binding protein 2 | P + T | eukaryotic initiation factor 4E binding\|negative regulation of protein biosynthesis\|negative regulation of translational initiation\|regulation of translation |
| miR-145 | NM_020909 | EPB41L5 | erythrocyte membrane protein band 4.1 like 5 | P + T | binding\|cytoplasm\|cytoskeletal protein binding\|cytoskeleton\|membrane |
| miR-145 | NM_005797 | EVA1 | epithelial V-like antigen 1 | P + T | cell adhesion\|cytoskeleton\|homophilic cell adhesion\|integral to membrane\|membrane\|morphogenesis\|protein binding |
| miR-145 | NM_022977 | FACL4 | fatty-acid-Coenzyme A ligase, long-chain 4 | M + P + T | fatty acid metabolism\|integral to membrane\|learning and/or memory\|ligase activity\|lipid metabolism\|long-chain-fatty-acid-CoA ligase activity\|magnesium ion binding\|metabolism |
| miR-145 | AL042120 | FHOD2 | formin homology 2 domain containing 2 | M + P | Rho GTPase binding\|actin binding\|actin cytoskeleton organization and biogenesis\|cell organization and biogenesis\|nucleus\|regulation of transcription, DNA-dependent\|transcription factor activity\|translation initiation factor activity\|translational initiation |
| miR-145 | NM_002013 | FKBP3 | FK506 binding protein 3, 25 kDa | P + T | FK506 binding\|isomerase activity\|nucleus\|peptidyl-prolyl cis-trans isomerase activity\|protein folding\|receptor activity |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-145 | NM_002017 | FLI1 | Friend leukemia virus integration 1 | M + P + T | hemostasis\|nucleus\|organogenesis\|regulation of transcription, DNA-dependent\|transcription\|transcription factor activity |
| miR-145 | NM_023071 | FLJ13117 | hypothetical protein FLJ13117 | P + T | |
| miR-145 | AL561281 | FLJ20373 | hypothetical protein FLJ20373 | M + P + T | ATP binding\|cellular_component unknown\|protein amino acid phosphorylation\|protein kinase cascade\|protein serine/threonine kinase activity\|response to stress\|signal transduction\|small GTPase regulator activity\|transferase activity |
| miR-145 | AK025444 | FLJ21791 | hypothetical protein FLJ21791 | M + T | |
| miR-145 | NM_024713 | FLJ22557 | hypothetical protein FLJ22557 | P + T | |
| miR-145 | AA872588 | FLJ36155 | likely ortholog of mouse Gli-similar 1 Kruppel-like zinc finger (Glis1) | P + T | DNA binding\|negative regulation of transcription from RNA polymerase II promoter\|nucleus\|positive regulation of transcription from RNA polymerase II promoter\|regulation of transcription, DNA-dependent\|specific RNA polymerase II transcription factor activity\|transcription\|zinc ion binding |
| miR-145 | AI434509 | FLJ38499 | Unnamed protein product [*Homo sapiens*], mRNA sequence | P + T | nucleic acid binding |
| miR-145 | M62994 | FLNB | filamin B, beta (actin binding protein 278) | P + T | actin binding\|actin binding\|actin cytoskeleton\|actin cytoskeleton organization and biogenesis\|cell differentiation\|cytoskeletal anchoring\|integral to plasma membrane\|myogenesis\|signal transduction |
| miR-145 | NM_002025 | FMR2 | fragile X mental retardation 2 | M + T | brain development\|learning and/or memory |
| miR-145 | N29672 | FOS | v-fos FBJ murine osteosarcoma viral oncogene homolog | M + T | proto-oncogene |
| miR-145 | NM_002015 | FOXO1A | forkhead box O1A (rhabdomyosarcoma) | M + P + T | anti-apoptosis\|nucleus\|regulation of transcription from RNA polymerase II promoter\|transcription\|transcription factor activity |
| miR-145 | NM_003507 | FZD7 | frizzled homolog 7 (*Drosophila*) | M + P + T | G-protein coupled receptor activity\|G-protein coupled receptor protein signaling pathway\|Wnt receptor activity\|development\|frizzled signaling pathway\|integral to membrane\|plasma membrane |
| miR-145 | AL049709 | GGTL3 | gamma-glutamyltransferase-like 3 | M + P + T | |
| miR-145 | NM_022735 | GOCAP1 | golgi complex associated protein 1, 60 kDa | M + P + T | Golgi apparatus\|acyl-CoA binding\|catalytic activity\|intracellular protein transport\|membrane\|mitochondrion\|protein carrier activity\|steroid biosynthesis |
| miR-145 | NM_020806 | GPHN | gephyrin | P + T | Mo-molybdopterin cofactor biosynthesis\|catalytic activity\|cytoskeleton |
| miR-145 | NM_015071 | GRAF | GTPase regulator associated with focal adhesion kinase pp125(FAK) | P + T | Rho GTPase activator activity\|actin cytoskeleton organization and biogenesis\|cellular_component unknown\|neurogenesis |
| miR-145 | NM_017913 | HARC | Hsp90-associating relative of Cdc37 | P + T | cytokinesis\|regulation of cell cycle |
| miR-145 | BC006237 | HECTD1 | HECT domain containing 1 | M + T | intracellular\|ligase activity\|receptor activity\|ubiquitin cycle\|ubiquitin-protein ligase activity |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-145 | U64317 | HEF1 | enhancer of filamentation 1 (cas-like docking; Crk-associated substrate related) | P + T | actin filament bundle formation\|cell adhesion\|cytokinesis\|cytoplasm\|cytoskeleton\|cytoskeleton organization and biogenesis\|integrin-mediated signaling pathway\|mitosis\|nucleus\|protein binding\|regulation of cell cycle\|regulation of cell growth\|signal transduction\|spindle |
| miR-145 | NM_016258 | HGRG8 | high-glucose-regulated protein 8 | P + T | |
| miR-145 | AL162003 | HIC2 | hypermethylated in cancer 2 | P + T | DNA binding\|negative regulation of transcription, DNA-dependent\|nucleus\|protein C-terminus binding\|transcription\|zinc ion binding |
| miR-145 | NM_014212 | HOXC11 | homeo box C11 | M + P + T | RNA polymerase II transcription factor activity\|development\|endoderm development\|nucleus\|regulation of transcription, DNA-dependent\|transcription factor activity |
| miR-145 | NM_002193 | INHBB | inhibin, beta B (activin AB beta polypeptide) | M + P + T | cell differentiation\|cytokine activity\|defense response\|extracellular region\|growth\|growth factor activity hormone activity\|host cell surface receptor binding\|negative regulation of follicle-stimulating hormone secretion\|negative regulation of hepatocyte growth factor biosynthesis\|ovarian follicle development\|positive regulation of follicle-stimulating hormone secretion\|protein binding\|protein homodimerization activity\|response to external stimulus |
| miR-145 | NM_005544 | IRS1 | insulin receptor substrate 1 | M + P + T | cytoplasm\|insulin receptor binding\|protein binding\|signal transducer activity\|signal transduction\|transmembrane receptor protein tyrosine kinase docking protein activity |
| miR-145 | NM_006459 | KEO4 | similar to *Caenorhabditis elegans* protein C42C1.9 | P + T | catalytic activity |
| miR-145 | NM_014686 | KIAA0355 | KIAA0355 gene product | P + T | |
| miR-145 | NM_015176 | KIAA0483 | KIAA0483 protein | P + T | ubiquitin cycle |
| miR-145 | NM_014871 | KIAA0710 | KIAA0710 gene product | M + P + T | cysteine-type endopeptidase activity\|exonuclease activity\|nucleus\|ubiquitin cycle\|ubiquitin thiolesterase activity\|ubiquitin-dependent protein catabolism |
| miR-145 | AA772278 | KIAA1673 | KIAA1673 | M + P + T | |
| miR-145 | AB051495 | KIAA1708 | KIAA1708 protein | P + T | ATP binding\|microtubule associated complex\|microtubule motor activity\|microtubule-based movement |
| miR-145 | AI814587 | KIAA1715 | KIAA1715 protein | M + T | |
| miR-145 | AI187364 | KIAA1894 | KIAA1894 protein | P + T | integral to membrane |
| miR-145 | AF155117 | KIF21A | kinesin family member 21A | P + T | ATP binding\|microtubule associated complex\|microtubule motor activity\|microtubule-based movement |
| miR-145 | NM_004235 | KLF4 | Kruppel-like factor 4 (gut) | M + T | mesodermal cell fate determination\|negative regulation of cell proliferation\|negative regulation of transcription, DNA-dependent\|negative regulation of |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| | | | | | transcription, DNA-dependent\|nucleic acid binding\|nucleus\|transcription factor activity\|transcription factor activity\|transcriptional activator activity\|transcriptional activator activity\|transcriptional repressor activity\|transcriptional repressor activity\|zinc ion binding\|zinc ion binding |
| miR-145 | T68150 | LL5beta | hypothetical protein FLJ21791 | M + T | |
| miR-145 | AI797833 | LOC285148 | a disintegrin and metalloproteinase domain 17 (tumor necrosis factor, alpha, converting enzyme) | P + T | catalytic activity |
| miR-145 | NM_025146 | MAK3P | likely ortholog of mouse Mak3p homolog (*S. cerevisiae*) | P + T | N-acetyltransferase activity |
| miR-145 | BF971923 | MAP3K3 | mitogen-activated protein kinase kinase kinase 3 | M + P | ATP binding\|MAP kinase kinase kinase activity\|MAPKKK cascade\|magnesium ion binding\|positive regulation of 1-kappaB kinase/NF-kappaB cascade\|protein amino acid phosphorylation\|protein kinase activity\|protein serine/threonine kinase activity\|signal transducer activity\|transferase activity |
| miR-145 | NM_004834 | MAP4K4 | mitogen-activated protein kinase kinase kinase kinase 4 | M + P + T | ATP binding\|cellular_component unknown\|protein amino acid phosphorylation\|protein kinase cascade\|protein serine/threonine kinase activity\|response to stress\|signal transduction\|small GTPase regulator activity\|transferase activity |
| miR-145 | BF382281 | MGC10120 | *Homo sapiens* cDNA FLJ30135 fis, clone BRACE2000061, mRNA sequence | P + T | |
| miR-145 | BG231756 | MGC10986 | hypothetical protein MGC10986 | M + P | ATP binding\|MAP kinase kinase kinase activity\|MAPKKK cascade\|magnesium ion binding\|positive regulation of I-kappaB kinase/NF-kappaB cascade\|protein amino acid phosphorylation\|protein kinase activity\|protein serine/threonine kinase activity\|signal transducer activity\|transferase activity |
| miR-145 | BC004869 | MGC2817 | hypothetical protein MGC2817 | P + T | outer membrane\|protein transport |
| miR-145 | BC002712 | MYCN | v-myc myelocytomatosis viral related oncogene, neuroblastoma derived (avian) | M + T | chromatin\|nucleus\|protein binding\|regulation of transcription from RNA polymerase II promoter\|transcription factor activity |
| miR-145 | AB007899 | NEDD4L | neural precursor cell expressed, developmentally down-regulated 4-like | P + T | excretion\|intracellular\|intracellular\|ligase activity\|positive regulation of endocytosis\|protein binding\|protein ubiquitination\|regulation of protein catabolism\|response to metal ion\|sodium channel regulator activity\|sodium ion homeostasis\|sodium ion transport\|ubiquitin cycle\|ubiquitin-protein ligase activity\|ubiquitin-protein ligase activity\|water homeostasis |
| miR-145 | NM_005863 | NET1 | neuroepithelial cell transforming gene 1 | P + T | guanyl-nucleotide exchange factor activity\|nucleus\|regulation of cell growth\|signal transduction |
| miR-145 | NM_003204 | NFE2L1 | nuclear factor (erythroid-derived 2)-like 1 | P + T | DNA binding\|heme biosynthesis\|inflammatory response\|morphogenesis\|nucleus\|nucleus\| |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-145 | NM_006469 | NS1-BP | NS1-binding protein | M + P + T | regulation of transcription, DNA-dependent\|transcription\|transcription cofactor activity\|transcription factor activity\|transcription from RNA polymerase II promoter\|RNA splicing\|protein binding\|response to virus\|spliceosome complex\|transcription factor complex\|transcription from RNA polymerase III promoter |
| miR-145 | NM_019094 | NUDT4 | nudix (nucleoside diphosphate linked moiety X)-type motif 4 | P + T | calcium-mediated signaling\|cyclic nucleotide metabolism cyclic-nucleotide-mediated signaling\|diphosphoinositol-polyphosphate diphosphatase activity\|hydrolase activity\|intracellular\|intracellular signaling cascade\|intracellular transport\|magnesium ion binding\|regulation of RNA-nucleus export |
| miR-145 | AW149417 | OAZ | OLF-1/EBF associated zinc finger gene | P + T | nucleic acid binding\|nucleus\|zinc ion binding |
| miR-145 | NM_024586 | OSBPL9 | oxysterol binding protein-like 9 | M + P | lipid transport\|steroid metabolism |
| miR-145 | AB040812 | PAK7 | p21(CDKN1A)-activated kinase 7 | M + T | ATP binding protein amino acid phosphorylation\|protein serine/threonine kinase activity\|transferase activity |
| miR-145 | NM_014456 | PDCD4 | programmed cell death 4 (neoplastic transformation inhibitor) | M + P + T | apoptosis |
| miR-145 | NM_002657 | PLAGL2 | pleiomorphic adenoma gene-like 2 | M + P + T | nucleus\|regulation of transcription, DNA-dependent\|transcription\|transcription factor activity\|zinc ion binding |
| miR-145 | AK023546 | PLCL2 | phospholipase C-like 2 | P + T | calcium ion binding\|intracellular signaling cascade\|lipid metabolism\|phosphoinositide phospholipase C activity |
| miR-145 | AI274352 | PLN | phospholamban | P + T | |
| miR-145 | NM_000944 | PPP3CA | protein phosphatase 3 (formerly 2B), catalytic subunit, alpha isoform (calcineurin A alpha) | P + T | calcineurin complex\|calcium ion binding\|calmodulin binding\|hydrolase activity\|protein amino acid dephosphorylation\|protein serine/threonine phosphatase activity |
| miR-145 | BF247371 | PRO1843 | hypothetical protein PRO1843 | M + T | |
| miR-145 | NM_000959 | PTGFR | prostaglandin F receptor (FP) | P + T | G-protein coupled receptor protein signaling pathway\|G-protein coupled receptor protein signaling pathway\|integral to membrane\|integral to plasma membrane\|parturition\|prostaglandin F receptor activity\|prostaglandin F receptor activity\|receptor activity\|rhodopsin-like receptor activity\|signal transduction\|thromboxane receptor activity |
| miR-145 | NM_002890 | RASA1 | RAS p21 protein activator (GTPase activating protein) 1 | P + T | Ras GTPase activator activity\|intracellular signaling cascade |
| miR-145 | NM_006506 | RASA2 | RAS p21 protein activator 2 | P + T | Ras GTPase activator activity\|intracellular signaling cascade |
| miR-145 | NM_002912 | REV3L | REV3-like, catalytic subunit of DNA polymerase zeta (yeast) | M + P + T | 3'-5' exonuclease activity\|DNA binding\|DNA repair\|DNA replication\|DNA-dependent DNA replication\|DNA-directed DNA polymerase activity\|nucleotide binding\|nucleus\|transferase |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-145 | NM_002924 | RGS7 | regulator of G-protein signalling 7 | P + T | activity\|zeta DNA polymerase activity\|zeta DNA polymerase complex heterotrimeric G-protein complex\|intracellular signaling cascade\|regulation of G-protein coupled receptor protein signaling pathway\|regulator of G-protein signaling activity\|signal transducer activity |
| miR-145 | AL136924 | RIN2 | Ras and Rab interactor 2 | P + T | GTPase activator activity\|Rab guanyl-nucleotide exchange factor activity\|cellular_component unknown\|endocytosis\|intracellular signaling cascade\|small GTPase mediated signal transduction\|small GTPase regulator activity |
| miR-145 | BE463945 | RTKN | rhotekin | P + T | intracellular\|protein binding\|signal transduction\|signal transduction |
| miR-145 | AF225986 | SCN3A | sodium channel, voltage-gated, type III, alpha polypeptide | P + T | cation channel activity\|cation transport\|integral to membrane\|membrane\|sodium ion transport\|voltage-gated sodium channel activity\|voltage-gated sodium channel complex |
| miR-145 | NM_006080 | SEMA3A | sema domain, immunoglobulin domain (Ig), short basic domain, secreted, (semaphorin) 3A | P + T | cell differentiation\|extracellular region\|neurogenesis |
| miR-145 | NM_020796 | SEMA6A | sema domain, transmembrane domain (TM), and cytoplasmic domain, (semaphorin) 6A | P + T | apoptosis\|axon\|axon guidance\|cell differentiation\|cell surface receptor linked signal transduction\|cytoskeleton organization and biogenesis\|development\|integral to membrane\|membrane\|neurogenesis\|protein binding\|receptor activity |
| miR-145 | NM_004171 | SLC1A2 | solute carrier family 1 (glial high affinity glutamate transporter), member 2 | P + T | L-glutamate transport\|L-glutamate transporter activity\|dicarboxylic acid transport\|integral to membrane\|membrane\|membrane fraction\|sodium:dicarboxylate symporter activity\|symporter activity\|synaptic transmission\|transport |
| miR-145 | NM_003759 | SLC4A4 | solute carrier family 4, sodium bicarbonate cotransporter, member 4 | P + T | anion transport\|inorganic anion exchanger activity\|integral to membrane\|integral to plasma membrane\|membrane\|sodium:bicarbonate symporter activity\|transport |
| miR-145 | NM_030918 | SNX27 | hypothetical protein My014 | M + P + T | intracellular signaling cascade\|protein binding\|protein transport |
| miR-145 | AI360875 | SOX11 | SRY (sex determining region Y)-box 11 | M + T | DNA binding\|neurogenesis\|nucleus\|regulation of transcription, DNA-dependent\|transcription |
| miR-145 | NM_000346 | SOX9 | SRY (sex determining region Y)-box 9 (campomelic dysplasia, autosomal sex-reversal) | P + T | DNA binding\|cartilage condensation\|nucleus\|regulation of transcription from RNA polymerase II promoter\|skeletal development\|specific RNA polymerase II transcription factor activity\|transcription |
| miR-145 | AK023899 | SRGAP1 | SLIT-ROBO Rho GTPase activating protein 1 | P + T | GTPase activator activity |
| miR-145 | NM_003155 | STC1 | stanniocalcin 1 | M + T | calcium ion homeostasis\|cell surface receptor linked signal transduction\|cell-cell signaling\|extracellular region\|hormone activity\|response to nutrients |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-145 | BE219311 | TIMM22 | translocase of inner mitochondrial membrane 22 homolog (yeast) | M + P + T | integral to membrane\|mitochondrial inner membrane\|mitochondrion\|protein transport\|protein transporter activity |
| miR-145 | AA705845 | TLE4 | transducin-like enhancer of split 4 (E(sp1) homolog, *Drosophila*) | M + P | frizzled signaling pathway\|molecular_function unknown\|nucleus\|nucleus\|regulation of transcription\|regulation of transcription, DNA-dependent |
| miR-145 | BC005016 | TRIM2 | tripartite motif-containing 2 | P + T | cytoplasm\|myosin binding\|protein ubiquitination\|ubiquitin ligase complex\|ubiquitin-protein ligase activity\|zinc ion binding |
| miR-145 | NM_025076 | UXS1 | UDP-glucuronate decarboxylase 1 | M + P + T | carbohydrate metabolism\|isomerase activity\|nucleotide-sugar metabolism |
| miR-145 | NM_005433 | YES1 | v-yes-1 Yamaguchi sarcoma viral oncogene homolog 1 | P + T | ATP binding\|intracellular signaling cascade\|protein amino acid phosphorylation\|protein-tyrosine kinase activity\|transferase activity |
| miR-145 | BC003128 | ZDHHC9 | zinc finger, DHHC domain containing 9 | P + T | integral to membrane\|metal ion binding |
| miR-155 | NM_019903 | ADD3 | adducin 3 (gamma) | P + T | calmodulin binding\|cytoskeleton\|membrane\|structural constituent of cytoskeleton |
| miR-155 | NM_020661 | AICDA | activation-induced cytidine deaminase | P + T | B-cell differentiation\|cellular_component unknown\|cytidine deaminase. activity\|hydrolase activity\|mRNA processing\|zinc ion binding |
| miR-155 | NM_007202 | AKAP10 | A kinase (PRKA) anchor protein 10 | P + T | kinase activity\|mitochondrion\|protein binding\|protein localization\|signal transducer activity\|signal transduction |
| miR-155 | AI806395 | ALFY | ALFY | P + T | binding\|zinc ion binding |
| miR-155 | NM_000038 | APC | adenomatosis polyposis coli | P + T | Wnt receptor signaling pathway\|beta-catenin binding\|cell adhesion\|microtubule binding\|negative regulation of cell cycle\|protein complex assembly\|signal transduction |
| miR-155 | NM_017610 | ARK | Arkadia | P + T | protein ubiquitination\|ubiquitin ligase complex\|ubiquitin-protein ligase activity\|zinc ion binding |
| miR-155 | BG032269 | ARL8 | ADP-ribosylation-like factor 8 | M + P + T | GTP binding\|small GTPase mediated signal transduction |
| miR-155 | AB000815 | ARNTL | aryl hydrocarbon receptor nuclear translocator-like | P + T | circadian rhythm\|nucleus\|regulation of transcription, DNA-dependent\|signal transducer activity\|signal transduction\|transcription\|transcription factor activity |
| miR-155 | NM_001670 | ARVCF | armadillo repeat gene deletes in velocardiofacial syndrome | P + T | cell adhesion\|cytoskeleton\|development\|protein binding\|structural molecule activity |
| miR-155 | AK024064 | ASTN2 | astrotactin 2 | P + T | integral to membrane |
| miR-155 | M95541 | ATP2B1 | ATPase, Ca + + transporting, plasma membrane 1 | M + P + T | ATP binding\|calcium ion binding\|calcium ion transport\|calcium-transporting ATPase activity\|calmodulin binding\|cation transport\|hydrolase activity\|hydrolase activity, acting on acid anhydrides, catalyzing transmembrane movement of substances\|integral to plasma membrane\|magnesium ion binding\|membrane\|metabolism |
| miR-155 | NM_001186 | BACH1 | BTB and CNC homology 1, basic leucine zipper transcription factor 1 | P + T | DNA binding\|nucleus\|protein binding\|regulation of transcription, DNA-dependent\|transcription\|transcription factor activity |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-155 | NM_007005 | BCE-1 | BCE-1 protein | P + T | frizzled signaling pathway\|molecular_function unknown\|nucleus\|nucleus\|regulation of transcription\|regulation of transcription, DNA-dependent |
| miR-155 | NM_022893 | BCL11A | B-cell CLL/lymphoma 11A (zinc finger protein) | P + T | cytoplasm\|hemopoiesis\|nucleic acid binding\|nucleus\|nucleus\|regulation of transcription, DNA-dependent\|transcription\|zinc ion binding |
| miR-155 | NM_001709 | BDNF | brain-derived neurotrophic factor | M + T | growth factor activity\|growth factor activity\|neurogenesis |
| miR-155 | NM_014577 | BRD1 | bromodomain containing 1 | P + T | DNA binding\|cell cycle\|nucleus\|nucleus\|regulation of transcription, DNA-dependent |
| miR-155 | NM_024529 | C1orf28 | chromosome 1 open reading frame 28 | M + P + T | |
| miR-155 | NM_000719 | CACNA1C | calcium channel, voltage-dependent, L type, alpha 1C subunit | P + T | calcium ion binding\|calcium ion transport\|cation transport\|integral to membrane\|ion channel activity\|ion transport\|membrane\|regulation of heart contraction rate\|voltage-gated calcium channel activity\|voltage-gated calcium channel activity\|voltage-gated calcium channel complex\|voltage-gated calcium channel complex |
| miR-155 | AL118798 | CD47 | CD47 antigen (Rh-related antigen, integrin-associated signal transducer) | P + T | cell-matrix adhesion\|integral to plasma membrane\|integrin-mediated signaling pathway\|plasma membrane\|protein binding |
| miR-155 | AL564683 | CEBPB | CCAAT/enhancer binding protein (C/EBP), beta | M + P + T | acute-phase response\|inflammatory response\|nucleus\|regulation of transcription, DNA-dependent\|transcription\|transcription factor activity\|transcription from RNA polymerase II promoter |
| miR-155 | NM_007023 | CGEF2 | cAMP-regulated guanine nucleotide exchange factor II | M + P | 3',5'-cAMP binding\|G-protein coupled receptor protein signaling pathway\|cAMP-dependent protein kinase complex\|cAMP-dependent protein kinase regulator activity\|exocytosis\|guanyl-nucleotide exchange factor activity\|membrane fraction\|nucleotide binding\|protein amino acid phosphorylation\|small GTPase mediated signal transduction |
| miR-155 | AU152178 | CMG2 | capillary morphogenesis protein 2 | P + T | integral to membrane\|receptor activity |
| miR-155 | NM_005776 | CNIH | cornichon homolog (*Drosophila*) | P + T | immune response\|integral to membrane\|intracellular signaling cascade\|membrane |
| miR-155 | AW241703 | CNTN4 | *Homo sapiens* cDNA FLJ32716 fis, clone TESTI2000808, highly similar to *Rattus norvegicus* neural cell adhesion protein BIG-2 precursor (BIG-2) mRNA, mRNA sequence | P + T | cell adhesion\|membrane\|protein binding |
| miR-155 | NM_000094 | COL7A1 | collagen, type VII, alpha 1 (epidermolysis bullosa, dystrophic, dominant and recessive) | P + T | basement membrane\|cell adhesion\|collagen type VII\|cytoplasm\|epidermis development\|phosphate transport\|protein binding\|serine-type endopeptidase inhibitor activity\|structural molecule activity |
| miR-155 | NM_003653 | COPS3 | COP9 constitutive photomorphogenic homolog subunit 3 (*Arabidopsis*) | P + T | signalosome complex |
| miR-155 | NM_005211 | CSF1R | colony stimulating factor 1 receptor, formerly McDonough feline sarcoma viral (v-fms) oncogene homolog | M + P + T | ATP binding\|antimicrobial humoral response (sensu Vertebrata)\|cell proliferation\|development\|integral to plasma membrane\|macrophage colony stimulating factor receptor activity\|plasma membrane\|protein |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-155 | NM_001892 | CSNK1A1 | casein kinase 1, alpha 1 | P + T | amino acid phosphorylation\|receptor activity\|signal transduction\|transferase activity\|transmembrane receptor protein tyrosine kinase signaling pathway ATP binding\|Wnt receptor signaling pathway\|casein kinase I activity\|protein amino acid phosphorylation\|protein amino acid phosphorylation\|protein serine/threonine kinase activity\|protein-tyrosine kinase activity\|transferase activity |
| miR-155 | NM_005214 | CTLA4 | cytotoxic T-lymphocyte-associated protein 4 | P + T | immune response\|immune response\|integral to plasma membrane\|membrane |
| miR-155 | U69546 | CUGBP2 | CUG triplet repeat, RNA binding protein 2 | M + P + T | RNA binding\|RNA binding\|RNA processing\|neuromuscular junction development\|nucleotide binding\|regulation of heart contraction rate |
| miR-155 | NM_030927 | DC-TM4F2 | tetraspanin similar to TM4SF9 | P + T | integral to membrane |
| miR-155 | NM_015652 | DKFZP564P1916 | DKFZP564P1916 protein | P + T | |
| miR-155 | AF151831 | DKFZP566C134 | DKFZP566C134 protein | P + T | protein binding |
| miR-155 | NM_004411 | DNCI1 | dynein, cytoplasmic, intermediate polypeptide 1 | P + T | cytoplasmic dynein complex\|motor activity |
| miR-155 | NM_001400 | EDG1 | endothelial differentiation, sphingolipid G-protein-coupled receptor, 1 | P + T | G-protein coupled receptor protein signaling pathway\|cell adhesion\|integral to plasma membrane\|lysosphingolipid and lysophosphatidic acid receptor activity\|plasma membrane\|receptor activity\|signal transduction |
| miR-155 | NM_006795 | EHD1 | EH-domain containing 1 | P + T | ATP binding\|GTP binding\|GTPase activity\|biological_process unknown\|calcium ion binding\|cellular_component unknown |
| miR-155 | NM_012081 | ELL2 | ELL-related RNA polymerase II, elongation factor | M + P + T | RNA elongation from RNA polymerase II promoter\|RNA polymerase II transcription factor activity\|nucleus\|regulation of transcription, DNA-dependent\|transcription\|transcription elongation factor complex |
| miR-155 | NM_005238 | ETS1 | v-ets erythroblastosis virus E26 oncogene homolog 1 (avian) | P + T | RNA polymerase II transcription factor activity\|immune response\|negative regulation of cell proliferation\|nucleus\|regulation of transcription, DNA-dependent\|transcription\|transcription factor activity\|transcription from RNA polymerase II promoter |
| miR-155 | NM_002009 | FGF7 | fibroblast growth factor 7 (keratinocyte growth factor) | P + T | cell proliferation\|cell-cell signaling\|epidermis development\|extracellular region\|growth factor activity\|positive regulation of cell proliferation\|regulation of cell cycle\|response to wounding\|signal transduction |
| miR-155 | NM_018208 | FLJ10761 | hypothetical protein FLJ10761 | P + T | biological_process unknown\|cellular_component unknown\|choline kinase activity\|transferase activity |
| miR-155 | NM_018243 | FLJ10849 | hypothetical protein FLJ10849 | P + T | GTP binding\|cell cycle\|cytokinesis |
| miR-155 | NM_022064 | FLJ12565 | hypothetical protein FLJ12565 | P + T | ligase activity\|protein ubiquitination\|ubiquitin ligase complex\|ubiquitin-protein ligase activity\|zinc ion binding |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-155 | NM_018391 | FLJ23277 | FLJ23277 protein | P + T | |
| miR-155 | NM_021078 | GCN5L2 | GCN5 general control of amino-acid synthesis 5-like 2 (yeast) | M + P + T | N-acetyltransferase activity\|chromatin remodeling\|histone acetyltransferase activity\|histone deacetylase binding\|nucleus\|protein amino acid acetylation\|regulation of transcription from RNA polymerase II promoter\|transcription\|transcription coactivator activity\|transferase activity |
| miR-155 | NM_018178 | GPP34R | hypothetical protein FLJ10687 | P + T | |
| miR-155 | AF019214 | HBP1 | HMG-box containing protein 1 | M + P | DNA binding\|nucleus\|regulation of transcription, DNA-dependent |
| miR-155 | NM_006037 | HDAC4 | histone deacetylase 4 | P + T | B-cell differentiation\|cell cycle\|chromatin modification\|cytoplasm\|development\|histone deacetylase activity\|histone deacetylase complex\|hydrolase activity\|inflammatory response\|negative regulation of myogenesis\|neurogenesis\|nucleus\|regulation of transcription, DNA-dependent\|transcription\|transcription factor binding\|transcriptional repressor activity |
| miR-155 | NM_001530 | HIF1A | hypoxia-inducible factor 1, alpha subunit (basic helix-loop-helix transcription factor) | P + T | RNA polymerase II transcription factor activity, enhancer binding\|electron transport\|histone acetyltransferase binding\|homeostasis\|nucleus\|nucleus\|protein heterodimerization activity\|protein heterodimerization activity\|regulation of transcription, DNA-dependent\|response to hypoxia\|signal transducer activity\|signal transduction\|signal transduction\|transcription factor activity |
| miR-155 | AL023584 | HIVEP2 | human immunodeficiency virus type I enhancer binding protein 2 | P + T | |
| miR-155 | AI682088 | HLCS | holocarboxylase synthetase (biotin-[proprionyl-Coenzyme A-carboxylase (ATP-hydrolysing)] ligase) | P + T | biotin-[acetyl-CoA-carboxylase] ligase activity\|biotin-[methylcrotonoyl-CoA-carboxylase] ligase activity\|biotin-[methylmalonyl-CoA-carboxytransferase] ligase activity\|biotin-[propionyl-CoA-carboxylase (ATP-hydrolyzing)] ligase activity\|ligase activity\|protein modification |
| miR-155 | NM_020190 | HNOEL-iso | HNOEL-iso protein | P + T | |
| miR-155 | NM_014002 | IKBKE | inhibitor of kappa light polypeptide gene enhancer in B-cells, kinase epsilon | P + T | ATP binding\|NF-kappaB-inducing kinase activity\|cytoplasm\|immune response\|positive regulation of I-kappaB kinase/NF-kappaB cascade\|protein amino acid phosphorylation\|protein serine/threonine kinase activity\|signal transducer activity\|transferase activity |
| miR-155 | D13720 | ITK | IL2-inducible T-cell kinase | P + T | ATP binding\|cellular defense response\|intracellular signaling cascade\|non-membrane spanning protein tyrosine kinase activity\|protein amino acid phosphorylation\|transferase activity |
| miR-155 | NM_002249 | KCNN3 | potassium intermediate/small conductance calcium- | P + T | calcium-activated potassium channel activity\|calcium-activated potassium channel activity\|calmodulin |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| | | | activated channel, subfamily N, member 3 | | binding|integral to membrane|ion channel activity|ion transport|membrane|membrane fraction|neurogenesis|potassium ion transport|potassium ion transport|small conductance calcium-activated potassium channel activity|synaptic transmission|voltage-gated potassium channel complex |
| miR-155 | AB033100 | KIAA1274 | KIAA protein (similar to mouse paladin) | P + T | protein tyrosine phosphatase activity |
| miR-155 | NM_017780 | KIAA1416 | KIAA1416 protein | P + T | ATP binding|chromatin|chromatin assembly or disassembly|chromatin binding|helicase activity|nucleus |
| miR-155 | NM_002264 | KPNA1 | karyopherin alpha 1 (importin alpha 5) | P + T | NLS-bearing substrate-nucleus import|cytoplasm|intracellular protein transport|nuclear localization sequence binding|nuclear pore|nucleus|protein binding|protein transporter activity|regulation of DNA recombination |
| miR-155 | AK021602 | KPNA4 | karyopherin alpha 4 (importin alpha 3) | P + T | NLS-bearing substrate-nucleus import|binding|intracellular protein transport|nucleus|protein transporter activity |
| miR-155 | NM_020354 | LALP1 | lysosomal apyrase-like protein 1 | M + P + T | hydrolase activity |
| miR-155 | AW242408 | LOC151531 | Similar to uridine phosphorylase [*Homo sapiens*], mRNA sequence | M + P + T | cytosol|nucleoside metabolism|nucleotide catabolism|protein binding|transferase activity, transferring glycosyl groups|type III intermediate filament|uridine metabolism|uridine phosphorylase activity |
| miR-155 | NM_016210 | LOC51161 | g20 protein | P + T | |
| miR-155 | NM_018557 | LRP1B | low density lipoprotein-related protein 1B (deleted in tumors) | P + T | calcium ion binding|integral to membrane|low-density lipoprotein receptor activity|membrane|protein transport|receptor activity|receptor mediated endocytosis |
| miR-155 | NM_002446 | MAP3K10 | mitogen-activated protein kinase kinase kinase 10 | M + P + T | ATP binding|JUN kinase kinase kinase activity|activation of JNK|autophosphorylation|induction of apoptosis|protein homodimerization activity|protein serine/threonine kinase activity|protein-tyrosine kinase activity|signal transduction|transferase activity |
| miR-155 | NM_003954 | MAP3K14 | mitogen-activated protein kinase kinase kinase 14 | P + T | ATP binding|protein amino acid phosphorylation|protein serine/threonine kinase activity|transferase activity |
| miR-155 | AL117407 | MAP3K7IP2 | mitogen-activated protein kinase kinase kinase 7 interacting protein 2 | P + T | kinase activity|positive regulation of I-kappaB kinase/NF-kappaB cascade|positive regulation of I-kappaB kinase/NF-kappaB cascade|signal transducer activity|signal transducer activity |
| miR-155 | NM_004992 | MECP2 | methyl CpG binding protein 2 (Rett syndrome) | M + P + T | DNA binding|negative regulation of transcription from RNA polymerase II promoter|nucleus|regulation of transcription, DNA-dependent|transcription|transcription corepressor activity |
| miR-155 | NM_002398 | MEIS1 | Meis1, myeloid ecotropic viral integration site 1 homolog (mouse) | M + P + T | RNA polymerase II transcription factor activity|nucleus|regulation of transcription, DNA-dependent|transcription factor activity |
| miR-155 | NM_016289 | MO25 | MO25 protein | P + T | |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-155 | AA621962 | MYO1D | myosin ID | M + P + T | ATP binding\|actin binding\|calmodulin binding\|motor activity\|myosin |
| miR-155 | NM_030571 | N4WBP5 | likely ortholog of mouse Nedd4 WW binding protein 5 | P + T | positive regulation of I-kappaB kinase/NF-kappaB cascade\|signal transducer activity |
| miR-155 | NM_014903 | NAV3 | neuron navigator 3 | P + T | ATP binding\|mitochondrion\|nucleoside-triphosphatase activity\|nucleotide binding |
| miR-155 | NM_030571 | NDFIP1 | likely ortholog of mouse Nedd4 WW binding protein 5 | P + T | positive regulation of I-kappaB kinase/NF-kappaB cascade\|signal transducer activity |
| miR-155 | NM_006599 | NFAT5 | nuclear factor of activated T-cells 5, tonicity-responsive | M + P + T | RNA polymerase II transcription factor activity\|excretion\|nucleus\|regulation of transcription, DNA-dependent\|signal transduction\|transcription factor activity\|transcription from RNA polymerase II promoter |
| miR-155 | NM_002515 | NOVA1 | neuro-oncological ventral antigen 1 | M + P + T | RNA binding\|RNA binding\|RNA splicing\|RNA splicing\|locomotory behavior\|locomotory behavior\|nucleus\|synaptic transmission\|synaptic transmission |
| miR-155 | AI373299 | PANK1 | pantothenate kinase 1 | P + T | ATP binding\|coenzyme A biosynthesis\|pantothenate kinase activity\|transferase activity |
| miR-155 | BG110231 | PAPOLA | poly(A) polymerase alpha | P + T | RNA binding\|cytoplasm\|mRNA polyadenylylation\|mRNA processing\|nucleus\|polynucleotide adenylyltransferase activity\|transcription\|transferase activity |
| miR-155 | NM_020403 | PCDH9 | protocadherin 9 | M + P + T | calcium ion binding\|cell adhesion\|homophilic cell adhesion\|integral to membrane\|membrane\|protein binding |
| miR-155 | NM_002655 | PLAG1 | pleiomorphic adenoma gene 1 | P + T | nucleic acid binding\|nucleus\|transcription factor activity\|zinc ion binding |
| miR-155 | AJ272212 | PSKH1 | protein serine kinase H1 | P + T | ATP binding\|Golgi apparatus\|nucleus\|protein amino acid phosphorylation\|protein serine/threonine kinase activity\|transferase activity |
| miR-155 | NM_014904 | Rab11-FIP2 | KIAA0941 protein | P + T | |
| miR-155 | AF322067 | RAB34 | RAB34, member RAS oncogene family | P + T | GTP binding\|Golgi apparatus\|protein transport\|small GTPase mediated signal transduction |
| miR-155 | NM_002869 | RAB6A | RAB6A, member RAS oncogene family | M + P + T | GTP binding\|GTPase activity\|Golgi apparatus\|protein transport\|small GTPase mediated signal transduction |
| miR-155 | AL136727 | RAB6C | RAB6C, member RAS oncogene family | M + P + T | GTP binding\|GTPase activity\|intracellular\|protein transport\|response to drug\|small GTPase mediated signal transduction |
| miR-155 | NM_002902 | RCN2 | reticulocalbin 2, EF-hand calcium binding domain | P + T | calcium ion binding\|endoplasmic reticulum\|protein binding |
| miR-155 | AJ223321 | RP58 | zinc finger protein 238 | M + P + T | |
| miR-155 | NM_002968 | SALL1 | sal-like 1 (*Drosophila*) | P + T | morphogenesis\|nucleus\|regulation of transcription, DNA-dependent\|transcription\|transcription factor activity\|zinc ion binding |
| miR-155 | NM_002971 | SATB1 | special AT-rich sequence binding protein 1 (binds to nuclear matrix/scaffold-associating DNA's) | P + T | double-stranded DNA binding\|establishment and/or maintenance of chromatin architecture\|nucleus\|regulation of transcription, DNA-dependent\|transcription factor activity |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-155 | NM_003469 | SCG2 | secretogranin II (chromogranin C) | P + T | calcium ion binding|protein secretion |
| miR-155 | NM_005625 | SDCBP | syndecan binding protein (syntenin) | P + T | actin cytoskeleton organization and biogenesis|adherens junction|cytoskeletal adaptor activity|cytoskeleton|endoplasmic reticulum|interleukin-5 receptor binding|interleukin-5 receptor complex|intracellular signaling cascade|metabolism|neurexin binding|nucleus|oxidoreductase activity|plasma membrane|protein binding|protein heterodimerization activity|protein-membrane targeting|substrate-bound cell migration, cell extension|synaptic transmission|syndecan binding |
| miR-155 | NM_000232 | SGCB | sarcoglycan, beta (43 kDa dystrophin-associated glycoprotein) | P + T | cytoskeleton|cytoskeleton organization and biogenesis|integral to plasma membrane|muscle development|sarcoglycan complex |
| miR-155 | NM_013257 | SGKL | serum/glucocorticoid regulated kinase-like | P + T | ATP binding|intracellular signaling cascade|protein amino acid phosphorylation|protein amino acid phosphorylation|protein serine/threonine kinase activity|protein serine/threonine kinase activity|protein-tyrosine kinase activity|response to stress|transferase activity |
| miR-155 | NM_005069 | SIM2 | single-minded homolog 2 (*Drosophila*) | P + T | cell differentiation|neurogenesis|nucleus|regulation of transcription, DNA-dependent|signal transducer activity|signal transduction|transcription|transcription factor activity |
| miR-155 | AA927480 | SKI | v-ski sarcoma viral oncogene homolog (avian) | P + T | |
| miR-155 | NM_006748 | SLA | Src-like-adaptor | P + T | SH3/SH2 adaptor activity|intracellular signaling cascade |
| miR-155 | AI684141 | SMARCA4 | SWI/SNF related, matrix associated, actin dependent regulator of chromatin, subfamily a, member 4 | P + T | ATP binding|DNA binding|helicase activity|helicase activity|hydrolase activity|nucleoplasm|nucleus|regulation of transcription from RNA polymerase II promoter|transcription|transcription coactivator activity|transcription factor activity |
| miR-155 | AB005043 | SOCS1 | suppressor of cytokine signaling 1 | M + P + T | JAK-STAT cascade|cytoplasm|insulin-like growth factor receptor binding|intracellular signaling cascade|negative regulation of JAK-STAT cascade|protein kinase binding|protein kinase inhibitor activity|regulation of cell growth|ubiquitin cycle |
| miR-155 | NM_004232 | SOCS4 | suppressor of cytokine signaling 4 | M + P | JAK-STAT cascade|cytoplasm|defense response|intracellular signaling cascade|regulation of cell growth |
| miR-155 | NM_005986 | SOX1 | SRY (sex determining region Y)-box 1 | P + T | DNA binding|establishment and/or maintenance of chromatin architecture|nucleus|regulation of transcription, DNA-dependent|regulation of transcription, DNA-dependent|transcription factor activity |
| miR-155 | AI360875 | SOX11 | SRY (sex determining region Y)-box 11 | M + T | DNA binding|neurogenesis|nucleus|regulation of transcription, DNA-dependent|transcription |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-155 | AL136780 | SOX6 | SRY (sex determining region Y)-box 6 | P + T | establishment and/or maintenance of chromatin architecture\|heart development\|muscle development\|nucleus\|regulation of transcription, DNA-dependent\|transcription\|transcription factor activity |
| miR-155 | AW470841 | SP3 | Sp3 transcription factor | P + T | DNA binding\|nucleus\|regulation of transcription, DNA-dependent\|transcription\|transcriptional activator activity\|transcriptional repressor activity\|zinc ion binding |
| miR-155 | BF224259 | SPF30 | splicing factor 30, survival of motor neuron-related | P + T | RNA splicing\|RNA splicing factor activity, transesterification mechanism\|apoptosis\|cytoplasm\|induction of apoptosis\|spliceosome assembly\|spliceosome complex |
| miR-155 | NM_003120 | SPI1 | spleen focus forming virus (SFFV) proviral integration oncogene spi1 | M + T | negative regulation of transcription from RNA polymerase II promoter\|nucleus\|regulation of transcription, DNA-dependent\|transcription\|transcription factor activity |
| miR-155 | BE676214 | SSH2 | slingshot 2 | P + T | protein amino acid dephosphorylation\|protein tyrosine/serine/threonine phosphatase activity |
| miR-155 | AF159447 | SUFU | suppressor of fused homolog (*Drosophila*) | P + T | cell cycle\|cytoplasm\|development\|negative regulation of cell cycle\|nucleus\|proteolysis and peptidolysis\|signal transducer activity\|signal transduction\|skeletal development\|transcription corepressor activity |
| miR-155 | NM_006754 | SYPL | synaptophysin-like protein | M + P + T | integral to plasma membrane\|membrane\|synaptic transmission\|synaptic vesicle\|transport\|transporter activity |
| miR-155 | NM_006286 | TFDP2 | transcription factor Dp-2 (E2F dimerization partner 2) | P + T | DNA metabolism\|nucleus\|regulation of cell cycle\|regulation of transcription from RNA polymerase II promoter\|transcription\|transcription cofactor activity\|transcription factor activity\|transcription factor complex |
| miR-155 | AA705845 | TLE4 | transducin-like enhancer of split 4 (E(sp1) homolog, *Drosophila*) | P + T | frizzled signaling pathway\|molecular_function unknown\|nucleus\|nucleus\|regulation of transcription\|regulation of transcription, DNA-dependent |
| miR-155 | NM_014765 | TOMM20 | translocase of outer mitochondrial membrane 20 (yeast) homolog | P + T | integral to membrane\|mitochondrial outer membrane translocase complex\|mitochondrion\|outer membrane\|protein translocase activity\|protein-mitochondrial targeting |
| miR-155 | AW341649 | TP53INP1 | tumor protein p53 inducible nuclear protein 1 | P + T | apoptosis\|nucleus |
| miR-155 | BC005016 | TRIM2 | tripartite motif-containing 2 | P + T | cytoplasm\|myosin binding\|protein ubiquitination\|ubiquitin ligase complex\|ubiquitin-protein ligase activity\|zinc ion binding |
| miR-155 | AA524505 | TSGA | zinc finger protein | P + T | nucleus |
| miR-155 | AW157525 | TSGA14 | testis specific, 14 | M + P + T | centrosome |
| miR-155 | X62048 | WEE1 | WEE1 homolog (*S. pombe*) | P + T | ATP binding\|cytokinesis\|mitosis\|nucleus\|protein amino acid phosphorylation\|protein serine/threonine kinase activity\|protein-tyrosine kinase activity\|regulation of cell cycle\|transferase activity |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-155 | AC005539 | WUGSC:H_NH0335J18.1 | Similar to uridine phosphorylase [Homo sapiens], mRNA sequence | M + P + T | |
| miR-155 | NM_003413 | ZIC3 | Zic family member 3 heterotaxy 1 (odd-paired homolog, Drosophila) | P + T | DNA binding\|determination of left/right symmetry\|nucleus\|regulation of transcription, DNA-dependent\|transcription\|zinc ion binding |
| miR-155 | NM_007345 | ZNF236 | zinc finger protein 236 | P + T | nucleus\|regulation of transcription, DNA-dependent\|transcription\|transcription factor activity\|zinc ion binding |
| miR-155 | NM_006352 | ZNF238 | zinc finger protein 238 | M + P + T | chromosome organization and biogenesis (sensu Eukaryota)\|negative regulation of transcription from RNA polymerase II promoter\|nuclear chromosome\|nucleic acid binding\|nucleus\|protein binding\|protein binding\|regulation of transcription, DNA-dependent\|specific RNA polymerase II transcription factor activity\|transcription\|transcription factor activity\|transport\|zinc ion binding |
| miR-21 | NM_005164 | ABCD2 | ATP-binding cassette, sub-family D (ALD), member 2 | M + P | ATP binding\|ATP-binding cassette (ABC) transporter complex\|ATPase activity\|ATPase activity, coupled to transmembrane movement of substances\|fatty acid metabolism\|integral to plasma membrane\|membrane\|peroxisome\|transport |
| miR-21 | NM_001616 | ACVR2 | activin A receptor, type II | P + T | ATP binding\|integral to plasma membrane\|membrane\|protein amino acid phosphorylation\|receptor activity\|transferase activity\|transforming growth factor beta receptor activity\|transmembrane receptor protein serine/threonine kinase signaling pathway |
| miR-21 | NM_015339 | ADNP | activity-dependent neuroprotector | P + T | nucleus\|regulation of transcription, DNA-dependent\|transcription factor activity\|zinc ion binding |
| miR-21 | AI990366 | ARHGEF7 | Rho guanine nucleotide exchange factor (GEF) 7 | P + T | guanyl-nucleotide exchange factor activity\|signal transduction |
| miR-21 | NM_017610 | ARK | Arkadia | P + T | protein ubiquitination\|ubiquitin ligase complex\|ubiquitin-protein ligase activity\|zinc ion binding |
| miR-21 | NM_014034 | ASF1A | DKFZP547E2110 protein | P + T | chromatin binding\|loss of chromatin silencing\|nucleus |
| miR-21 | NM_017680 | ASPN | asporin (LRR class 1) | P + T | |
| miR-21 | NM_000657 | BCL2 | B-cell CLL/lymphoma 2 | P + T | anti-apoptosis\|endoplasmic reticulum\|humoral immune response\|integral to membrane\|membrane\|mitochondrial outer membrane\|mitochondrial outer membrane\|mitochondrion\|negative regulation of cell proliferation\|nucleus\|protein binding\|regulation of apoptosis\|regulation of cell cycle\|release of cytochrome c from mitochondria |
| miR-21 | NM_014577 | BRD1 | bromodomain containing 1 | P + T | DNA binding\|cell cycle\|nucleus\|nucleus\|regulation of transcription, DNA-dependent |
| miR-21 | AA902767 | BRD2 | bromodomain containing 2 | P + T | nucleus\|protein serine/threonine kinase activity\|spermatogenesis |
| miR-21 | NM_014962 | BTBD3 | BTB (POZ) domain containing 3 | P + T | protein binding |
| miR-21 | NM_006763 | BTG2 | BTG family, member 2 | P + T | DNA repair\|negative regulation of cell proliferation\|regulation of transcription, DNA- |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-21 | AK025768 | C20orf99 | chromosome 20 open reading frame 99 | P + T | dependent\|transcription\|transcription factor activity nucleic acid binding |
| miR-21 | AI671238 | CAPN3 | Homo sapiens cDNA FLJ23750 fis, clone HEP16527, mRNA sequence | P + T | calcium ion binding\|calpain activity\|calpain activity\|intracellular\|intracellular\|muscle development\|proteolysis and peptidolysis\|proteolysis and peptidolysis\|signal transducer activity |
| miR-21 | NM_002981 | CCL1 | chemokine (C-C motif) ligand 1 | P + T | calcium ion homeostasis\|cell-cell signaling\|chemokine activity\|chemotaxis\|extracellular space\|inflammatory response\|sensory perception\|signal transduction\|viral life cycle |
| miR-21 | BF939071 | CCM1 | cerebral cavernous malformations 1 | M + P | binding\|catalytic activity\|cytoskeleton\|small GTPase mediated signal transduction\|small GTPase regulator activity |
| miR-21 | NM_001789 | CDC25A | cell division cycle 25A | P + T | cell proliferation\|cytokinesis\|hydrolase activity\|intracellular\|mitosis\|protein amino acid dephosphorylation\|protein tyrosine phosphatase activity\|regulation of cyclin dependent protein kinase activity |
| miR-21 | NM_001842 | CNTFR | ciliary neurotrophic factor receptor | M + P + T | ciliary neurotrophic factor receptor activity\|cytokine binding\|extrinsic to membrane\|neurogenesis\|receptor activity\|signal transduction |
| miR-21 | NM_001310 | CREBL2 | cAMP responsive element binding protein-like 2 | P + T | nucleus\|regulation of transcription, DNA-dependent\|signal transduction\|transcription\|transcription factor activity |
| miR-21 | NM_016441 | CRIM1 | cysteine-rich motor neuron 1 | M + P + T | insulin-like growth factor receptor activity\|integral to membrane\|membrane fraction\|neurogenesis\|serine-type endopeptidase inhibitor activity |
| miR-21 | NM_015396 | DKFZP434A043 | DKFZP434A043 protein | P + T | cell adhesion\|cytoskeleton\|mitotic chromosome condensation\|protein binding\|structural molecule activity |
| miR-21 | AL047650 | DKFZp434A2417 | endozepine-related protein precursor | P + T | acyl-CoA binding |
| miR-21 | AB028628 | DKFZP547E2110 | DKFZP547E2110 protein | P + T | chromatin binding\|loss of chromatin silencing\|nucleus |
| miR-21 | NM_031305 | DKFZP564B1162 | hypothetical protein DKFZp564B1162 | P + T | GTPase activator activity |
| miR-21 | NM_004405 | DLX2 | distal-less homeo box 2 | P + T | brain development\|development\|nucleus\|regulation of transcription, DNA-dependent\|transcription factor activity |
| miR-21 | NM_001949 | E2F3 | E2F transcription factor 3 | M + P + T | nucleus\|protein binding\|regulation of cell cycle\|regulation of transcription, DNA-dependent\|transcription\|transcription factor activity\|transcription factor complex\|transcription initiation from RNA polymerase II promoter |
| miR-21 | NM_006795 | EHD1 | EH-domain containing 1 | P + T | ATP binding\|GTP binding\|GTPase activity\|biological_process unknown\|calcium ion binding\|cellular_component unknown |
| miR-21 | NM_001412 | EIF1A | eukaryotic translation initiation factor 1A | P + T | RNA binding\|eukaryotic translation initiation factor 4F complex\|protein biosynthesis\|translation initiation factor activity\|translational initiation\|translational initiation |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-21 | AI832074 | EIF2C2 | eukaryotic translation initiation factor 2C, 2 | P + T | cellular_component unknown\|protein biosynthesis\|translation initiation factor activity |
| miR-21 | NM_006874 | ELF2 | E74-like factor 2 (ets domain transcription factor) | P + T | nucleus\|nucleus\|protein binding\|protein binding\|regulation of transcription from RNA polymerase II promoter\|regulation of transcription, DNA-dependent\|transcription factor activity\|transcriptional activator activity\|transcriptional activator activity |
| miR-21 | NM_004438 | EPHA4 | EphA4 | P + T | ATP binding\|ephrin receptor activity\|integral to plasma membrane\|membrane\|protein amino acid phosphorylation\|receptor activity\|signal transduction\|transferase activity\|transmembrane receptor protein tyrosine kinase signaling pathway |
| miR-21 | BE888593 | FLJ11220 | hypothetical protein FLJ11220 | P + T | |
| miR-21 | NM_017637 | FLJ20043 | hypothetical protein FLJ20043 | P + T | nucleic acid binding\|nucleus\|zinc ion binding |
| miR-21 | AF019214 | HBP1 | HMG-box containing protein 1 | M + P + T | DNA binding\|nucleus\|regulation of transcription, DNA-dependent |
| miR-21 | NM_000214 | JAG1 | jagged 1 (Alagille syndrome) | M + P + T | Notch binding\|Notch signaling pathway\|angiogenesis\|calcium ion binding\|calcium ion binding\|cell communication\|cell fate determination\|development\|endothelial cell differentiation\|extracellular region\|growth factor activity\|hemopoiesis\|integral to plasma membrane\|keratinocyte differentiation\|membrane\|myoblast differentiation\|neurogenesis\|regulation of cell migration\|regulation of cell proliferation\|structural molecule activity |
| miR-21 | NM_002232 | KCNA3 | potassium voltage-gated channel, shaker-related subfamily, member 3 | M + P + T | cation transport\|delayed rectifier potassium channel activity\|integral to membrane\|membrane\|membrane fraction\|potassium ion transport\|voltage-gated potassium channel complex |
| miR-21 | NM_014766 | KIAA0193 | KIAA0193 gene product | P + T | cellular_component unknown\|dipeptidase activity\|exocytosis\|proteolysis and peptidolysis |
| miR-21 | NM_014912 | KIAA0940 | KIAA0940 protein | M + P + T | nucleic acid binding |
| miR-21 | NM_014952 | KIAA0945 | KIAA0945 protein | P + T | DNA binding |
| miR-21 | NM_017780 | KIAA1416 | KIAA1416 protein | P + T | ATP binding\|chromatin\|chromatin assembly or disassembly\|chromatin binding\|helicase activity\|nucleus |
| miR-21 | AB040901 | KIAA1468 | KIAA1468 protein | P + T | binding\|mitotic chromosome condensation |
| miR-21 | U90268 | Krit1 | cerebral cavernous malformations 1 | M + P | binding\|catalytic activity\|cytoskeleton\|small GTPase mediated signal transduction\|small GTPase regulator activity |
| miR-21 | BF591611 | LOC147632 | hypothetical protein BC010734 | P + T | oxidoreductase activity\|zinc ion binding |
| miR-21 | NM_005904 | MADH7 | MAD, mothers against decapentaplegic homolog 7 (*Drosophila*) | P + T | intracellular\|protein binding\|receptor signaling protein serine/threonine kinase signaling protein activity\|regulation of transcription, DNA-dependent\|response to stress\|transcription\|transforming growth factor beta receptor signaling pathway\|transforming growth factor beta receptor, inhibitory cytoplasmic mediator activity |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-21 | NM_025146 | MAK3P | likely ortholog of mouse Mak3p homolog (*S. cerevisiae*) | P + T | N-acetyltransferase activity |
| miR-21 | NM_014319 | MAN1 | integral inner nuclear membrane protein | P + T | integral to membrane\|integral to nuclear inner membrane\|membrane fraction\|nuclear membrane\|nucleotide binding |
| miR-21 | AW025150 | MAP3K12 | mitogen-activated protein kinase kinase kinase 12 | M + T | ATP binding\|JNK cascade\|cytoplasm\|magnesium ion binding\|plasma membrane\|protein amino acid phosphorylation\|protein kinase cascade\|protein serine/threonine kinase activity\|protein-tyrosine kinase activity\|transferase activity |
| miR-21 | NM_012325 | MAPRE1 | microtubule-associated protein, RP/EB family, member 1 | P + T | cell proliferation\|cytokinesis\|microtubule binding\|mitosis\|protein C-terminus binding\|regulation of cell cycle |
| miR-21 | NM_002380 | MATN2 | matrilin 2 | P + T | biological_process unknown\|calcium ion binding\|extracellular matrix (sensu Metazoa) |
| miR-21 | NM_018834 | MATR3 | matrin 3 | M + P + T | RNA binding\|nuclear inner membrane\|nucleotide binding\|nucleus\|structural molecule activity\|zinc ion binding |
| miR-21 | NM_021038 | MBNL1 | muscleblind-like (*Drosophila*) | M + P + T | cytoplasm\|double-stranded RNA binding\|embryonic development (sensu Mammalia)\|embryonic limb morphogenesis\|muscle development\|myoblast differentiation\|neurogenesis\|nucleic acid binding\|nucleus\|nucleus |
| miR-21 | AI139252 | MGC16063 | ribosomal protein L35a | P + T | JAK-STAT cascade\|acute-phase response\|calcium ion binding\|cell motility\|cytoplasm\|hematopoietin/interferon-class (D200-domain) cytokine receptor signal transducer activity\|intracellular signaling cascade\|negative regulation of transcription from RNA polymerase II promoter\|neurogenesis\|nucleus\|nucleus\|regulation of transcription, DNA-dependent\|signal transducer activity\|transcription\|transcription factor activity\|transcription factor activity |
| miR-21 | BC004162 | MGC2452 | hypothetical protein MGC2452 | P + T | fatty acid metabolism\|generation of precursor metabolites and energy\|ligand-dependent nuclear receptor activity\|lipid metabolism\|nucleus\|nucleus\|regulation of transcription, DNA-dependent\|steroid hormone receptor activity\|transcription\|transcription factor activity\|transcription factor activity\|transcription from RNA polymerase II promoter |
| miR-21 | NM_024052 | MGC3048 | hypothetical protein MGC3048 | P + T | |
| miR-21 | AB049636 | MRPL9 | mitochondrial ribosomal protein L9 | P + T | mitochondrion\|protein biosynthesis\|ribosome\|structural constituent of ribosome |
| miR-21 | NM_015678 | NBEA | neurobeachin | P + T | Golgi trans face\|cytosol\|endomembrane system\|plasma membrane\|post-Golgi transport\|postsynaptic membrane\|protein kinase A binding |
| miR-21 | AI700518 | NFIB | nuclear factor I/B | M + T | DNA replication\|nucleus\|nucleus\|regulation of transcription, DNA-dependent\|transcription\|transcription factor activity\|transcription factor activity |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-21 | NM_002527 | NTF3 | neurotrophin 3 | M + P | anti-apoptosis\|cell motility\|cell-cell signaling\|growth factor activity\|neurogenesis\|signal transduction |
| miR-21 | U24223 | PCBP1 | poly(rC) binding protein 1 | M + P + T | RNA binding\|catalytic activity\|cytoplasm\|mRNA metabolism\|nucleus\|ribonucleoprotein complex\|single-stranded DNA binding |
| miR-21 | NM_005016 | PCBP2 | poly(rC) binding protein 2 | M + T | DNA binding\|RNA binding\|cytoplasm\|mRNA metabolism\|nucleic acid binding\|nucleus\|ribonucleoprotein complex |
| miR-21 | NM_014456 | PDCD4 | programmed cell death 4 (neoplastic transformation inhibitor) | P + T | apoptosis |
| miR-21 | AF338650 | PDZD2 | PDZ domain containing 2 | P + T | |
| miR-21 | NM_000325 | PITX2 | paired-like homeodomain transcription factor 2 | M + P + T | determination of left/right symmetry\|development\|nucleus\|organogenesis\|regulation of transcription, DNA-dependent\|transcription factor activity |
| miR-21 | NM_002655 | PLAG1 | pleiomorphic adenoma gene 1 | P + T | nucleic acid binding\|nucleus\|transcription factor activity\|zinc ion binding |
| miR-21 | NM_005036 | PPARA | peroxisome proliferative activated receptor, alpha | P + T | fatty acid metabolism\|generation of precursor metabolites and energy\|ligand-dependent nuclear receptor activity\|lipid metabolism\|nucleus\|nucleus\|regulation of transcription, DNA-dependent\|steroid hormone receptor activity\|transcription\|transcription factor activity\|transcription factor activity\|transcription from RNA polymerase II promoter |
| miR-21 | NM_002711 | PPP1R3A | protein phosphatase 1, regulatory (inhibitor) subunit 3A (glycogen and sarcoplasmic reticulum binding subunit, skeletal muscle) | P + T | carbohydrate metabolism\|glycogen metabolism\|hydrolase activity\|integral to membrane\|phosphoprotein phosphatase activity\|type 1 serine/threonine specific protein phosphatase inhibitor activity |
| miR-21 | NM_000944 | PPP3CA | protein phosphatase 3 (formerly 2B), catalytic subunit, alpha isoform (calcineurin A alpha) | P + T | calcineurin complex\|calcium ion binding\|calmodulin binding\|hydrolase activity\|protein amino acid dephosphorylation\|protein serine/threonine phosphatase activity |
| miR-21 | NM_018569 | PRO0971 | hypothetical protein PRO0971 | P + T | |
| miR-21 | AA156948 | PRPF4B | PRP4 pre-mRNA processing factor 4 homolog B (yeast) | M + T | ATP binding\|RNA splicing\|nuclear mRNA splicing, via spliceosome\|nucleus\|protein amino acid phosphorylation\|protein serine/threonine kinase activity\|transferase activity |
| miR-21 | BF337790 | PURB | purine-rich element binding protein B | M + P + T | |
| miR-21 | NM_002869 | RAB6A | RAB6A, member RAS oncogene family | P + T | GTP binding\|GTPase activity\|Golgi apparatus\|protein transport\|small GTPase mediated signal transduction |
| miR-21 | AL136727 | RAB6C | RAB6C, member RAS oncogene family | P + T | GTP binding\|GTPase activity\|intracellular\|protein transport\|response to drug\|small GTPase mediated signal transduction |
| miR-21 | NM_002890 | RASA1 | RAS p21 protein activator (GTPase activating protein) 1 | P + T | Ras GTPase activator activity\|intracellular signaling cascade |
| miR-21 | NM_005739 | RASGRP1 | RAS guanyl releasing protein 1 (calcium and DAG-regulated) | P + T | Ras guanyl-nucleotide exchange factor activity\|Ras protein signal transduction\|calcium ion binding\|calcium ion binding\|diacylglycerol |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-21 | NM_021111 | RECK | reversion-inducing-cysteine-rich protein with kazal motifs | M + P + T | binding\|guanyl-nucleotide exchange factor activity\|membrane fraction\|small GTPase mediated signal transduction cell cycle\|membrane\|membrane fraction\|metalloendopeptidase inhibitor activity\|negative regulation of cell cycle\|serine-type endopeptidase inhibitor activity |
| miR-21 | NM_006915 | RP2 | retinitis pigmentosa 2 (X-linked recessive) | P + T | beta-tubulin folding\|membrane\|sensory perception\|unfolded protein binding\|visual perception |
| miR-21 | AA906056 | RPS6KA3 | ribosomal protein S6 kinase, 90 kDa, polypeptide 3 | M + T | ATP binding\|central nervous system development\|protein amino acid phosphorylation\|protein serine/threonine kinase activity\|signal transduction\|skeletal development\|transferase activity |
| miR-21 | NM_002971 | SATB1 | special AT-rich sequence binding protein 1 (binds to nuclear matrix/scaffold-associating DNA's) | M + P + T | double-stranded DNA binding\|establishment and/or maintenance of chromatin architecture\|nucleus\|regulation of transcription, DNA-dependent\|transcription factor activity |
| miR-21 | NM_014191 | SCN8A | sodium channel, voltage gated, type VIII, alpha polypeptide | M + P + T | ATP binding\|cation channel activity\|cation transport\|integral to membrane\|membrane\|neurogenesis\|sodium ion transport\|voltage-gated sodium channel activity\|voltage-gated sodium channel complex |
| miR-21 | AA927480 | SKI | v-ski sarcoma viral oncogene homolog (avian) | M + P + T | |
| miR-21 | NM_003983 | SLC7A6 | solute carrier family 7 (cationic amino acid transporter, y + system), member 6 | P + T | amino acid metabolism\|amino acid transport\|amino acid-polyamine transporter activity\|integral to plasma membrane\|plasma membrane\|protein complex assembly\|transport |
| miR-21 | NM_006359 | SLC9A6 | solute carrier family 9 (sodium/hydrogen exchanger), isoform 6 | P + T | antiporter activity\|endoplasmic reticulum membrane\|integral to membrane\|integral to membrane\|ion transport\|microsome\|mitochondrion\|regulation of pH\|sodium ion transport\|sodium:hydrogen antiporter activity\|solute:hydrogen antiporter activity |
| miR-21 | NM_003076 | SMARCD1 | SWI/SNF related, matrix associated, actin dependent regulator of chromatin, subfamily d, member 1 | P + T | chromatin remodeling\|chromatin remodeling complex\|regulation of transcription from RNA polymerase II promoter\|transcription coactivator activity |
| miR-21 | AI669815 | SOX2 | SRY (sex determining region Y)-box 2 | P + T | establishment and/or maintenance of chromatin architecture\|nucleus\|regulation of transcription, DNA-dependent\|transcription\|transcription factor activity |
| miR-21 | NM_006940 | SOX5 | SRY (sex determining region Y)-box 5 | P + T | nucleus\|regulation of transcription, DNA-dependent\|transcription\|transcription factor activity\|transcription from RNA polymerase II promoter |
| miR-21 | AI808807 | SOX7 | SRY (sex determining region Y)-box 7 | P + T | DNA binding\|nucleus\|regulation of transcription, DNA-dependent\|transcription |
| miR-21 | NM_006717 | SPIN | Spindling | P + T | gametogenesis\|ribonucleoprotein complex |
| miR-21 | NM_005842 | SPRY2 | sprouty homolog 2 (*Drosophila*) | P + T | cell-cell signaling\|development\|membrane\|organogenesis\|regulation of signal transduction |
| miR-21 | NM_006751 | SSFA2 | sperm specific antigen 2 | P + T | plasma membrane |
| miR-21 | NM_006603 | STAG2 | stromal antigen 2 | P + T | cell cycle\|chromosome segregation\|cytokinesis\|meiosis\|mitosis\| |

TABLE 4-continued

Putative gene targets of differentially-expressed miRNA identified by at least two prediction methods

| miRNA | Genbank | Gene Symbol | Gene Name | Prediction algorithm | Gene Ontology condensed |
|---|---|---|---|---|---|
| miR-21 | BC000627 | STAT3 | signal transducer and activator of transcription 3 (acute-phase response factor) | P + T | molecular_function unknown\|nucleus JAK-STAT cascade\|acute-phase response\|calcium ion binding\|cell motility\|cytoplasm\|hematopoietin\|interferon-class (D200-domain) cytokine receptor signal transducer activity\|intracellular signaling cascade\|negative regulation of transcription from RNA polymerase II promoter\|neurogenesis\|nucleus\|nucleus\|regulation of transcription, DNA-dependent\|signal transducer activity\|transcription\|transcription factor activity\|transcription factor activity |
| miR-21 | AW138827 | TAF5 | TAF5 RNA polymerase II, TATA box binding protein (TBP)-associated factor, 100 kDa | P + T | nucleus\|regulation of transcription, DNA-dependent\|transcription factor TFIID complex\|transcription factor activity |
| miR-21 | BF591040 | TAGAP | T-cell activation GTPase activating protein | P + T | GTPase activator activity |
| miR-21 | NM_000358 | TGFBI | transforming growth factor, beta-induced, 68 kDa | M + P + T | cell adhesion\|cell proliferation\|extracellular matrix (sensu Metazoa)\|extracellular space\|integrin binding\|negative regulation of cell adhesion\|protein binding\|sensory perception\|visual perception |
| miR-21 | NM_000362 | TIMP3 | tissue inhibitor of metalloproteinase 3 (Sorsby fundus dystrophy, pseudoinflammatory) | P + T | enzyme inhibitor activity\|extracellular matrix (sensu Metazoa)\|extracellular matrix (sensu Metazoa)\|induction of apoptosis by extracellular signals\|metalloendopeptidase inhibitor activity\|sensory perception\|visual perception |
| miR-21 | AA149745 | TRIM2 | tripartite motif-containing 2 | M + P + T | cytoplasm\|myosin binding\|protein ubiquitination\|ubiquitin ligase complex\|ubiquitin-protein ligase activity\|zinc ion binding |
| miR-21 | AF346629 | TRPM7 | transient receptor potential cation channel, subfamily M, member 7 | P + T | ATP binding\|calcium channel activity\|calcium ion transport\|cation transport\|integral to membrane\|membrane\|protein amino acid phosphorylation\|protein serine/threonine kinase activity\|transferase activity |
| miR-21 | AI745185 | YAP1 | Yes-associated protein 1, 65 kDa | P + T | |
| miR-21 | NM_005667 | ZFP103 | zinc finger protein 103 homolog (mouse) | P + T | central nervous system development\|integral to membrane\|protein ubiquitination\|ubiquitin ligase complex\|ubiquitin-protein ligase activity\|zinc ion binding |
| miR-21 | N62196 | ZNF367 | zinc finger protein 367 | M + P + T | nucleic acid binding\|nucleus\|zinc ion binding |

M = MiRanda
P = PicTar
T = TargetScan

EXAMPLE 3

Bio-pathological Features and microRNA Expression

Materials and Methods
Immunohistochemical Analysis of Breast Cancer Samples.
Staining procedures were performed as described (Querzoli, P., et al., *Anal. Quant. Cytol. Histol.* 21:151-160 (1999)).

Hormonal receptors were evaluated with 6F11 antibody for estrogen receptor a (ER) and PGR-1A6 antibody for progesterone receptor (PR) (Ventana, Tucson, Ariz., U.S.A.). The proliferation index was assessed with MIB1 antibody (DAKO, Copenhagen). ERBB2 was detected with CB 11 antibody (Ventana, Tucson, Ariz., U.S.A.) and p53 protein expression was examined with D07 antibody (Ventana, Tucson, Ariz., U.S.A.). Only tumor cells with distinct nuclear immunostaining for ER, PR, Mib1 and p53 were recorded as positive. Tumor cells were considered positive for ERBB2 when they showed distinct membrane immunoreactivity.

To perform a quantitative analysis of the expression of these various biological markers, the Eureka Menarini computerized image analysis system was used. For each tumor section, at least 20 microscopic fields of invasive carcinoma were measured using a 40× objective. The following cut-off values were employed: 10% of positive nuclear area for ER, PR, c-erbB2 and p53, 13% of nuclei expressing Mib1 was introduced to discriminate cases with high and low proliferative activity.

Results

To evaluate whether a correlation exists between various bio-pathological features associated with breast cancer and the expression of particular miRNAs, we generated and compared miRNA expression profiles for various cancer samples associated with the presence or absence of a particular breast cancer feature. In particular, we analyzed breast cancers with lobular or ductal histotypes, breast cancers with differential expression of either estrogen receptor alpha (ER) or progesterone receptor, and breast cancers with differences in lymph node metastasis, vascular invasion, proliferation index, and expression of ERBB2 and p53.

Expression profiles of lobular or ductal and +/−ERBB2 expression classes did not reveal any microRNAs that were differentially-expressed, while all other comparisons revealed a small number of differentially-expressed microRNAs (P<0.05). Tumor grade was not analyzed. The results of this analysis are shown in FIG. 4.

Differentially-expressed miRNA families were identified for various bio-pathological features that are associated with human breast cancer. For example, all miR-30 miRNAs are down-regulated in both ER- and PR-tumors, suggesting that expression of miR-30 miRNAs is regulated by these hormones. In addition, the expression of various let-7 miRNAs was down-regulated in breast cancer samples with either lymph node metastasis or a high proliferation index, suggesting that reduced let-7 expression could be associated with a poor prognosis, a result that is consistent with previous findings (Takamizawa, J., et al., Cancer Res. 39: 167-169 (2004)). The discovery that the let-7 family of miRNAs regulates the expression of members of the RAS oncogene family provides a potential explanation for the role of let-7 miRNAs in human cancer (Johnson, S. M., et al., Cell 120:635-647 (2005)).

miR-145 and miR-21, two miRNAs whose expression could differentiate cancer or normal tissues, were also differentially-expressed in cancers with a different proliferation index or different tumor stage. In particular, miR-145 is progressively down-regulated from normal breast to cancers with a high proliferation index. Similarly, miR-21 is progressively up-regulated from normal breast to cancers with high tumor stage. These findings suggest that deregulation of these two miRNAs may affect critical molecular events involved in tumor progression.

Another miRNA potentially involved in cancer progression is miR-9-3. miR-9-3 was downregulated in breast cancers with either high vascular invasion or lymph node metastasis, suggesting that its down-regulation was acquired during the course of tumor progression and, in particular, during the acquisition of metastatic potential.

The relevant teachings of all publications cited herein that have not explicitly been incorporated by reference, are incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method of diagnosing whether a subject has, or is at risk for developing, breast cancer, comprising measuring the level of at least one miR-155 gene product in a test sample from said subject, wherein an increase in the level of the miR-155 gene product in the test sample, relative to the level of a corresponding miR-155 gene product in a control sample, is indicative of the subject either having, or being at risk for developing, breast cancer.

2. The method of claim 1, which further comprises measuring at least one miR-125b-1 gene product.

3. The method of claim 1, which further comprises measuring at least one miR-145 gene product.

4. The method of claim 1, which further comprises measuring at least one miR-21 gene product.

5. The method of claim 1, which further comprises measuring at least one miR-125b-2 gene product.

6. The method of claim 1, which further comprises measuring at least one miR-10b gene product.

7. The method of claim 1, which further comprises measuring at least one miR gene product selected from the group consisting of miR-125b, miR-145, miR-21, miR-10b, miR-009-1 (miR131-1), miR-34 (miR-170), miR-102 (miR-29b), miR-123 (miR-126), miR-140-as, miR-125a, miR-125b-1, miR-125b-2, miR-194, miR-204, miR-213, let-7a-2, let-7a-3, let-7d (let-7d-v1), let-7f-2, let-7i (let-7d-v2), miR-101-1, miR-122a, miR-128b, miR-136, miR-143, miR-149, miR-191, miR-196-1, miR-196-2, miR-202, miR-203, miR-206, miR-210 and combinations thereof.

8. The method of claim 1, wherein the level of the at least one miR-155 gene product is measured using Northern blot analysis.

9. The method of claim 1, wherein the level of the at least one miR-155 gene product in the test sample is less than the level of the corresponding miR-155 gene product in the control sample.

10. The method of claim 1, wherein the level of the at least one miR-155 gene product in the test sample is greater than the level of the corresponding miR-155 gene product in the control sample.

* * * * *